US011505809B2

(12) United States Patent
Pearlman et al.

(10) Patent No.: US 11,505,809 B2
(45) Date of Patent: Nov. 22, 2022

(54) ORGANISMS AND BIOSYNTHETIC PROCESSES FOR HYDROCARBON SYNTHESIS

(71) Applicant: INV Nylon Chemicals Amercias, LLC, Wilmington, DE (US)

(72) Inventors: Paul S. Pearlman, Redcar (GB); Alex Van Eck Conradie, Redcar (GB); Gary Smith, Redcar (GB)

(73) Assignee: INV Nylon Chemicals Americas LLC, Wilmington, DE (US)

( * ) Notice: Subject to any disclaimer, the term of this patent is extended or adjusted under 35 U.S.C. 154(b) by 0 days.

(21) Appl. No.: 16/144,035

(22) Filed: Sep. 27, 2018

(65) Prior Publication Data

US 2019/0093130 A1 Mar. 28, 2019

Related U.S. Application Data

(60) Provisional application No. 62/564,369, filed on Sep. 28, 2017.

(51) Int. Cl.

| | |
|---|---|
| ***C12P 5/02*** | (2006.01) |
| ***C12N 9/10*** | (2006.01) |
| ***C08F 36/08*** | (2006.01) |
| ***C12N 9/00*** | (2006.01) |
| ***C12N 9/88*** | (2006.01) |
| ***C12P 5/00*** | (2006.01) |
| ***C12N 15/52*** | (2006.01) |

(52) U.S. Cl.

CPC .............. *C12P 5/026* (2013.01); *C08F 36/08* (2013.01); *C12N 9/1025* (2013.01); *C12N 9/1029* (2013.01); *C12N 9/88* (2013.01); *C12N 9/93* (2013.01); *C12N 15/52* (2013.01); *C12P 5/007* (2013.01); *C12Y 101/01027* (2013.01); *C12Y 203/01* (2013.01); *C12Y 203/01009* (2013.01); *C12Y 203/01016* (2013.01); *C12Y 401/01005* (2013.01); *C12Y 402/01134* (2015.07); *C12Y 604/00* (2013.01)

(58) Field of Classification Search

CPC ........ C12P 5/026; C12P 5/007; C12N 9/1029; C12N 15/52; C12N 9/1025; C12N 9/93; C12N 9/88; C12Y 401/01005; C12Y 101/01027; C12Y 203/01009; C12Y 203/01; C12Y 203/01016; C12Y 402/01134; C12Y 604/00; C08F 36/08

See application file for complete search history.

(56) References Cited

U.S. PATENT DOCUMENTS

| | | | | |
|---|---|---|---|---|
| 4,605,620 | A | 8/1986 | Andersch et al. | 435/148 |
| 5,830,714 | A | 11/1998 | Swaminathan et al. | 435/91.2 |
| 8,703,455 | B2 | 4/2014 | Marliere | 435/167 |
| 8,741,612 | B2 | 6/2014 | Campbell et al. | 435/167 |
| 9,297,026 | B2 | 3/2016 | Koepke et al. | |
| 9,422,578 | B2 | 8/2016 | Pearlman et al. | C12P 5/02 |
| 9,422,580 | B2 | 8/2016 | Pearlman et al. | C12P 5/026 |
| 9,777,300 | B2 | 10/2017 | Yeh et al. | C12P 7/6409 |
| 9,862,973 | B2 | 1/2018 | Botes et al. | C12P 5/007 |
| 10,167,487 | B2 | 1/2019 | Conradie | C12P 5/007 |
| 10,538,788 | B2 | 1/2020 | Cartman et al. | 435/232 |
| 10,538,789 | B2 | 1/2020 | Kamionka et al. | C12P 5/007 |
| 2003/0148416 | A1 | 8/2003 | Berry et al. | |
| 2008/0311640 | A1 | 12/2008 | Cox et al. | 435/168 |
| 2009/0117629 | A1 | 5/2009 | Schmidt-Dannert et al. | 435/134 |
| 2011/0053216 | A1 | 3/2011 | Vermass | 435/69.1 |
| 2011/0160501 | A1 | 6/2011 | Martin et al. | 585/14 |
| 2011/0165644 | A1 | 7/2011 | Marliere | 435/167 |
| 2011/0300597 | A1 | 12/2011 | Burk et al. | 435/167 |
| 2012/0015427 | A1 | 1/2012 | Green et al. | 435/257.2 |
| 2012/0021478 | A1 | 1/2012 | Osterhout et al. | 435/167 |
| 2012/0045807 | A1 | 2/2012 | Simpson et al. | 435/148 |
| 2012/0055081 | A1 | 3/2012 | Aravanis et al. | |
| 2012/0122563 | A1 | 5/2012 | Walker et al. | |
| 2012/0164711 | A1 | 6/2012 | Muir et al. | |
| 2012/0225466 | A1 | 9/2012 | Burk et al. | 435/167 |
| 2012/0329119 | A1 | 12/2012 | Burgard et al. | 435/167 |
| 2013/0189753 | A1 | 7/2013 | Pearlman et al. | 435/167 |
| 2013/0210104 | A1 | 8/2013 | Pearlman et al. | 435/167 |
| 2013/0252300 | A1 | 9/2013 | Green et al. | 435/161 |
| 2013/0309742 | A1 | 11/2013 | Campbell et al. | |
| 2013/0323820 | A1 | 12/2013 | Chen et al. | 435/252.3 |
| 2013/0330709 | A1 | 12/2013 | Beatty et al. | 435/4 |
| 2014/0065686 | A1 | 3/2014 | Marliere | 435/167 |
| 2014/0141482 | A1 | 5/2014 | Pearlman et al. | 435/167 |
| 2014/0148622 | A1 | 5/2014 | Nair et al. | |
| 2014/0186913 | A1 | 7/2014 | Botes et al. | 435/167 |

(Continued)

FOREIGN PATENT DOCUMENTS

| | | |
|---|---|---|
| CN | 103602626 | 2/1916 |
| EP | 2336340 | 6/2011 |

(Continued)

OTHER PUBLICATIONS

Tan et al. Activating Phosphoenolpyruvate Carboxylase and Phosphoenolpyruvate Carboxykinase in Combination for Improvement of Succinate Production. Appl and Environ Microbiol (2013), 79(16): p. 4838-4844.*

Islam et al., "Investigating Moorella thermoacetica Metabolism with a Genome-Scale Constraint-Based Metabolic Model", Integrative Biology, 2015, 26 pages.

Kuzuyama, Tomohiisa, "Mevalonate and Nonmevalonate Pathways for the Biosynthesis of Isoprene Units", Bioscience Biotechnology Biochemistry, vol. 66, No. 8, 2002, pp. 1619-1627.

(Continued)

*Primary Examiner* — Iqbal H Chowdhury

(57) ABSTRACT

Methods for biosynthesising hydrocarbons from a gaseous substrate in non-naturally occurring acetogens as well as non-naturally occurring acetogens for production of hydrocarbons are provided.

17 Claims, 7 Drawing Sheets

Specification includes a Sequence Listing.

(56) References Cited

U.S. PATENT DOCUMENTS

2014/0206901 A1* 7/2014 Koepke .................... C12P 7/40 562/577
2014/0234926 A1 8/2014 Beck et al.
2014/0242649 A1 8/2014 Yeh et al. .................... 435/134
2014/0335576 A1 11/2014 Chotani et al. ............... 435/131
2015/0017694 A1 1/2015 Kurek et al.
2015/0037860 A1 2/2015 Botes et al. ................. 435/167
2015/0037869 A1 2/2015 Savile et al.
2015/0079654 A1 3/2015 Botes et al. ................. 435/167
2015/0140640 A1 5/2015 Reed et al.
2015/0191747 A1 7/2015 Chen et al. ............. C12P 5/007
2015/0210987 A1 7/2015 Nagaraju et al.
2015/0284742 A1 10/2015 Furutani et al. ........ C12P 5/007
2015/0291981 A1 10/2015 Marliere et al. ........ C12P 5/026
2016/0002672 A1 1/2016 Beck et al. ............. C12P 5/007
2016/0017374 A1 1/2016 Leonard et al. ........ C12P 5/007
2016/0130618 A1* 5/2016 Hara ...................... C12P 13/04 435/107
2017/0051314 A1 2/2017 Conradie ................ C12P 5/007
2017/0106054 A1 4/2017 Summar et al. ....... A61K 38/44
2017/0145441 A1 5/2017 Conradie ................ C12P 5/007
2017/0260552 A1 9/2017 Haas et al.
2018/0094282 A1 4/2018 Cartman et al. ........ C12P 5/007
2018/0127788 A1 5/2018 Kamionka et al. ..... C12P 5/007
2018/0208952 A1 7/2018 Koepke et al.
2018/0291401 A1 10/2018 Conradie ................ C12P 5/007
2019/0002926 A1 1/2019 Cartman et al. ........ C12P 5/007
2019/0002927 A1 1/2019 Foster et al. ........... C12P 5/007
2019/0017076 A1 1/2019 Conradie ................ C12P 5/007
2019/0093130 A1 3/2019 Pearlman et al.
2019/0218577 A1 7/2019 Cartman et al. ........ C12P 5/007
2019/0271009 A1 9/2019 Conradie ................ C12P 5/007

FOREIGN PATENT DOCUMENTS

EP 2336341 6/2011
EP 12190039 10/2012
EP 2857509 A1 4/2015
EP 2913392 9/2015
KR 20150006097 1/2015
WO 2017/029549 2/1917
WO 2017/029553 2/1917
WO 2018/064105 4/1918
WO 2019/006255 1/1919
WO 2019/006257 1/1919
WO 2006/014837 2/2006
WO 2009/064910 5/2009
WO 2009/111513 A1 9/2009
WO 2009/132220 10/2009
WO 2009/155382 12/2009
WO 2010/001078 1/2010
WO 2010/031062 3/2010
WO 2010/099201 9/2010
WO 2010/115838 10/2010
WO 2011/011689 1/2011
WO 2011/076261 6/2011
WO 2011/076689 6/2011
WO 2011/076691 6/2011
WO 2011/079314 6/2011
WO 2011/140171 11/2011
WO 2012/018624 2/2012
WO 2012/052427 4/2012
WO 2012/174439 12/2012
WO 2013/007786 1/2013
WO 2013/020118 2/2013
WO 2013/028519 2/2013
WO 2013/036812 3/2013
WO 2013/040383 3/2013
WO 2013/057194 4/2013
WO 2013/082542 6/2013
WO 2013/090915 6/2013
WO 2013/092567 6/2013
WO 2013096863 A1 6/2013
WO 2013/119340 8/2013
WO 2013/150100 10/2013
WO 2013/173437 11/2013
WO 2013/180584 12/2013
WO 2013/180584 A1 12/2013
WO 2013/181647 12/2013
WO 2013/188546 12/2013
WO 2013/192183 12/2013
WO 2014/001517 1/2014
WO 2014/015210 1/2014
WO 2014/033129 3/2014
WO 2014/064198 5/2014
WO 2014/085612 6/2014
WO 2014/100726 6/2014
WO 2014/193473 12/2014
WO 2015/172972 11/2015

OTHER PUBLICATIONS

Marcellin et al., "Low Carbon Fuels and Commodity Chemicals From Waste Gases—Systematic Approach to Understand Energy Metabolism in a Model Acetogen", Green Chemistry, Royal Society of Chemistry, Jan. 5, 2016, 10 pages.

Nagarajan, Harish et al., "Characterizing Acetogenic Metabolism Using a Genome-Scale Metabolic Reconstruction of Clostridium Ijungdahlii", Microbial Cell Factories, Nov. 25, 2013, pp. 1-13.

Pereira et al., "Improving the Flux Distributions Simulated with Genome-Scale Metabolic Models of Saccharomy Cescerevisiae", Metabolic Engineering Communications 3, 2016, pp. 153-163.

Valgepea et al., "Maintenance of ATP Homeostasis Triggers Metabolic Shifts in Gas-Fermenting Acetogens", Cell Systems, No. 4, 2017, pp. 505-515.

Whited et al., "Development of a Gas-Phase Bioprocess for Isoprene-Monomer Production Using Metabolic Pathway Engineering", Peer Review, Technology Update, Industrial Biotechnology, vol. 6, No. 3, 2010, pp. 152-163.

Akatsuka et al. "The Serratia marcescens bioH gene encodes an esterase" Gene 2003 302:185-192.

Barta et al. "Structural basis for nucleotide binding and reaction catalysis in mevalonate diphosphate decarboxylase" Biochemistry 2012 51(28):5611-5621.

Becker et al. "Metabolic flux engineering of L-lysine production in Corynebacterium glutamicum—over expression and modification of G6P dehydrogenase" Journal of Biotechnology 2007 132:99-109.

Bischoff, K.M & Rodwell, V.W. "Biosynthesis and characterization of (S)-and (R)-3-hydroxy-3-methylglutaryl coenzyme A" Biochem Med Metab Biol 1992 48(2):149-58.

Boucher et al. "Bacterial origin for the isoprenoid biosynthesis enzyme HMG-CoA reductase of the archaeal orders Thermoplasmatales and Archaeoglobales" Mol. Biol. Evol. 2011 18(7):1378-1388.

Brigham et al. Advanced Biofuels and Bioproducts, Springer New York, Chapter 39 2013 pp. 1065-1090.

Brodkorb et al. "Linalool dehydratase-isomerase, a bifunctional enzyme in the anaerobic degradation of monoterpenes" J Biol Chem 285(40):30436-30442.

Buckel et al. "Glutaconate CoA-transferase from Acidaminococcus fermentans" Eur J Biochem 1981 118(2):315-321.

Buckel et al. "2-Hydroxyl-CoA Dehydratases, a novel family of moybdeum enzymes" J Inorganic Biochemistry 2003 96(1):53.

Bugg et al. "The emerging role for bacteria in lignin degradation and bio-product formation" Current Opinion in Biotechnology 2011 22:394-400.

Byrd et al. "Bacterial Control of Agromyces ramosus in soil" Can J Microbiol 1985 31:1157-1163.

Chayabutra & Ju "Degradation of n-hexadecane and its metabolites by Pseudomonas aeruginosa under microaerobic and anaerobic denitrifying conditions" Appl Environ Microbiol 2000 66(2):493-498.

Chica et al. "Semi-rational approaches to engineering enzyme activity: combining the benefits of directed evolution and rational design" Current Opinion in Biotechnology 2005 16:378-384.

Chung & Rhee "Overexpression of the (R)-specific enoyl-CoA hydratase gene from Pseudomonas chlororaphis HS21 in Pseudomonas

(56) References Cited

OTHER PUBLICATIONS strains for the biosynthesis of polyhydroxyalkanoates of altered monomer composition" Biosci Biotechnol Biochem 2012 76(3):613-616.
Daniel et al. "Biochemistry of coenzyme B12-dependent glycerol and diol dehydratases and organization of the encoding genes" FEMS Microbiology Reviews 1999 22:553-566.
Devos & Valencia "Practical Limits of Function Prediction" Proteins-:Structure, Function and Genetics 2000 41:98-107.
Demain et al. "Manual of Industrial Microbiology and Biotechnology", 2nd Edition, Scale-Up of Microbial Process, ASM Press, 1999, 5 pages.
Dhe-Paganon et al. "Mechanism of mevalonate pyrophosphate decarboxylase: evidence for a carbocationic transition state" Biochemistry 1994 33(45):13355-1336.
Eikmanns & Buckel "Crystalline green 5-hydroxyvaleryl-CoA dehydratase from Clostridium aminovalericum" Eur J Biochem 1991 197(3):661-668.
Eriksen et al. "Protein design for pathway engineering" Journal of Structural Biology 2013 185(2):234-242.
Ferrandez et al. "Genetic characterization and expression in heterologous hosts of the 3-(3-hydroxyphenyl)propionate catabolic pathway of *Escherichia coli* K-12" J Bacteriol 1997 179(8):2573-2581.
Forster-Fromme et al. "Biochemical characterization of isovaleryl-CoA dehydrogenase (LiuA) of Pseudomonas aeruginosa and the importance of liu genes fora functional catabolic pathway of methyl-branched compounds" FEMS Microbiol Lett 2008 286(1):78-8.
Fukui et al. "Expression and characterization of (R)-specific enoyl coenzyme A hydratase involved in polyhydroxyalkanoate biosynthesis by Aeromonas caviae" J Bacteriology 1998 180(3):667-673.
Gehret et al. "Terminal alkene formation by the thioesterase of curacin A biosynthesis: structure of a decarboxylating thioesterase" J Biol Chem 2011 186(16):14445-14454.
Genbank Accession No. AAD44196.1, Oct. 15, 1999 1 page.
Genbank Accession No. AAG02436.1, Aug. 29, 2000, 1 page.
Genbank Accession No. AAG05403.1, Jan. 31, 2014 2 pages.
Genbank Accession No. AAK99143.1, Jan. 30, 2014, 2 pages.
Genbank Accession No. AAV40818.1, Feb. 4, 2005, 1 page.
Genbank Accession No. AAV40819.1, Feb. 4, 2005, 1 page.
Genbank Accession No. AAV40820.1, Feb. 4, 2005, 1 page.
Genbank Accession No. ABX19602.1, Dec. 11, 2013, 2 pages.
Genbank Accession No. BAA21816.1, Aug. 19, 1997, 2 pages.
Genbank Accession No. BAA92740.1, Aug. 1, 2007, 2 pages.
Genbank Accession No. BAB56752.1, Oct. 7, 2016, 2 pages.
Genbank Accession No. BAB56754.1, Oct. 7, 2016, 1 page.
Genbank Accession No. BAB58707.1, Oct. 7, 2016, 2 pages.
Genbank Accession No. BAD98243.1, May 10, 2005, 2 pages.
Genbank Accession No. CAA32465.1, Jul. 26, 1995, 1 page.
Genbank Accession No. CAA32466.1, Jul. 26, 1995, 1 page.
Genbank Accession No. CAA42196.1, Oct. 16, 1995, 1 page.
Genbank Accession No. CAA99573.1, Nov. 14, 2006, 2 pages.
UniProtKB/Swiss-Prot. E1XUJ2.1, Sep. 5, 2012, 2 pages.
NCBI Reference Sequence NP 746661, Jun. 27, 2013, 2 pages.
Gogerty & Bobik "Formation of isobutene from 3-hydroxy-3-methylbutyrate by diphosphomevalonate decarboxylase" Appl Environ Microbiol 2010 76(24):8004-8010.
Gu et al. "Polyketide decarboxylative chain termination preceded by o-sulfonation in curacin a biosynthesis" Am J Chem Soc 2009 131(44):16033-1603.
Guan et al. "Cytochrome P450-dependent desaturation of lauric acid: isoform selectivity and mechanism of formation of 11-dodecenoic acid"Chem Biol Interact 1998 110(1-2):103-12.
Gupta et al. "Phylogenomics and signature proteins for the alpha Protobacteria and its main groups" BMC Microbiol. 2007 7:106:1-2.
He & Spain "A novel 2-aminomuconate deaminase in the nitrobenzene degradation pathway of Pseudomonas pseudoalcaligenes JS45" J Bacteriol 1998 180(9):2502-2506.
Hermann, T. "Industrial production of amino acids by coryneform bacteria" Journal of Biotechnology 2003 104:155-172.
Ishizaki et al. "Microbial production of poly-D-3-hydroxybutyrate from CO2" Appl Microbiol Biotechnol 2001 57(1-2):6-12.
Jang et al. "Bio-based production of C2-C6 platform chemicals" Biotechnol Bioeng 2012 109(10)::2437-2459.
Jaremko et al. "The initial metabolic conversion of levulinic acid in Cupriavidus necator" Journal of Biotechnology 2011 155:293-298.
Jin et al. "The selective addition of water to C=C bonds; enzymes are the best chemists" Chem Commun. 2011 47:2502-2510.
Kasai et al. "Uncovering the protocatechuate 2,3-cleavage pathway genes" J Bacteriol 2009 191(21):6758-6768.
Kelada et al. "Delta-aminolevulinic acid dehydratase genotype and lead toxicity: a HuGE review" Am. J. Epidemiology 2001 154(1):1-1.
Kim et al. "An allylic ketyl radical intermediate in clostridial amino-acid fermentation" Nature 2008 452(7184):239-24.
Kim et al. :Dehydration of (R)-2-hydroxyacyl-CoA to enoyl-CoA in the fermentation of α-amino acids by anaerobic bacteria FEMS Microbiol Rev 2004 28(4):445-468.
Kim, "On the enzymatic mechanism of 2-hydroxyisocaproyl-CoA dehydratase from Clostridium difficile" 2004 Ph.D. dissertation, Phillipps-Universitat, Marburg, 200.
Kisselev "Polypeptide release factors in prokaryotes and eukaryotes: same function, different structure" Structure 2002 10:8-9.
Kizer et al. "Application of functional genomics to pathway optimization for increased isoprenoid production" Applied and Environmental Microbiology 2008 74(10):3229-3241.
Kneen et al. "Characterization of a thiamin diphosphate-dependent phenylpyruvate decarboxylase from *Saccharomyces cerevisiae*" FEBS J. 2011 278:1842-1853.
Kopke et al. "2,3-butanediol production by acetogenic bacteria, an alternative route to chemical synthesis, using industrial waste gas" Applied and Environmental Microbiology 2011 77(15):5467-5475.
Kuzma et al. "Bacteria produce the volatile hydrocarbon isoprene" Curr Microbiol 1995 30(2):97-103.
Kuzuyuma et al. "Mevalonate and Nonmevalonate Pathways for the Biosynthesis of Isoprene Units" Biosci. Biotechnol. Biochem. 2002 66(8):1619-1627.
Lan et al. "ATP drives direct photosynthetic production of 1-butanol in cyanobacteria" PNAS 2012 109(16):6018-6023.
Lee et al. "Conversion of β-Methylbutyrinc Acid to β-Hydroxy-β-Methylbutyrin Acid by Galactomyces reessii" Applied and Environmental Microbiology 1997 63(11):4191-4195.
Lee et al. "Synthesis of pure meso-2,3-butanediol from crude glycerol using an engineered metabolic pathway in *Escherichia coli*" Applied Biochemistry and Biotechnology 2012 166(7):1801-1813.
Li et al. "Cupriavidus necator JMP134 rapidly reduces furfural with a Zn-dependent alcohol dehydrogenase" Biodegradation 2011 22(6):1215-122.
Lim et al. "Amplification of the NADPH-related genes zwf and gnd for the oddball biosynthesis of PHB in an *E. coli* transformant harboring a cloned phbCAB operon" Journal of Bioscience and Bioengineering 2002 93(6):543-54.
Lin et al. "The BioC O-methyltransferase catalyzes methyl esterification of malonyl-acyl carrier protein, an essential step in biotin synthesis" Journal of Biological Chemistry 2012 287(440::37010-37020.
Lin et al. "Biotin synthesis begins by hijacking the fatty acid synthetic pathway" Nature Chem Biol 2010 6:682-68.
Liu et al. "Microbial production of R-3-hydroxybutyric.acid by recombinant *E. coli* harboring genes of phbA, phbB, and tesB" Appl Microbiol Biotechnol 2007 76(4):811-181.
Liu et al. "Zirconia microbial hollow fibre bioreactor for *Esherichia coli* culture" Ceramics International 2010 36:2087-2093.
Lo, H. & Chen, Y.J. "Gene cloning and biochemical characterization of a Nad(P)+-dependent aldehyde dehydrogenase from Bacillus licheniformis" Mol. Biotechnol 2010 46(2):157-67.
Luddeke et al. "Geraniol and geranial dehydrogenases induced in anaerobic monoterpene degradation by Castellaniella defragrans" Appl and Environmental Microbiology 2012 78(7):2128-2136.
Luddeke et al. "Enantiospecific (S)-(+)-linalool formation from beta-myrcene by linalool dehydratase-isomerase" Z. Naturforsch C 2011 66(708):409-412.

(56) References Cited

OTHER PUBLICATIONS

Luo et al. "Production of 3-hydroxypropionic acid through propionaldehyde dehydrogenase PduP mediated biosynthetic pathway in Klebsiella pneumonia" Bioresour Technol 2011 103(1):1-6.
Makkar et al. "*Cupriavidus necator* gen. nov., sp, nov.: a Non Obligate Bacterial Predator of Bacteria in Soil" Bacteriology 1987 37(4):323-326.
Martin et al. "High-titer production of monomeric hydroxyvalerates from levulinic acid in Pseudomonas putida" Journal of Biotechnology 2009 139(1):61-67.
Martin et al. "Engineering a mevalonate pathway in *Escherichia coli* for production of terpenoids" Nature Biotechnology 2003 21:796-802.
McCarthy et al. "Structural basis of functional group activation by sulfotransferases in complex metabolic pathways" ACS Chem Biol 2012 7:1994-2003.
Meijnen et al. "Improved p-hydroxybenzoate production by engineered Pseudomonas putida S12 by using a mixed-substrate feeding strategy" Applied Microbiology and Biotechnology 2011 90(3):885-893.
Mo et al. "Biosynthesis of the Allylmalonyl-CoA Extended Unit for the FK506 Polyketide Synthase (PKS) Proceeds Through a Dedicated PKS and Faciliates the Mutasynthesis of Novel Analogs" J Am Chem Soc 2010 1333(4):976-985.
Morrone et al. "Increasing diterpene yield with a modular metabolic engineering system in *E. coli*: comparison of MEV and MEP isoprenoid precursor pathway engineering" Applied Microbiology and Biotechnology 2010 85:1893-1906.
Muraki et al. "Prokaryotic homologs of the eukaryotic 3-hydroxyanthranilate 3,4-dioxygenase and 2-amino-3-carboxymuconate-6-semialdehyde decarboxylase in the 2-nitrobenzoate degradation pathway of Pseudomonas fluorescens strain KU-7" Appl Environ Microbiol 2003 69(3):1564-1572.
Ohashi et al. "Continuous production of lactic acid from molasses by perfusion culture of Lactococcus lactis using a stirred ceramic membrane reactor" Journal of Bioscience and Bioengineering 1999 87(5): 647-654.
Papanikolaou et al. "Citric acid production by Yarrowia lipolytica cultivated on olive-mill wastewater-based media" Bioresource Technology 2008 99(7):2419-2428.
Perez-Pantoja et al. "Metabolic reconstruction of aromatic compounds degradation from the genome of the amazing pollutant-degrading bacterium Cupriavidus necator JMP134" FEMS Microbiology Reviews 2008 32:736-794.
Pitera et al. "Balancing a heterologous mevalonate pathway for improved isoprenoid production in *Escherichia coli*" Metabolic Engineering 2007 9:193-207.
Prather et al. "De novo biosynthetic pathways: rational design of microbial chemical factories" Curr Opin Biotechnol 2008 19:468-474.
"Production of Butadiene" China Synthetic Rubber Industry, Special Issue of 1978, 21 pages (with partial English translation).
Przybylski et al. "Third-generation feed stocks for the clean and sustainable biotechnological production of bulk chemicals: Synthesis of 2-hydroxyisobutyric acid" Energy, Sustainability and Society 2012. 2(11):1-9.
Ramsay et al. "Use of a nylon manufacturing waste as an industrial fermentation substrate" Applied and Environmental Microbiology 1986 52(1):152-156.
Rettie et al. "CYP4 isozyme specificity and the relationship between omega-hydroxylation and terminal desaturation of valproic acid" Biochemistry 1995 34(24):7889-7895.
Rodruguez-Zavala et al. "Characterization of *E. coli* tetrameric aldehyde dehydrogenases with atypical properties compared to other aldehyde dehydrogenases" Protein Science 2006 15:1387-1396.
Rude et al. "Terminal olefin (1-alkene) biosynthesis by a novel p450 fatty acid decarboxylase from *Jeotgalicoccus species*" Appl Environ Microbiol 2011 77(5):1718-1727.
Schafer et al. "Synthesis of short-chain diols and unsaturated alcohols from secondary alcohol substrates by the Rieske nonheme mononuclear iron oxygenase MdpJ" Appl Environ Microbiol 2012 78(17):6280-6284.
Scherf & Buckel "Purification and properties of an iron-sulfur and FAD-containing 4-hydroxybutyryl-CoA dehydratase/vinylacetyl-CoA delta 3-delta 2-isomerase from Clostridium aminobutyricum" Eur J Biochem 1993 215(2):421-429.
Scherf et al. "Succinate-ethanol fermentation in Clostridium kluyveri: purification and characterisation of 4-hydroxybutyryl-CoA dehydratase/vinylacetyl-CoA delta 3-delta 2-isomerase" Arch Microbiol 1994 161(3):239-245.
Seedorf et al. "The genome of Clostridium kluyveri, a strict anaerobe with unique metabolic features" PNAS USA 2008 105:2128-2133.
Sen et al. "Developments in directed evolution for improving enzyme functions" Appl Biochem Biotechnol 2007 143:212-223.
Shen et al. "Driving forces enable high-titer anaerobic 1-butanol synthesis in *Escherichia coli*" Appl Environ Microbiol 2011 77(9):2905-2915.
Sillman et al. "Isolation of nonobligate bacterial predators of bacteria from soil" Can J Microbiol 1986 32:760-762.
Silver & Fall "Characterization of aspen isoprene synthase, an enzyme responsible for leaf isoprene emission to the atmosphere" J Biol Chem 1995 270(22):13010-13016.
Slater et al. "Multiple beta-ketothiolases mediate poly(beta-hydroxyalkanoate) copolymer synthesis in Ralstonia eutropha" J. Bacter. 1998 180(8):1979-1987.
Studier "Protein production by auto-induction in high density shaling cultures" Protein Expression and Purification 2005 41:207-234.
Sweeney et al. "Physiologically based pharmacokinetic modeling of 1,3-butadiene, 1,2-epoxy-3-butene, and 1,2:3,4-diepoxybutane toxicokinetic in miace and rats" Carcinogenesis 1997 18(4):611-625.
Toraya et al. "Radical catalysis of B12 enzymes: structure, mechanism, inactivation, and reactivation of diol and glycerol dehydratases" Cellular and Molecular Life Sciences 2000 57:106-127.
Tseng et al. "Biosynthesis of chiral 3-hydroxyvalerate from single propionate-unrelated carbon sources in metabolically engineered *E. coli*" Microb Cell Fact 2010 9:96.
Tsuge et al. "Molecular characterization and properties of (R)-specific enoyl-CoA hydratases from Pseudomonas aeruginosa: metabolic tools for synthesis of polyhydroxyalkanoates via fatty acid beta-oxidation" Int J. Biol Macromol 2003 31(4-5):195-205.
Ulmer et al. "Bacterial Production of Poly(β-hydroxyalkanoates) Contaning Unsaturated Repeating Units by Rhodospirillum rubrum" Macromolecules 1994 27(7):1675-1679.
Uniprot Accession No. 032472, Jun. 11, 2014, 2 pages.
Uniprot Accession No. B8ZLF3, Jun. 15, 2010, 2 pages.
Uniprot Accession No. I3RA72, Sep. 5, 2012, 2 pages.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A6Q6, Jun. 11, 2014, 3 pages.
Uniprot Accession No. P0A953, Jun. 11, 2014, 4 pages.
Uniprot Accession No. P0AEK2, May 14, 2014, 4 pages.
Uniprot Accession No. P13001, Jun. 11, 2014, 4 pages.
Uniprot Accession No. P32377, Jun. 15, 2010, 4 pages.
Uniprot Accession No. Q5EU90, Feb. 19, 2014, 2 pages.
Uniprot Accession No. Q73A47, May 14, 2014, 2 pages.
Uniprot Accession No. Q7CCL9, Jun. 15, 2010, 2 pages.
Uniprot Accession No. Q818X2, Jun. 11, 2014, 2 pages.
Upton & McKinney "Role of the methylcitrate cycle in propionate metabolism and detoxification in *Mycobacterium smegmatis*" Microbiology 2007 153(Pt 12):3973-3982.
Van Leeuwen et al. "Fermentative production of isobutene" Appl Microbiol Biotechnol 2012 93(4):1377-1387.
Wang & Liao "Alteration of product specificity of Rhodobacter sphaeroides phytoene desaturase by directed evolution" J Biol Chem 2001 276(44):41161-41164.

(56) References Cited

OTHER PUBLICATIONS

Wee et al. "Biotechnological Production of Lactic Acid and Its Recent Applications" Food Technology and Biotechnology 2006 44(2):163-172.
Wendt et al. "Crystal structure of the carboxyltransferase subunit of the bacterial sodium ion pump glutaconyl-coenzyme A decarboxylase" EMBO J 2003 22(14):3493-3502.
Westin et al. "The identification of a succinyl-CoA thioesterase suggests a novel pathway for succinate production in peroxisomes" J Biol Chem 2005 280:38125-38132.
Whisstock et al. "Prediction of protein function from protein sequence and structure" Quarterly Reviews of BioPhysics 2003 36(3):307-340.
White "Butadiene production process overview" Chem Biol Interact 2007 166(1-3):10-14.
Witkowski et al. "Conversion of a beta-ketoacyl synthase to a malonyl decarboxylase by replacement of the active-site cysteine with glutamine" Biochemistry 1999 38:11643-1165.
Yang et al. Enhancing Production of Bio-Isoprene Using Hybrid MVA Pathway and Isoprene Synthase in *E. coli*: PLoS One 2012 7:1-7.
Yang et al. "Value-added uses for crude glycerol—a byproduct of biodiesel production" Biotechnology for Biofuels 2012 5(10):1-10.
Zeph et al. "Gram-negative versus gram-positive (actinomycete) nonobligate bacterial predators of bacteria in soil" Appl Environ Microbiol 1986 522:819-823.
Zhang et al. "Genes encoding acyl-CoA dehydrogenase (AcdH) homologues from Streptomyces coelicolor and Streptomyces avermitilis provide insights into the metabolism of small branched-chain fatty acids and macrolide antibiotic production" Microbiology 1999 145(9):2323-2334.
Zhao et al. "Biosynthesis of isoprene in *Escherichia coli* via methylerythritol phosphate (MEP) pathway" Applied Microbiology and Biotechnology 2011 90:1915-1922.
Zhou et al. "Isopentenyl diphosphate and dimethylallyl diphosphate/isopentenyl diphosphate ratio measured with recombinant isopentenyl diphosphate isomerase and isoprene synthase" Analytical Biochemistry 2013 440:130-136.
Zhuang et al. "Structure of YciA from Haemophilus influenzae (HI0827), a hexameric broad specificity acyl-coenzyme A thioesterase" Biochemistry 2008 47(9):2789-2796.
Chinese Office Action in Chinese Application No. 201280040122.2 dated Jul. 17, 2015.
Office Communication in CN201280068870.1 dated Aug. 23, 2016.
Office Communication in CN201280040122.2 dated Jun. 8, 2016.
Office Communication in CN201380043586.3 dated Nov. 8, 2016.
European Communication pursuant to Rules 161(1) and 162 EPC in application No. EP 12799032.3 dated Jun. 25, 2014.
Office Communication in EP 12799032.3 dated Dec. 10, 2015.
Office Communication in EP 12799032.3 dated Mar. 3, 2016.
Office Communication in EP 12799032.3 dated Jun. 16, 2016.
Office Communication in EP12731825.1 dated Nov. 17, 2015.
Office Communication in EP12731825.1 dated Feb. 4, 2019.
Office Communication in EP 13812263.5 dated Jan. 12, 2017.
Office Communication in EP 13812263.5 dated Sep. 26, 2018.
Office Communication in U.S. Appl. No. 13/524,973 dated Jun. 11, 2014.
Office Communication in U.S. Appl. No. 13/524,973 dated Dec. 22, 2014.
Office Communication in U.S. Appl. No. 13/524,973 dated Jul. 23, 2015.
Office Communication in U.S. Appl. No. 13/524,973 dated Apr. 20, 2016.
Office Communication in U.S. Appl. No. 13/524,973 dated Aug. 30, 2016.
Office Communication in U.S. Appl. No. 13/524,973 dated Jan. 26, 2017.
Office Communication in U.S. Appl. No. 13/691,623 dated Mar. 4, 2014.
Office Communication in U.S. Appl. No. 13/691,623 dated Jun. 25, 2014.
Office Communication in U.S. Appl. No. 13/691,623 dated Dec. 9, 2014.
Office Communication in U.S. Appl. No. 13/691,623 dated Mar. 16, 2015.
Office Communication in U.S. Appl. No. 13/691,623 dated Apr. 23, 2015.
Office Communication in U.S. Appl. No. 13/691,623 dated Jul. 17, 2015.
Office Communication in U.S. Appl. No. 13/691,623 dated Dec. 7, 2015.
Office Communication in U.S. Appl. No. 13/691,623 dated May 4, 2016.
Office Communication in U.S. Appl. No. 13/916,156 dated Jan. 9, 2015.
Office Communication in U.S. Appl. No. 13/916,156 dated Jul. 14, 2015.
Office Communication in U.S. Appl. No. 13/916,156 dated Dec. 3, 2015.
Office Communication in U.S. Appl. No. 13/916,156 dated Mar. 15, 2016.
Office Communication in U.S. Appl. No. 13/916,156 dated Apr. 7, 2016.
Office Communication in U.S. Appl. No. 13/916,156 dated Apr. 20, 2016.
Office Communication in U.S. Appl. No. 13/916,156 dated May 17, 2016.
Office Communication in U.S. Appl. No. 14/092,115 dated Apr. 1, 2015.
Office Communication in U.S. Appl. No. 14/092,115 dated Oct. 27, 2015.
Office Communication in U.S. Appl. No. 14/092,115 dated Feb. 2, 2016.
Office Communication in U.S. Appl. No. 14/092,115 dated Mar. 21, 2016.
Office Communication in U.S. Appl. No. 14/092,115 dated Jul. 12, 2016.
Office Communication in U.S. Appl. No. 14/092,115 dated Oct. 12, 2016.
Office Communication in U.S. Appl. No. 14/092,115 dated Apr. 6, 2017.
Office Communication in U.S. Appl. No. 14/092,115 dated Jul. 27, 2017.
Office Communication in U.S. Appl. No. 14/334,190 dated Feb. 5, 2016.
Office Communication in U.S. Appl. No. 14/334,190 dated Jul. 27, 2016.
Office Communication in U.S. Appl. No. 14/334,190 dated Jan. 20, 2017.
Office Communication in U.S. Appl. No. 14/334,190 dated May 9, 2017.
Office Communication in U.S. Appl. No. 14/334,190 dated Oct. 5, 2017.
Office Communication in U.S. Appl. No. 14/334,190 dated Mar. 13, 2018.
Office Communication in U.S. Appl. No. 14/334,190 dated Apr. 25, 2018.
Office Communication in U.S. Appl. No. 14/334,190 dated Jul. 30, 2018.
Office Communication in U.S. Appl. No. 14/334,190 dated Sep. 10, 2018.
Office Communication in U.S. Appl. No. 14/334,190 dated Sep. 28, 2018.
Office Communication in U.S. Appl. No. 14/334,190 dated Nov. 16, 2018.
Office Communication in U.S. Appl. No. 14/334,190 dated Jan. 9, 2019.
Office Communication in U.S. Appl. No. 14/452,201 dated May 20, 2016.
Office Communication in U.S. Appl. No. 14/452,201 dated Oct. 28, 2016.

(56) References Cited

OTHER PUBLICATIONS

Office Communication in U.S. Appl. No. 14/452,201 dated Apr. 5, 2017.
Office Communication in U.S. Appl. No. 14/452,201 dated Aug. 30, 2017.
Office Communication in U.S. Appl. No. 14/914,741 dated Nov. 17, 2016.
Office Communication in U.S. Appl. No. 14/914,741 dated Feb. 7, 2017.
Office Communication in U.S. Appl. No. 14/914,741 dated Aug. 17, 2017.
Office Communication in U.S. Appl. No. 14/914,741 dated Jul. 24, 2018.
Office Communication in U.S. Appl. No. 14/914,741 dated Apr. 19, 2019.
Office Communication in U.S. Appl. No. 14/914,741 dated Sep. 16, 2019.
Office Communication in U.S. Appl. No. 15/238,225 dated Dec. 18, 2018.
Office Communication in U.S. Appl. No. 15/238,225 dated Mar. 11, 2019.
Office Communication in U.S. Appl. No. 15/238,225 dated Oct. 10, 2019.
Office Communication in U.S. Appl. No. 15/238,225 dated Feb. 27, 2020.
Office Communication in U.S. Appl. No. 15/238,234 dated Nov. 30, 2017.
Office Communication in U.S. Appl. No. 15/238,234 dated May 2, 2018.
Office Communication in U.S. Appl. No. 15/238,234 dated Aug. 13, 2018.
Office Communication in U.S. Appl. No. 15/238,234 dated Nov. 16, 2018.
Office Communication in U.S. Appl. No. 15/717,065 dated Nov. 8, 2018.
Office Communication in U.S. Appl. No. 15/717,065 dated Feb. 13, 2019.
Office Communication in U.S. Appl. No. 15/717,065 dated Jun. 19, 2019.
Office Communication in U.S. Appl. No. 15/717,065 dated Oct. 1, 2019.
Office Communication in U.S. Appl. No. 15/808,409 dated May 8, 2019.
Office Communication in U.S. Appl. No. 15/808,409 dated Sep. 5, 2019.
Office Communication in U.S. Appl. No. 15/932,217 dated Jun. 10, 2019.
Office Communication in U.S. Appl. No. 15/932,217 dated Sep. 13, 2019.
Office Communication in U.S. Appl. No. 15/932,189 dated Dec. 5, 2019.
Office Communication in U.S. Appl. No. 16/188,673 dated Dec. 10, 2019.
Office Communication in U.S. Appl. No. 16/022,878 dated Feb. 12, 2019.
Office Communication in U.S. Appl. No. 16/022,878 dated Aug. 28, 2019.
Office Communication in U.S. Appl. No. 16/022,878 dated Apr. 16, 2020.
Office Communication in U.S. Appl. No. 16/023,055 dated Oct. 7, 2019.
Office Communication in U.S. Appl. No. 16/023,055 dated Feb. 5, 2020.
International Search Report in PCT/US2012/042757 dated Mar. 6, 2013.
International Preliminary Report on Patentability in PCT/US2012/042757 dated Dec. 17, 2013.
International Search Report in PCT/US2012/064407 dated Feb. 7, 2013.
International Preliminary Report on Patentability in PCT/US2012/064407 dated May 13, 2014.
International Search Report in PCT/US2012/067463 dated Jun. 17, 2013.
International Preliminary Report on Patentability in PCT/US2012/067463 dated Jun. 3, 2014.
International Search Report and Written Opinion in PCT/US2013/045430 dated Feb. 3, 2014.
International Preliminary Report on Patentability in PCT/US2013/045430 dated Dec. 16, 2014.
International Search Report and Written Opinion in PCT/US2013/072275 dated Mar. 6, 2014.
International Preliminary Report on Patentability in PCT/US2013/072275 dated Jun. 2, 2015.
International Search Report and Written Opinion in PCT/US2014/048606 dated Oct. 31, 2014.
International Preliminary Report on Patentability in PCT/US2014/048606 dated Feb. 2, 2016.
International Search Report and Written Opinion in PCT/US2014/049786 dated Sep. 11, 2015.
International Preliminary Report on Patentability in PCT/US2014/049786 dated Feb. 9, 2016.
International Search Report and Written Opinion in PCT/US2014/049807 dated Nov. 5, 2014.
International Report on Patentability in PCT/US2014/049807 dated Feb. 9, 2016.
International Search Report and Written Opinion in PCT/IB2016/001233 dated Feb. 28, 2017.
International Report on Patentability in PCT/IB2016/001233 dated Feb. 20, 2018.
International Search Report and Written Opinion in PCT/IB2016/001245 dated Feb. 27, 2017.
International Report on Patentability in PCT/IB2016/001245 dated Feb. 20, 2018.
International Search Report and Written Opinion in PCT/US2017/053607 dated Dec. 22, 2017.
International Report on Patentability in PCT/ US2017/053607 dated Apr. 2, 2019.
International Search Report and Written Opinion in PCT/US2018/040213 dated Sep. 21, 2018.
International Report on Patentability in PCT/US2018/040213 dated Dec. 31, 2019.
International Search Report and Written Opinion in PCT/US2018/040218 dated Oct. 3, 2018.
International Report on Patentability in PCT/US2018/040218 dated Dec. 31, 2019.
Kuzuyuma & Seto "Two distinct pathways for essential metabolic precursors for isoprenoid biosynthesis" Proc Jap Acad. Ser B 88 2012 3:41-52.
Lv et al. "Significantly enhanced production of isoprene by ordered coexpression of genes dxs, dxr, and idi in *Escherichia coli*" Appl Microbio. Biotechnol 2013 97:2357-2365.
Office Communication in U.S. Appl. No. 16/023,055 dated Jun. 25, 2020.
Office Communication in U.S. Appl. No. 16/022,878 dated Sep. 30, 2020.
Final Office Action received for U.S. Appl. No. 15/238,225, dated Aug. 6, 2021, 20 Pages.
Non Final Rejection received for U.S. Appl. No. 16/022,878, dated Jul. 28, 2021, 17 Pages.
Non-Final office action received for U.S. Appl. No. 16/022,878, dated May 31, 2022, 17 pages.
Brigham, C J., et al., "Whole-genome microarray and gene deletion studies reveal regulation of the polyhydroxyalkanoate production cycle by the stringent response in Ralstonia eutropha H16", Appl Environ Microbiol., vol. 78, Issue 22, 2012, pp. 8033-8044.
Genbank Accession No. AAA21972.1, Apr. 24, 1993, 1 page.
Genbank Accession No. AAA24665.1, Apr. 26, 1993, 1 page.
GenBank Accession No. AAG43513.1, Jul. 14, 2016, 1 page.
Genbank Accession No. AAK33797.1, Apr. 1, 2014, 2 pages.
GenBank Accession No. AAO77182.1, Jan. 31, 2014, 2 pages.
Genbank Accession No. ACA99172.1, Dec. 11, 2013, 3 pages.
Genbank Accession No. ACT54545.1, Jul. 21, 2009, 2 pages.

(56) References Cited

OTHER PUBLICATIONS

Genbank Accession No. ACV42478.1, Feb. 12, 2014, 2 pages.
Genbank Accession No. ADU56236.1, Apr. 8, 2011, 2 pages.
Genbank Accession No. ADU56239.1, Apr. 8, 2011, 2 pages.
Genbank Accession No. AER12131.1, Oct. 29, 2011, 2 pages.
Genbank Accession No. AFY98994.1, Aug. 27, 2013, 2 pages.
Genbank Accession No. AHF01884.1, Jan. 3, 2014, 2 pages.
Genbank Accession No. BAA14785.1, Sep. 29, 2018, 12 pages.
Genbank Accession No. BAB58708.1, Oct. 7, 2016, 2 pages.
Genbank Accession No. CAA44858.1, Apr. 28, 1992, 2 pages.
Genbank Accession No. CAA66158.1, Oct. 29, 1997, 2 pages.
Genbank Accession No. CAC12426.1, Feb. 27, 2015, 2 pages.
Genbank Accession No. CAR68209.1, Feb. 6, 2015, 2 pages.
Genbank Accession No. CBW30776.1, Jan. 19, 2012, 1 page.
GenBank Accession No. CCC78182.1, Feb. 27, 2015, 2 pages.
Genbank Accession No. Q835L4, Oct. 31, 2006, 2 pages.
Genbank accession No. AEK70970.1, Apr. 15, 2013, 2 pages.
Invitation to pay additional fees and, where applicable, protest fee for PCT/US2012/067463, dated Mar. 13, 2013, 17 pages.
Invitation to pay additional fees and, where applicable, protest fee for PCT/US2013/045430, dated Nov. 25, 2013, 6 pages.
Invitation to pay additional fees and, where applicable, protest fee for PCT/US2015/036095, dated Sep. 18, 2015, 13 pages.
Lechner, A. et al., "Designed biosynthesis of 36-methyl-FK506 by polyketide precursor pathway engineering", ACS Synthetic Biology, vol. 2, Issue 7, Jul. 19, 2013, pp. 379-383.
Lefurgy, S.T. et al., "Probing ligand-binding pockets of the mevalonate pathway enzymes from *Streptococcus pneumoniae* ". The Journal of Biological Chemistry, vol. 285, Issue 27, pp. 20654-20663.
NCBI Reference Sequence: WP_000163323.1, Oct. 12, 2019, 2 pages.
NCBI Reference Sequence: WP_000210618.1, Mar. 22, 2021, 2 pages.
NCBI Reference Sequence: WP_000373455.1, Jun. 3, 2019, 1 page.
NCBI Reference Sequence: WP_000562415.1, Jun. 20, 2019, 1 page.
NCBI Reference Sequence: WP_002382276.1, Jun. 3, 2019, 2 Pages.
Non Final office action received for U.S. Appl. No. 15/238,225, dated Apr. 1, 2022, 17 pages.
Non Final Office Action received for U.S. Appl. No. 15/238,225, dated Dec. 14, 2020, 17 Pages.
Park, S.J., et al., "Identification and Characterization of a New Enoyl Coenzyme A Hydratase Involved in Biosynthesis of Medium-Chain-Length Polyhydroxyalkanoates in Recombinant *Escherichia coli*", Journal of Bacteriology, vol. 185, No. 18, Sep. 15, 2003, pp. 5391-5397.
Peoples et al., "Poly-beta-hydroxybutyrate biosynthesis in Alcaligenes eutrophus H16. Characterization of the genes encodingbeta-ketothiolase and acetoacetyl-CoA reductase", Journal of Biological Chemistry, vol. 264, No. 26, 1989, pp. 15293-15297.
Reference "NCBI" (2019, updated) https://www.ncbi.nlnn.nih.gov/protein/ANO50205.1, "hydroxymethylglutaryl-CoA synthase", June 0, 2016, pp. 1-2.
Reference "NCBI" (2019, updated) https://www.ncbi.nlm.nih.gov/protein/WP_000786547.1, "acetyl-CoA acetyltransferase [Proteobacteria]", Oct. 6, 2015, 1 page.
Schafer, F., et al., "Formation of Alkenes via Degradation of tert-Alkyl Ethers and Alcohols by Aquincola tertiaricarbonis L108 and *Methylibium* spp.", Applied and environmental Microbiology, vol. 77, Issue 17, Sep. 2011, pp. 5981-5987.
Uniprot Accession No. Q73Q47, May 14, 2014, 2 pages.
UniProtKB/Swiss-Prot: Q50L36.1, Feb. 23, 2022, 3 pages.
Valgepea, K., et al., "Arginine deiminase pathway provides ATP and boosts growth of the gas-fermenting acetogen Clostridium autoethanogenum", Metabolic Engineering, vol. 41, May 2017, 44 Pages.
Vinokur, J.M., et al., "Evidence of a novel mevalonate pathway in archaea", Biochemistry, vol. 53, Issue 25, Jul. 1, 2014, pp. 4161-4168.
Willis, M. A. et al., "Structure of YciA from Haemophilus influenzae (H10827), a Hexameric Broad Specificity Acyl-Coenzyme A Thioesterase," Biochemistry, 2008, vol. 47, Issue 9, pp. 2797-2805.
Zhuang, Z., et al., "Divergence of function in the hotdog fold enzyme superfamily: the bacterial thioesterase YciA", Biochemistry, vol. 47, No. 9, Mar. 4, 2008, pp. 2789-2796.
"A9AST0 UniProtKB" ,UniProt enzyme classification 5.3.3.2, IDI_BURM1, Isopentenyl-diphosphate delta-isomerase, Retrieved on on Sep. 13, 2022, 05 pages.
Non Final Rejection received for U.S. Appl. No. 15/238,225, dated Oct. 3, 2022, 16 Pages.
Pohlmann et al.,"Genome sequence of the bioplastic-producing "Knallgas" bacterium Ralstonia eutropha H16", Nature Biotechnology, vol. 24, 07 Pages, 2006.
Wilding et al., "Identification, Evolution, and Essentiality of the Mevalonate Pathway for Isopentenyl Diphosphate Biosynthesis in Gram-Positive Cocci", Journal of Bacteriology, vol. 182, No. 15, 4319-4327, Aug. 2000.

* cited by examiner

ORGANISMS AND BIOSYNTHETIC PROCESSES FOR HYDROCARBON SYNTHESIS

This patent application claims the benefit of priority from U.S. Provisional Application Ser. No. 62/564,369, filed Sep. 28, 2017, the content of which is hereby incorporated by reference in its entirety.

FIELD

The present invention provides methods for biosynthesizing hydrocarbons from a gaseous substrate in non-naturally occurring organisms, such as, acetogens as well as non-naturally occurring acetogens and other means for production of hydrocarbons.

BACKGROUND

Hydrocarbons are known as important monomers for the production of polymers, including specialty elastomers, such as motor mounts/fittings, surgical gloves, rubber bands, golf balls and shoes. For example, styrene-isoprene-styrene block copolymers form a key component of hot-melt pressure-sensitive adhesive formulations and cis-poly-isoprene is utilized in the manufacture of tires (Whited et al. *Industrial Biotechnology* 2010 6(3):152-163).

Manufacturers of rubber goods depend on either imported natural rubber from the Brazilian rubber tree or petroleum-based synthetic rubber polymers (Whited et al. 2010 supra).

Given a reliance on petrochemical feedstocks and the harvesting of trees, biotechnology offers an alternative approach via biocatalysis. Biocatalysis is the use of biological catalysts, such as enzymes, to perform biochemical transformations of organic compounds.

Accordingly, against this background, it is clear that there is a need for sustainable methods for producing hydrocarbon intermediates such as isoprene wherein the methods are biocatalysis based.

Both bioderived feedstocks and petrochemical feedstocks are viable starting materials for biocatalysis processes. The introduction of vinyl groups into medium carbon chain length enzyme substrates is a key consideration in synthesizing isoprene via biocatalysis processes.

There are some known metabolic pathways leading to the synthesis of isoprene in prokaryotes such as *Bacillus subtillis* and eukaryotes such as *Populus alba* (Whited et al. 2010 supra).

Isoprene may be synthesized via two routes leading to the precursor dimethylvinyl-PP including the mevalonate and the non-mevalonate pathway (Kuzuyama, T. *Biosci. Biotechnol. Biochem.* 2002 66(8):1619-1627). The mevalonate pathway incorporates a decarboxylase enzyme, mevalonate diphosphate decarboxylase (hereafter MDD), that introduces the first vinyl-group into the precursors leading to isoprene. The second vinyl-group is introduced by isoprene synthase (hereafter ISPS) in the final step in synthesizing isoprene.

The mevalonate pathway has been exploited in the biocatalytic production of isoprene using *E. coli* as the host. *E. coli* engineered with the mevalonate pathway requires three moles of acetyl-CoA, three moles of ATP and two moles of NAD(P)H to produce a mole of isoprene. Given a theoretical maximum yield of 25.2% (w/w) for the mevalonate pathway, isoprene has been produced biocatalytically at a volumetric productivity of 2 g/(L·h) with a yield of 11% (w/w) from glucose (Whited et al. 2010 supra). Particularly, the phosphate activation of mevalonate to 5-diphosphomevalonate is energy intensive metabolically, requiring two moles of ATP per mole of isoprene synthesis. Accordingly, reducing the ATP consumption can improve the efficiency of the pathway.

Published U.S. Patent Application No. 2015/0037869 discloses biochemical pathways for production of isoprene by forming two vinyl groups in a central precursor produced from isobutyryl-CoA, 3-methyl-2-oxopentanoate, or 4-methyl-2-oxopentanoate as well as recombinant hosts for producing isoprene. The isoprene synthesis pathways include a beta-ketothiolase route via pyruvate via ldh, a 2-hydroxyacyl-CoA dehydratase route via ldh, a 2-hydroxyacyl-CoA dehydratase route via mdd and a polyketide synthase route via ldh.

Published PCT Application PCT/US2009/035937 identified pathways and mechanisms to confer direct carbon-based products producing capacity to photoautotrophic organisms.

Published PCT Application PCT/NZ2013/000095 discloses carboxydotrophic, acetogenic, recombinant microorganisms containing exogenous mevalonate pathway enzymes and/or DXS pathway enzymes.

A genome scale metabolic network for the acetogen *C. ljungdahlii* was disclosed by Nagarajan et al. (Microbiol. Cell Factories 2013 212:118) and a systemic description of the metabolism of the acetogen *C. autoethanogenum* at a transcriptional, translational and metabolome level was disclosed by Marcellin et al. (Green Chem. The Royal Society of Chemistry 2016 DOI:10.1039/c5gc02708).

U.S. Pat. No. 9,297,026 discloses genetically modified acetogenic microorganisms capable of using carbon monoxide to produce, for example, ethanol with reduced amounts of 2,3-butanediol. The microorganisms comprise one or more genetic modifications which disrupt the 2,3-butanediol biosynthesis pathway compared to a parental microorganism.

Published U.S. Patent Application No. 2015/0210987 discloses carboxydotrophic acetogenic bacterium comprising a disrupting mutation in a lactate biosynthesis pathway enzyme and a method of producing a product such as ethanol, 2,3-butanediol, formate pyruvate, succinate, valine, leucine, isoleucine, malate, fumarate, 2-oxogluterate, citrate and citramate by culturing the bacterium in the presence of a substrate comprising carbon monoxide.

There is therefore a need for organisms, including non-naturally occurring hosts, capable of increased hydrocarbon production.

SUMMARY

An aspect of the present invention relates to non-naturally occurring organisms, such as acetogens, capable of producing hydrocarbons from a gaseous substrate.

In one nonlimiting embodiment, the hydrocarbon comprises any saturated or unsaturated 5 carbon branched structure derived from an isoprenoid including, isoprene as well as other isoprenoids, terpenes and terpenoids and derivatives such as, but not limited to isoprenols, and salts thereof.

In one nonlimiting embodiment, the hydrocarbon is isoprene produced in a non-naturally occurring acetogen via a beta-ketothiolase route via pyruvate via ldh, a 2-hydroxyacyl-CoA dehydratase route via ldh, a 2-hydroxyacyl-CoA dehydratase route via mdd or a polyketide synthase route utilizing ldh.

In one nonlimiting embodiment, at least one polynucleotide of the non-naturally occurring acetogen has been altered. In one nonlimiting embodiment, at least two polynucleotides of the non-naturally occurring acetogen have been altered. In one nonlimiting embodiment, at least three polynucleotides of the non-naturally occurring acetogen have been altered. In one nonlimiting embodiment, at least five polynucleotides of the non-naturally occurring acetogen have been altered. In one nonlimiting embodiment, alteration of the polynucleotide eliminates activity of a polypeptide encoded by the polynucleotide.

In one nonlimiting embodiment, the non-naturally occurring acetogen capable of producing hydrocarbons from a gaseous substrate comprises either an alteration of at least one polynucleotide encoding a polypeptide having an activity of an alpha-acetolactate decarboxylase or encoding a polypeptide having an activity of a lactate dehydrogenase; or an alteration of at least two polynucleotides, the first polynucleotide encoding a polypeptide having an activity of an alpha-acetolactate decarboxylase and the second polynucleotide encoding a polypeptide having an activity of a lactate dehydrogenase.

In one nonlimiting embodiment, the non-naturally occurring acetogen further comprises an alteration of a polynucleotide encoding a polypeptide having an activity of one or more members of an aldehyde:ferredoxin oxidoreductase, a purine nucleoside phosphorylase, a dihydrolipoylprotein: NAD+ oxidoreductase, an L-Aspartate ammonia-lyase, a 2,6-Diaminoheptanedioate: 2-oxoglutarate aminotransferase, a glutamate synthase, an L-Threonine acetaldehyde-lyase, a N2-Acetyl-L-ornithine:L-glutamate N-acetyltransferase/Acetyl-CoA:L-glutamate N-acetyltransferase, an N2-Acetyl-L-ornithine amidohydrolase, a formate dehydrogenase or a Nfn complex.

In one nonlimiting embodiment, the non-naturally occurring acetogen is a *Clostridium* species.

Another aspect of the present invention relates to a composition comprising a means for producing a hydrocarbon via a beta-ketothiolase route via pyruvate via ldh, a 2-hydroxyacyl-CoA dehydratase route via ldh, a 2-hydroxyacyl-CoA dehydratase route via mdd or a polyketide synthase route utilizing ldh.

Another aspect of the present invention relates to genetic constructs comprising at least one polynucleotide encoding a polypeptide having an activity of an alpha-acetolactate decarboxylase or encoding a polypeptide having an activity of a lactate dehydrogenase, wherein said polynucleotide is altered to eliminate activity of the encoded polypeptide.

In one nonlimiting embodiment, the genetic construct comprises at least two polynucleotides, wherein a first polynucleotide encodes a polypeptide having an activity of an alpha-acetolactate decarboxylase and a second polynucleotide encodes a polypeptide having an activity of a lactate dehydrogenase, wherein the polynucleotides are altered to eliminate the activity of the encoded polypeptides.

In one nonlimiting embodiment, the genetic construct further comprises a polynucleotide encoding a polypeptide having an activity of one or more members selected from the group consisting of an aldehyde:ferredoxin oxidoreductase, a purine nucleoside phosphorylase, a dihydrolipoylprotein: NAD+ oxidoreductase, an L-Aspartate ammonia-lyase, a 2,6-Diaminoheptanedioate: 2-oxoglutarate aminotransferase, a glutamate synthase, an L-Threonine acetaldehyde-lyase, a N2-Acetyl-L-ornithine:L-glutamate N-acetyltransferase/Acetyl-CoA:L-glutamate N-acetyltransferase, an N2-Acetyl-L-ornithine amidohydrolase, a formate dehydrogenase and a Nfn complex, wherein the polynucleotide is altered to eliminate the activity of the encoded polypeptide.

Another aspect of the present invention relates to a method for biosynthesising hydrocarbons from a gaseous substrate in a non-naturally occurring acetogen or other means capable of producing hydrocarbons from a gaseous substrate.

In one nonlimiting embodiment, the hydrocarbon comprises any saturated or unsaturated 5 carbon branched structure derived from an isoprenoid including, isoprene as well as other isoprenoids, terpenes and terpenoids and derivatives such as, but not limited to isoprenols, and salts thereof.

In one nonlimiting embodiment, the hydrocarbon is isoprene produced in a non-naturally occurring acetogen via a beta-ketothiolase route via pyruvate via lactate hydrogenase (hereinafter ldh), a 2-hydroxyacyl-CoA dehydratase route via ldh, a 2-hydroxyacyl-CoA dehydratase route via mdd or a polyketide synthase route utilizing ldh.

In one nonlimiting embodiment, the method comprises synthesizing isoprene via a non-naturally occurring acetogen having at least one altered polynucleotide. In one nonlimiting embodiment, at least two polynucleotides of the non-naturally occurring acetogen have been altered. In one nonlimiting embodiment, the non-naturally occurring acetogen has at least three altered polynucleotides. In one nonlimiting embodiment, the non-naturally occurring acetogen has at least five altered polynucleotides. In one nonlimiting embodiment, alteration of the polynucleotide eliminates activity of a polypeptide encoded by the polynucleotide.

In one nonlimiting embodiment, the non-naturally occurring acetogen used in this method comprises either an alteration of at least one polynucleotide encoding a polypeptide having an activity of an alpha-acetolactate decarboxylase or encoding a polypeptide having an activity of a lactate dehydrogenase; or an alteration of at least two polynucleotides, the first polynucleotide encoding a polypeptide having an activity of an alpha-acetolactate decarboxylase and the second polynucleotide encoding a polypeptide having an activity of a lactate dehydrogenase.

In one nonlimiting embodiment, the non-naturally occurring acetogen used in this method further comprises an alteration of a polynucleotide encoding a polypeptide having an activity of one or more members of an aldehyde:ferredoxin oxidoreductase, a purine nucleoside phosphorylase, a dihydrolipoylprotein:NAD+ oxidoreductase, an L-Aspartate ammonia-lyase, a 2,6-Diaminoheptanedioate: 2-oxoglutarate aminotransferase, a glutamate synthase, an L-Threonine acetaldehyde-lyase, a N2-Acetyl-L-ornithine:L-glutamate N-acetyltransferase/Acetyl-CoA:L-glutamate N-acetyltransferase, an N2-Acetyl-L-ornithine amidohydrolase, a formate dehydrogenase or a Nfn complex.

In one nonlimiting embodiment, the non-naturally occurring acetogen is a *Clostridium* species.

Another aspect of the present invention relates to a method for producing a non-naturally occurring acetogen capable of producing hydrocarbons from a gaseous substrate.

In one nonlimiting embodiment, at least one polynucleotide of the non-naturally acetogen is altered. In one nonlimiting embodiment, at least two polynucleotides are altered. In one nonlimiting embodiment at least three polynucleotides are altered. In another nonlimiting embodiment, at least five polynucleotides are altered. In one nonlimiting embodiment, alteration of the polynucleotide eliminates activity of a polypeptide encoded by the polynucleotide.

In one nonlimiting embodiment, the non-naturally occurring acetogen produced comprises either an alteration of at least one polynucleotide encoding a polypeptide having an activity of an alpha-acetolactate decarboxylase or encoding a polypeptide having an activity of a lactate dehydrogenase; or an alteration of at least two polynucleotides, the first polynucleotide encoding a polypeptide having an activity of an alpha-acetolactate decarboxylase and the second polynucleotide encoding a polypeptide having an activity of a lactate dehydrogenase.

In one nonlimiting embodiment, the non-naturally occurring acetogen produced further comprises an alteration of a polynucleotide encoding a polypeptide having an activity of one or more members of an aldehyde:ferredoxin oxidoreductase, a purine nucleoside phosphorylase, a dihydrolipoylprotein:NAD+ oxidoreductase, an L-Aspartate ammonia-lyase, a 2,6-Diaminoheptanedioate: 2-oxoglutarate aminotransferase, a glutamate synthase, an L-Threonine acetaldehyde-lyase, a N2-Acetyl-L-ornithine:L-glutamate N-acetyltransferase/Acetyl-CoA:L-glutamate N-acetyltransferase, an N2-Acetyl-L-ornithine amidohydrolase, a formate dehydrogenase or a Nfn complex.

In one nonlimiting embodiment, the non-naturally occurring acetogen is a *Clostridium* species.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

BRIEF DESCRIPTION OF FIGURES

In FIGS. 5A and 5B Reference refers to mevalonate pathway and isoprene synthase, 1 refers to Pathway 1—β-ketothiolaseroute via pyruvate via ldh, 2 refers to Pathway 2—2-hydroxyacyl-CoA dehydratase route via ldh, 3 refers to Pathway 3—2-hydroxyacyl-CoAdehydratase route via mdd and 4 refers to Pathway 4—Polyketide synthase route via ldh. Suboptimal growth results in FIG. 5A indicate that all supplied pathways are superior to the references. These range from 1.4× to 1.9× higher than the reference mevalonate pathway. Evolved growth-optimality depicted in FIG. 5B indicate that all supplied pathways also offer better growth-coupled yields than the reference during growth-optimal conditions. These growth-coupled predicted yields range from 1.7× to 9× higher than the reference mevalonate pathway.

DETAILED DESCRIPTION

The present invention provides organisms, such as non-naturally occurring acetogens and other means derived therefrom or related thereto capable of producing hydrocarbons, as well as methods for the production of these acetogens and methods for their use in production of hydrocarbons and derivatives thereof.

Accordingly, disclosed herein are acetogens genetically engineered by alteration of one or more polynucleotides to produce hydrocarbons from gaseous substrates, as well as methods for their production and their use in biosynthesis of hydrocarbons. The non-naturally occurring acetogens and methods disclosed herein provide low cost processes for conversion of industrial gases to chemicals in a fermenter. In the methods of the present invention, the non-naturally occurring acetogens are introduced into a fermenter, mixed with gas feedstocks which are enzymatically converted to a hydrocarbon by the non-naturally occurring acetogens, and the hydrocarbon is then separated from the off-gases from the fermenter.

By "hydrocarbon" or hydrocarbons" as used herein, it is meant to encompass any organic compound comprised of carbons and hydrogens which can be enzymatically synthesized from a gas and is inclusive of saturated as well as unsaturated structures with double or triple bonds formed between carbon atoms, ring structures, salts and derivatives thereof. In one nonlimiting embodiment, the hydrocarbon comprises one or more isoprene units as depicted in Formula I (I)

or a salt or derivative thereof.

By the phrase "one or more isoprene units as depicted in Formula I" it is meant to encompass any saturated or unsaturated 5 carbon branched structure derived from an isoprenoid including, isoprene as well as other isoprenoids, terpenes and terpenoids and derivatives such as, but not limited to isoprenols, and salts thereof.

Nonlimiting examples of hydrocarbons comprising one or more isoprene units produced in accordance with the present invention include isoprene as well as other isoprenoids, terpenes or terpenoid derivatives of 5, including C5, C10, C15, C20, C25, C30, C35, C40, C45, C50, etc. Nonlimiting examples include hemiterpene, monoterpene, diterpene, triterpene, tetraterpene, polyterpene, lycopene, abietadiene, amorphadiene, carene, alpha-farnesene, beta-farnesene, farnesol, geraniol, geranylgeraniol, isoprene, linalool, limonene, myrcene, nerolidol, ocimene, patchoulol, beta-pinene, sabinene, gamma-terpinene, terpinolene and valencene, as well as derivatives and salts thereof.

The present invention provides non-naturally occurring acetogens capable of producing hydrocarbons from a gaseous substrate.

In one nonlimiting embodiment, the hydrocarbon comprises any saturated or unsaturated 5 carbon branched structure derived from an isoprenoid including, isoprene as well as other isoprenoids, terpenes and terpenoids and derivatives such as, but not limited to isoprenols, and salts thereof.

Figure 1:
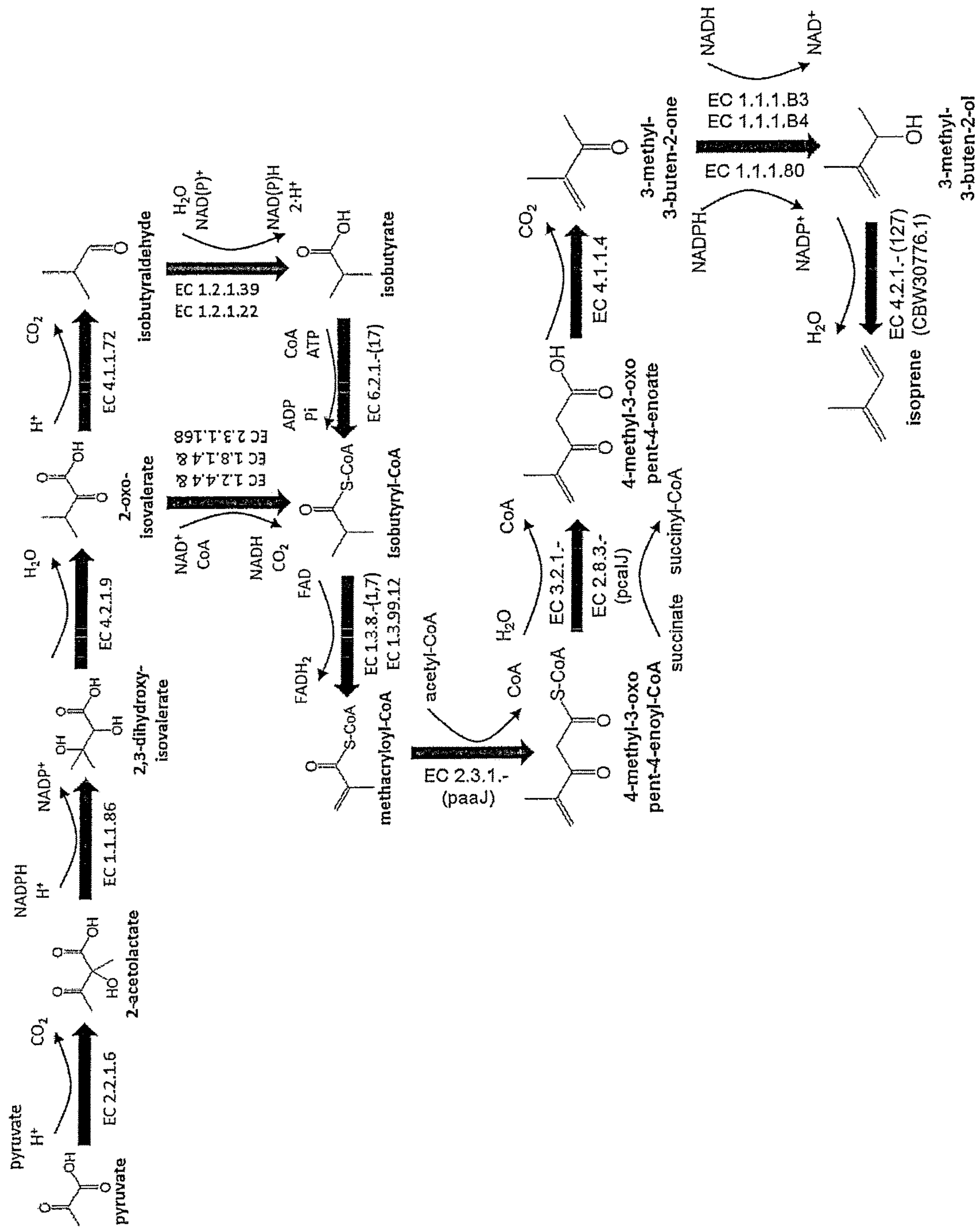
FIG. 1 is a biosynthetic schematic of isoprene synthesis using via a beta-ketothiolase route utilizing pyruvate and ldh.
Figure 2:
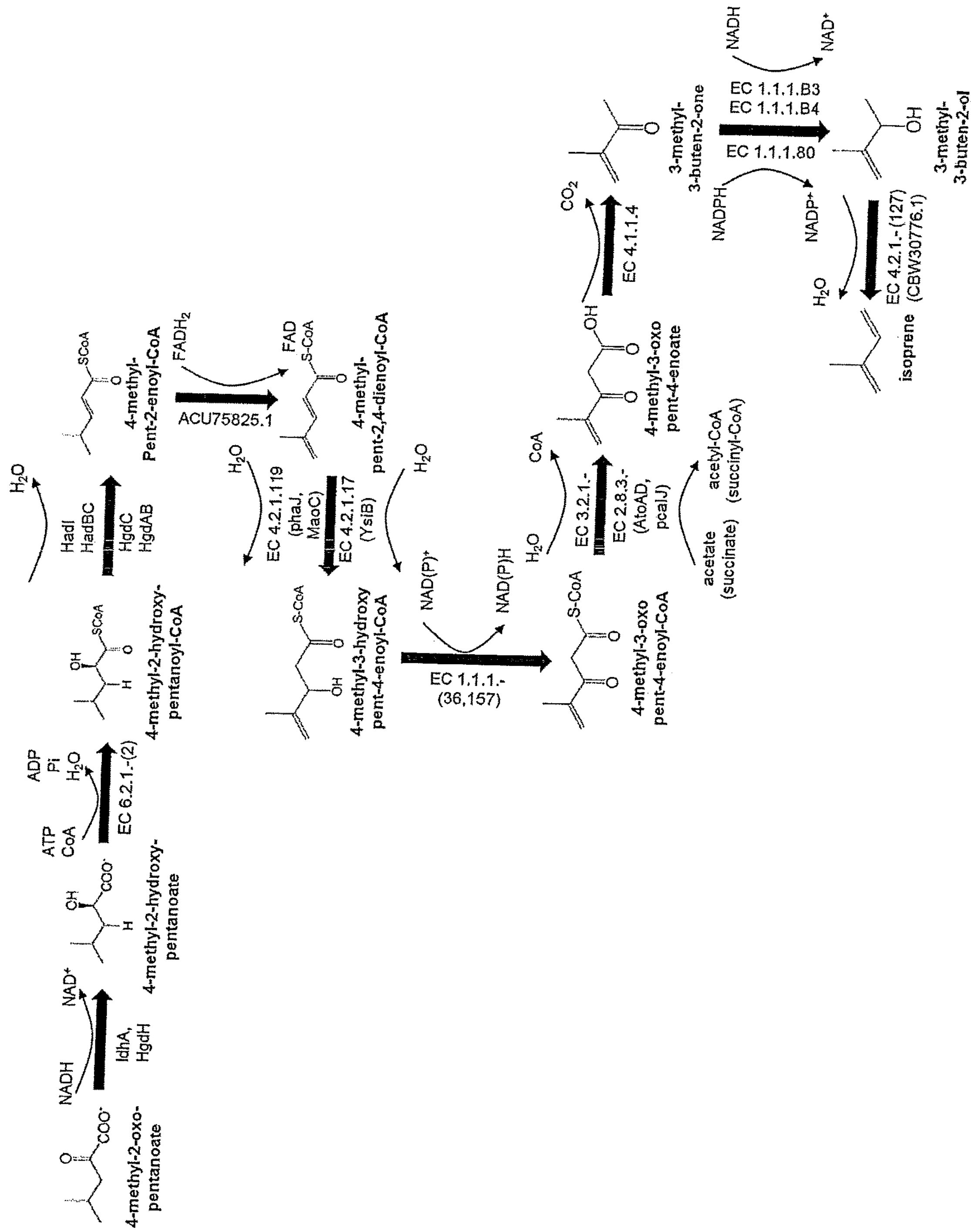
FIG. 2 is a biosynthetic schematic of isoprene synthesis via a 2-hydroxyacyl-CoA dehydratase route utilizing ldh.
Figure 3:
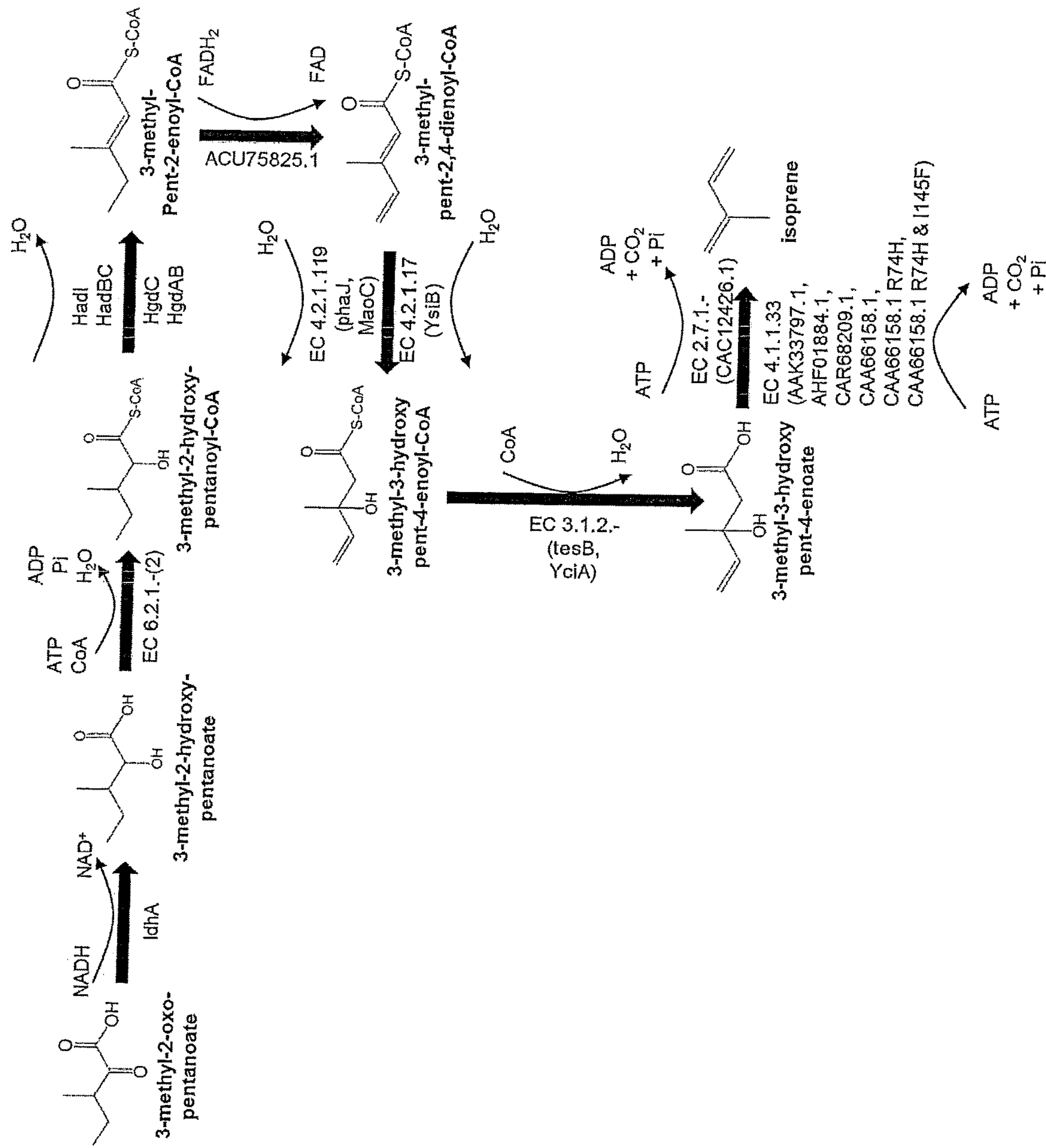
FIG. 3 is a biosynthetic schematic of isoprene synthesis via a 2-hydroxyacyl-CoA dehydratase route utilizing mdd.
Figure 7:
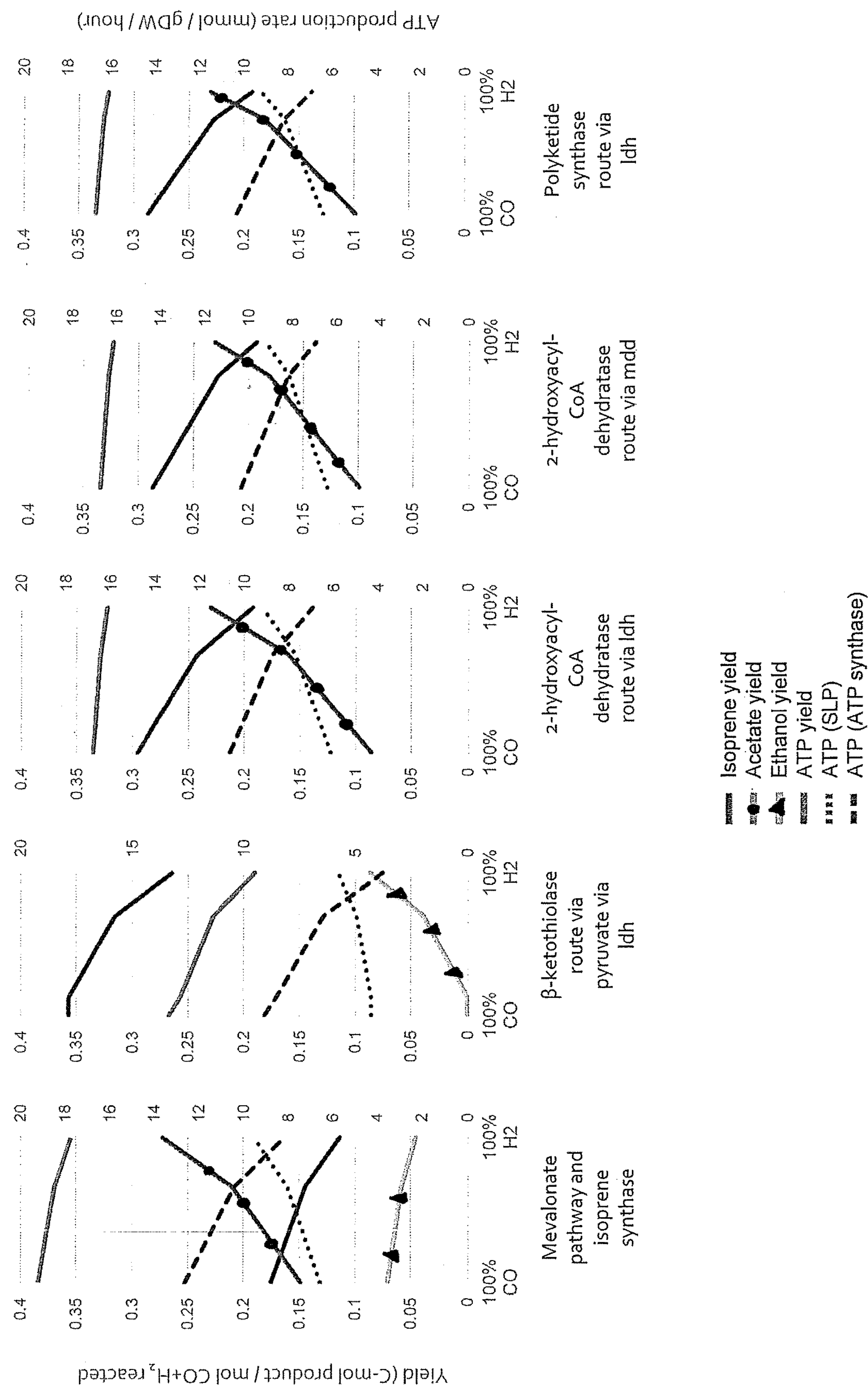
FIG. 7 shows isoprene yields of *C. autoethanogenum* LZ1561 across different gas uptake ratios.

In one nonlimiting embodiment, the hydrocarbon is isoprene produced in a non-naturally occurring acetogen via a beta-ketothiolase route via pyruvate via ldh (see FIG. 1), a 2-hydroxyacyl-CoA dehydratase route via ldh (see FIG. 2), a 2-hydroxyacyl-CoA dehydratase route via mdd (see FIG. 3) or a polyketide synthase route utilizing ldh (FIG. 4) as these pathways to isoprene offer considerably higher maximum predicted yields than the reference pathway (mevalonate pathway with isoprene synthase). For example, the beta-ketothiolase route via pyruvate via ldh pathway offers a maximum predicted yield which is two times higher than the mevalonate pathway with isoprene synthase wherein maximum yield is defined as the maximum isoprene yield in *C. autoethanogenum* LZ1561 with no growth. *C. autoethanogenum* LZ1561 is deposited under DSMZ accession DSM23693. As shown in FIG. 7, *C. autoethanogenum* LZ1561 can grow on a mixture of CO, $CO_2$ and $H_2$ as a carbon and energy source. Growth on CO offers the highest yield.

The non-naturally occurring acetogens of the present invention have at least one altered polynucleotide. In one nonlimiting embodiment, the alteration in the polynucleotide eliminates an activity of a polypeptide encoded by the polynucleotide. In one nonlimiting embodiment, the alteration comprises knock-out of an endogenous polynucleotide of the acetogen. By "knock-out" it is meant replacement or disruption of an existing gene with an artificial piece of DNA. In one nonlimiting embodiment, at least two polynucleotides of the non-naturally occurring acetogen have been altered. In one nonlimiting embodiment, at least three polynucleotides of the non-naturally occurring acetogen have been altered. In one nonlimiting embodiment, at least five polynucleotides of the non-naturally occurring acetogen have been altered.

In one nonlimiting embodiment, the non-naturally occurring acetogen capable of producing hydrocarbons from a gaseous substrate comprises either an alteration of at least one polynucleotide encoding a polypeptide having an activity of an alpha-acetolactate decarboxylase or encoding a polypeptide having an activity of a lactate dehydrogenase; or an alteration of at least two polynucleotides, the first polynucleotide encoding a polypeptide having an activity of an alpha-acetolactate decarboxylase and the second polynucleotide encoding a polypeptide having an activity of a lactate dehydrogenase.

In one nonlimiting embodiment, at least two polynucleotides of the non-naturally occurring acetogen have been altered. In one nonlimiting embodiment, at least one polynucleotide encoding a polypeptide having activity of a member selected from an alpha-acetolactate decarboxylase and/or a lactate dehydrogenase and at least one polynucleotide encoding a polypeptide having activity of a member selected from an aldehyde:ferredoxin oxidoreductase, a purine nucleoside phosphorylase, a dihydrolipoylprotein: NAD+ oxidoreductase, an L-Aspartate ammonia-lyase, a 2,6-Diaminoheptanedioate: 2-oxoglutarate aminotransferase, a glutamate synthase, an L-Threonine acetaldehyde-lyase, a N2-Acetyl-L-ornithine:L-glutamate N-acetyltransferase/Acetyl-CoA:L-glutamate N-acetyltransferase, an N2-Acetyl-L-ornithine amidohydrolase, a formate dehydrogenase and/or a Nfn complex have been altered.

In one nonlimiting embodiment, wherein at least three polynucleotides are altered, the polynucleotides may encode polypeptides having an activity of a member selected from an alpha-acetolactate decarboxylase, a lactate dehydrogenase and an aldehyde:ferredoxin oxidoreductase. In another nonlimiting embodiment, wherein at least three polynucleotides are altered, the polynucleotides may encode polypeptides having an activity of a member selected from an alpha-acetolactate decarboxylase, a lactate dehydrogenase, a pyruvate formate lyase and/or a dihydrolipoylprotein:NAD+ oxidoreductase.

In one nonlimiting embodiment wherein at least five polynucleotides are altered, the polynucleotides may encode polypeptides having an activity of a member selected from an alpha-acetolactate decarboxylase, a lactate dehydrogenase, a pyruvate formate lyase, an aldehyde dehydrogenase and/or a purine nucleoside phosphorylase. In another nonlimiting embodiment wherein at least five polynucleotides are altered, the polynucleotides may encode polypeptides having an activity of a member selected from an alpha-acetolactate decarboxylase, a lactate dehydrogenase, a pyruvate formate lyase, a L-Aspartate ammonia-lyase, a 2,6-Diaminoheptanedioate:2-oxoglutarate aminotransferase and/or a N2-Acetyl-L-ornithine:L-glutamate N-acetyltransferase/Acetyl-CoA:L-glutamate N-acetyltransferase. In yet another nonlimiting embodiment wherein at least five polynucleotides are altered, the polynucleotides may encode polypeptides having an activity of a member selected from an alpha-acetolactate decarboxylase, a lactate dehydrogenase, a pyruvate formate lyase, a glutamate synthase, an L-Threonine acetaldehyde-lyase, an 2,6-Diaminoheptanedioate: 2-oxoglutarate aminotransferase, an N2-Acetyl-L-ornithine:L-glutamate N-acetyltransferase/Acetyl-CoA:L-glutamate N-acetyltransferase and/or a Nfn complex. In yet another nonlimiting embodiment wherein at least five polynucleotides are altered, the polynucleotides may encode polypeptides having an activity of a member selected from an alpha-acetolactate decarboxylase, a lactate dehydrogenase, 2,6-Diaminoheptanedioate:2-oxoglutarate aminotransferase, an N2-Acetyl-L-ornithine amidohydrolase and/or a formate dehydrogenase.

In one nonlimiting embodiment, the non-naturally occurring acetogen is a *Clostridium* species. Examples of *Clostridium* species which can be used include, but are not limited to *Clostridium autoethanogenum, Clostridium ljungdahlii, Clostridium coskatii* or *Clostridium ragsdalei.*

Also provided by the present invention are methods for producing the above-described non-naturally occurring acetogens. While various methods known to those skilled in the art, in one nonlimiting embodiment, the non-naturally occurring acetogen is altered by a knock-out procedure such as described in the Examples herein.

The present invention also relates to compositions comprising a means for producing a hydrocarbon via a beta-ketothiolase route via pyruvate via ldh, a 2-hydroxyacyl-CoA dehydratase route via ldh, a 2-hydroxyacyl-CoA dehydratase route via mdd or a polyketide synthase route utilizing ldh. In one nonlimiting embodiment, the means is derived from or related to the non-naturally occurring acetogens disclosed herein. Nonlimiting examples include the non-naturally occurring acetogen, a cell lysate thereof or one or more polypeptides derived therefrom.

In addition, the present invention provides genetic constructs comprising at least one polynucleotide encoding a polypeptide having an activity of an alpha-acetolactate decarboxylase or encoding a polypeptide having an activity of a lactate dehydrogenase, wherein said polynucleotide is altered to eliminate activity of the encoded polypeptide. In one nonlimiting embodiment, the genetic construct comprises at least two polynucleotides, wherein a first polynucleotide encodes a polypeptide having an activity of an alpha-acetolactate decarboxylase and a second polynucleotide encodes a polypeptide having an activity of a lactate dehydrogenase, wherein the polynucleotides are altered to eliminate the activity of the encoded polypeptides. In one nonlimiting embodiment, the genetic construct further comprises a polynucleotide encoding a polypeptide having an activity of one or more members selected from the group consisting of an aldehyde:ferredoxin oxidoreductase, a purine nucleoside phosphorylase, a dihydrolipoylprotein: NAD+ oxidoreductase, an L-Aspartate ammonia-lyase, a 2,6-Diaminoheptanedioate: 2-oxoglutarate aminotransferase, a glutamate synthase, an L-Threonine acetaldehyde-lyase, a N2-Acetyl-L-ornithine:L-glutamate N-acetyltransferase/Acetyl-CoA:L-glutamate N-acetyltransferase, an N2-Acetyl-L-ornithine amidohydrolase, a formate dehydrogenase and a Nfn complex, wherein the polynucleotide is altered to eliminate the activity of the encoded polypeptide.

The present invention also provides methods for biosynthesising hydrocarbons from a gaseous substrate in a non-naturally occurring acetogen or other means as disclosed herein capable of producing hydrocarbons from a gaseous substrate.

In one nonlimiting embodiment, the hydrocarbon produced via the present invention comprises a saturated or unsaturated 5 carbon branched structure derived from an isoprenoid. Examples include, but are not limited to, isoprene as well as other isoprenoids, terpenes and terpenoids and derivatives such as, but not limited to isoprenols, and salts thereof.

Figure 4:
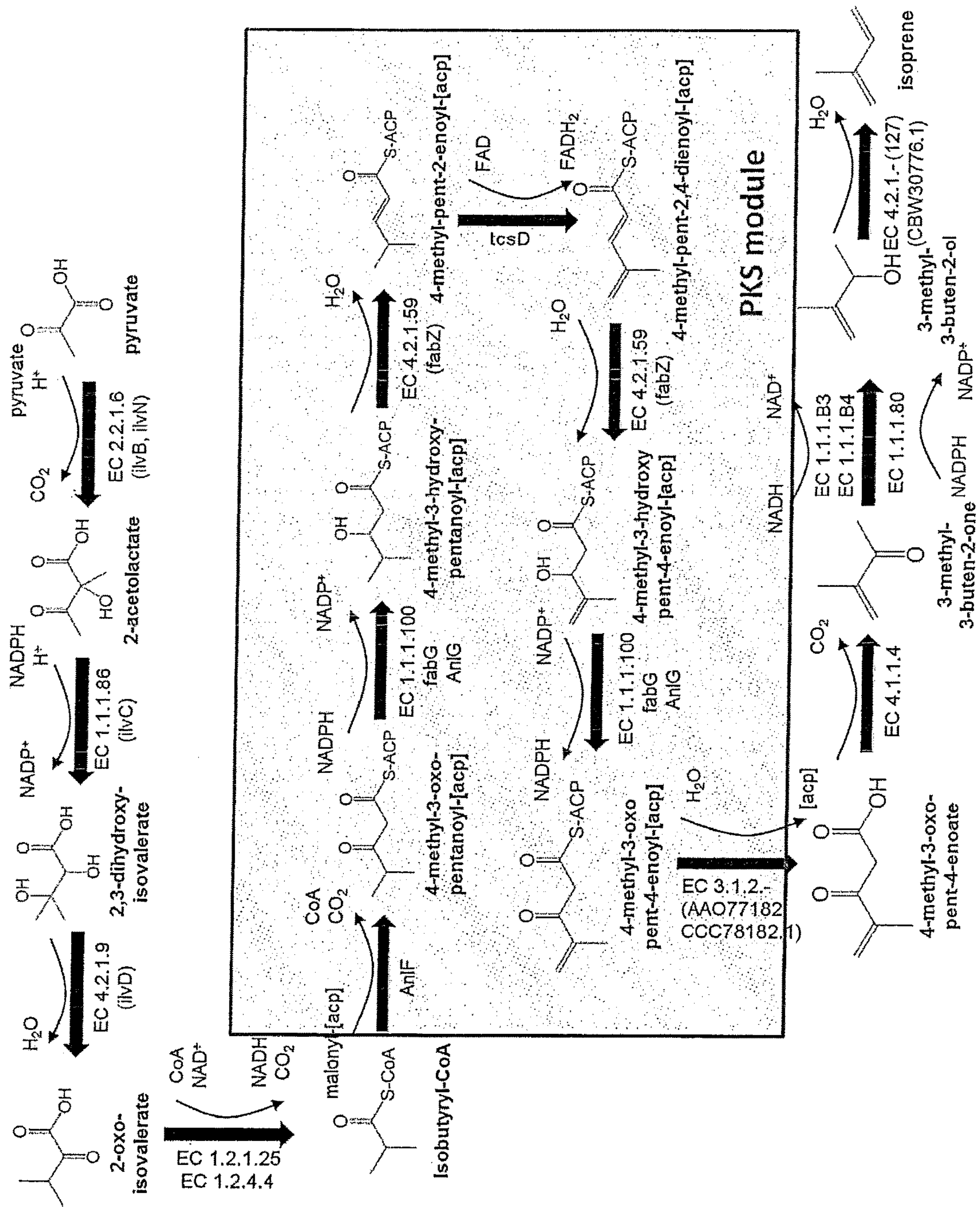
FIG. 4 is a biosynthetic schematic of isoprene synthesis via a polyketide synthase route utilizing ldh.

In one nonlimiting embodiment, the hydrocarbon is isoprene produced in a non-naturally occurring acetogen via a beta-ketothiolase route via pyruvate via ldh (see FIG. 1), a 2-hydroxyacyl-CoA dehydratase route via ldh (see FIG. 2), a 2-hydroxyacyl-CoA dehydratase route via mdd (see FIG. 3) or a polyketide synthase route utilizing ldh (see FIG. 4).

In these methods of isoprene production, the non-naturally occurring acetogen has at least one altered polynucleotide. In one nonlimiting embodiment, at least two polynucleotides of the non-naturally occurring acetogen have been altered. In one nonlimiting embodiment, the non-naturally occurring acetogen has at least three altered polynucleotides. In another nonlimiting embodiment, the non-naturally occurring acetogen has at least five altered polynucleotides. In one nonlimiting embodiment, the alteration in the polynucleotide eliminates an activity of a polypeptide encoded by the polynucleotide.

In one nonlimiting embodiment, the non-naturally occurring acetogen used in this method comprises either an alteration of at least one polynucleotide encoding a polypeptide having an activity of an alpha-acetolactate decarboxylase or encoding a polypeptide having an activity of a lactate dehydrogenase; or an alteration of at least two polynucleotides, the first polynucleotide encoding a polypeptide having an activity of an alpha-acetolactate decarboxylase and the second polynucleotide encoding a polypeptide having an activity of a lactate dehydrogenase.

In one nonlimiting embodiment, at least two polynucleotides of the non-naturally occurring acetogen have been altered. In one nonlimiting embodiment, at least one polynucleotide encoding a polypeptide having activity of members selected from an alpha-acetolactate decarboxylase and/or a lactate dehydrogenase and at least one polynucleotide encoding a polypeptide having activity of members selected from an aldehyde:ferredoxin oxidoreductase, a purine nucleoside phosphorylase, a dihydrolipoylprotein:NAD+ oxidoreductase, an L-Aspartate ammonia-lyase, a 2,6-Diaminoheptanedioate: 2-oxoglutarate aminotransferase, a glutamate synthase, an L-Threonine acetaldehyde-lyase, a N2-Acetyl-L-ornithine:L-glutamate N-acetyltransferase/Acetyl-CoA:L-glutamate N-acetyltransferase, an N2-Acetyl-L-ornithine amidohydrolase, a formate dehydrogenase and/or a Nfn complex have been altered.

In one nonlimiting embodiment, wherein the method comprises use of a non-naturally occurring acetogen with at least three altered polynucleotides, the polynucleotides may encode polypeptides having activities of members selected from an alpha-acetolactate decarboxylase, a lactate dehydrogenase and an aldehyde:ferredoxin oxidoreductase. In another nonlimiting embodiment, wherein the method comprises use of a non-naturally occurring acetogen with at least three altered polynucleotides, the polynucleotides may encode polypeptides having activities of members selected from an alpha-acetolactate decarboxylase, a lactate dehydrogenase, a pyruvate formate lyase and/or a dihydrolipoylprotein:NAD+ oxidoreductase.

In one nonlimiting embodiment, wherein the method comprises use of a non-naturally occurring acetogen with at least five altered polynucleotide, the altered polynucleotides, the polynucleotides may encode polypeptides having activities of members selected from an alpha-acetolactate decarboxylase, a lactate dehydrogenase, a pyruvate formate lyase, an aldehyde dehydrogenase and/or a purine nucleoside phosphorylase. In another nonlimiting embodiment, wherein the method comprises use of a non-naturally occurring acetogen with at least five altered polynucleotides, the polynucleotides may encode polypeptides having activities of members selected from an alpha-acetolactate decarboxylase, a lactate dehydrogenase, a pyruvate formate lyase, a L-Aspartate ammonia-lyase, a 2,6-Diaminoheptanedioate:2-oxoglutarate aminotransferase and a N2-Acetyl-L-ornithine:L-glutamate N-acetyltransferase/Acetyl-CoA:L-glutamate N-acetyltransferase. In yet another nonlimiting embodiment, wherein the method comprises use of a non-naturally occurring acetogen with at least five altered polynucleotides, the polynucleotides may encode polypeptides having activities of members selected from an alpha-acetolactate decarboxylase, a lactate dehydrogenase, a pyruvate formate lyase, a glutamate synthase, an L-Threonine acetaldehyde-lyase, an 2,6-Diaminoheptanedioate:2-oxoglutarate aminotransferase, an N2-Acetyl-L-ornithine:L-glutamate N-acetyltransferase/Acetyl-CoA:L-glutamate N-acetyltransferase and/or a Nfn complex. In yet another nonlimiting embodiment wherein at least five polynucleotides are altered, the polynucleotides may encode polypeptides having an activity of members selected from an alpha-acetolactate decarboxylase, a lactate dehydrogenase, 2,6-Diaminoheptanedioate:2-oxoglutarate aminotransferase, an N2-Acetyl-L-ornithine amidohydrolase and/or a formate dehydrogenase.

For nonlimiting embodiments of the present invention where isoprene is produced via a beta-ketothiolase route via pyruvate via ldh, nonlimiting examples of useful non-naturally occurring acetogens include those having at least one altered polynucleotide encoding a polypeptide in an alpha-acetolactate decarboxylase and/or a lactate dehydrogenase, those having at least two polynucleotides altered in polypeptides in an alpha-acetolactate decarboxylase and/or a lactate dehydrogenase and those having at least 3 or at least 5 altered polynucleotides.

For nonlimiting embodiments of the present invention where isoprene is produced via a 2-hydroxyacyl-CoA dehydratase route via ldh, nonlimiting examples of useful non-naturally occurring acetogens include those having at least one altered polynucleotide encoding a polypeptide in an alpha-acetolactate decarboxylase and/or a lactate dehydrogenase, those having at least two polynucleotides altered in polypeptides in an alpha-acetolactate decarboxylase and/or a lactate dehydrogenase and those having at least 3 or at least 5 altered polynucleotides. A nonlimiting example of a non-naturally occurring acetogen useful in this embodiment with at least three altered polynucleotides is that having polynucleotides encoding polypeptides having activities of members selected from an alpha-acetolactate decarboxylase, a lactate dehydrogenase, a pyruvate formate lyase and/or a dihydrolipoylprotein:NAD+ oxidoreductase altered. A nonlimiting example of a non-naturally occurring acetogen useful in this embodiment with at least five altered polynucleotides is that having polynucleotides encoding polypeptides having activities of members selected from an alpha-acetolactate decarboxylase, a lactate dehydrogenase, a pyruvate formate lyase, a L-Aspartate ammonia-lyase, a 2,6-Diaminoheptanedioate:2-oxoglutarate aminotransferase and/or a N2-Acetyl-L-ornithine:L-glutamate N-acetyltransferase/Acetyl-CoA:L-glutamate N-acetyltransferase altered.

For nonlimiting embodiments of the present invention where isoprene is produced via a 2-hydroxyacyl-CoA dehydratase route via mdd, nonlimiting examples of useful non-naturally occurring acetogens include those having one altered polynucleotide encoding a polypeptide in an alpha-acetolactate decarboxylase and/or a lactate dehydrogenase, those having at least two polynucleotides altered in polypeptides in an alpha-acetolactate decarboxylase and a lactate dehydrogenase and those having at least 3 or at least 5 altered polynucleotides. A nonlimiting example of a non-naturally occurring acetogen useful in this embodiment with at least three altered polynucleotides is that having polynucleotides encoding polypeptides having activities of members selected from an alpha-acetolactate decarboxylase, a lactate dehydrogenase, and an aldehyde:ferredoxin oxidoreductase altered. A nonlimiting example of a non-naturally occurring acetogen useful in this embodiment with at least five altered polynucleotides is that having polynucleotides encoding polypeptides having activities of members selected from an alpha-acetolactate decarboxylase, a lactate dehydrogenase, a pyruvate formate lyase, a glutamate synthase, an L-Threonine acetaldehyde-lyase, an 2,6-Diaminoheptanedioate: 2-oxoglutarate aminotransferase, an N2-Acetyl-L-ornithine:L-glutamate N-acetyltransferase/Acetyl-CoA:L-glutamate N-acetyltransferase and/or a Nfn complex altered.

For nonlimiting embodiments of the present invention where isoprene is produced via a polyketide synthase route utilizing ldh, nonlimiting examples of useful non-naturally occurring acetogens include those having at least one altered polynucleotide encoding a polypeptide in an alpha-acetolactate decarboxylase and/or a lactate dehydrogenase, those having at least two polynucleotides altered in polypeptides in an alpha-acetolactate decarboxylase and a lactate dehydrogenase and those having at least 3 or at least 5 altered polynucleotides. A nonlimiting example of a non-naturally occurring acetogen useful in this embodiment with at least three altered polynucleotides is that having polynucleotides encoding polypeptides having activities of members selected from an alpha-acetolactate decarboxylase, a lactate dehydrogenase, and an aldehyde:ferredoxin oxidoreductase altered. A nonlimiting example of a non-naturally occurring acetogen useful in this embodiment with at least five altered polynucleotides is that having polynucleotides encoding polypeptides having activities of members selected from an alpha-acetolactate decarboxylase, a lactate dehydrogenase, a 2,6-Diaminoheptanedioate:2-oxoglutarate aminotransferase, a N2-Acetyl-L-ornithine amidohydrolase and/or a formate dehydrogenase altered.

In one nonlimiting embodiment, the non-naturally occurring acetogen used in the method of the present invention is a *Clostridium* species. Examples of *Clostridium* species which can be used include, but are not limited to, *Clostridium autoethanogenum, Clostridium ljungdahlii, Clostridium coskatii* and *Clostridium ragsdalei.*

In any the methods described herein, a fermentation strategy can be used that entails anaerobic, micro-aerobic or aerobic cultivation. A fermentation strategy can entail nutrient limitation such as nitrogen, phosphate or oxygen limitation. A cell retention strategy using a ceramic hollow fiber membrane can be employed to achieve and maintain a high cell density during fermentation. The principal gaseous substrate fed to the fermentation can derive from a biological or non-biological feedstock. The biological feedstock can be, or can derive from, monosaccharides, disaccharides, lignocellulose, hemicellulose, cellulose, lignin, levulinic acid and formic acid, triglycerides, glycerol, fatty acids, agricultural waste, condensed distillers' solubles or municipal waste. The non-biological feedstock can be, or can derive from, natural gas, syngas, $CO_2/H_2$, methanol, ethanol, non-volatile residue (NVR) a caustic wash waste stream from cyclohexane oxidation processes or waste stream from a chemical industry such as, but not limited to a carbon black industry or a hydrogen-refining industry, or petrochemical industry.

In one nonlimiting embodiment, at least one of the enzymatic conversions of the hydrocarbon production method comprises fermentation of the gaseous substrate within the non-naturally occurring acetogen. In this embodiment, the gaseous substrate fermentation may comprise at least one of natural gas, syngas, $CO_2/H_2$, methanol, ethanol, non-volatile residue, caustic wash from cyclohexane oxidation processes, or waste stream from a chemical industry such as, but not limited to a carbon black industry or a hydrogen-refining industry, or petrochemical industry. In one nonlimiting embodiment, the gas substrate comprises a mixture of CO, $CO_2$ and $H_2$. In one nonlimiting embodiment, the gas substrate comprises CO.

The methods of the present invention may further comprise recovering produced hydrocarbons from the non-naturally occurring host.

Once produced, any method can be used to isolate hydrocarbons. For example, hydrocarbons can be recovered from the fermenter off-gas stream as a volatile product as the boiling point of isoprene is 34.1° C. At a typical fermentation temperature of approximately 30° C., hydrocarbons have a high vapor pressure and can be stripped by the gas flow rate through the broth for recovery from the off-gas. Hydrocarbons can be selectively adsorbed onto, for example, an adsorbent and separated from the other off-gas components. Membrane separation technology may also be employed to separate hydrocarbons from the other off-gas compounds. Hydrocarbons may be desorbed from the adsorbent using, for example, nitrogen and condensed at low temperature and high pressure.

Because of the gaseous nature of isoprene, in embodiments of the present invention wherein the hydrocarbon produced is isoprene, an advantage is easy separation of the product.

Also provided by the present invention are hydrocarbons bioderived from a non-naturally occurring acetogen or other means according to any of the methods described herein.

In addition, the present invention provides bio-derived, bio-based, or fermentation-derived product produced using the methods and/or compositions disclosed herein. Examples of such products include, but are not limited to, compositions comprising at least one bio-derived, bio-based, or fermentation-derived compound or any combination thereof, as well as polymers, rubbers such as cis-polyisoprene rubber, trans-polyisoprene rubber, or liquid polyisoprene rubber, molded substances, formulations and semi-solid or non-semi-solid streams comprising one or more of the bio-derived, bio-based, or fermentation-derived compounds or compositions, combinations or products thereof.

Although specific advantages have been enumerated above, various embodiments may include some, none, or all of the enumerated advantages. Further, other technical advantages may become readily apparent to one of ordinary skill in the art after review of the figures and description herein. It should be understood at the outset that, although exemplary embodiments are described herein, the principles of the present disclosure may be implemented using any number of techniques, whether currently known or not. The present disclosure should in no way be limited to the exemplary implementations and techniques described herein.

Modifications, additions, or omissions may be made to the compositions, systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, “each” refers to each member of a set or each member of a subset of a set.

To aid the Patent Office and any readers of any patent issued on this application in interpreting the claims appended hereto, applicants wish to note that they do not intend any of the appended claims or claim elements to invoke 35 U.S.C. 112(f) unless the words “means for” or “step for” are explicitly used in the particular claim.

The following section provides further illustration of the methods and compositions of the present invention. These working examples are illustrative only and are not intended to limit the scope of the invention in any way.

EXAMPLES

Example 1: Isoprene Yields

Pathways to isoprene, e.g., a beta-ketothiolase route via pyruvate via ldh, a 2-hydroxyacyl-CoA dehydratase route via ldh, a 2-hydroxyacyl-CoA dehydratase route via mdd and a polyketide synthase route via ldh, as depicted in FIGS. 1-4 were subjected to a strain optimisation pipeline to calculate predicted yields for various genetic variants (e.g., gene knock-out) strain designs that are predicted to favour isoprene production in *Clostridium.*

Genome scale model (GSM) simulations and flux balance analysis (FBA) were carried out to identify strategies to increase isoprene production from CO, $CO_2$, and $H_2$ containing substrate in acetogens via beta-ketothiolase route via pyruvate via ldh, 2-hydroxyacyl-CoA dehydratase route via ldh and 2-hydroxyacyl-CoA dehydratase route via mdd). Genome scale models exist for a number of acetogens including *Clostridium ljungdahlii* (Nagarajan et al. Microb. Cell Fact. 2013 12:118 doi:10.1186/1475-2859-12-118), *Clostridium autoethanogenum* (Marcellin et al. Green Chem. 2016 doi:10.1039/C5GC02708J; Valgepea et al. Metab. Eng. 2017 41: 202-211. doi:10.1016/j.ymben.2017.04.007; Valgepea et al. Cell Syst. 2017 4:505-515.e5. doi:10.1016/j.cels.2017.04.008) or *Moorella thermoacetica* (Islam et al. Integr. Biol. 2015 doi:10.1039/C5IB00095E).

A genome-scale metabolic model of *C. autoethanogenum* similar to the one described by Marcellin et al. (Green Chem. 2016 doi:10.1039/C5GC02708J) was utilized. Growth was simulated by flux balance analysis (FBA), using scripts from the COBRA Toolbox v2.0 in MATLAB R2014a (The Mathworks, Inc.) with Gurobi version 6.0.4 as the solver (Gurobi Optimization, Inc.). Maximum theoretical yield of isoprene was calculated using FBA.

Figure 5B:
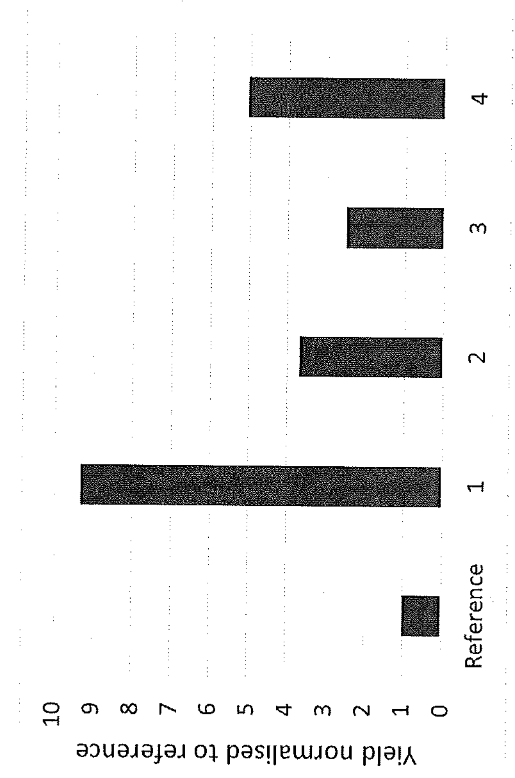
FIG. 5A and FIG. 5B show results simulated for suboptimal growth by MOMA and evolved growth-optimality by FBA for the reference pathway and the beta-ketothiolase route via pyruvate via ldh, the 2-hydroxyacyl-CoA dehydratase route via ldh, the 2-hydroxyacyl-CoA dehydratase route via mdd and the polyketide synthase route via ldh.
Figure 5A:
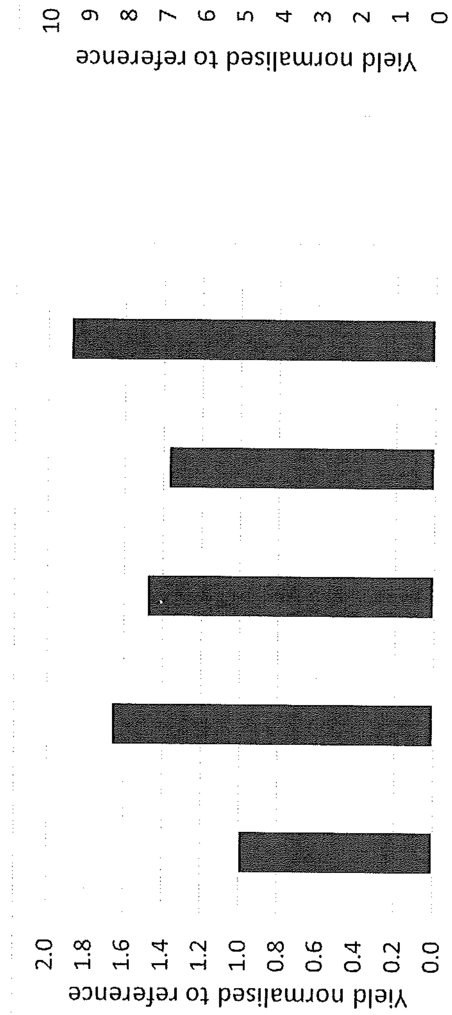

Strain optimizations were obtained using OptFluxlibrary running on a high performance computing cluster with IBM ILOG CPLEX (version 12.6). Ten million simulations for each pathway option were assessed using Strength Pareto Evolutionary Algorithm 2. Simulation methods used were ParsimoniousFBA (pFBA), minimization of metabolic adjustment (MOMA), LMOMA, ROOM (Pereira et al. Metab. Eng. Commun. 2016 3:153-163 doi:10.1016/j.meteno. 2016.05.002) and for each strain three classes of strain designs (1-2 gene knock-outs, 3-4 gene KO, 5-10 gene KO) were simulated. Results simulated by MOMA and FBA for the reference pathway and the beta-ketothiolase route via pyruvate via ldh, the 2-hydroxyacyl-CoA dehydratase route via ldh, the 2-hydroxyacyl-CoA dehydratase route via mdd and the polyketide synthase route via ldh are depicted in FIG. 5A and FIG. 5B, respectively.

Reactions and associated genes that are predicted to improve isoprene in acetogens, when knocked-out, are listed in Tables 1 through 12 for a representative beta-ketothiolase route via pyruvate via ldh, a 2-hydroxyacyl-CoA dehydratase route via ldh, a 2-hydroxyacyl-CoA dehydratase route via mdd pathways and a polyketide synthase route utilizing ldh. Genbank gene locus tags are provided in the tables and can be accessed via ncbi with the extension . nlm.nih.gov/gene of the world wide web.

TABLE 1

Reaction/gene knock-outs in acetogens to improve isoprene production via beta-ketothiolase route via pyruvate via ldh, incorporates 1-2 reaction knock-outs

| Reaction | Gene in *C. autoethanogenum* | Gene in *C. ljungdahlii* | Gene in *C. coskatii* | Gene in *C. ragsdalei* |
|---|---|---|---|---|
| Alpha-acetolactate decarboxylase | CAETHG_RS14410 (SEQ ID NO: 1) | CLJU_c08380 (SEQ ID NO: 2) | CLCOS_42470 (SEQ ID NO: 3) | CLRAG_08070 (SEQ ID NO: 4) |

TABLE 1-continued

Reaction/gene knock-outs in acetogens to improve isoprene production via beta-ketothiolase route via pyruvate via ldh, incorporates 1-2 reaction knock-outs

| Reaction | Gene in *C. autoethanogenum* | Gene in *C. ljungdahlii* | Gene in *C. coskatii* | Gene in *C. ragsdalei* |
|---|---|---|---|---|
| Lactate dehydrogenase | CAETHG_RS05500 (SEQ ID NO: 5) | CLJU_c32190 (SEQ ID NO: 6) | CLCOS_24090 (SEQ ID NO: 7) | CLRAG_02820 (SEQ ID NO: 8) |

TABLE 2

Reaction/gene knock-outs in acetogens to improve isoprene production via beta-ketothiolase route via pyruvate via ldh, incorporates 3-4 reaction knock-outs.

| Reaction | Gene in *C. autoethanogenum* | Gene in *C. ljungdahlii* | Gene in *C. coskatii* | Gene in *C. ragsdalei* |
|---|---|---|---|---|
| Alpha-acetolactate decarboxylase | CAETHG_RS14410 (SEQ ID NO: 1) | CLJU_c08380 (SEQ ID NO: 2) | CLCOS_42470 (SEQ ID NO: 3) | CLRAG_08070 (SEQ ID NO: 4) |
| Lactate dehydrogenase | CAETHG_RS05500 (SEQ ID NO: 5) | CLJU_c32190 (SEQ ID NO: 6) | CLCOS_24090 (SEQ ID NO: 7) | CLRAG_02820 (SEQ ID NO: 8) |
| Aldehyde: ferredoxin oxidoreductase (AOR) | CAETHG_RS00440 (SEQ ID NO: 9) | CLJU_c20110 (SEQ ID NO: 10) | — | CLRAG_29650 (SEQ ID NO: 11) |
| | CAETHG_RS00490 (SEQ ID NO: 12) | CLJU_c20210 (SEQ ID NO: 13) | — | — |

TABLE 3

Reaction/gene knock-outs in acetogens to improve isoprene production via beta-ketothiolase route via pyruvate via ldh, incorporates 5-10 reaction knock-outs.

| Reaction | Gene in *C. autoethanogenum* | Gene in *C. ljungdah1ii* | Gene in *C. coskatii* | Gene in *C. ragsdalei* |
|---|---|---|---|---|
| Alpha-acetolactate decarboxylase | CAETHG_RS14410 (SEQ ID NO: 1) | CLJU_c08380 (SEQ ID NO: 2) | CLCOS_42470 (SEQ ID NO: 3) | CLRAG_08070 (SEQ ID NO: 4) |
| Lactate dehydrogenase | CAETHG_RS05500 (SEQ ID NO: 5) | CLJU_c32190 (SEQ ID NO: 6) | CLCOS_24090 (SEQ ID NO: 7) | CLRAG_02820 (SEQ ID NO: 8) |
| Pyruvate formate lyase (Acetyl-CoA:formate C-acetyltransferase) | CAETHG_RS08855 (SEQ ID NO: 14) | CLJU_c39820 (SEQ ID NO: 15) | CLCOS_22680 (SEQ ID NO: 16) | CLRAG_22070 (SEQ ID NO: 17) |
| | CAETHG_RS03170 (SEQ ID NO: 18) | CLJU_c25980 (SEQ ID NO: 19) | CLCOS_16780 (SEQ ID NO: 20) | CLRAG_04120 (SEQ ID NO: 21) |
| | CAETHG_RS16075 (SEQ ID NO: 22) | CLJU_c11830 (SEQ ID NO: 23) | CLCOS_41080 (SEQ ID NO: 24) | — |
| Aldehyde dehydrogenase (CoA acetylating) | CAETHG_RS08810 (SEQ ID NO: 25) | CLJU_c39730 (SEQ ID NO: 26) | CLCOS_24220 (SEQ ID NO: 27) | CLRAG_21980 (SEQ ID NO: 28) |
| | CAETHG_RS16140 (SEQ ID NO: 29) | — | — | — |
| | CAETHG_RS08865 (SEQ ID NO: 30) | CLJU_c39840 (SEQ ID NO: 31) | — | — |
| purine nucleoside phosphorylase | CAETHG_RS00760 (SEQ ID NO: 32) | CLJU_c20750 (SEQ ID NO: 33) | CLCOS_19750 (SEQ ID NO: 34) | CLRAG_19250 (SEQ ID NO: 35) |

TABLE 4

Reaction/gene knock-outs in acetogens to improve isoprene production via 2-hydroxyacyl-CoA dehydratase route via ldh, incorporates 1-2 reaction knock-outs.

| Reaction | Gene in *C. autoethanogenum* | Gene in *C. ljungdahlii* | Gene in *C. coskatii* | Gene in *C. ragsdalei* |
|---|---|---|---|---|
| Alpha-acetolactate decarboxylase | CAETHG_RS14410 (SEQ ID NO: 1) | CLJU_c08380 (SEQ ID NO: 2) | CLCOS_42470 (SEQ ID NO: 3) | CLRAG_08070 (SEQ ID NO: 4) |

TABLE 4-continued

Reaction/gene knock-outs in acetogens to improve isoprene production via 2-hydroxyacyl-CoA dehydratase route via ldh, incorporates 1-2 reaction knock-outs.

| Reaction | Gene in *C. autoethanogenum* | Gene in *C. ljungdahlii* | Gene in *C. coskatii* | Gene in *C. ragsdalei* |
|---|---|---|---|---|
| Lactate dehydrogenase | CAETHG_RS05500 (SEQ ID NO: 5) | CLJU_c32190 (SEQ ID NO: 6) | CLCOS_24090 (SEQ ID NO: 7) | CLRAG_02820 (SEQ ID NO: 8) |

TABLE 5

Reaction/gene knock-outs in acetogens to improve isoprene production via 2-hydroxyacyl-CoA dehydratase route via ldh, incorporates 3-4 reaction knock-outs.

| Reaction | Gene in *C. autoethanogenum* | Gene in *C. ljungdahlii* | Gene in *C. coskatii* | Gene in *C. ragsdalei* |
|---|---|---|---|---|
| Alpha-acetolactate decarboxylase | CAETHG_RS14410 (SEQ ID NO: 1) | CLJU_c08380 (SEQ ID NO: 2) | CLCOS_42470 (SEQ ID NO: 3) | CLRAG_08070 (SEQ ID NO: 4) |
| Lactate dehydrogenase | CAETHG_RS05500 (SEQ ID NO: 5) | CLJU_c32190 (SEQ ID NO: 6) | CLCOS_24090 (SEQ ID NO: 7) | CLRAG_02820 (SEQ ID NO: 8) |
| Pyruvate formate lyase | CAETHG_RS08855 (SEQ ID NO: 14) | CLJU_c39820 (SEQ ID NO: 15) | CLCOS_22680 (SEQ ID NO: 16) | CLRAG_22070 (SEQ ID NO: 17) |
| (Acetyl-CoA:formate C-acetyltransferase) | CAETHG_RS03170 (SEQ ID NO: 18) | CLJU_c25980 (SEQ ID NO: 19) | CLCOS_16780 (SEQ ID NO: 20) | CLRAG_04120 (SEQ ID NO: 21) |
| | CAETHG_RS16075 (SEQ ID NO: 22) | CLJU_C11830 (SEQ ID NO: 23) | CLCOS_41080 (SEQ ID NO: 24) | — |
| Dihydrolipoylprotein: NAD + oxidoreductase | CAETHG_RS07795 (SEQ ID NO: 36) | — | — | — |
| | CAETHG_RS07825 (SEQ ID NO: 37) | CLJU_c37600 (SEQ ID NO: 38) | CLCOS_09450 (SEQ ID NO: 39) | CLRAG_37010 (SEQ ID NO: 40) |

TABLE 6

Reaction/gene knock-outs in acetogens to improve isoprene production via 2-hydroxyacyl-CoA dehydratase route via ldh, incorporates 5-10 reaction knock-outs.

| Reaction | Gene in *C. autoethanogenum* | Gene in *C. ljungdahlii* | Gene in *C. coskatii* | Gene in *C. ragsdalei* |
|---|---|---|---|---|
| Alpha-acetolactate decarboxylase | CAETHG_RS14410 (SEQ ID NO: 1) | CLJU_c08380 (SEQ ID NO: 2) | CLCOS_42470 (SEQ ID NO: 3) | CLRAG_08070 (SEQ ID NO: 4) |
| Lactate dehydrogenase | CAETHG_RS05500 (SEQ ID NO: 5) | CLJU_c32190 (SEQ ID NO: 6) | CLCOS_24090 (SEQ ID NO: 7) | CLRAG_02820 (SEQ ID NO: 8) |
| Pyruvate formate lyase | CAETHG_RS08855 (SEQ ID NO: 14) | CLJU_c39820 (SEQ ID NO: 15) | CLCOS_22680 (SEQ ID NO: 16) | CLRAG_22070 (SEQ ID NO: 17) |
| (Acetyl-CoA:formate C-acetyltransfer ase) | CAETHG_RS03170 (SEQ ID NO: 18) | CLJU_c25980 (SEQ ID NO: 19) | CLCOS_16780 (SEQ ID NO: 20) | CLRAG_04120 (SEQ ID NO: 21) |
| | CAETHG_RS16075 (SEQ ID NO: 22) | CLJU_C11830 (SEQ ID NO: 23) | CLCOS_41080 (SEQ ID NO: 24) | — |
| L-Aspartate ammonia-lyase/Fumarase | CAETHG_RS10085 (SEQ ID NO: 41) | CLJU_c42370 (SEQ ID NO: 42) | CLCOS_38200 (SEQ ID NOL43) | CLRAG_05490 (SEQ ID NO: 44) |
| | CAETHG_RS12205 (SEQ ID NO: 45) | CLJU_c04170 (SEQ ID NO: 46) | CLCOS_14400 (SEQ ID NO: 47) | CLRAG_26890 (SEQ ID NO: 48) |
| 2,6-Diaminoheptanedioate: 2-oxoglutarate aminotransferase | CAETHG_RS17235 (SEQ ID NO: 49) | CLJU_c14280 (SEQ ID NO: 50) | CLCOS_27270 (SEQ ID NO: 51) | CLRAG_09600 (SEQ ID NO: 52) |
| N2-Acetyl-L-ornithine:L-glutamate N-acetyltransferase/ Acetyl-CoA:L-glutamate N-acetyltransferase | CAETHG_RS01140 (SEQ ID NO: 53) | CLJU_c21530 (SEQ ID NO: 54) | CLCOS_33330 (SEQ ID NO: 55) | CLRAG_31090 (SEQ ID NO: 56) |

TABLE 7

Reaction/gene knock-outs in acetogens to improve isoprene production via 2-hydroxyacyl-CoA dehydratase route via mdd, incorporates 1-2 reaction knock-outs.

| Reaction | Gene in *C. autoethanogenum* | Gene in *C. ljungdahlii* | Gene in *C. coskatii* | Gene in *C. ragsdalei* |
|---|---|---|---|---|
| Alpha-acetolactate decarboxylase | CAETHG_RS14410 (SEQ ID NO: 1) | CLJU_c08380 (SEQ ID NO: 2) | CLCOS_42470 (SEQ ID NO: 3) | CLRAG_08070 (SEQ ID NO: 4) |
| Lactate dehydrogenase | CAETHG_RS05500 (SEQ ID NO: 5) | CLJU_c32190 (SEQ ID NO: 6) | CLCOS_24090 (SEQ ID NO: 7) | CLRAG_02820 (SEQ ID NO: 8) |

TABLE 8

Reaction/gene knock-outs in acetogens to improve isoprene production via 2-hydroxyacyl-CoA dehydratase route via mdd, incorporates 3-4 reaction knock-outs.

| Reaction | Gene in *C. autoethanogenum* | Gene in *C. ljungdahlii* | Gene in *C. coskatii* | Gene in *C. ragsdalei* |
|---|---|---|---|---|
| Alpha-acetolactate decarboxylase | CAETHG_RS14410 (SEQ ID NO: 1) | CLJU_c08380 (SEQ ID NO: 2) | CLCOS_42470 (SEQ ID NO: 3) | CLRAG_08070 (SEQ ID NO: 4) |
| Lactate dehydrogenase | CAETHG_RS05500 (SEQ ID NO: 5) | CLJU_c32190 (SEQ ID NO: 6) | CLCOS_24090 (SEQ ID NO: 7) | CLRAG_02820 (SEQ ID NO: 8) |
| Aldehyde: ferredoxin oxidoreductase (AOR) | CAETHG_RS00440 (SEQ ID NO: 9) | CLJU_c20110 (SEQ ID NO: 10) | — | CLRAG_29650 (SEQ ID NO: 11) |
| | CAETHG_RS00490 (SEQ ID NO: 12) | CLJU_c20210 (SEQ ID NO: 13) | — | — |

TABLE 9

Reaction/gene knock-outs in acetogens to improve isoprene production via 2-hydroxyacyl-CoA dehydratase route via mdd, incorporates 5-10 reaction knock-outs.

| Reaction | Gene in *C. autoethanogenum* | Gene in *C. ljungdahlii* | Gene in *C. coskatii* | Gene in *C. ragsdalei* |
|---|---|---|---|---|
| Alpha-acetolactate decarboxylase | CAETHG_RS14410 (SEQ ID NO: 1) | CLJU_c08380 (SEQ ID NO: 2) | CLCOS_42470 (SEQ ID NO: 3) | CLRAG_08070 (SEQ ID NO: 4) |
| Lactate dehydrogenase | CAETHG_RS05500 (SEQ ID NO: 5) | CLJU_c32190 (SEQ ID NO: 6) | CLCOS_24090 (SEQ ID NO: 7) | CLRAG_02820 (SEQ ID NO: 8) |
| Pyruvate formate lyase (Acetyl-CoA:formate C-acetyltransferase) | CAETHG_RS08855 (SEQ ID NO: 14) | CLJU_c39820 (SEQ ID NO: 15) | CLCOS_22680 (SEQ ID NO: 16) | CLRAG_22070 (SEQ ID NO: 17) |
| | CAETHG_RS03170 (SEQ ID NO: 18) | CLJU_c25980 (SEQ ID NO: 19) | CLCOS_16780 (SEQ ID NO: 20) | CLRAG_04120 (SEQ ID NO: 21) |
| | CAETHG_RS16075 (SEQ ID NO: 22) | CLJU_c11830 (SEQ ID NO: 23) | CLCOS_41080 (SEQ ID NO: 24) | — |
| Glutamate synthase | CAETHG_ RS18885 (SEQ ID NO: 57) | CLJU_c17370 (SEQ ID NO: 58) | CLCOS_13150 (SEQ ID NO: 59) | CLRAG_29210 (SEQ ID NO: 60) |
| | CAETHG_RS18890 (SEQ ID NO: 61) | CLJU_c17380 (SEQ ID NO: 62) | CLCOS_13160 (SEQ ID NO: 63) | CLRAG_29200 (SEQ ID NO: 64) |
| | CAETHG_RS02275 (SEQ ID NO: 65) | CLJU_c24190 (SEQ ID NO: 66) | CLCOS_32470 (SEQ ID NO: 67) | CLRAG_24880 (SEQ ID NO: 68) |
| L-Threonine acetaldehyde-lyase | CAETHG_RS03265 (SEQ ID NO: 69) | CLJU_c26170 (SEQ ID NO: 70) | CLCOS_16980 (SEQ ID NO: 71) | CLRAG_04250 (SEQ ID NO: 72) |
| 2,6-Diaminoheptanedioate: 2-oxoglutarate aminotransferase | CAETHG_RS17235 (SEQ ID NO: 49) | CLJU_c14280 (SEQ ID NO: 50) | CLCOS_27270 (SEQ ID NO: 51) | CLRAG_09600 (SEQ ID NO: 52) |
| N2-Acetyl-L-ornithine:L-glutamate N-acetyltransferase/Acetyl-CoA:L-glutamate N-acetyltransferase | CAETHG_RS01140 (SEQ ID NO: 53) | CLJU_c21530 (SEQ ID NO: 54) | CLCOS_33330 (SEQ ID NO: 55) | CLRAG_31090 (SEQ ID NO: 56) |

TABLE 9-continued

| Reaction/gene knock-outs in acetogens to improve isoprene production via 2-hydroxyacyl-CoA dehydratase route via mdd, incorporates 5-10 reaction knock-outs. | | | | |
|---|---|---|---|---|
| Reaction | Gene in *C. autoethanogenum* | Gene in *C. ljungdahlii* | Gene in *C. coskatii* | Gene in *C. ragsdalei* |
| Nfn complex | CAETHG_RS07665<br>(SEQ ID NO: 73) | CLJU_c37240<br>(SEQ ID NO: 74) | CLCOS_09810<br>(SEQ ID NO: 75) | CLRAG_36680<br>(SEQ ID NO: 76) |

TABLE 10

| Reaction/gene knock-outs in acetogens to improve isoprene production via polyketide synthase route, incorporates 1-2 reaction knock-outs. | | | | |
|---|---|---|---|---|
| Reaction | Gene in *C. autoethanogenum* | Gene in *C. ljungdah1ii* | Gene in *C. coskatii* | Gene in *C. ragsdalei* |
| Alpha-acetolactate decarboxylase | CAETHG_RS14410<br>(SEQ ID NO: 1) | CLJU_c08380<br>(SEQ ID NO: 2) | CLCOS_42470<br>(SEQ ID NO: 3) | CLRAG_08070<br>(SEQ ID NO: 4) |
| Lactate dehydrogenase | CAETHG_RS05500<br>(SEQ ID NO: 5) | CLJU_c32190<br>(SEQ ID NO: 6) | CLCOS_24090<br>(SEQ ID NO: 7) | CLRAG_02820<br>(SEQ ID NO: 8) |

TABLE 11

| Reaction/gene knock-outs in acetogens to improve isoprene production via polyketide synthase route, incorporates 3-4 reaction knock-outs. | | | | |
|---|---|---|---|---|
| Reaction | Gene in *C. autoethanogenum* | Gene in *C. ljungdahlii* | Gene in *C. coskatii* | Gene in *C. ragsdalei* |
| Alpha-acetolactate decarboxylase | CAETHG_RS14410<br>(SEQ ID NO: 1) | CLJU_c08380<br>(SEQ ID NO: 2) | CLCOS_42470<br>(SEQ ID NO: 3) | CLRAG_08070<br>(SEQ ID NO: 4) |
| Lactate dehydrogenase | CAETHG_RS05500<br>(SEQ ID NO: 5) | CLJU_c32190<br>(SEQ ID NO: 6) | CLCOS_24090<br>(SEQ ID NO: 7) | CLRAG_02820<br>(SEQ ID NO: 8) |
| Aldehyde: ferredoxin oxidoreductase (AOR) | CAETHG_RS00440<br>(SEQ ID NO: 9) | CLJU_c20110<br>(SEQ ID NO: 10) | — | CLRAG_29650<br>(SEQ ID NO: 11) |
| | CAETHG_RS00490<br>(SEQ ID NO: 12) | CLJU_c20210<br>(SEQ ID NO: 13) | — | — |

TABLE 12

| Reaction/gene knock-outs in acetogens to improve isoprene production via polyketide synthase route, incorporates 5-10 reaction knock-outs. | | | | |
|---|---|---|---|---|
| Reaction | Gene in *C. autoethanogenum* | Gene in *C. ljungdahlii* | Gene in *C. coskatii* | Gene in *C. ragsdalei* |
| Alpha-acetolactate decarboxylase | CAETHG_RS14410<br>(SEQ ID NO: 1) | CLJU_c08380<br>(SEQ ID NO: 2) | CLCOS_42470<br>(SEQ ID NO: 3) | CLRAG_08070<br>(SEQ ID NO: 4) |
| Lactate dehydrogenase | CAETHG_RS05500<br>(SEQ ID NO: 5) | CLJU_c32190<br>(SEQ ID NO: 6) | CLCOS_24090<br>(SEQ ID NO: 7) | CLRAG_02820<br>(SEQ ID NO: 8) |
| 2,6-Diaminoheptanedioate: 2-oxoglutarate aminotransferase | CAETHG_RS17235<br>(SEQ ID NO: 49) | CLJU_c14280<br>(SEQ ID NO: 50) | CLCOS_27270<br>(SEQ ID NO: 51) | CLRAG_09600<br>(SEQ ID NO: 52) |
| N2-Acetyl-L-ornithine amidohydrolase | CAETHG_RS04740<br>(SEQ ID NO: 77) | CLJU_c29950<br>(SEQ ID NO: 78) | — | CLRAG_35950<br>(SEQ ID NO: 79) |
| | CAETHG_RS02125<br>(SEQ ID NO: 80) | CLJU_c23810<br>(SEQ ID NO: 81) | CLCOS_28660<br>(SEQ ID NO: 82) | CLRAG_17360<br>(SEQ ID NO: 83) |
| Formate dehydrogenase | CAETHG_RS14690<br>(SEQ ID NO: 84) | CLJU_c20040<br>(SEQ ID NO: 85) | CLCOS_13030<br>(SEQ ID NO: 86) | CLRAG_29330<br>(SEQ ID NO: 87) |
| | CAETHG_RS13725<br>(SEQ ID NO: 88) | CLJU_c08930<br>(SEQ ID NO: 89) | CLCOS_19340<br>(SEQ ID NO: 90) | CLRAG_18840<br>(SEQ ID NO: 91) |

Figure 6:
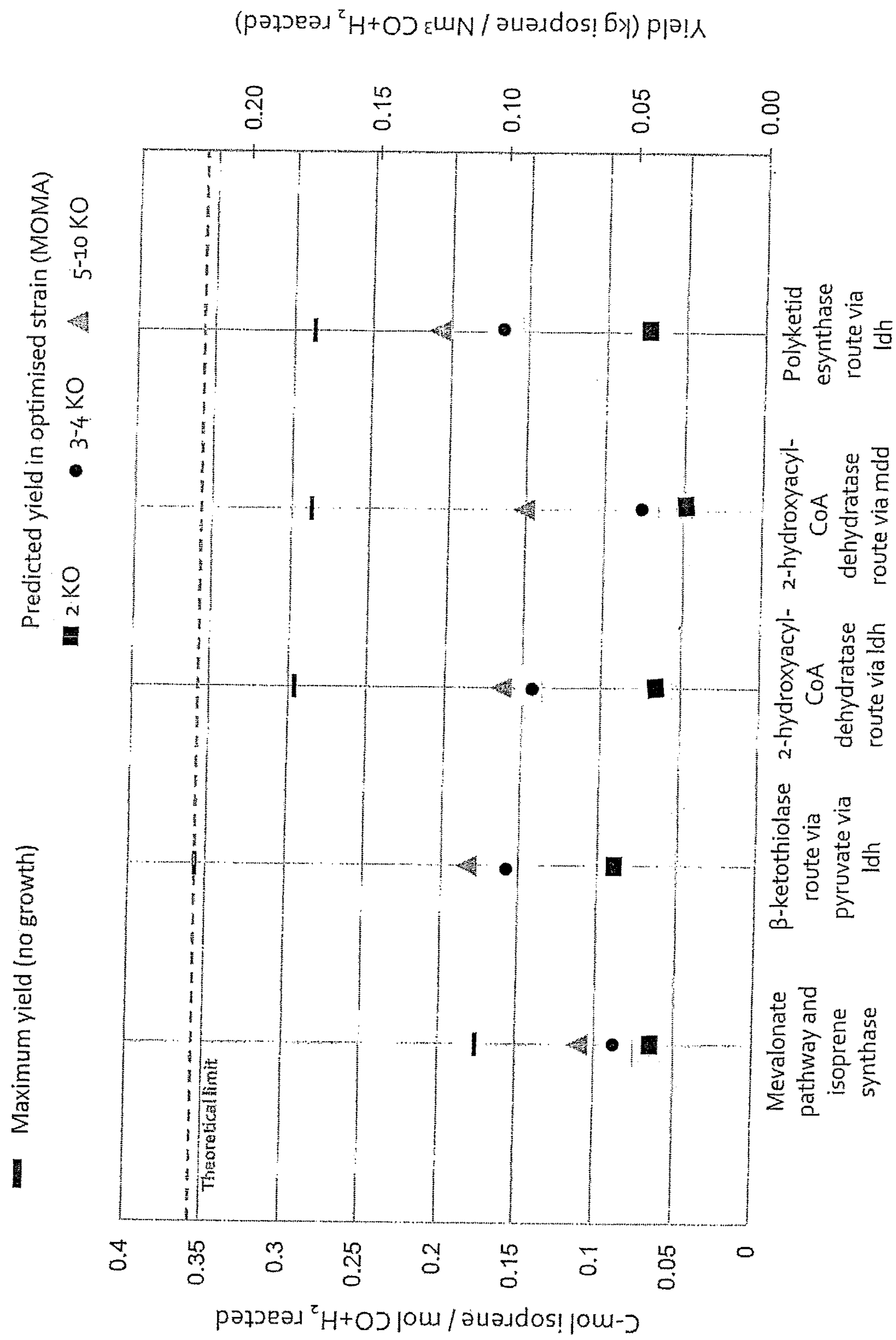
FIG. 6 shows predicted yield of isoprene in *Clostridium autoethanogenum* in strains genetically engineered with different numbers of knock-outs (2 KO, 3-4 KO and 5-10 KO).

FIG. 6 shows predicted yield of isoprene in *Clostridium autoethanogenum* in strains genetically engineered with different numbers of knock-outs (2 KO, 3-4 KO and 5-10 KO). It can be seen that the 5-10 knockout strains give the highest predicted yield of isoprene.

What is claimed is:

1. A non-naturally occurring acetogen which produces hydrocarbons comprising one or more isoprene units or isoprenoid, terpene or functionally active terpenoid derivatives thereof from a gaseous substrate, said acetogen comprising: an alteration of at least five polynucleotides, wherein a first polynucleotide encodes a polypeptide having an activity of an alpha-acetolactate decarboxylase, a second polynucleotide encodes a polypeptide having an activity of a lactate dehydrogenase, and alterations of three or more polynucleotides encoding polypeptides having activities selected from the group consisting of an aldehyde:ferredoxin oxidoreductase, a purine nucleoside phosphorylase, a dihydrolipoylprotein: nicotinamide adenine dinucleotide (NAD+) oxidoreductase, an L-Aspartate ammonia-lyase, a 2,6- Diaminoheptanedioate: 2-oxoglutarate aminotransferase, a glutamate synthase, an L-Threonine acetaldehyde-lyase, a N2-Acetyl-L-ornithine:L-glutamate N-acetyltransferase/Acetyl-CoA:L- glutamate N-acetyltransferase, an N2-Acetyl-L-ornithine amidohydrolase, a formate dehydrogenase and a nicotinamide adenine dinucleotide hydrogen (H)-dependent reduced ferredoxin:NADP+ oxidoreductase (Nfn) complex, wherein the polynucleotide alteration eliminates the activity of the encoded polypeptide, wherein the non-naturally occurring acetogen is a Clostridium species, and wherein the non-naturally occurring acetogen produces said hydrocarbons via a beta-ketothiolase route via pyruvate via lactate dehydrogenase (ldh), a 2-hydroxyacyl-CoA dehydratase route via ldh, or a polyketide synthase route utilizing ldh at a higher yield as compared to a mevalonate pathway with isoprene synthase.

2. The non-naturally occurring acetogen of claim 1, wherein said *Clostridium* species is any one of *Clostridium autoethanogenum, Clostridium ljungdahlii, Clostridium coskatii* or *Clostridium ragsdalei.*

3. A method for producing the non-naturally occurring acetogen of claim 1, said method comprising:

altering at least five polynucleotides, wherein a first polynucleotide encodes a polypeptide having an activity of an alpha-acetolactate decarboxylase, a second polynucleotide encodes a polypeptide having an activity of a lactate dehydrogenase, and three or more polynucleotides encode polypeptides having activities selected from the group consisting of an aldehyde:

ferredoxin oxidoreductase, a purine nucleoside phosphorylase, a dihydrolipoylprotein:nicotinamide adenine dinucleotide (NAD+) oxidoreductase, an L-Aspartate ammonia-lyase, a 2,6-Diaminoheptanedioate: 2-oxoglutarate aminotransferase, a glutamate synthase, an L-Threonine acetaldehyde-lyase, a N2-Acetyl-L-ornithine:L-glutamate N-acetyltransferase/Acetyl-CoA:L-glutamate N-acetyltransferase, an N2-Acetyl-L-ornithine amidohydrolase, a formate dehydrogenase and a nicotinamide adenine dinucleotide hydrogen (H)-dependent reduced ferredoxin: NADP+ oxidoreductase (Nfn) complex, wherein the polynucleotide alteration eliminates the activity of the encoded polypeptide.

4. The method of producing the non-naturally occurring acetogen of claim 3, wherein said altered polynucleotides encode:

polypeptides having an activity of members selected from the group consisting of an alpha-acetolactate decarboxylase, a lactate dehydrogenase and an aldehyde: ferredoxin oxidoreductase;

polypeptides having an activity of members selected from the group consisting of an alpha-acetolactate decarboxylase, a lactate dehydrogenase, a pyruvate formate lyase or a dihydrolipoylprotein:NAD+ oxidoreductase;

polypeptides having an activity of members selected from the group consisting of an alpha-acetolactate decarboxylase, a lactate dehydrogenase, a pyruvate formate lyase, an aldehyde dehydrogenase and a purine nucleoside phosphorylase;

polypeptides having an activity of members selected from the group consisting of an alpha-acetolactate decarboxylase, a lactate dehydrogenase, a pyruvate formate lyase, a L-Aspartate ammonia-lyase, a 2,6-Diaminoheptanedioate:2-oxoglutarate aminotransferase and a N2-Acetyl-L-ornithine:L-glutamate N-acetyltransferase/Acetyl-CoA:L-glutamate N-acetyltransferase;

polypeptides having an activity of members selected from the group consisting of an alpha-acetolactate decarboxylase, a lactate dehydrogenase, a pyruvate formate lyase, a glutamate synthase, an L-Threonine acetaldehyde-lyase, an 2,6-Diaminoheptanedioate: 2-oxoglutarate aminotransferase, an N2-Acetyl-L-ornithine:L-glutamate N-acetyltransferase/Acetyl-CoA: L-glutamate N-acetyltransferase and a Nfn complex; or polypeptides having an activity of members selected from the group consisting of an alpha-acetolactate decarboxylase, a lactate dehydrogenase, a 2,6-Diaminoheptanedioate:2-oxoglutarate aminotransferase, an N2-Acetyl-L-ornithine amidohydrolase and a formate dehydrogenase.

5. The method of producing the non-naturally occurring acetogen of claim 3 wherein said *Clostridium* species is any one of *Clostridium autoethanogenum, Clostridium ljungdahlii, Clostridium coskatii* or *Clostridium ragsdalei.*

6. A method for biosynthesizing a hydrocarbon or functionally active derivatives thereof in the non- naturally occurring acetogen of claim 1, said method comprising enzymatically producing the hydrocarbon from a gaseous substrate in the non-naturally occurring acetogen.

7. The method of claim 6 wherein the hydrocarbon is a saturated or unsaturated 5 carbon branched structure derived from an isoprenoid.

8. The method of claim 6 wherein the hydrocarbon is isoprene.

9. The method of claim 6, wherein said altered polynucleotides encode:

polypeptides having an activity of members selected from the group consisting of an alpha-acetolactate decarboxylase, a lactate dehydrogenase and an aldehyde: ferredoxin oxidoreductase;

polypeptides having an activity of members selected from the group consisting of an alpha-acetolactate decarboxylase, a lactate dehydrogenase, a pyruvate formate lyase and a dihydrolipoylprotein:NAD+ oxidoreductase;

polypeptides having an activity of members selected from the group consisting of an alpha-acetolactate decarboxylase, a lactate dehydrogenase, a pyruvate formate lyase, an aldehyde dehydrogenase and a purine nucleoside phosphorylase;

polypeptides having an activity of members selected from the group consisting of an alpha-acetolactate decarboxylase, a lactate dehydrogenase, a pyruvate formate lyase, a L-Aspartate ammonia-lyase, a 2,6-Diaminoheptanedioate:2-oxoglutarate aminotransferase and a N2-Acetyl-L-ornithine:L-glutamate N-acetyltransferase/Acetyl-CoA:L-glutamate N-acetyltransferase;

polypeptides having an activity of members selected from the group consisting of an alpha-acetolactate decarboxylase, a lactate dehydrogenase, a pyruvate formate lyase, a glutamate synthase, an L-Threonine acetaldehyde-lyase, an 2,6-Diaminoheptanedioate: 2-oxoglutarate aminotransferase, an N2-Acetyl-L-ornithine:L-glutamate N-acetyltransferase/Acetyl-CoA:L-glutamate N-acetyltransferase and a Nfn complex; or polypeptides having an activity of members selected from the group consisting of an alpha-acetolactate decarboxylase, a lactate dehydrogenase, a 2,6-Diaminoheptanedioate:2-oxoglutarate aminotransferase, an N2-Acetyl-L-ornithine amidohydrolase and a formate dehydrogenase.

10. The method of claim 8 wherein isoprene is produced via a 2-hydroxyacyl-CoA dehydratase route via ldh and the altered polynucleotides encode polypeptides having an activity of members selected from the group consisting of an alpha-acetolactate decarboxylase, a lactate dehydrogenase, a pyruvate formate lyase, a L-Aspartate ammonia-lyase, a 2,6-Diaminoheptanedioate:2-oxoglutarate aminotransferase and a N2-Acetyl-L-ornithine:L-glutamate N-acetyltransferase/Acetyl-CoA:L-glutamate N-acetyltransferase.

11. The method of claim 8 wherein isoprene is produced via a polyketide synthase route utilizing ldh and wherein said altered polynucleotides encode polypeptides having an activity of members selected from the group consisting an alpha-acetolactate decarboxylase, a lactate dehydrogenase and an aldehyde:ferredoxin oxidoreductase.

12. The method of claim 8 wherein isoprene is produced via a polyketide synthase route utilizing ldh and wherein said altered polynucleotides encode polypeptides having an activity of members selected from the group consisting of an alpha-acetolactate decarboxylase, a lactate dehydrogenase, a 2,6-Diaminoheptanedioate:2-oxoglutarate aminotransferase, an N2-Acetyl-L-ornithine amidohydrolase and a formate dehydrogenase.

13. The method of claim 6 wherein the gaseous substrate comprises a mixture of CO, $CO_2$ and $H_2$.

14. The method of claim 6 wherein the gaseous substrate comprises CO.

15. The method of claim 6, wherein said *Clostridium* species is any one of *Clostridium autoethanogenum, Clostridium ljungdahlii, Clostridium coskatii* or *Clostridium ragsdalei.*

16. A bio-derived hydrocarbon produced with an acetogen of claim 1.

17. A bio-derived, bio-based, or fermentation-derived product produced from an acetogen of claim 1, wherein said product comprises:

(i) a composition comprising at least one bio-derived, bio-based, or fermentation-derived compound or any combination thereof;

(ii) a bio-derived, bio-based, or fermentation-derived polymer comprising the bio-derived, bio-based, or fermentation-derived composition or compound of (i), or any combination thereof;

(iii) a bio-derived, bio-based, or fermentation-derived cis-polyisoprene rubber, trans-polyisoprene rubber, or liquid polyisoprene rubber, comprising the bio-derived, bio-based, or fermentation-derived compound or bio-derived, bio-based, or fermentation-derived composition of (i), or any combination thereof or the bio-derived, bio-based, or fermentation-derived polymer of (ii), or any combination thereof;

(iv) a molded substance obtained by molding the bio-derived, bio-based, or fermentation-derived polymer of (ii), or the bio-derived, bio-based, or fermentation-derived rubber of (iii), or any combination thereof;

(v) a bio-derived, bio-based, or fermentation-derived formulation comprising the bio-derived, bio-based, or fermentation-derived composition of (i), the bio-derived, bio-based, or fermentation-derived compound of (i), the bio-derived, bio-based, or fermentation-derived polymer of (ii), the bio-derived, bio-based, or fermentation-derived rubber of (iii), or the bio-derived, bio-based, or fermentation-derived molded substance of (iv), or any combination thereof; or (vi) a bio-derived, bio-based, or fermentation-derived semi-solid or a non-semi-solid stream, comprising the bio-derived, bio-based, or fermentation-derived composition of (i), the bio-derived, bio-based, or fermentation-derived compound of (i), the bio-derived, bio-based, or fermentation-derived polymer of (ii), the bio-derived, bio-based, or fermentation-derived rubber of (iii), the bio-derived, bio-based, or fermentation-derived formulation of (iv), or the bio-derived, bio-based, or fermentation-derived molded substance of (v), or any combination thereof.

* * * * *

SEQUENCE LISTING

<160> NUMBER OF SEQ ID NOS: 91

<210> SEQ ID NO 1
<211> LENGTH: 720
<212> TYPE: DNA
<213> ORGANISM: Clostridium autoethanogenum

<400> SEQUENCE: 1
atggatgatg aggtgaaagt cccaaaccat atatatcaaa tgtctacaat aaatgcactt 60
gtttcggggc tgtatgatgg ctgtgtttca ttatctaaac ttcttaaaaa aggaaacttt 120
ggtataggta cttttaaagg tctagatggt gaactaactc ttttaaatgg aactttttat 180
aggactaaac ctgatggcag cgtatacgta tgttccaaaa acgtatccgt tccttttgct 240
gtagtcactg aactggaaaa ttataatact tataatattc aaaatcgtac ttcttatgaa 300
gatataagaa aagaattgga cagctttata gaaagcaaaa atatatttta tgctttctat 360
atggaaggta aatttaatta tgtaaaaaca cgtactgttg taaaacagaa tatgccttat 420
aagcctatgg ctgaagttgt taaagatcag cctatgtttg aatataacgg tgttgatgga 480
tatgtggttg gatttaggtg tcctgattat gttgaaggcc ttaatgtccc tggatatcat 540
tttcatttca taaataaaga taagaaattt ggtggacata taagtgaatt ttccattgaa 600
aatgcgaagg tttatgtaca gaactgttct tgctttagga tggaacttcc taaaaatgaa 660
agtttttata atatggaagt acaagataga aacgatgaga taacaagtgt tgaaaaataa 720

<210> SEQ ID NO 2
<211> LENGTH: 720
<212> TYPE: DNA
<213> ORGANISM: Clostridium ljungdahlii

<400> SEQUENCE: 2
atggatgatg aggtgaaagt cccaaaccat atatatcaaa tgtctacaat aaatgcactt 60
gtttcggggc tgtatgatgg ctgtgtttca ttatctaaac ttcttaaaaa aggaaacttt 120
ggtataggta cttttaaagg tctagatggt gaactaactc ttttaaatgg aactttttat 180
aggactaaac ctgatggcag cgtatacgta tgttccaaaa acgtatccgt tccttttgct 240
gtagtcactg aactggaaaa ttataatact tataatattc aaaatcgtac ttcttatgaa 300
gatataagaa aagaattgga cagctttata gaaagcaaaa atatatttta tgctttctat 360
atggaaggta aatttaatta tgtaaaaaca cgtactgttg taaaacagaa tatgccttat 420
aagcctatgg ctgaagttgt taaagatcag cctatgtttg aatataacgg tgttgatgga 480
tatgtggttg gatttaggtg tcctgattat gttgaaggcc ttaatgtccc tggatatcat 540
tttcatttca taaataaaga taagaaattt ggtggacata taagtgaatt ttccattgaa 600
aatgcgaagg tttatgtaca gaactgttct tgctttagga tggaacttcc taaaaatgaa 660
agtttttata atatggaagt acaagataga aacgatgaga taacaagtgt tgaaaaataa 720

<210> SEQ ID NO 3
<211> LENGTH: 719
<212> TYPE: DNA
<213> ORGANISM: Clostridium coskatii

<400> SEQUENCE: 3
atggatgatg aggtgaaagt cccaaaccat atatatcaaa tgtctacaat aaatgcactt 60
gtttcggggc tgatgatggc tgtgtttcat tatctaaact tcttaaaaaa ggaaactttg 120
gtataggtac ttttaaaggt ctagatggtg aactaactct tttaaatgga actttttata 180

```
ggactaaacc tgatggcagc gtatacgtat gttccaaaaa cgtatccgtt ccttttgctg    240

tagtcactga actggaaagt tataatactt ataatattca aaatcgtact tcttatgaag    300

atataagaaa agaattggac agctttatag aaagcaaaaa tatattttat gctttctata    360

tggaaggtaa atttaattat gtaaaaacac gtactgttgt aaaacagaat atgccttata    420

agcctatggc tgaagttgtt aaagatcagc ctatgtttga atataacggt gttgatggat    480

atgtggttgg atttaggtgt cctgattatg ttgaaggcct taatgtccct ggatatcatt    540

ttcatttcat aaataaagat aagaaatttg gtggacatat aagtgaattt tccattgaaa    600

atgcgaaggt ttatgtacag aactgttctt gctttaggat ggaacttcct aaaaatgaaa    660

gtttttataa tatggaagta caagatagaa acgatgagat aacaagtgtt gaaaaataa     719
```

<210> SEQ ID NO 4
<211> LENGTH: 720
<212> TYPE: DNA
<213> ORGANISM: Clostridium ragsdalei

<400> SEQUENCE: 4

```
atggatgatg aggtgaaagt cccaaaccat atatatcaaa tgtctacaat aaatgcactt     60

gtttcgggac tatatgatgg ctgtgtttca ttatctaaac ttctaaaaaa aggaaatttt    120

ggtataggta cttttaaagg tctagatggt gaactaactc tcttaaatgg aactttttat    180

aggactaaac ctgatggcag tgtatacgta tgttccaaaa acgtatccgt tccttttgct    240

gtagtcactg aaatggagaa ttataacact tataatattc aaaattgtac ttcttatgaa    300

gatataagaa aagaattgga cagctttata gaaagtaaaa atatatttta tgctttctat    360

atggaaggta aatttaatta tgtaaaaaca cgtactgttg taaaacagaa tatgccttat    420

aagcctatgg ctgaagctgt taaaaatcaa cctatgtttg aatataatga tgttgatgga    480

tatgtggttg gatttagatg tcccgattat gttgaaggtc ttaatgtccc tggataccac    540

ttccatttta taaataaaga taagaaattt ggtggacatg taagcgaatt ttctattgaa    600

agtgtaaagg cttatgtaca gaattgctct tgctttagaa tggaacttcc taaaaatgaa    660

aatttttaca atatggaagt gaaagataga aacgatgaga taacaagtgt tgaaaaataa    720
```

<210> SEQ ID NO 5
<211> LENGTH: 981
<212> TYPE: DNA
<213> ORGANISM: Clostridium autoethanogenum

<400> SEQUENCE: 5

```
atgaaagttt tggcatatag tcatagacaa gatgaaactg aatatttcaa aaaattcagt     60

aaaaaatacg acgtggaggt tgtattgtgt gatgatccac caactatgga aaatgcagac    120

ttggccaagg gatttgactg catcagcatt atcacaacta aaatttcaga taaattagta    180

gaaaaatttc atgaaattgg agtaaaattt atatctacaa gaacaatagg atatgaccat    240

atagacataa aaaaggcaaa agagctaggt gtccatatag gcaatgtaaa ctattcacca    300

aatagtgtag ccgattatac aattatgatg attcttatgg ctataagaaa aacgaaagct    360

attatagaac gaagtaatgt acaggattat tctttaaaag gtgttcaagg taaagagctt    420

cacaatttaa ctgtaggtgt tattggtaca ggaagaattg gccgtgcagt tataagtcgc    480

ttaagtggat ttggctgcaa aatattagct tatgatttat atgagaatga agaaataaag    540

aagtatgtta catatgttac actagaagat ctctttaaaa acagtgacat tattacaatg    600
```

```
catgcacctg caacagatga caattatcac atgataaata aggattccat agcacttatg    660

aaagatggta catttattat caatatagcc cgaggctcac ttatcaatac tgaagatctt    720

atagatgcca ttgaaaataa aaaaattggt ggtgcagcta tagacgttat tgaaaatgaa    780

ttcggacttt gctataacga tttaaaatgt gagatactag ataaaaggga aatggcaatt    840

ttaaaatctt ttccaaatgt aattgtaaca cctcacacag ctttttatac agatcaagct    900

gtaagtgata tggtagaaca ttctatttta agttgtgttt tattcatgga aggcaaagaa    960

aatccatggc aaattgaata a                                                981
```

<210> SEQ ID NO 6
<211> LENGTH: 981
<212> TYPE: DNA
<213> ORGANISM: Clostridium ljungdahlii

<400> SEQUENCE: 6

```
atgaaagttt tggcatatag tcatagacaa gatgaaactg aatatttcaa aaaattcagt     60

aaaaaatacg acgtggaggt tgtattgtgt gatgatccac caactatgga aaatgcagac    120

ttggccaagg gatttgactg catcagcatt atcacaacta aaatttcaga taaattagta    180

gaaaaatttc atgaaattgg agtaaaattt atatctacaa gaacaatagg atatgaccat    240

atagacataa aaaaggcaaa agagctaggt gtccatatag gcaatgtaaa ctattcacca    300

aatagtgtag ccgattatac aattatgatg attcttatgg ctataagaaa aacgaaagct    360

attatagaac gaagtaatgt acaggattat tctttaaaag gtgttcaagg taaagagctt    420

cacaatttaa ctgtaggtgt tattggtaca ggaagaattg gccgtgcagt tataagtcgc    480

ttaagtggat ttggctgcaa aatattagct tatgatttat atgagaatga agaaataaag    540

aagtatgtta catatgttac actagaagat ctctttaaaa acagtgacat tattacaatg    600

catgcacctg caacagatga caattatcac atgataaata aggattccat agcacttatg    660

aaagatggta catttattat caatatagcc cgaggctcac ttatcaatac tgaagatctt    720

atagatgcca ttgaaaataa aaaaattggt ggtgcagcta tagacgttat tgaaaatgaa    780

ttcggacttt gctataacga tttaaaatgt gagatactag ataaaaggga aatggcaatt    840

ttaaaatctt ttccaaatgt aattgtaaca cctcacacag ctttttatac agatcaagct    900

gtaagtgata tggtagaaca ttctatttta agttgtgttt tattcatgga aggcaaagaa    960

aatccatggc aaattgaata a                                                981
```

<210> SEQ ID NO 7
<211> LENGTH: 981
<212> TYPE: DNA
<213> ORGANISM: Clostridium coskatii

<400> SEQUENCE: 7

```
atgaaagttt tggcatatag tcatagacaa gatgaaactg aatatttcaa aaaattcagt     60

aaaaaatacg acgtggaggt tgtattgtgt gatgatccac caactatgga aaatgcagac    120

ttggccaagg gatttgactg catcagcatt atcacaacta aaatttcaga taaattagta    180

gaaaaatttc atgaaattgg agtaaaattt atatctacaa gaacaatagg atatgaccat    240

atagacataa aaaaggcaaa agagctaggt gtccatatag gcaatgtaaa ctattcacca    300

aatagtgtag ccgattatac aattatgatg attcttatgg ctataagaaa aacgaaagct    360

attatagaac gaagtaatgt acaggattat tctttaaaag gtgttcaagg taaagagctt    420

cacaatttaa ctgtaggtgt tattggtaca ggaagaattg gccgtgcagt tataagtcgc    480
```

```
ttaagtggat ttggctgcaa aatattagct tatgatttat atgagaatga agaaataaag    540

aagtatgtta catatgttac actagaagat ctctttaaaa acagtgacat tattacaatg    600

catgcacctg caacagatga caattatcac atgataaata aggattccat agcacttatg    660

aaagatggta catttattat caatatagcc cgaggctcac ttatcaatac tgaagatctt    720

atagatgcca ttgaaaataa aaaaattggt ggtgcagcta tagacgttat tgaaaatgaa    780

ttcggacttt gctataacga tttaaaatgt gagatactag ataaaaggga aatggcaatt    840

ttaaaatctt ttccaaatgt aattgtaaca cctcacacag ctttttatac agatcaagct    900

gtaagtgata tggtagaaca ttctatttta agttgtgttt tattcatgga aggcaaagaa    960

aatccatggc aaattgaata a                                              981
```

```
<210> SEQ ID NO 8
<211> LENGTH: 981
<212> TYPE: DNA
<213> ORGANISM: Clostridium ragsdalei

<400> SEQUENCE: 8

atgaaagttt tggcatatag tcatagacaa gatgaaactg aatatttcaa aaaattcagt     60

gaaaaatacg acgtggaggt tgtattgtgt gatgatccac caactatgga aaatgcagac    120

ttggccaaag gatttgactg catcagcatt atcacaacta aaatttcaga taaattagta    180

gaaaaatttc atgaaattgg agtaaaattt atatccacaa gaacaatagg atatgaccat    240

atagacataa aaaaggcgaa agagctaggt gtccatatag gcaatgtaaa ctattcacca    300

aatagtgtag ccgattatac aattatgatg attcttatgg ctataagaaa aatgaaagct    360

attatggaac gaagtaatgt acaggattat tctttaaaag gtgttcaagg taaagagctt    420

cacaatttaa ctgtaggtgt tattggtaca ggaagaattg gccgtgcagt tataagtcgt    480

ttaagtggat tcggctgcaa aatattggct tatgatttat acgaaaatga agaaataaag    540

aagtatgtta catatgttac actagaagat ctctttaaaa acagtgacat tattacaatg    600

catgcacctg caacagatga caattatcac atgataaata aggattccat agcacttatg    660

aaagatggta catttattat caatatagcc cgaggctcac ttatcaatac tgaagatctc    720

atagacgcca ttgaaaataa aaaaattggt ggtgcagcta tagacgttat tgaaaatgaa    780

ttcggacttt gctataacga tttaaaatgt gagatactag ataaaaggga aatggcaatt    840

ttaaagtctt ttccaaatgt aattgttaca cctcacacag cgttttatac agatcaagct    900

gtaagtgaca tggtagaaca ttctatttta agttgtgttt tattcatgga aggcaaagaa    960

aatccatggc aaattgaata a                                              981
```

```
<210> SEQ ID NO 9
<211> LENGTH: 1824
<212> TYPE: DNA
<213> ORGANISM: Clostridium autoethanogenum

<400> SEQUENCE: 9

atgtatggtt atgatggtaa agtattaaga attaatttaa aagaaagaac ttgcaaatca     60

gaaaatttag atttagataa agctaaaaag tttataggtt gtaggggact aggtgttaaa    120

actttatttg atgaaataga tcctaaaata gatgcattat caccagaaaa taaatttata    180

attgtaacag gtcctttaac tggagctccg gttccaacta gtggaaggtt tatggtagtt    240

actaaagcac cgcttacagg aactatagga atttcaaatt cgggtggaaa atggggagta    300
```

```
gacttaaaaa aagctggttg ggatatgata atagtagagg ataaggctga ttcaccagtt    360

tacattgaaa tagtagatga taaggtagaa attaaagacg cgtcacagct ttggggaaaa    420

gttacatcag aaactacaaa agagttagaa aagataactg agaataaatc aaaggtatta    480

tgtataggac ctgctggtga acgattgtct cttatggcag cagttatgaa tgatgtagat    540

agaactgcag caagaggcgg cgttggtgca gttatgggat ctaaaaactt aaaagctatt    600

acagttaaag gaactggaaa aatagcttta gctgataaag aaaaagtaaa aaaagtgtcc    660

gtagaaaaaa ttacaacatt aaaaaatgat ccagtagctg gtcagggaat gccaacttat    720

ggtacagcta tactggttaa tataataaat gaaaatggag ttcatcctgt aaagaatttt    780

caagagtctt atacgaatca agcagataaa ataagtggag agactcttac tgctaaccaa    840

ctagtaagga aaaatccttg ttacagctgt cctataggtt gtggaagatg ggttagacta    900

aaagatggca cagagtgcgg aggaccagaa tatgaaacac tgtggtgttt tggatctgac    960

tgtggttcat atgatttaga tgctataaat gaagctaata tgttatgtaa tgaatatggt   1020

attgatacta ttacttgtgg tgcaacaatt gctgcagcta tggaacttta tcaaagagga   1080

tatataaaag acgaagaaat agctggagat aacctatctc tcaagtgggg tgatacggaa   1140

tctatgattg gctggataaa gagaatggta tatagtgaag gctttggagc aaagatgaca   1200

aatggttcat ataggctttg tgaaggttat ggagcaccgg agtattctat gacagttaaa   1260

aagcaggaaa ttccagcata tgatccaagg ggaatacagg gacacggtat tacctatgca   1320

gttaataata gaggaggctg tcatattaag ggatacatga ttaaccctga aatattaggt   1380

tatcctgaaa aacttgatag atttgcatta gatggtaaag cagcttatgc caaattattt   1440

catgatttaa ctgctgtaat tgattcttta ggattgtgca tattcactac atttgggctt   1500

ggaatacagg attatgtaga tatgtataat gcagtagtag gagaatctac ttatgatgca   1560

gattcactat tagaggcagg agatagaatc tggactcttg agaaattatt taatcttgca   1620

gctggaatag acagcagcca ggatactcta ccaaagagat tgttagaaga acctattcca   1680

gatggcccat caaagggaga agttcatagg ctagatgttc ttctgccaga atattactca   1740

gtacgaggat ggagtaaaga gggtatacct acagaagaaa cattaaagaa attaggatta   1800

gatgaatata taggtaagtt ctag                                          1824
```

<210> SEQ ID NO 10
<211> LENGTH: 1824
<212> TYPE: DNA
<213> ORGANISM: Clostridium ljungdahlii

<400> SEQUENCE: 10

```
atgtatggtt atgatggtaa agtattaaga attaatttaa aagaaagaac ttgcaaatca     60

gaaaatttag atttagataa agctaaaaag tttataggtt gtaggggact aggtgttaaa    120

actttatttg atgaaataga tcctaaaata gatgcattat caccagaaaa taaatttata    180

attgtaacag gtcctttaac tggagctccg gttccaacta gtggaaggtt tatggtagtt    240

actaaagcac cgcttacagg aactatagga atttcaaatt cgggtggaaa atggggagta    300

gacttaaaaa aagctggttg ggatatgata atagtagagg ataaggctga ttcaccagtt    360

tacattgaaa tagtagatga taaggtagaa attaaagacg cgtcacagct ttggggaaaa    420

gttacatcag aaactacaaa agagttagaa aagataactg agaataaatc aaaggtatta    480

tgtataggac ctgctggtga acgattgtct cttatggcag cagttatgaa tgatgtagat    540

agaactgcag caagaggcgg cgttggtgca gttatgggat ctaaaaactt aaaagctatt    600
```

```
acagttaaag gaactggaaa aatagcttta gctgataaag aaaaagtaaa aaaagtgtcc    660
gtagaaaaaa ttacaacatt aaaaaatgat ccagtagctg gtcagggaat gccaacttat    720
ggtacagcta tactggttaa tataataaat gaaaatggag ttcatcctgt aaagaatttt    780
caagagtctt atacgaatca agcagataaa ataagtggag agactcttac tgctaaccaa    840
ctagtaagga aaaatccttg ttacagctgt cctataggtt gtggaagatg ggttagacta    900
aaagatggca cagagtgcgg aggaccagaa tatgaaacac tgtggtgttt tggatctgac    960
tgtggttcat atgatttaga tgctataaat gaagctaata tgttatgtaa tgaatatggt   1020
attgatacta ttacttgtgg tgcaacaatt gctgcagcta tggaacttta tcaaagagga   1080
tatataaaag acgaagaaat agctggagat aacctatctc tcaagtgggg tgatacggaa   1140
tctatgattg gctggataaa gagaatggta tatagtgaag gctttggagc aaagatgaca   1200
aatggttcat ataggctttg tgaaggttat ggagcaccgg agtattctat gacagttaaa   1260
aagcaggaaa ttccagcata tgatccaagg ggaatacagg gacacggtat tacctatgca   1320
gttaataata gaggaggctg tcatattaag ggatatatga ttaaccctga aatattaggt   1380
tatcctgaaa aacttgatag atttgcatta gatggtaaag cagcttatgc caaattattt   1440
catgatttaa ctgctgtaat tgattcttta ggattgtgca tattcactac atttgggctt   1500
ggaatacagg attatgtaga tatgtataat gcagtagtag gagaatctac ttatgatgca   1560
gattcactat tagaggcagg agatagaatc tggactcttg agaaattatt taatcttgca   1620
gctggaatag acagcagcca ggatactcta ccaaagagat tgttagaaga acctattcca   1680
gatggcccat caaagggaga agttcatagg ctagatgttc ttctgccaga atattactca   1740
gtacgaggat ggagtaaaga gggtatacct acagaagaaa cattaaagaa attaggatta   1800
gatgaatata taggtaagtt ctag                                          1824
```

<210> SEQ ID NO 11
<211> LENGTH: 1824
<212> TYPE: DNA
<213> ORGANISM: Clostridium ragsdalei

<400> SEQUENCE: 11

```
atgtatggtt ataatggtaa agtattaaga attaatttaa aagaaagaac ttgcaaatca     60
gaaaatttag atttagataa agctaaaaag tttataggct gtaggggact aggtgttaaa    120
actttatttg atgaaataga tcctaaaata gatgcattat caccagaaaa taaatttata    180
attgtaacag gtccgttaac tggagctcca gttccaacta gtggaaggtt tatggtagtt    240
actaaagcac cgcttacagg aactatagga atttcaaatt cgggtggaaa atggggagta    300
gacttgaaaa aagctggctg ggatatgata atagtagagg ataaggctga ttcaccagtt    360
tacattgaaa tagtagatga taaagtagaa attaaagatg cgtcacagct ttggggaaaa    420
gttacatcag aaactacaaa agagttagaa aagataactg agaatagatc aaaggtatta    480
tgtataggac ctgctggtga aagattgtcc cttatggcag cagttatgaa tgatgtagat    540
agaactgcag caagaggcgg cgttggtgca gttatgggat ctaaaaactt aaaagctatt    600
acagttaaag gaactggaaa aatagcttta gctgataaag aaaaagtaaa aaaagtgtcc    660
gtagaaaaaa ttacaacatt aaaaaatgat ccagtagctg gtcagggaat gccaacttat    720
ggtacagcta tactggttaa tataataaat gaaaatggag ttcatcctgt aaataatttt    780
caagaatctt atacggatca agcagataaa ataagtggag agactcttac tgctaaccaa    840
```

-continued

```
ctagtaagga aaaatccttg ttacagctgt cctataggtt gtggaagatg ggttagacta    900

aaagatggta cagagtgcgg aggaccggag tatgaaacac tgtggtgttt tggctctgac    960

tgtggttcat atgatttaga tgctataaat gaagctaata tgttatgtaa tgaatatggt   1020

attgatacta ttacctgtgg tgcaacaatt gctgcagcta tggaacttta tcaaagagga   1080

tatgtaaaag atgaagaaat agccggagat aacctatctc tcaagtgggg agatacggag   1140

tctatgattg gctggataaa gaaaatggta tatagtgaag gctttggagc aaagatgaca   1200

aatggttcat ataggctttg tgaaggttat ggagtacctg agtattctat gacagttaaa   1260

aaacaagaaa ttccagcata tgatccaagg ggaatacagg gacatggtat tacctatgca   1320

gttaataata gaggaggatg tcatattaag ggatatatga ttaatcctga aatattaggt   1380

tatccggaaa aacttgatag atttgcatta gatggtaaag cagcctatgc caaaatgatg   1440

catgatttaa ctgctgtaat tgattcttta ggattgtgca tattcactac atttgggctt   1500

ggaatacagg attatgtaga tatgtataat gcagtagtag gagaatctac ttgtgattca   1560

gattcactat tagaggcagg agatagagta tggactcttg aaaaattatt taatcttgca   1620

gctggaatag acagcagcca ggatactcta ccaaagagat tgttagaaga acctattcca   1680

gatggtccat caaagggaca cgttcatagg ctagatgttc ttctgccaga atattactca   1740

gtacgaggat ggagtaaaga gggtatacct acagaagaaa cattaaagaa attaggatta   1800

gatgaatata taggtaagtt ctag                                          1824
```

<210> SEQ ID NO 12
<211> LENGTH: 1824
<212> TYPE: DNA
<213> ORGANISM: Clostridium autoethanogenum

<400> SEQUENCE: 12

```
atgtacggat ataagggtaa ggtattaaga attaatctaa gtagtaaaac ttatatagtg     60

gaagaattga aaattgacaa agctaaaaaa tttataggtg caagagggtt aggcgtaaaa    120

accttatttg acgaagtaga tccaaaggta gatccattat cacctgataa caaatttatt    180

atagcagcgg gaccacttac aggtgcacct gttccaacaa gcggaagatt catggtagtt    240

actaaatcac ctttaacagg aactattgct attgcaaatt caggtggaaa atggggagca    300

gaattcaaag cagctggata cgatatgata atcgttgaag gtaaatctga taaagaagtt    360

tatgtaaata tagtagatga taaagtagaa tttagggatg cttctcatgt ttggggaaaa    420

ctaacagaag aaactacaaa aatgcttcaa caggaaacag attcgagagc taaggtttta    480

tgcataggac cagctgggga aaagttatca cttatggcag cagttatgaa tgatgttgat    540

agaacagcag gacgtggtgg tgttggagct gttatgggtt caaagaactt aaaagctatt    600

gtagttaaag gaagcggaaa agtaaaatta tttgatgaac aaaaagtgaa ggaagtagca    660

cttgagaaaa caaatatttt aagaaaagat ccagtagctg gtggaggact tccaacatac    720

ggaacagctg tacttgttaa tattataaat gaaaatggtg tacatccagt aaagaatttt    780

caaaaatctt atacagatca agcagataag atcagtggag aaactttaac taaagattgc    840

ttagttagaa aaaatccttg ctataggtgt ccaattgcct gtggaagatg ggtaaaactt    900

gatgatggaa ctgaatgtgg aggaccagaa tatgaaacat tatggtcatt tggatctgat    960

tgtgatgtat acgatataaa tgctgtaaat acagcaaata tgttgtgtaa tgaatatgga   1020

ctagatacca ttacagcagg atgtactatt gcagcagcta tggaacttta tcaaagaggt   1080

tatattaagg atgaagaaat agcagcagat ggattgtcac ttaattgggg agatgctaag   1140
```

```
tccatggttg aatgggtaaa gaaaatggga cttagagaag gatttggaga caagatggca   1200
gatggttcat acagactttg tgactcatac ggtgtacctg agtattcaat gactgtaaaa   1260
aaacaggaac ttccagcata tgacccaaga ggaatacagg gacatggcat tacttatgct   1320
gttaacaata ggggaggatg tcacattaag ggatatatgg taagtcctga aatacttggc   1380
tatccagaaa aacttgatag acttgcagtg gaaggaaaag caggatatgc tagagtattc   1440
catgatttaa cagctgttat agattcactt ggattatgta tttttacaac atttggtctt   1500
ggtgcacagg attatgttga tatgtataat gcagtagttg gtggagaatt acatgatgta   1560
aattctttaa tgttagctgg agatagaata tggactttag aaaaaatatt taacttaaaa   1620
gcaggcatag atagttcaca ggatactctt ccaaagagat tgcttgaaga acaaattcca   1680
gaaggaccat caaaaggaga agttcataag ttagatgtac tactacctga atattattca   1740
gtacgtggat gggataaaaa tggtattcct acagaggaaa cgttaaagaa attaggatta   1800
gatgaatacg taggtaagct ttag                                          1824
```

<210> SEQ ID NO 13
<211> LENGTH: 1824
<212> TYPE: DNA
<213> ORGANISM: Clostridium ljungdahlii

<400> SEQUENCE: 13

```
atgtacggat ataagggtaa ggtattaaga attaatctaa gtagtaaaac ttatatagtg     60
gaagaattga aaattgacaa agctaaaaaa tttataggtg caagagggtt aggcgtaaaa    120
accttatttg acgaagtaga tccaaaggta gatccattat cacctgataa caaatttatt    180
atagcagcgg gaccacttac aggtgcacct gttccaacaa gcggaagatt catggtagtt    240
actaaatcac ctttaacagg aactattgct attgcaaatt caggtggaaa atggggagca    300
gaattcaaag cagctggata cgatatgata atcgttgaag gtaaatctga taaagaagtt    360
tatgtaaata tagtagatga taaagtagaa tttagggatg cttctcatgt ttggggaaaa    420
ctaacagaag aaactacaaa aatgcttcaa caggaaacag attcgagagc taaggtttta    480
tgcataggac cagctgggga aaagttatca cttatggcag cagttatgaa tgatgttgat    540
agaacagcag gacgtggtgg tgttggagct gttatgggtt caaagaactt aaaagctatt    600
gtagttaaag gaagcggaaa agtaaaatta tttgatgaac aaaaagtgaa ggaagtagca    660
cttgagaaaa caaatatttt aagaaaagat ccagtagctg gtggaggact tccaacatac    720
ggaacagctg tacttgttaa tattataaat gaaaatggtg tacatccagt aaagaatttt    780
caaaaatctt atacagatca agcagataag atcagtggag aaactttaac taaagattgc    840
ttagttagaa aaaatccttg ctataggtgt ccaattgcct gtggaagatg ggtaaaactt    900
gatgatggaa ctgaatgtgg aggaccagaa tatgaaacat tatggtcatt tggatctgat    960
tgtgatgtat acgatataaa tgctgtaaat acagcaaata tgttgtgtaa tgaatatgga   1020
ttagatacca ttacagcagg atgtactatt gcagcagcta tggaacttta tcaaagaggt   1080
tatattaagg atgaagaaat agcagcagat ggattgtcac ttaattgggg agatgctaag   1140
tccatggttg aatgggtaaa gaaaatggga cttagagaag gatttggaga caagatggca   1200
gatggttcat acagactttg tgactcatac ggtgtacctg agtattcaat gactgtaaaa   1260
aaacaggaac ttccagcata tgacccaaga ggaatacagg gacatggtat tacttatgct   1320
gttaacaata ggggaggatg tcacattaag ggatatatgg taagtcctga aatacttggc   1380
```

```
tatccagaaa aacttgatag acttgcagtg gaaggaaaag caggatatgc tagagtattc   1440

catgatttaa cagctgttat agattcactt ggattatgta tttttacaac atttggtctt   1500

ggtgcacagg attatgttga tatgtataat gcagtagttg gtggagaatt acatgatgta   1560

aattctttaa tgttagctgg agatagaata tggactttag aaaaaatatt taacttaaag   1620

gcaggcatag atagttcaca ggatactctt ccaaagagat tgcttgaaga acaaattcca   1680

gaaggaccat caaaaggaga agttcataag ttagatgtac tactacctga atattattca   1740

gtacgtggat gggataaaaa tggtattcct acagaggaaa cgttaaagaa attaggatta   1800

gatgaatacg taggtaagct ttag                                          1824
```

<210> SEQ ID NO 14
<211> LENGTH: 951
<212> TYPE: DNA
<213> ORGANISM: Clostridium autoethanogenum

<400> SEQUENCE: 14

```
atgagtaatg cgaaggcagc aatgattgaa agaaaagcag tcatttttaa tgtgcaaaaa     60

tacaatatgt atgatggacc gggagtaagg acactggtat tctttaaagg atgcccattg    120

cgttgcaagt ggtgtgccaa tcctgaagga caattacgaa aatatgaagt tatgttcaaa    180

aaaaattcat gcattaattg cggtgcttgt gtctctgttt gtccggttgg aatacataca    240

atgtcaaaag gaatggaaca tgaggtagat catagtattg attgtttagg ttgccgtaag    300

tgtgagaatg cttgtaccga gtcagcaata tccattatgg gacaagaaaa aactgtttct    360

gaaattatgg aaattataga agaggacaga cagttttatg aaatttcagg tggtggtgtc    420

acactaggtg gcggcgaggt attgatgcag tgggaatttg cagcaaattt gcttatggta    480

tgtaagcagg aaggaatcaa tacagccatt gaaacttgtg gtcatgcaaa attagaagca    540

atacttaagg ttgctgagtt cacagatttg ttccttttg atataaagca tattgatcct     600

gaacgacact atcaactgac aggagtgcat aatgaacaaa ttttgaagaa cttgaaggaa    660

cttcttaatc acagatataa cgtgaagatt aggatgcccc tgttaaaagg cctgaatgat    720

agcaaagaag agtttgatgg tgtaattaac tttttgatgc ctttccgtga ttacaaaaac    780

tttaaaggta tagatttact tccttatcat aaattaggcg taaataaata tacacagcta    840

ggaatagagt atccaataga gggagatcca agcttaagca gtgatgattt ggatagaatt    900

gaaggctgga ttaaagaata tgatttcccg gtttcggtta ttaagcatta a             951
```

<210> SEQ ID NO 15
<211> LENGTH: 951
<212> TYPE: DNA
<213> ORGANISM: Clostridium ljungdahlii

<400> SEQUENCE: 15

```
atgagtaatg cgaaggcagc aatgattgaa agaaaagcag tcatttttaa tgtgcaaaaa     60

tacaatatgt atgatggacc gggagtaagg acactggtat tctttaaagg atgcccattg    120

cgttgcaagt ggtgtgccaa tcctgaagga caattacgaa aatatgaagt tatgttcaaa    180

aaaaattcat gcattaattg cggtgcttgt gtctctgttt gtccggttgg aatacataca    240

atgtcaaaag gaatggaaca tgaggtagat catagtattg attgtttagg ttgccgtaag    300

tgtgagaatg cttgtaccga gtcagcaata tccattatgg gacaagaaaa aactgtttct    360

gaaattatgg aaattataga agaggacaga cagttttatg aaatttcagg tggtggtgtc    420

acactaggtg gcggcgaggt attgatgcag tgggaatttg cagcaaattt gcttatggta    480
```

```
tgtaagcagg aaggaatcaa tacagccatt gaaacttgtg gtcatgcaaa attagaagca    540

atacttaagg ttgctgagtt cacagatttg ttcctttttg atataaagca tattgatcct    600

gaacgacact atcaactgac aggagtgcat aatgaacaaa ttttgaagaa cttgaaggaa    660

cttcttaatc acagatataa cgtgaagatt aggatgcccc tgttaaaagg cctgaatgat    720

agcaaagaag agtttgatgg tgtaattaac tttttgatgc ctttccgtga ttacaaaaac    780

tttaaaggta tagatttact tccttatcat aaattaggcg taaataaata tacacagcta    840

ggaatagagt atccaataga gggagatcca agcttaagca gtgatgattt ggatagaatt    900

gaaggctgga ttaaagaata tgatttcccg gtttcggtta ttaagcatta a             951
```

<210> SEQ ID NO 16
<211> LENGTH: 951
<212> TYPE: DNA
<213> ORGANISM: Clostridium coskatii

<400> SEQUENCE: 16

```
atgagtaatg cgaaggcagc aatgattgaa agaaaagcag tcatttttaa tgtgcaaaaa     60

tacaatatgt atgatggacc gggagtaagg acactggtat tctttaaagg atgcccattg    120

cgttgcaagt ggtgtgccaa tcctgaagga caattacgaa aatatgaagt tatgttcaaa    180

aagaattcat gcattaattg cggtgcttgt gtctctgttt gtccggttgg aatacataca    240

atgtcaaaag gaatggaaca tgaggtagat catagtattg attgtttagg ttgccgcaag    300

tgtgagaatg cttgtaccga gtctgcaata tccattatgg gagaagaaaa gactgtttct    360

gaaattatgg aagttataga agaggacagg cagttttatg aaatttcagg tggtggtgtc    420

acactaggtg gcggcgaggt attgatgcag tgggaatttg cagcaaattt gcttatggta    480

tgtaagcagg aaggaatcaa tacagccatt gaaacttgtg gtcatgcaaa attagaagca    540

atacttaagg ttgctgagtt cacagatttg ttcctttttg atataaagca tattgatcct    600

gaacgacact atcaattgac aggagtgcat aatgaacaaa ttttgaagaa cttgaaggaa    660

cttcttaatc acagatataa cgtgaagatt aggatgcccc tgttaaaagg cttgaatgat    720

agcaaagaag aatttgatgg tgtaattaac ttcttgatgc ctttccgtga ttacaaaaac    780

tttaaaggta tagatctgct tccttatcat aaattaggcg taaataaata tacacagctg    840

ggtatagatt atccaataga gggagatcca agcttaagca gtgatgattt ggataggatt    900

gaaggctgga ttaaagaata tgatttccca gttgcggtta ttaagcatta a             951
```

<210> SEQ ID NO 17
<211> LENGTH: 950
<212> TYPE: DNA
<213> ORGANISM: Clostridium ragsdalei

<400> SEQUENCE: 17

```
atgagtaatg cgaaggcagc aatgattgaa agaaaagcag tcatttttaa tgtgcaaaaa     60

tacaatatgt atatggaccg ggagtaagga cactggtatt ctttaaagga tgcccattgc    120

gttgcaagtg gtgtgccaat cctgaaggac aattacgaaa atatgaagtt atgttcaaaa    180

agaattcatg cattaattgc ggtgcttgtg tctctgtttg tccggttgga atacatacaa    240

tgtcaaaagg aatggaacat gaggtagatc atagtattga ttgtttaggt tgccgcaagt    300

gtgagaatgc ttgtaccgag tctgcaatat ccattatggg acaagaaaaa actgtttctg    360

aaattatgga agttatagaa gaggacaggc agttttatga aatttcaggt ggtggtgtca    420
```

```
cactaggtgg cggcgaggta ttgatgcagt gggaatttgc agcaaatttg cttatggtat    480

gtaagcagga aggaatcaat acagccattg aaacttgtgg tcatgcaaaa ttggaagcaa    540

tacttaaggt tgctgagttc acagatttgt tcctttttga tataaagcat attgatcctg    600

aacgacacta tcaactgaca ggagtgcata atgagcaaat tttgaagaac ttgaaagaac    660

ttcttaacca caggtataac gtgaagatta ggatgcccct gttaaaaggc ttgaatgata    720

gcaaagaaga gtttgatggt gtaattaact tcttgatgcc tttccgtgat tacaaaaact    780

ttaaaggtat agatctgctt ccttatcata aattaggcgt aaataaatat acacagctgg    840

gtatagatta cccaatagag ggagatccaa gcttaagtag tgatgatttg gataggattg    900

aaggctggat taaagaatat gatttcccag ttgcggttat taagcattaa               950
```

```
<210> SEQ ID NO 18
<211> LENGTH: 2355
<212> TYPE: DNA
<213> ORGANISM: Clostridium autoethanogenum

<400> SEQUENCE: 18

atggaagagt taattcaaac tgacagaata gcttggctga agaaaaaaat gatggatgag     60

ccgagatacg tatctattga gcaagcactt attatcacaa aaacatataa agaaaatgaa    120

gataaaccca ttattattaa aagggcactt gctctaaaaa atgcattgac acacttaaat    180

atcgcggtag aaccagaaga gatgattgtt ggaaatcgta caatgggtgt aagatatggt    240

gttgtatttc ctgaaagcgg aagctcttgg gttgatcgtg aaatagaaac ccttccaaca    300

aggcctcaag atagatttaa tgtaagaaaa gaagatatta ctacttttag agaaattatt    360

aaaccatatt ttaatggaaa atccttagaa gatgtaatta gaaaacggta tggaaaagag    420

atagatgaaa ttgcaaaggt agttaaaatc aatcaaaaag atcatgcgca ggggcatatt    480

tgtccagatt gtgaaagctg gttaaaatac ggacctgagg gattaaaaaa tcaagctgct    540

gtgagattaa aagatgctag taaaaagcag caggattttt ataacagtgt tattttggta    600

atggaaggta cccaaaggtt tatgatgcga tatcatgatc ttttaataga gagatcaaag    660

gaagaatcaa atgaagaaaa tagggccaac atgcttcaga ttgcagcaaa ttgtaaaagc    720

ttgagtatga atcctccaaa gtcttttcat gaagctgtac agtctgtttg gtttttattt    780

gttattcttc acatggaatc aaatgcatct tctttttcac caggtagaat ggataaattc    840

ttgtatccat tttataaaaa agacattgac agtggaaaaa ttgataatca aaaagcttta    900

gaaattatag aatgtctttg gcttaaattc aatcaaattg tctatttgag aaactcacac    960

agtgcaaagt tttttgcagg ttttccaatt ggattcaatg ttgtaattgg cggccaagat   1020

gaaaaaggta atgatttttt taatgagtta tcttttatat tttaaaagc acaagagcat   1080

ttaggattac cacagcctaa cttatcagta aggcttcaca aaaaaactaa tgagaggttt   1140

ttaaaggaag cagtgaaagt agtgtcaaag ggaagtggaa tgccgcaatt ttttaacgat   1200

gaagctatta tttcttccat gatgaagtta ggtgtaaaag aaaaagatgc aagggattac   1260

gctgttgtag gatgtgtgga aatcactacc caaggcaata atcttggctg gagtgatgct   1320

gctatgttta atttagacaa aacattggag ttaactttaa acaatggaaa gtctctatta   1380

agtggggaca aaattggccc tgatttagga aatttaactg attatgaaac ttttgaagaa   1440

ttggaaggag cttttgcaaa gaatataact tattttatgg ataaaatgat actagcttgt   1500

gaagagatag aaaaagcaca catggatata ttgccatccc catttttatc ttctgtaatt   1560

gacaattgta ttgaaaaggg aatggatgtt acaaaaggag gagctgttta taacttttca   1620
```

```
ggaattcaga tgatacaaat agctaacctg gcagacagtt tagctgctat taaactttta   1680
gtatatgaag aaaagagaat atcaaaagaa gatttactaa aagcactgca aaataatttt   1740
gaaggatatg aagtaatacg tactatgctg cttaagcgtg caccaaagta tggcaatgac   1800
attgactatg ttgatgaact tggcgcaaag tgggcaagat ttttcagtaa aaagttaagt   1860
tgctatacaa attatcgtgg cggcagatat catacaggaa tgtatacagt ctctgctcac   1920
gtacctatgg gagaaaatgt tggagcttcg tcagatggaa gatatgcaaa aacacctctg   1980
gcagatggag gtatgtctcc tgtatatggg agagatatcg ccggccccac agcagtatta   2040
aagtctgttt cttcattgga caattactta actactaatg gtggactctt aaatatgaag   2100
tttttacctg aattctttaa gactgaaagc aatatagata agtttgctaa atttttaaga   2160
acttttgtgg atttagaaat accacatata caattcaacg tagtgagaaa agaagatttg   2220
attgcagcac aaaagaatcc tgaaaattat agaagtttaa ctgttagagt tgcaggatat   2280
actgcttatt ttacagaatt ggcaggagaa cttcaaaatg aaattattgc tagaacaagt   2340
tatggtaata tataa                                                    2355
```

<210> SEQ ID NO 19
<211> LENGTH: 2355
<212> TYPE: DNA
<213> ORGANISM: Clostridium ljungdahlii

<400> SEQUENCE: 19

```
atggaagagt taattcaaac tgacagaata gcttggctga agaaaaaaat gatggatgag     60
ccgagatacg tatctattga gcaagcactt attatcacaa aacatataa agaaaatgaa     120
gataaaccca ttattattaa aagggcactt gctctaaaaa atgcattgac acacttaaat    180
atcgcggtag aaccagaaga gatgattgtt ggaaatcgta caatgggtgt aagatatggt    240
gttgtatttc ctgaaagcgg aagctcttgg gttgatcgtg aaatagaaac ccttccaaca    300
aggcctcaag atagatttaa tgtaagaaaa gaagatatta ctacttttag agaaattatt    360
aaaccatatt ttaatggaaa atccttagaa gatgtaatta gaaaacggta tggaaaagag    420
atagatgaaa ttgcaaaggt agttaaaatc aatcaaaaag atcatgcgca ggggcatatt    480
tgtccagatt gtgaaagctg gttaaaatac ggacctgagg gattaaaaaa tcaagctgct    540
gtgagattaa aagatgctag taaaaagcag caggattttt ataacagtgt tattttggta    600
atggaaggta cccaaaggtt tatgatgcga tatcatgatc ttttaataga gagatcaaag    660
gaagaatcaa atgaagaaaa tagggccaac atgcttcaga ttgcagcaaa ttgtaaaagc    720
ttgagtatga atcctccaaa gtcttttcat gaagctgtac agtctgtttg gtttttattt    780
gttattcttc acatggaatc aaatgcatct tctttttcac caggtagaat ggataaattc    840
ttgtatccat tttataaaaa agacattgac agtggaaaaa ttgataatca aaaagcttta    900
gaaattatag aatgtctttg gcttaaattc aatcaaattg tctatttgag aaactcacac    960
agtgcaaagt tttttgcagg ttttccaatt ggattcaatg ttgtaattgg cggccaagat   1020
gaaaaaggta atgatttttt taatgagtta tcttttatat ttttaaaagc acaagagcat   1080
ttaggattac cacagcctaa cttatcagta aggcttcaca aaaaaactaa tgagaggttt   1140
ttaaaggaag cagtgaaagt agtgtcaaag ggaagtggaa tgccgcaatt ttttaacgat   1200
gaagctatta tttcttccat gatgaagtta ggtgtaaaag aaaaagatgc aagggattac   1260
gctgttgtag gatgtgtgga aatcactacc caaggcaata atcttggctg gagtgatgct   1320
```

```
gctatgttta atttagacaa aacattggag ttaactttaa acaatggaaa gtctctatta   1380

agtggggaca aaattggccc tgatttagga aatttaactg attatgaaac ttttgaagaa   1440

ttggaaggag cttttgcaaa gaatataact tattttatgg ataaaatgat actagcttgt   1500

gaagagatag aaaaagcaca catggatata ttgccatccc catttttatc ttctgtaatt   1560

gacaattgta ttgaaaaggg aatggatgtt acaaaaggag gagctgttta taacttttca   1620

ggaattcaga tgatacaaat agctaacctg gcagacagtt tagctgctat taaactttta   1680

gtatatgaag aaaagagaat atcaaaagaa gatttactaa aagcactgca aaataatttt   1740

gaaggatatg aagtaatacg tactatgctg cttaagcgtg caccaaagta tggcaatgac   1800

attgactatg ttgatgaact tggcgcaaag tgggcaagat tttcagtaa aaagttaagt   1860

tgctatacaa attatcgtgg cggcagatat catacaggaa tgtatacagt ctctgctcac   1920

gtacctatgg gagaaaatgt tggagcttcg tcagatggaa gatatgcaaa aacacctctg   1980

gcagatggag gtatgtctcc tgtatatggg agagatatcg ccggccccac agcagtatta   2040

aagtctgttt cttcattgga caattactta actactaatg gtggactctt aaatatgaag   2100

tttttacctg aattctttaa gactgaaagc aatatagata agtttgctaa atttttaaga   2160

acttttgtgg atttagaaat accacatata caattcaacg tagtgagaaa agaagatttg   2220

attgcagcac aaaagaatcc tgaaaattat agaagtttaa ctgttagagt tgcaggatat   2280

actgcttatt ttacagaatt ggcaggagaa cttcaaaatg aaattattgc tagaacaagt   2340

tatggtaata tataa                                                     2355
```

<210> SEQ ID NO 20
<211> LENGTH: 2355
<212> TYPE: DNA
<213> ORGANISM: Clostridium coskatii

<400> SEQUENCE: 20

```
atggaagagt taattcaaac tgacagaata gcttggctga agaaaaaaat gatggatgag     60

ccgagatacg tatctattga gcaagcactt attatcacaa aaacatataa agaaaatgaa    120

gataaaccca ttattattaa aagggcactt gctctaaaaa atgcattgac acacttgaat    180

atcgcggtag aaccagaaga gatgattgtt ggaaatcgta caatgggtgt aagatatggt    240

gttgtatttc ctgaaagcgg aagttcttgg gttgatcgtg aaatagaaac ccttccaaca    300

aggcctcaag atagatttaa tgtaagaaaa gaagatatta ctacttttag agaaattatt    360

aaaccatatt ttaatggaaa atccttagaa gatgtaatta gaaaacggta tggaaaagag    420

atagatgaaa ttgcaaaggt agttaaaatc aatcaaaaag atcatgcgca ggggcatatt    480

tgtccagatt gtgaaagctg gttaaaatac ggacctgagg gattaaaaaa tcaagctgct    540

gtgagattaa aagatgctag taaaaagcag caggattttt ataacagtgt tattttggta    600

atggaaggta cccaaaggtt tatgatgcga tatcatgatc ttttaataga gagatcaaag    660

gaagaatcaa atgaagaaaa tagggccaac atgcttcagg ttgcagcaaa ttgtaaaagc    720

ttgagtatga atcctccaaa gtcttttcat gaagctgtac agtctgtttg gtttttattt    780

gttattcttc acatggaatc aaatgcatct tctttttcac caggtagaat ggataaattc    840

ttgtatccct tttataaaaa agacattgac agtggaaaaa ttgataatca aaaagctttg    900

gaaattatag aatgtctttg gcttaaattc aatcaaattg tctatttgag aaactcacac    960

agtgcaaagt tttttgcagg ttttccaatt ggattcaatg ttgtaattgg cggccaagat   1020

gaaaaaggta atgatttttt taatgagtta tcttttctat ttttaaaagc acaagagcat   1080
```

```
ttaggattac cacagcctaa cttatcagta aggcttcaca aaaaaactaa tgagaggttt   1140

ttaaaggaag cagtaaaagt agtgtcaaag ggaagtggaa tgccacaatt ttttaacgat   1200

gaagctatta tttcttccat gatgaagtta ggtgtaaaag aaaaagatgc aagggattac   1260

gctgttgtag gatgtgtgga aatcactacc caaggcaata atcttggctg gagtgatgct   1320

gctatgttta atttagacaa aacattggag ttaactttaa acaatggaaa gtctctatta   1380

agtggggaca aaattggccc tgatttagga aatttaactg attatgaaac ttttgaagaa   1440

ttggaaggag cttttgcaaa gaatataact tattttatgg ataaaatgat actagcttgt   1500

gaagagatag aaaaagcaca catggatata ttgccatccc catttttatc ttctgtaatt   1560

gacaattgta ttgaaaaggg aatggatgtt acaaaaggag gagctgttta taacttttca   1620

ggaattcaga tgatacaaat agctaacctg gcagacagtt tagctgctat taaactttta   1680

gtatatgaag aaaagagaat atcaaaagaa gatttactaa aagcactgca aaataatttt   1740

gaaggatatg aagtaatacg tactatgctg cttaagcgtg caccaaagta tggcaatgac   1800

attgactatg ttgatgaact tggcgcaaag tgggcaagat tttcagtaa aaagttaagt   1860

tgctatacaa attatcgtag cggcagatat catacaggaa tgtatacagt ctctgctcac   1920

gtacctatgg gagaaaatgt tggagcttcg tcagatggaa gatatgcaaa aacacctctg   1980

gcagatggag gtatgtctcc tgtatatggg agagatatcg ccggccccac agcagtatta   2040

aagtctgttt cttcattgga caattactta actactaatg gtggactctt aaatatgaag   2100

tttttacctg aattctttaa gactgaaaac aatatagata agtttgctaa atttctaaga   2160

acttttgtgg atttagaaat accacatata caattcaacg tagtgagaaa agaagatttg   2220

attgcagcac aaaagaatcc tgaaaattat agaagtttaa ctgttagagt tgcaggatat   2280

actgcttatt ttacagaatt ggcaggagaa cttcaaaatg aaattattgc tagaacaagt   2340

tatggtaata tataa                                                    2355
```

<210> SEQ ID NO 21
<211> LENGTH: 2355
<212> TYPE: DNA
<213> ORGANISM: Clostridium ragsdalei

<400> SEQUENCE: 21

```
atggaagagt taattcaaac ggacagaata gcctggctaa agaaaaaaat gatggatgag     60

ccaaaatacg tatctattga acaagcactt attatcacca aaacatataa agaaaatgaa    120

gataaaccca ttattattaa aagggcactt gctctaaaaa atgtattgac acacttgaat    180

attgcggtag agccagaaga gatgattgtt ggaaatcgta caatgggtgt aagacatggt    240

gttgtatttc ctgaaagcgg aagttcttgg gttgatcgtg aaatagaaac ccttccaaca    300

aggcctcaag atagatttaa tgtaagaaaa gaagatatta ctacttttag agaagttatt    360

aagccatatt ttaacggaaa atccttggaa gatgtaatta gaaaacggta tggaaaagag    420

atagatgaaa ttgcaaaggt agttaaaatc aatcaaaaag atcatgcaca aggtcatatt    480

tgtccagatt gtgaaagctg gttaaaatac ggacctgagg gattaaaaaa tcaagctgtt    540

ttgagattag aaggtgcttc taaagagcag cagcattttt ataacagtgt tattttggta    600

atggaaggta ctcaaaggtt tatgatgcga tatcatgatc ttttaataga aaaatcaaag    660

gaagaatcaa atgaagaaaa taaggccaat atgcttcaag ttgcattaaa ttgtaaaagt    720

ttgagtatga attctccaaa ttcttttcat gaagctgtac agtctatttg gtttttattt    780
```

```
gttattcttc acatggaatc aaatgcatct tctttttcac caggcagaat ggataaattc    840

ttatatccct tttataagaa agatattgac agtggaaaaa ttgataatca aaaagctttg    900

gaaattatag aatgtctttg gcttaaattc aatcaaattg tctatttgag aaattcacac    960

agtgcaaagt tttttgcagg ttttccaatt gggttcaatg ttgtaattgg cggccaagat   1020

gaaaaaggca atgatttttt taatgaacta tcttttctgt ttttaaaagc acaagagcat   1080

ttaggattac cacagcctaa cttatcagta aggcttcata aaaaaactaa cgagtggctt   1140

ttaaaggaag cagtaaaagt agtgtcaaag ggaagtggaa tgccgcaatt ttttaatgat   1200

gaggctatta tttcttccat gatgaagtta ggtgtaaaag aaaaagatgc aagggattac   1260

gctgttgtag gatgcgtgga aatcactacc cagggcaata atcttgggtg gagtgatgct   1320

gctatgttca atttagacaa agtattggag ctaaccttaa acaatggaag gtctctatta   1380

agtggagata aaattggccc tgatttaggg aatttaactg attatgaaac ttttgaagaa   1440

ttagaagaag cttttgcaaa tagtatcact tattttatgg ataaaatgat actagcctgt   1500

gaagaagtag aaaaagcaca tatagatata ttgccatccc catttttatc ttctgtaatt   1560

gacaattgca ttgaaaaggg aatggatgtt acaaaaggag gagctgttta taacttttca   1620

ggaattcaga tgatacaaat agctaacctg gcagacagtt tagctgctat taaactttta   1680

gtatatgaag aaaagagaat atcaaaagaa gatttactaa aagcactgca aaataatttt   1740

gaaggatatg aagtaatacg tactatgctg cttaagcgtg caccaaagta tggcaatgac   1800

attgactatg ttgatgaact tggtgcgaag tgggcaagat tttcagtaaa aaagttaagc   1860

tgctatacaa attatcgcgg gggcaggtat catacaggaa tgtatacagt ctctgctcat   1920

gtacctatgg gagaaaatgt tggagcttca ccagatggaa gatatgcaaa aacacctctg   1980

gcagatgggg gtatgtctcc cgtatatgga agagatattg ccggtccaac agcagtacta   2040

aagtcagttt cttcattaga caattactta actactaatg gtggactctt aaatatgaag   2100

tttttacctg aattctttaa gaccgaaagt aatatagata agtttgctaa atttttaaga   2160

acttttgtgg atttagaaat accacatata caattcaacg tagtgagaaa agaagatttg   2220

attgcagcac aaaagaatcc tgaaaattat agaagtttaa ctgttagagt tgcaggatat   2280

actgcttatt ttacagaact ggcaggagaa cttcaaaatg aaattattgc tagaacaagt   2340

tatggtaata tataa                                                    2355
```

```
<210> SEQ ID NO 22
<211> LENGTH: 2565
<212> TYPE: DNA
<213> ORGANISM: Clostridium autoethanogenum

<400> SEQUENCE: 22
```

```
ttgaatgatg ttttaaacaa actttatact gcaaatcaaa gtaaaagaat agaaaaatta     60

actaacgatt tatactcggt aactcctgaa atcgaagcgc aaagagcagt tttaataacg    120

gaatctttta aggaaactga agcttatcct atgattatta gaagagctaa agctttagaa    180

aaaatactaa atgaaatgga tatagttatt cgtgatgaag aacttattgt aggaaattta    240

actaaaaaac ctagagcggc ttcaatattt ccggaatttt caaataagtg gcttttggag    300

gaatttgata ctcttgcaaa aagaactggt gatgtatttc ttattagtga agatgtaaaa    360

tcacaactta gagaagtatt caaatattgg gatggaaaaa caacaaatga gcttgcaaca    420

gagtatatgt tttcagaaac gaaggaagca atggaagcag ggtatttac tgttggaaat    480

tattacttca atggtatagg tcatatttct gtagattatg caaaagtatt atctaaagga    540
```

```
tttaacggta taattgaaga tgcagaaagt gaaaaggcta aagcagataa agcagatcca     600
gattacataa agaaggatca gtttttaaca gctgtaatca taacttcaaa agctgttatt     660
aagtttgcta gacgttttgc tgaattagct agaaatttag caagtcaatc attggattca     720
cgaagacgtg aagagttaat gcaaatagct gaaaattgtc agtgggtacc tgaaagacca     780
gctagaacgt tttatgaggc tctacaatca ttttggtttg tacaatctat tattcaaata     840
gaatctaatg gacattcaat atcacctatg cgttttgacc aatacatgta tccttatttt     900
aagaaggatg tatcaaatgg acttattaca caagaaaaag cccaagaact tttagattgt     960
ctatgggtta aatttaatga tgttaataag gttcgtgatg aaggatcaac aaaagcattt    1020
ggtggatatc caatgttcca gaacttaatt gtaggtggac aaactattga tggaagagat    1080
gctacaaatg agctttcatt tatgtgcctt gaagctactg cacataccaa attaccgcaa    1140
ccatcaattt caataagagc ttggaacaaa actccagatg agttattatt aaaagctgct    1200
gaagtaactc gtttaggttt aggtatgcca gcttactata atgatgaagt tatcattcct    1260
tctttgacaa gccgcggtct tacgttagaa gatgctagag attatggtat tattggatgt    1320
gtagaacctc aaaaaggtgg aaagacggaa ggatggcatg atgctgcatt ctttaatatt    1380
gtaaaggtat tagagataac tataaataat ggtatggata atggcaaaca gataggatta    1440
agaactggag acttcacttc ttttacatca tttgagaaat tatttgatgc atacaaatta    1500
cagatggagt attttgttaa acttttagtt aatgcagata acagtgtaga tttagcacat    1560
ggagagagag caccattacc attcttatct tcaatggcag acgattgtat agctagagga    1620
aagtcattac aagaaggagg agcacattac aactttacag gaccacaagg agtaggagtt    1680
gcaaatgcag cagactcgtt agaagctatt aagaaacttg tttttgaaga taagaagata    1740
actttacagg atttaaagaa tgcgttagac actaattttg gtgaatgtaa gaaaaaccca    1800
atatctgaac ttgctaatag cataaatgaa gtgggtgata tgaaaggatt aacacctgaa    1860
actatattga aagttattga gaaattatta tcagaagaaa agaaaacctc attagaagga    1920
ttggagccgg gtaaagatat taatttaggt agttatggaa ataaagagag tattcgtcaa    1980
atgctattaa atagagcacc taagtttggt aatgatatag atgaggttga tgatttagca    2040
cgagaagccg cattaattta ctgtaatgaa gttgaaaaat acactaatcc acgtaatggt    2100
caattccaac caggacttta tcctgtttct gcaaatgttc caatgggatc acagacagga    2160
gcaacaccag atggaagaaa agctggggaa ccactagcag atggtgtatc accagtttca    2220
ggaagagatg caatgggacc aactgcagct gctaattctg ttgcgaaaat agaccattgt    2280
aaagcttcaa atggtacatt atttaatcaa aagtttcatc catctgcttt agaaggtcag    2340
actggtttac agaatttatc ttctctagta agaacctttt tcgatgaaaa aggattacat    2400
gtacaattta atgtagtaag tagagaaacg cttttagatg ctcaaaagaa tcctgaaaat    2460
tatagaaatc tggtagtacg tgtagccgga tatagtgctc actttacttc tttagataag    2520
tcaattcagg atgatattat aaaaagaaca gaacatactt tttag                    2565
```

<210> SEQ ID NO 23
<211> LENGTH: 2565
<212> TYPE: DNA
<213> ORGANISM: Clostridium ljungdahlii

<400> SEQUENCE: 23

```
ttgaatgatg ttttaaacaa actttatact gcaaatcaaa gtaaaagaat agaaaaatta      60
```

-continued

```
actaacgatt tatactcggt aactcctgaa atcgaagcgc aaagagcagt tttaataacg    120
gaatctttta aggaaactga agcttatcct atgattatta gaagagctaa agctttagaa    180
aaaatactaa atgaaatgga tatagttatt cgtgatgaag aacttattgt aggaaattta    240
actaaaaaac ctagagcggc ttcaatattt ccagaatttt caaataagtg gcttttggag    300
gaatttgata ctcttgcaaa aagaactggt gatgtatttc ttattagtga agatgtaaaa    360
tcacaactta gagaagtatt caaatattgg gatggaaaaa caacaaatga gcttgcaaca    420
gagtatatgt tttcagaaac gaaggaagca atggaagcag gggtatttac tgttggaaat    480
tattacttca atggtatagg tcatatttct gtagattatg caaaagtatt atctaaagga    540
tttaacggta taattgaaga tgcagaaagt gaaaaggcta aagcagataa agcagatcca    600
gattacataa agaaggatca gtttttaaca gctgtaatca taacttcaaa agctgttatt    660
aagtttgcta gacgttttgc tgaattagct agaaatttag caagtcaatc attggattca    720
cgaagacgtg aagagttaat gcaaatagct gaaaattgtc agtgggtacc tgaaagacca    780
gctagaacgt tttatgaggc tctacaatca ttttggtttg tacaatctat tattcaaata    840
gaatctaatg gacattcaat atcacctatg cgttttgacc aatacatgta tccttatttt    900
aagaaggatg tatcaaatgg acttattaca caagaaaaag cccaagaact tttagattgt    960
ctatgggtta aatttaatga tgttaataag gttcgtgatg aaggatcaac aaaagcattt   1020
ggtggatatc caatgttcca gaacttaatt gtaggtggac aaactattga tggaagagat   1080
gctacaaatg agctttcatt tatgtgcctt gaagctactg cacataccaa attaccgcaa   1140
ccatcaattt caataagagc ttggaacaaa actccagatg agttattatt aaaagctgct   1200
gaagtaactc gtttaggttt aggtatgcca gcttactata atgatgaagt tatcattcct   1260
tctttgacaa gccgcggtct tacgttagaa gatgctagag attatggtat tattggatgt   1320
gtagaacctc aaaaaggtgg aaagacggaa ggatggcatg atgctgcatt ctttaatatt   1380
gtaaaggtat tagagataac tataaataat ggtatggata atggcaaaca gataggatta   1440
agaactggag acttcacttc ttttacatca tttgagaaat tatttgatgc atacaaatta   1500
cagatggagt attttgttaa acttttagtt aatgcagata acagtgtaga tttagcacat   1560
ggagagagag caccattacc attcttatct tcaatggcag acgattgtat agctagagga   1620
aagtcattac aagaaggagg agcacattac aactttacag gaccacaagg agtaggagtt   1680
gcaaatgcag cagactcgtt agaagctatt aagaaacttg tttttgaaga taagaagata   1740
actttacagg atttaaagaa tgcgttagac actaattttg gtggatgtaa gaaaaaccca   1800
atatctgaac ttgctaatag cataaatgaa gtgggtgata tgaaaggatt aacacctgaa   1860
actatattga aagttattga gaaattatta tcagaagaaa agaaaacctc attagaagga   1920
ttggagccgg gtaaagatat taatttaggt agttatggaa ataaagagag tattcgtcaa   1980
atgctattaa atagagcacc taagtttggt aatgatatag atgaggttga tgatttagca   2040
cgagaagccg cattaattta ctgtaatgaa gttgaaaaat acactaatcc acgtaatggt   2100
caattccaac caggacttta tcctgtttct gcaaatgttc caatgggatc acagacagga   2160
gcaacaccag atggaagaaa agctggggaa ccactagcag atggtgtatc accagtttca   2220
ggaagagatg caatgggacc aactgcagct gctaattctg ttgcgaaaat agaccattgt   2280
aaagcttcaa atggtacatt atttaatcaa aagtttcatc catctgcttt agaaggtcag   2340
actggtttac agaatttatc ttctctagta agaacctttt tcgatgaaaa aggattacat   2400
gtacaattta atgtagtaag tagagaaacg cttttagatg ctcaaaagaa tcctgaaaat   2460
```

```
tatagaaatc tggtagtacg tgtagccgga tatagtgctc actttacttc tttagataag   2520

tcaattcagg atgatattat aaaaagaaca gaacatactt tttag                   2565


<210> SEQ ID NO 24
<211> LENGTH: 2565
<212> TYPE: DNA
<213> ORGANISM: Clostridium coskatii

<400> SEQUENCE: 24

ttgaatgatg ttttaaacaa actttatact gcaaatcaaa gtaaaagaat agaaaaatta     60

actaacgatt tatactcggt aactcctgaa atcgaagcgc aaagagcagt tttaataacg    120

gaatctttta aggaaactga agcttatcct atgattatta gaagagctaa agctttagaa    180

aaaatactaa atgaaatgga tatagttatt cgtgatgaag aacttattgt aggaaattta    240

actaaaaaac ctagagcggc ttcaatattt ccggaatttt caaataagtg gcttttggag    300

gaatttgata ctcttgcaaa aagaactggt gatgtatttc ttattagtga agatgtaaaa    360

tcacagctta gagaagtatt caaatattgg gatggaaaaa caacaaatga gcttgcaaca    420

gagtatatgt tttcagaaac gaaggaagca atggaagcag gagtatttac tgttggaaat    480

tattacttca atggtatagg tcatatttct gtagattatg caaaagtatt atctaaagga    540

tttaacggta taattgaaga tgcagaaagt gaaaaggcta aagcagataa agcagatcca    600

gattacataa agaaggatca gtttttaaca gctgtaatca taacttcaaa agctgttatt    660

aagtttgcta gacgttttgc tgaattagct agaaatttag caagtcaatc attggattca    720

cgaagacgtg aagagttaat gcaaatagct gaaaattgtc agtgggtacc tgaaagacca    780

gctagaacgt tttatgaggc tctacaatca ttttggtttg tacaatctat tattcagata    840

gaatctaatg gacattcaat atcacctatg cgttttgatc aatatatgta tccttatttt    900

aaaaaggata tatcaaacgg acttattaca caagaaaaag ctcaagaact tttagattgc    960

ctatgggtta agtttaatga tgttaataaa gttcgtgatg aaggatcaac aaaagcattt   1020

ggtgggtatc caatgttcca gaacttaatt gtaggtgggc aaactattga tggaagagat   1080

gctacaaatg aactttcatt tatgtgtctt gaagctactg cacataccaa gttaccacaa   1140

ccgtcaattt caataagagc ttggaacaaa actccagatg agttattatt aaaagctgct   1200

gaagtaactc gtttaggatt aggtatgcca gcttactata atgatgaagt tatcatccct   1260

tctttgacaa gtagaggtct tacattagaa gatgctagag attatggtat tattgggtgc   1320

gtagaacctc aaaaaggtgg aaagactgaa ggatggcatg atgctgcatt ttttaatatt   1380

gtaaaggtat tagagataac tataaataat ggtatggata atggaaaaca gataggatta   1440

agaactggag acttcacttc ttttacatca tttgagaaac tatttgatgc gtacaaatta   1500

cagatggaat actttgttaa actcttggtt aatgcagata acagtgtaga tttagcacac   1560

ggagagagag cgccattacc attcttatct tcaatggcag acgattgtat agctagagga   1620

aaatcattac aagaaggagg agcgcattac aactttacgg gtccacaagg agtaggagtt   1680

gcaaatgcag cagactcgtt agaagctatt aagaaacttg tttttgaaga taagaagata   1740

actttacagg atttaaagaa tgcgttagat actaattttg gtgaatgtaa gaaaagccca   1800

atgtctgaac ttgctaatag cataaatgaa gtgggtgata tgaaaggatt aacacctgaa   1860

actatattga aagttattga aaaattatta tcagaagaaa agaaaacctc attagaagga   1920

ttggaaccgg gtaaagatat taacttaggt agttatggaa ataaagagag tattcgccag   1980
```

```
atgctattaa atagagcacc taagtttggt aatgatatag atgaggttga tgatttagca   2040

cgagaagccg cattaattta ctgtaatgaa gttgaaaaat acactaatcc acgtaatggt   2100

caattccaac caggacttta tcctgtttct gcaaatgttc caatgggatc acagacagga   2160

gcaacaccag atggaagaaa agctggggaa ccactagcag atggtgtatc accagtttca   2220

ggaagagatg caatgggacc aactgcagct gctaattctg ttgcgaaaat agaccattgt   2280

aaagcttcaa atggtacatt atttaatcaa aagtttcatc catctgcttt agaaggtcag   2340

actggtttac agaatttatc ttctctagta agaacctttt tcgatgaaaa aggattacat   2400

gtacaattta atgtagtaag tagagaaacg cttttagatg ctcaaaagaa tcctgaaaat   2460

tatagaaatc tggtagtacg tgtagccgga tatagtgctc actttacttc tttagataag   2520

tcaattcagg atgatattat aaaaagaaca gaacatactt tttag                   2565
```

<210> SEQ ID NO 25
<211> LENGTH: 1554
<212> TYPE: DNA
<213> ORGANISM: Clostridium autoethanogenum

<400> SEQUENCE: 25

```
ttggaaaatt ttgataaaga cttacgttct atacaagaag caagagatct tgcacgttta     60

ggaaaaattg cagcagacca aattgctgat tatactgaag aacaaattga taaaatccta    120

tgtaatatgg ttagggtagc agaagaaaat gcagtttgcc ttggtaaaat ggctgcagaa    180

gaaactggtt ttggaaaagc tgaagataag gcttataaga accatatggc tgctactaca    240

gtatataatt acatcaagga tatgaagact attggtgtta taaaagaaga taaaagtgaa    300

ggtgtaattg aatttgcaga accagttggt ttattaatgg gtattgtacc atctacaaat    360

ccaacatcta ctgttattta taaatcaatc attgcaatta aatcaagaaa tgcaattgta    420

ttctcaccac acccagctgc attaaaatgt tcaacaaaag caatagaact tatgcgtgat    480

gcagcagtag cagcaggagc tcctgcaaat gtaattggtg gtattgttac accatctata    540

caagctacaa atgaacttat gaaagctaaa gaagttgcta tgataattgc aactggaggc    600

cctggaatgg taaaggctgc atatagttca ggaacacctg caataggcgt tggtgctggt    660

aactctccat cctatattga aagaactgct gatgttcatc aatcagttaa agatataata    720

gctagtaaga gttttgacta tggtactatt tgtgcatccg agcagtctgt aattgcagaa    780

gaatgcaacc atgatgaaat agtagctgaa tttaagaaac aaggcggata tttcatgaca    840

gctgaagaaa ctgcaaaagt ttgcagcgta ctttttaaac ctggtacaca cagcatgagt    900

gctaagtttg taggaagagc tcctcaggtt atagcagaag ctgcaggttt cacagttcca    960

gaaggaacaa aagtattaat aggagaacaa ggcggagttg gtaatggtta ccctctatct   1020

tatgagaaac ttacaacagt acttgctttc tatacagtta aagattggca tgaagcatgt   1080

gagcttagta taagattact tcaaaatggt cttggacata caatgaacat tcatacaaat   1140

gatagagact tagtaatgaa gtttgctaaa aaaccagcat cccgtatctt agttaatact   1200

ggtggaagcc agggaggtac tggtgcaagc acaggattag cacctgcatt tacattaggt   1260

tgtggtacat ggggaggaag ctctgtttct gaaaatgtta ctccattaca tttaatcaat   1320

ataaagagag tagcatatgg tcttaaagat tgtactacat tagctgcaga cgatacaact   1380

ttcaatcatc ctgaactttg cggaagcaaa aatgacttag gattctgtgc tacaagccct   1440

gcagaatttg cagcaaagag caattgtgat agcactgctg cagatactac tgataatgat   1500

aaacttgcta gactcgtaag tgaattagta gctgcaatga agggagctaa ctaa          1554
```

<210> SEQ ID NO 26
<211> LENGTH: 1554
<212> TYPE: DNA
<213> ORGANISM: Clostridium ljungdahlii

<400> SEQUENCE: 26

```
ttggaaaatt ttgataaaga cttacgttct atacaagaag caagagatct tgcacgttta     60
ggaaaaattg cagcagacca aattgctgat tatactgaag aacaaattga taaaatccta    120
tgtaatatgg ttagggtagc agaagaaaat gcagtttgcc ttggtaaaat ggctgcagaa    180
gaaactggtt ttggaaaagc tgaagataag gcttataaga accatatggc tgctactaca    240
gtatataatt acatcaagga tatgaagact attggtgtta taaaagaaga taaaagtgaa    300
ggtgtaattg aatttgcaga accagttggt ttattaatgg gtattgtacc atctacaaat    360
ccaacatcta ctgttattta taaatcaatc attgcaatta aatcaagaaa tgcaattgta    420
ttctcaccac acccagctgc attaaaatgt tcaacaaaag caatagaact tatgcgtgat    480
gcagcagtag cagcaggagc tcctgcaaat gtaattggtg gtattgttac accatctata    540
caagctacaa atgaacttat gaaagctaaa gaagttgcta tgataattgc aactggaggc    600
cctggaatgg taaaggctgc atatagttca ggaacacctg caataggcgt tggtgctggt    660
aactctccat cctatattga aagaactgct gatgttcatc aatcagttaa agatataata    720
gctagtaaga gttttgacta tggtactatt tgtgcatccg agcagtctgt aattgcagaa    780
gaatgcaacc atgatgaaat agtagctgaa tttaagaaac aaggcggata tttcatgaca    840
gctgaagaaa ctgcaaaagt ttgcagcgta ctttttaaac ctggtacaca cagcatgagt    900
gctaagtttg taggaagagc tcctcaggtt atagcagaag ctgcaggttt cacagttcca    960
gaaggaacaa aagtattaat aggagaacaa ggcggagttg gtaatggtta ccctctatct   1020
tatgagaaac ttacaacagt acttgctttc tatacagtta aagattggca tgaagcatgt   1080
gagcttagta taagattact tcaaaatggt cttggacata caatgaacat tcatacaaat   1140
gatagagact tagtaatgaa gtttgctaaa aaaccagcat cccgtatctt agttaatact   1200
ggtggaagcc agggaggtac tggtgcaagc acaggattag cacctgcatt tacattaggt   1260
tgtggtacat ggggaggaag ctctgtttct gaaaatgtta ctccattaca tttaatcaat   1320
ataaagagag tagcatatgg tcttaaagat tgtactacat tagctgcaga cgatacaact   1380
ttcaatcatc ctgaactttg cggaagcaaa aatgacttag gattctgtgc tacaagccct   1440
gcagaatttg cagcaaagag caattgtgat agcactgctg cagatactac tgataatgat   1500
aaacttgcta gactcgtaag tgaattagta gctgcaatga agggagctaa ctaa         1554
```

<210> SEQ ID NO 27
<211> LENGTH: 1473
<212> TYPE: DNA
<213> ORGANISM: Clostridium coskatii

<400> SEQUENCE: 27

```
atggaaaata tggataggga tttgcaatct atacaagatg taagacggct tgttcaaaaa     60
gcaagacaag ctcaacagga atattgtaaa ttcagtcagg aaaagatgaa taaaattatt    120
gagcatgtag cagaatccgc tggtttacaa gctgaaagac tagcaaaact tgctgtagaa    180
gaaacaactt ttggaaattt acccgataag ataattaaaa acaaatttgc tagtgaaata    240
gtgtatgaaa atataaaaga catgaagtta gtaggcattt taagagatga caaagataga    300
```

```
aaaatattag agataggttc acctgtaggt attattgcag gacttgtacc atcaactaat    360

cctacttcta ccgttatata caaaagtctt atagctttaa aatcaggaaa tgcaattgta    420

tttagtcctc atcctaaggc aagacattgc attgcagaag ctataaaagt tgtaagtgat    480

gcagctgttg aggcaggagc acccttagga atggtttccg gaatgagcat acttactatg    540

gaaggaactc atgagcttat gaaaaacgtt gatctcatac tagcaacagg tggatcagct    600

atggtaaagg cagcatacag ttcaggaact cctgctatag gagttggacc tggaaatgga    660

cctgctttta ttgaaaaaac agcaaatata aagcttgcag taaaaagaat aatggatagt    720

aaaacttttg acaatggggt aatatgtgct tcagaacagt ccatagtagt tgaaaagtgt    780

ataaaagatg aagttgtaga tgagcttaaa cgtcaaggag catacttctt atctaaagaa    840

caatccgaaa aagtagcaaa gtttatattg agagcaaatg gtactatgaa tcctcaaatt    900

gtgggaaaat cagctcagaa aatagctgaa atggcagata taactgtaga tccaaatgca    960

agaatattga tttcagagca gacaacagtt ggaaaagata acccattttc aagggaaaag   1020

cttacaacaa ttttagcatt ctactgtgaa gaaaattggg aaaaagcttg cgagagatgt   1080

attgagcttt taaataatga aggtatagga catactctca taatacattc aaacaatgaa   1140

gaaatagtaa aagaatttgg gcttaaaaaa cctgtatcca gaatacttgt aaacacgccg   1200

ggatcacttg gaggaatagg agctactaca aatttagtgc ctgcacttac acttggatgc   1260

ggagcagttg gaggaagtgc aacttctgat aatgtagggc caaggaatct tataaatata   1320

agaagagttg cctatggagt aaaggaaata gaagatataa aaaattttgt aagtaattgt   1380

aatgacagag aaacctcaca tactgtttta gatatttctg atcagtacgt tgaacttata   1440

actaaaaaaa tagctgaaaa gcttagtttg taa                                1473
```

<210> SEQ ID NO 28
<211> LENGTH: 1554
<212> TYPE: DNA
<213> ORGANISM: Clostridium ragsdalei

<400> SEQUENCE: 28

```
ttggaaaatt ttgataaaga cttacgctct atacaagaag caagagatct tgcacgttta     60

ggaaaaattg cagcatgtga aattgctgat tatactgaag aacaaattga taaaatccta    120

tgtaatatgg ttagggtagc agaggaaaat gcagtttgcc ttggtaaaat ggctgcagaa    180

gaaactggtt ttggaaaagc tgaagataag gcttataaga accatatggc tgctactaca    240

gtatataatt atatcaagga tatgaagact attggtgtta taaaagaaga taaaagtcaa    300

ggtgtaattg aatttgctga accagttggt ttattaatgg gtattgtacc atctacaaat    360

ccaacatcta ctgttatcta taaatcaatc attgcaatta aatcaagaaa tgcaattgta    420

ttctcaccac acccagctgc attaaaatgt tcaacaaaag caatagaact tatgcgtgat    480

gcagcagtag cagcaggagc tcctgcaaat gtaattggcg gtattgttac accatctata    540

caagctacaa atgaacttat gaaagctaaa gaagttgcta tgataattgc cactggaggc    600

cctggaatgg taaaggctgc ttatagttca ggaacacctg caataggcgt tggtgctggt    660

aactctccat cttatataga aagaactgct gatgttcatc aatcagttaa agatataatt    720

gctagtaaga gttttgacta tggtactatt tgtgcatctg agcaatcaat aattgttgaa    780

gaatgcaacc atgatgaagt aatagctgag ttgaagaaac aaggcggata tttcatgaca    840

gctgaagaaa ctgcaaaagt ttgcagtata ctttttaagc ctggtacaca cagtatgagt    900

gctaagtttg taggaagagc tcctcaggtt atagcagcag ctgcaggttt ctcagttcca    960
```

```
gaaggaacaa aagttttagt aggagaacaa ggcggagttg gtaatggtta ccctctatct   1020

tatgagaaac ttacaacagt acttgctttc tatacagtta aagattggca tgaagcatgt   1080

gatcttagta taagattact tcaaaatggt cttggacata ctatgaacat tcatacaaat   1140

gacagagact tagtaatgaa gtttgctaaa aaaccagcat cccgtatatt agttaatact   1200

ggtggaagcc aaggaggtac tggtgcaagc acaggattag cacctgcatt tacattaggt   1260

tgtggtacat ggggaggaag ctctgtttcc gaaaatgtta ctccattaca tttaatcaat   1320

ataaagagag ttgcatatgg tcttaaagat tgttctacat tagctgcaga tgatacaact   1380

ttcaatcatc ctgaactttg tggaagcaaa aatgacttag gatgctgtgc tacaagccct   1440

gcagaatttg cagcaaatag caattgtgct agcactgctg cggatactac tgataatgat   1500

aaacttgcta gactcgtaag tgaattagta gctgcaatga agggagctaa ctaa         1554
```

<210> SEQ ID NO 29
<211> LENGTH: 1518
<212> TYPE: DNA
<213> ORGANISM: Clostridium autoethanogenum

<400> SEQUENCE: 29

```
ttggaaaatt ttgataaaga cttacgttct atacaagaag caagagatct tgcacgttta     60

ggaaaaattg cagcagacca aattgctgat tatactgaag aacaaattga taaaatccta    120

tgtaatatgg ttagagtagc agaagaaaat gcagtttgcc ttggtaaaat ggctgcagaa    180

gaaactggtt ttggaaaagc tgaagataag gcttataaga accatatggc tgctactaca    240

gtatataatt acatcaagga tatgaagact attggtgtta taaaagaaga taaaagtgaa    300

ggtgtaattg aatttgcaga accagttggt ttattgatgg gtattgtacc atctacaaat    360

ccaacatcta ctgttattta taaatcaatc attgcaatta aatcaagaaa tgcaattgta    420

ttctcaccac acccagctgc attaaaatgt tcaacaaaag caatagaact tatgcgtgat    480

gcagcagtag cagcaggagc tcctgcaaat gtaattggtg gtattgttac accatctata    540

caagctacaa atgaacttat gaaagctaaa gaagttgcta tgataattgc aactggaggc    600

cctggaatgg taaaggctgc atatagttca ggaacacctg caataggcgt cggtgctggt    660

aactctccat cttatattga aagaactgct gatgttcatc aatcagttaa agatataatt    720

gctagtaaga gctttgacta tggtactatt tgtgcatccg agcaatctgt aattgctgaa    780

gaatgcaacc atgatgaaat agtagctgaa tttaagaaac aaggcggata tttcatgaca    840

gctgaagaaa ctgcaaaagt ttgcagcgta ctttttaaac ctggtacaca cagcatgagt    900

gctaagtttg taggaagagc tcctcaggtt atagcagaag ctgcaggttt cacagttcca    960

gaaggaacaa aagtattaat aggagaacaa ggcggagttg gtaatggtta ccctctatct   1020

tatgagaaac ttacaacagt acttgctttc tatacagtta aagattggca tgaagcatgt   1080

gagcttagta taagattact tcaaaatggt cttggacata ctatgaacat tcatacaaat   1140

gacagggact tagtaatgaa gtttgctaaa aaaccagcat cccgtatatt agttaatact   1200

ggtggaagcc agggaggtac tggtgcaagc acaggattag cacctgcatt tacattaggt   1260

tgtggtacat ggggaggaag ctctgtttcc gaaaatgtta ctccattaca tttaattaat   1320

ataaagagag tagcatatgg tcttaaagac tgtactacat tagctgcaga cgatacaact   1380

ttcaatcatt gtgctacaag ccctgcagaa tttgcagcaa agagcaattg tgctagcaat   1440

gctgcggata ctactgataa tgataaactt gctagactcg taagtgaatt agtagctgca   1500
```

atgaagggag ctaactaa 1518

<210> SEQ ID NO 30
<211> LENGTH: 1497
<212> TYPE: DNA
<213> ORGANISM: Clostridium autoethanogenum

<400> SEQUENCE: 30
atgaatatta ttgataatga tttgctctcc atccaagaat cccgaatcct tgtggaaaat 60
gctgcacgag cacaaaaaat gttagcaacc tttccacaag aaaagctaga tgagattgtt 120
gaacgtatgg cggaagaaat cggaaaacat acccgagagc ttgctgtaat gtcacaggat 180
gaaactggtt atggaaaatg gcaggataaa tgcatcaaaa accgatttgc ctgtgagtat 240
ttgccagcta agcttagagg aatgcgatgt gtaggtatta ttaatgaaaa tggtcaggat 300
aagaccatgg atgtaggtgt acctatgggt gtaattattg cattatgtcc tgcaactagt 360
ccggtttcta ctaccatata taaggcattg attgcaatta agtctggtaa tgcaattatc 420
ttttctccac atcctagagc aaaggagaca atttgtaagg cgcttgacat catgattcgt 480
gcagctgaag gatatgggct tccagaagga gctcttgcat acttacatac tgtgacgcct 540
agtggaacaa tcgaattgat gaaccatatt gcgacttctt tgattatgaa tacaggtgtt 600
cccgggatgc ttaaagcagc atataattct gggaaacctg ttatatatgg aggaactggt 660
aatggaccag catttattga acgtacagct gacatcaaac aggcggtaaa agatattatt 720
gctagtaaga cctttgataa cggaatagta ccatcagctg aacaatctat tgttgtagat 780
agctgtgttg catctgatgt taaacgtgag ttgcaaaata atggtgcata tttcatgaca 840
gaggaggaag cacaaaaact aggttctctc tttttccgtt ctgatggcag tatggattca 900
gaaatggttg gcaaatccgc acaaagattg gctaaaaaag caggtttcag cattcctgaa 960
agtagcacag tgctaatttc agagcagaaa tatgtttctc aagataatcc ttattccaag 1020
gagaaacttt gtccggtact agcttactac attgaagatg attggatgca tgcatgtgaa 1080
aagtgtattg aactgctgtt aagtgagaga catggtcaca ctcttgttat acattcaaaa 1140
gacgaagatg taattcgcca gtttgcatta aaaaaacctg taggtaggat acttgttaat 1200
acgcctgctt cctttggtag tatgggtgct acaagtaatt tatttcctgc tttaacttta 1260
ggtagtggat cggcaggtaa aggtattacc tccgataatg tttcaccaat gaatcttatt 1320
tacgtccgca aagtcggata tggcgtacgg aatgtagaag agattgtcaa tactaatgga 1380
ttgtttacag aagaaaaaag tgatttgaat ggaatgacaa aaaagtcaga ctataatcca 1440
gaggatatac aaatgttaca gcatatttta aaaaaagcta tggaaaaaat taaatag 1497

<210> SEQ ID NO 31
<211> LENGTH: 1497
<212> TYPE: DNA
<213> ORGANISM: Clostridium ljungdahlii

<400> SEQUENCE: 31
atgaatatta ttgataatga tttgctctcc atccaagaat cccgaatcct tgtggaaaat 60
gctgcacgag cacaaaaaat gttagcaacc tttccacaag aaaagctaga tgagattgtt 120
gaacgtatgg cggaagaaat cggaaaacat acccgagagc ttgctgtaat gtcacaggat 180
gaaactggtt atggaaaatg gcaggataaa tgcatcaaaa accgatttgc ctgtgagtat 240
ttgccagcta agcttagagg aatgcgatgt gtaggtatta ttaatgaaaa tggtcaggat 300
aagaccatgg atgtaggtgt acctatgggt gtaattattg cattatgtcc tgcaactagt 360

```
ccggtttcta ctaccatata taaggcattg attgcaatta agtctggtaa tgcaattatc    420
ttttctccac atcctagagc aaaggagaca atttgtaagg cgcttgacat catgattcgt    480
gcagctgaag gatatgggct tccagaagga gctcttgcat acttacatac tgtgacgcct    540
agtggaacaa tcgaattgat gaaccatatt gcgacttctt tgattatgaa tacaggtgtt    600
cccgggatgc ttaaagcagc atataattct gggaaacctg ttatatatgg aggaactggt    660
aatggaccag catttattga acgtacagct gacatcaaac aggcggtaaa agatattatt    720
gctagtaaga cctttgataa cggaatagta ccatcagctg aacaatctat tgttgtagat    780
agctgtgttg catctgatgt taaacgtgag ttgcaaaata atggtgcata tttcatgaca    840
gaggaggaag cacaaaaact aggttctctc tttttccgtt ctgatggcag tatggattca    900
gaaatggttg gcaaatccgc acaaagattg gctaaaaaag caggtttcag cattcctgaa    960
agtagcacag tgctaatttc agagcagaaa tatgtttctc aagataatcc ttattccaag   1020
gagaaacttt gtccggtact agcttactac attgaagatg attggatgca tgcatgtgaa   1080
aagtgtattg aactgctgtt aagtgagaga catggtcaca ctcttgttat acattcaaaa   1140
gacgaagatg taattcgcca gtttgcatta aaaaaacctg taggtaggat acttgttaat   1200
acgcctgctt cctttggtag tatgggtgct acaagtaatt tatttcctgc tttaacttta   1260
ggtagtggat cggcaggtaa aggtattacc tccgataatg tttcaccaat gaatcttatt   1320
tacgtccgca aagtcggata tggcgtacgg aatgtagaag agattgtcaa tactaatgga   1380
ttgtttacag aagaaaaaag tgatttgaat ggaatgacaa aaaagtcaga ctataatcca   1440
gaggatatac aaatgttaca gcatatttta aaaaaagcta tggaaaaaat taaatag      1497
```

<210> SEQ ID NO 32
<211> LENGTH: 846
<212> TYPE: DNA
<213> ORGANISM: Clostridium autoethanogenum

<400> SEQUENCE: 32

```
atgcatttaa tgtttaaaca aaatggtaca gatttaaact caaatataga ggaagctgca     60
agttatataa gctctggaat aaaggtaaaa ccagagatag cacttatact tggatcgggt    120
cttgggcata tcgcagatga aattgaagac aaaaaaatat atccttatag tgaaatacca    180
aactttccta tttctacagt ggaaggtcat aaaagctgtc ttgttgtagg aaaacttcaa    240
ggtaaggtag tagctgcaat gcagggcaga tttcattatt atgaaggata ttcaatgaaa    300
gaagtgactt ttcctgttag agttatgaag atgttggaaa ttcaaaacct aatagtaact    360
aatgctgcag gaggaataaa taaaaattat aaaagtggag atctgatgct tataaaggat    420
cacataaatc tatcaggaca aaatccttta ataggacaga acttggaaaa atttggacct    480
agatttccag atatgtctga tgcatatgat agtcatctta gagaaatggt aaaaaaggtg    540
gcatatgaat tgcacatacc aattcaagaa ggagtatatg cttacatgag tgggccaagc    600
tatgaaacgc cagctgaaat aaagatgcta agtgtattag gaggggatgc agtgggaatg    660
tccacagttc ctgaggtgat tgtggcaaat cacagtggta tgagaactat tggaatatcc    720
tgcataacta atatggcagc agggatattg aaacaagccc taaatcatga agaagttata    780
aaaaattccc tctatgctag tgaaaagttt acgaaattga ttaaagcaat aatagaaaat    840
atatag                                                               846
```

<210> SEQ ID NO 33

<211> LENGTH: 846
<212> TYPE: DNA
<213> ORGANISM: Clostridium ljungdahlii

<400> SEQUENCE: 33

```
atgcatttaa tgtttaaaca aaatggtaca gatttaaact caaatataga ggaagctgca     60

agttatataa gctctggaat aaaggtaaaa ccagagatag cacttatact tggatcgggt    120

cttgggcata tcgcagatga aattgaagac aaaaaaatat atccttatag tgaaatacca    180

aactttccta tttctacagt ggaaggtcat aaaagctgtc ttgttgtagg aaaacttcaa    240

ggtaaggtag tagctgcaat gcagggcaga tttcattatt atgaaggata ttcaatgaaa    300

gaagtgactt ttcctgttag agttatgaag atgttggaaa ttcaaaacct aatagtaact    360

aatgctgcag gaggaataaa taaaaattat aaaagtggag atctgatgct tataaaggat    420

cacataaatc tatcaggaca aaatccttta ataggacaga acttggaaaa atttggacct    480

agatttccag atatgtctga tgcatatgat agtcatctta gagaaatggt aaaaaaggtg    540

gcatatgaat tgcacatacc aattcaagaa ggagtatatg cttacatgag tgggccaagc    600

tatgaaacgc cagctgaaat aaagatgcta agtgtattag gaggggatgc agtgggaatg    660

tccacagttc ctgaggtgat tgtggcaaat cacagtggta tgagaactat tggaatatcc    720

tgcataacta atatggcagc agggatattg aaacaagccc taaatcatga agaagttata    780

aaaaattccc tctatgctag tgaaaagttt acgaaattga ttaaagcaat aatagaaaat    840

atatag                                                               846
```

<210> SEQ ID NO 34
<211> LENGTH: 846
<212> TYPE: DNA
<213> ORGANISM: Clostridium coskatii

<400> SEQUENCE: 34

```
atgcatttaa tgtttaaaca aaatggtaca gatttaaact caaatataga ggaagctgca     60

agttatataa gctctggaat aaaggtaaaa ccagagatag cacttatact tggatcgggt    120

cttgggcata tcgcagatga aattgaagac aaaaaaatat atccttatag cgaaatacca    180

aactttccta tttctacagt ggaaggtcat aaaagctgtc ttgttgtagg aaaacttcaa    240

ggtaaggtag tagctgcaat gcagggcaga tttcattatt atgaaggata ttcaatgaaa    300

gaagtgactt ttcctgttag agttatgaag atgttggaaa ttcaaaacct aatagtaact    360

aatgctgcag gaggaataaa taaaaattat aaaagtggag atctgatgct tataaaggat    420

cacataaatc tatcaggaca aaatccttta ataggacaga atttggggaa atttggacct    480

agatttccag atatgtctga tgcatatgat agtcatctta gagaaatggt aaaaaaggtg    540

gcacatgaat tgcacatacc aattcaagaa ggagtatatg cttacatgag tgggccaagc    600

tatgaaacgc cagctgaaat aaagatgcta agtgtattag gaggggatgc agtgggaatg    660

tccacagttc ctgaggtgat tgtggcaaat cacagtggta tgagaactat tggaatatcc    720

tgcataacta atatggcagc agggatattg aaacaagccc taaatcatga agaagttata    780

aaaaattccc tctatgctag tgaaaagttt acgaaattga ttaaagcaat aatagaaaat    840

atatag                                                               846
```

<210> SEQ ID NO 35
<211> LENGTH: 846
<212> TYPE: DNA
<213> ORGANISM: Clostridium ragsdalei

<400> SEQUENCE: 35

```
atgcatttaa tgtttaaaca aaatggtacg gatttaaact caaatataga ggaagctgca     60
agttatataa gctctggtat aaaggtaaag ccagggatag cacttatact tggatcgggt    120
cttggacata ttgcagatga aattgaagac aaaaaaattt atccttatag tgaaatacca    180
aactttccta tttctacagt ggaaggtcat aaaagctgtc ttgttatagg aaagcttcaa    240
ggtaaggtag tagctgcaat gcagggcaga tttcattatt atgaaggata ttcaatgaaa    300
gaagtgactt ttcctattag agttatgaaa atgttgggaa ttcacaatct aatagtaact    360
aatgctgcag gggggaataaa taaaagttat aaaagtggag atctgatgct tataagggat    420
catctaaatc tatcaggaca aaatccttta ataggacaga attttgagaa atttggacct    480
aggtttccag atatgtctga tgcatatgat agtcatctta gagaaatggt aaaaaaggtg    540
gcaggtgaat tgcacatatc tattaaagaa ggagtatatg cttacatgag tgggccaagc    600
tatgaaacgc cagctgaaat aaaaatgtta agtgtattag gaggggatgc agtgggaatg    660
tccacagttc ctgaggtgat tgtggcaaat cacagtgata tgagaactat tggaatatct    720
tgcataacta atatggcagc aggaatattg aaacaaccct taaatcatga agaagttata    780
aaaaattccc tctatgcaag tgaaaaattt acaagactga ttaaagcagt aataggaagt    840
atatag                                                               846
```

<210> SEQ ID NO 36
<211> LENGTH: 375
<212> TYPE: DNA
<213> ORGANISM: Clostridium autoethanogenum

<400> SEQUENCE: 36

```
atgaatttcc caaaagaatt aaagtatagc aaagaacaca catgggcaaa gattgaagga     60
gacacagcac ttataggcat aagtgatttt gcacaggatc aacttggaga gatattattt    120
gtagaaatgc cagatgtagg agatgaaatt actcaaggag tttctcttgg agttgttgaa    180
tcatccaaaa aggcttcaga tgtaatatct ccattatctg gagaagtgct cgaaattaac    240
gaaaaactag atgatgaacc agaatatata aatgagaatg cttatgatgc atggatagta    300
aaaataaaag taaaagacag tggagaagtt aaaagcttag tagatgcttc tgaatacgaa    360
gcaggtttga aataa                                                     375
```

<210> SEQ ID NO 37
<211> LENGTH: 1383
<212> TYPE: DNA
<213> ORGANISM: Clostridium autoethanogenum

<400> SEQUENCE: 37

```
atgaaattag ttgtaattgg tggaggacca ggaggatatg tagctgcact gcaagctgca     60
attttaggag cagatgttac tgtagttgag aagaaagctg taggaggaac ttgcttaaat    120
gtaggatgta tacctacaaa agcactgctt gcttccacag atgttttaag cgtaataaaa    180
ggagcatcaa aatttggaat taatgttgaa ggtgaagcaa aacctgattt tgatgcaatt    240
atgaagagaa aagataaagt agtagatcaa cttgtaaaag gcatagaata tatgtttgaa    300
catagagggg taaagcttat aaggggaaca ggaaaactta taagcaataa agaggtagag    360
gttacaaagc aggatggatc taaagaatcc ataacggcag ataaaattat acttgctact    420
ggttctgtac ctgttacacc tggagtattc aagtatgatg gtaaaaaggt tataacttca    480
```

```
gatgaagttt tgaatttaga aaaacttcca aagtcaatga tattagttgg tggaggtcct    540

ataggctgtg aaataggata tttcctaaat agtatgggag tagaagttaa ggtagttgaa    600

gctcttccac atcttgcacc acttgaagat gaagatgttg caaaacaact tcagagaatt    660

ttcaaacaaa ataagattaa atattttgta ggtgatggta taactagtgt agaagttaaa    720

ggtgatacgg taactgctac attgggaagc ggaaaagttt tagaggctga aacacttctc    780

atagcagttg gaagaagagc ttatgctgaa ggtttaggtt tggatgatat aggtattaaa    840

aaagatcaaa aaggaagaat aattgtaaat gaatatttag aaactaatgt agagggagtt    900

tatgcaatag gtgatttaat tcctactgct gctcttgcac atgtagctga aagagaaggt    960

attgtagctg ttcaaaatgc agttttagat aaaaagaaga agatgagtta caaagcagta   1020

cctggttgta catttgtaga accagaaata gcttctgtag gtatgaaaga gaaagatgct   1080

gaaaaagcag gaatccagta caaggttgga aaatttgact ttagggggct tggaaaagct   1140

caagctatgg gtaaattaca aggatttgta aagattatta cagacgaaaa ggacgtaata   1200

attggagctg ctattgtagg tgatagagca acagatatga tttcagaact aggtgttgct   1260

tgtgagcttg gtttaacagc agaacgagtt ggtgaagtta ttcatccaca tccaacttta   1320

tctgaggcaa tgatggaagc tcttcatgat gtacacaaac aatgtgttca ttctgttgat   1380

taa                                                                 1383
```

<210> SEQ ID NO 38
<211> LENGTH: 1383
<212> TYPE: DNA
<213> ORGANISM: Clostridium ljungdahlii

<400> SEQUENCE: 38

```
atgaaattag ttgtaattgg tggaggacca ggaggatatg tagctgcact gcaagctgca     60

attttaggag cagatgttac tgtagttgag aagaaagctg taggaggaac ttgcttaaat    120

gtaggatgta tacctacaaa agcattactt gcttccacag atgttttaag cgtaataaaa    180

ggagcatcaa aatttggaat taatgttgaa ggtgaagcaa aacctgattt tgatgcaatt    240

atgaagagaa aagataaagt agtagatcaa cttgtaaaag gcatagaata tatgtttgaa    300

catagagggg taaagcttat aaggggaaca ggaaaactta taagcaataa agaggtagag    360

gttacaaagc aggatggatc taaagaatcc ataacggcag ataaaattat acttgctact    420

ggttctgtac ctgttacacc tggagtattc aagtatgatg gtaaaaaggt tataacttca    480

gatgaagttt tgaatttaga gaaacttcca aagtcaatga tactagttgg tggaggtcct    540

ataggatgtg aaataggatt cttcctgaat agtatgggag tagaagttaa ggtagttgaa    600

gctcttccac atcttgcacc acttgaagat gaagatgttg caaaacaact tcagagaatt    660

ttcaaacagc ataagattaa atactttgta ggtgatggta taactagtgt agaagttaaa    720

ggtgatacgg taactgctac attgggaagc ggaaaagttt tagaggctga aacacttctt    780

atagcagttg gaagaagagc ttatgctgaa ggtttaggtt tggatgatat aggtattgaa    840

aaagatcaaa aaggaagaat aattgtaaat gaatatttag aaactaatgt agagggagtt    900

tatgcaatag gtgatttaat tcctactgct gctcttgcac atgtagctga aagagaaggt    960

attgtagctg ttcaaaatgc agttttagat aaaaagaaga agatgagtta caaagcagta   1020

cctggttgta catttgtaga accagaaata gcttctgtag gtatgaaaga aaaagatgct   1080

gaaaaagcag gaatccagta caaggttgga aaatttgact ttagaggact tggaaaagct   1140

caagctatgg gtaaattaca aggatttgta aagattatta cagacgaaaa ggacgtaata   1200
```

attggagctg ctattgtagg tgatagagca acagatatga tttcagaact aggtgttgct 1260
tgtgagcttg gtttaacagc agaacgagtt ggtgaagtta ttcatccaca tccaacttta 1320
tctgaggcaa tgatggaagc tcttcatgat gtacacaaac aatgtgttca ttctgttgat 1380
taa 1383

<210> SEQ ID NO 39
<211> LENGTH: 1383
<212> TYPE: DNA
<213> ORGANISM: Clostridium coskatii

<400> SEQUENCE: 39
atgaaattag ttgtaattgg tggaggacca ggaggatatg tagctgcatt gcaagctgca 60
attttaggag cagatgttac tgtagttgag aagaaagctg taggaggaac ttgcttaaat 120
gtaggatgta tacctacaaa agcactgctt gcttccacag atgttttaag tgtaataaaa 180
ggagcatcaa aatttggaat taatgttgaa ggtgaagcaa aacctgattt tgatgcaatt 240
atgaagagaa aagataaagt agtagatcaa cttgtaaaag gtatagaata tatgtttgaa 300
catagagggg taaagcttat aaggggaaca ggaaaactta taagcaataa agaggtagag 360
gttacaaagc aggatggatc taaagaatcc ataacggcag ataaaattat acttgctact 420
ggttctgtac ctgttacacc tggagtattc aagtatgatg gtaaaaaggt tataacttca 480
gatgaagttt tgaatttaga gaaacttcca aagtcaatga tactagttgg tggaggtcct 540
ataggatgtg aaataggatt cttcttaaat agtatgggag tagaagttaa ggtagttgaa 600
gctcttccgc atcttgcacc acttgaagat gaagatgttg caaaacaact tcagagaatt 660
ttcaaacaaa ataagattaa atactttgtt ggtgatggta taactagtgt agaagttaaa 720
ggtgatacgg taactgctac attgggaagc ggaaaagttt tggaagctga aacacttctc 780
atagcagttg gaagaagagc ttatgctgaa ggtttaggtt tggatgatat aggtattgaa 840
aaagatcaaa aaggaagaat aattgtaaat gaatatttag aaactaatgt agagggagtt 900
tatgcaatag gtgatttaat tcctactgct gctcttgcac atgtagctga aagagaaggt 960
attgtagctg ttcaaaatgc agttttagat aaaaagaaga agatgagtta caaagcagta 1020
cctggttgta cgtttgtaga accagaaata gcttctgtag gtatgaaaga gaaagatgct 1080
gaaaaagcag gaatccagta caaggttgga aaatttgact ttagggggct tggaaaagct 1140
caagctatgg gtaaattaca aggatttgta aagattatta cagacgaaaa ggacgtaata 1200
attggagctg ctattgtagg tgatagagca acagatatga tttctgaact aggtgttgct 1260
tgtgagcttg gtttaacagc agaacgagtt ggtgaagtta ttcatccaca tccaacttta 1320
tctgaggcaa tgatggaagc tcttcatgat gtacacaaac aatgtgttca ttctgttgat 1380
taa 1383

<210> SEQ ID NO 40
<211> LENGTH: 1383
<212> TYPE: DNA
<213> ORGANISM: Clostridium ragsdalei

<400> SEQUENCE: 40
atgaaattag ttgtaattgg tggaggacca ggaggatatg tagctgcact gcaagctgca 60
attttaggag cagatgttac tgtagttgag aagaaagctg taggaggaac ttgcttaaat 120
gtaggatgta tacctacaaa agcactgctt gcttccacag atgttttaag tgtaataaaa 180
ggagcatcaa aatttggaat taatgttgaa ggtgaagtaa aacctgattt tgatgcaatt 240
atgaagagaa aagataaagt agtagatcaa cttgtaaaag gcatagaata tatgtttgaa 300
catagagggg taaagcttat aaggggaaca ggaaaactta taagcaataa agaggtagag 360
gttacaaagc aggatggatc taaagaatcc ataacggcag ataaaattat acttgctact 420
ggttctgtac ctgttacacc tggagtattc aagtatgatg gtaaaaaggt tataacttca 480
gatgaagttt tgaatttaga gaaacttcca aagtcaatga tactagttgg tggaggtcct 540
ataggatgtg aaataggatt cttcttaaat agtatgggag tagaagttaa ggtagttgaa 600
gctcttccac atcttgcacc acttgaagat gaagatgttg caaaacaact tcagagaatt 660
ttcaaacagc ataagattaa atactttgta ggcgatggta taactagtgt agaagttaaa 720
ggtgatacgg taactgctac attgggaagc ggaaaagttt tagaggctga aacacttctc 780
atagcagttg gaagaagagc ttatgctgaa ggtttaggtt tggatgatat tggtattaag 840
aaagatcaaa aaggaagaat aattgtaaat gaatatttag aaactaatgt agagggagtt 900
tatgcaatag gtgatttaat tcctactgct gctcttgcac atgtagctga aagagaaggt 960
attgtagctg ttcaaaatgc agttttagat aaaaagaaga agatgagtta caaagcagta 1020
cctggttgta catttgtaga accagaaata gcttctgtag gtatgaaaga gaaagatgct 1080
gaaaaagcag gaatccagta caaggttgga aaatttgact ttaggggggct tggaaaagct 1140 caagctatgg gtaaattaca aggatttgta aagattatta cagacgaaaa ggacgtaata 1200
attggagctg ctattgtagg tgatagagca acagatatga tttcagaatt aggtgttgct 1260
tgtgagcttg gtttaacagc agaacgagtt ggtgaagtta ttcatccaca tccgacttta 1320
tctgaggcaa tgatggaagc tcttcatgat gtacacaaac aatgtgttca ttctgttgat 1380
taa 1383

<210> SEQ ID NO 41
<211> LENGTH: 1398
<212> TYPE: DNA
<213> ORGANISM: Clostridium autoethanogenum

<400> SEQUENCE: 41
gtgaacttta gagtagaaaa agatttactt ggagaaaagg aagttgaagc ctcttcctat 60
tttggtatta atactgaaag agctttagaa aattttaatt tacagaacaa aactattaat 120
ttaaatttag ttaaagaaat tgcactcata aaaaaagcag ctgccctagt caataaagat 180
ttaggagaac ttaaaattga aaaagccgat gccataatta aagctagtga agaagttatc 240
ggcggcaaat ttgacaatca atttaagtta agtgcatttc aaggtggagc cggcacatcc 300
acaaatatga atgtaaatga agtcatagca aatagagcta tagaaatact tggcggcgaa 360
aagggaaact attcattagt acatccttta aatgatgtta atatgtctca atccacaaat 420
gacgtttatc ctactgctct tagaatcgca gctatacgac gcataagaaa actaagcagt 480
tgcctgtccg atcttcagga agaacttcaa gttaaagaaa acgatttttc agatatattg 540
aaattaggta gaactcagct aatggatgcg cttcccatga tggtaggaca aggttttggg 600
gcttacgcca aagcaatcgc tcgagataga tggagaatat ataaagtaga agaaagactc 660
agggaaatca acataggcgg taccgctata ggtacaggcc ttaatgcaac taataaattt 720
atatataaga taaccgatgt acttcaagac ttaaccggtc ttggaattgc ccgttccgat 780
tatcctatgg atgttactca aaattgcgat gtatttgttg aggtctcagg acttttaaag 840
tccctagcct gcaacctttt aaaaatctca aatgatttaa ggcttttaaa ttcaggacct 900

```
tttggaggaa taggagaaat cattcttcca aaggtacaag caggttctac tattatgcca    960
ggaaaagtaa atccagtcat agctgaaatg gtggcacaag taagtatgag agtaatatca   1020
aacgacacag caattactat ggccagcagt tcaggtcaat tggagttaaa tgcattcact   1080
cctctcattg cagaatgtct acttgaatct ctagaacttt tagaaagaac agttacacta   1140
tttagagaaa agtgcattaa cggaatcaaa gtaaatgaag aaaattgtaa aaaaaatctt   1200
gaaaattcca cagcactggt aactgcatta gtacattaca taggttatga taaagctagt   1260
gagcttgcaa agaaagcctt aaaaaatcat aaaactataa gagaaattct atatgaagaa   1320
aaaatactgc ctaaggaaaa aatagatgaa ataataaatc catatcagct gacaaaacca   1380
ggtatacctg gcaaataa                                                 1398
```

<210> SEQ ID NO 42
<211> LENGTH: 1398
<212> TYPE: DNA
<213> ORGANISM: Clostridium ljungdahlii

<400> SEQUENCE: 42

```
gtgaacttta gagtagaaaa agatttactt ggagaaaagg aagttgaagc ctcttcctat     60
tttggtatta atactgaaag agctttagaa aattttaatt tacagaacaa aactattaat    120
ttaaatttag ttaaagaaat tgcactcata aaaaaagcag ctgccctagt caataaagat    180
ttaggagaac ttaaaattga aaaagccgat gccataatta aagctagtga agaagttatc    240
ggcggcaaat ttgacaatca atttaagtta agtgcatttc aaggtggagc cggcacatcc    300
acaaatatga atgtaaatga agtcatagca aatagagcta tagaaatact tggcggcgaa    360
aagggaaact attcattagt acatccttta aatgatgtta atatgtctca atccacaaat    420
gacgtttatc ctactgctct tagaatcgca gctatacgac gcataagaaa actaagcagt    480
tgcctgtccg atcttcagga agaacttcaa gttaaagaaa acgatttttc agatatattg    540
aaattaggta gaactcagct aatggatgcg cttcccatga tggtaggaca aggttttggg    600
gcttacgcca aagcaatcgc tcgagataga tggagaaatat ataaagtaga agaaagactc   660
agggaaatca acataggcgg taccgctata ggtacaggcc ttaatgcaac taataaattt    720
atatataaga taaccgatgt acttcaagac ttaaccggtc ttggaattgc ccgttccgat    780
tatcctatgg atgttactca aaattgcgat gtatttgttg aggtctcagg acttttaaag    840
tccctagcct gcaacctttt aaaaatctca aatgatttaa ggcttttaaa ttcaggacct    900
tttggaggaa taggagaaat cattcttcca aaggtacaag caggttctac tattatgcca    960
ggaaaagtaa atccagtcat agctgaaatg gtggcacaag taagtatgag agtaatatca   1020
aacgacacag caattactat ggccagcagt tcaggtcaat tggagttaaa tgcattcact   1080
cctctcattg cagaatgtct acttgaatct ctagaacttt tagaaagaac agttacacta   1140
tttagagaaa agtgcattaa cggaatcaaa gtaaatgaag aaaattgtaa aaaaaatctt   1200
gaaaattcca cagcactggt aactgcatta gtacattaca taggttatga taaagctagt   1260
gagcttgcaa agaaagcctt aaaaaatcat aaaactataa gagaaattct atatgaagaa   1320
aaaatactgc ctaaggaaaa aatagatgaa ataataaatc catatcagct gacaaaacca   1380
ggtatacctg gcaaataa                                                 1398
```

<210> SEQ ID NO 43
<211> LENGTH: 1398
<212> TYPE: DNA

<213> ORGANISM: Clostridium coskatii

<400> SEQUENCE: 43

```
gtgaacttta gagtagaaaa agatttactt ggagaaaagg aagttgaagc ctcttcctat      60
tttggtatta atactgaaag agctttagaa aattttaatt tacagaacaa aactattaat     120
ttaaatttag ttaaagaaat tgcactcata aaaaaagcag ctgccctagt caataaagat     180
ttaggagaac ttaaaattga aaaagccgat gccataatta aagctagtga agaagttatc     240
ggcggcaaat ttgacaatca atttaagtta agtgcatttc aaggtggagc cggcacatcc     300
acaaatatga atgtaaatga agtcatagca aatagagcta tagaaatact tggcggcgaa     360
aagggaaact attcattagt acatccttta aatgatgtta atatgtctca atccacaaat     420
gacgtttatc ctactgctct tagaatcgca gctatacgac gcataagaaa actaagcagt     480
tgcctgtccg atcttcagga agaacttcaa gttaaagaaa acgatttttc agatatattg     540
aaattaggta gaactcagct aatggatgcg cttcccatga tggtaggaca aggttttggg     600
gcttacgcca aagcaatcgc tcgagataga tggagaaatat ataaagtaga agaaagactc     660
agggaaatca acataggcgg taccgctata ggtacaggcc ttaatgcaac taataaattt     720
atatataaga taaccgatgt acttcaagac ttaaccggtc ttggaattgc ccgttccgat     780
tatcctatgg atgttactca aaattgcgat gtatttgttg aggtctcagg acttttaaag     840
tccctagcct gcaacctttt aaaaatctca aatgatttaa ggcttttaaa ttcaggacct     900
tttggaggaa taggagaaat cattcttcca aaggtacaag caggttctac tattatgcca     960
ggaaaagtaa atccagtcat agctgaaatg gtggcacaag taagtatgag agtaatatca    1020
aacgacacag caattactat ggccagcagt tcaggtcaat tggagttaaa tgcattcact    1080
cctctcattg cagaatgtct acttgaatct ctagaacttt tagaaagaac agttacacta    1140
tttagagaaa agtgcattaa cggaatcaaa gtaaatgaag aaaattgtaa aaaaaatctt    1200
gaaaattcca cagcactggt aactgcatta gtacattaca taggttatga taaagctagt    1260
gagcttgcaa agaaagcctt aaaaaatcat aaaactataa gagaaattct atatgaagaa    1320
aaaatactgc ctaaggaaaa aatagatgaa ataataaatc catatcagct gacaaaacca    1380
ggtatacctg gcaaataa                                                   1398
```

<210> SEQ ID NO 44
<211> LENGTH: 1398
<212> TYPE: DNA
<213> ORGANISM: Clostridium ragsdalei

<400> SEQUENCE: 44

```
gtgaacttta gagtagaaaa agatttactt ggagaaaagg aaattgaaac ctcttcctat      60
tttggtatta ataccgaaag agctttagaa aattttaatt tacagggcaa aaccgttaat     120
ttaaatttag ttaaagaaat tgcactcata aaaaaagcag ctgccctagt caataaagat     180
ttaagagaac ttaaaattga aaaagctgat gccataatta aagctagtga agaagttatc     240
ggtggcaaat ttgacgatca atttaagtta agtgcatttc aaggtggagc cggcacatcc     300
acaaatatga atgtaaatga agtcatagca aacagagcta tagagctact aggtggtaaa     360
aagggagatt actcattagt acatccttta aatgatgtaa atatgtctca atctacaaat     420
gatgtttatc ctactgctct tagaattgca gctatacgcc gcataagaaa gttaagcagt     480
tgtctgtctg atcttcagga agagcttcaa gttaaagaaa acgatttttc agatatattg     540
aaattaggta gaacccaact aatggatgcg cttcccatga tggtaggaca aggttttggt     600
```

```
gcttacgcca aagcaatatc tcgagataga tggagaatat ataaagtaga agaaagactc    660

agggaaatca acataggcgg taccgctata ggtacaggtc ttaatgcaac taataaattt    720

atatataaga taacagatgt acttcaagac ttaaccggcc ttggaattgc ccgttccgat    780

tatcctatgg atgttactca aaattgtgat gtatttgttg aggtctcagg acttttaaag    840

tccctagcct gcaatctttt aaaaatttca aatgatttaa ggcttttaaa ttcgggaccc    900

cggggaggaa taggagaaat cattcttcca aaggtacaag caggttcaac catcatgccg    960

ggaaaagtca atccagtcat agctgaaatg gtagcacagg taagtatgag agtaatatca   1020

aacgacacag caattactat ggccagcagt tcaggtcaat tggagttaaa tgcattcact   1080

ccactcattg cagaatgtct acttgaatcc ctagaacttt tagaaagaac agttacacta   1140

tttagggaaa agtgcattag cggaatcaaa gtaaatgaag aaaattgtaa aaaaaatctt   1200

gaaaattcca cagcactggt aactgcatta gtacattaca taggttatga taaggctagt   1260

gagcttgcaa agaaagcctt gaaaaatcat aaaactataa gagaaattct atatgaagaa   1320

aaaatactgc ctaaggaaaa aatagatgaa ataataaatc catatcagct gacaaaacca   1380

ggtatacctg gcaaataa                                                 1398
```

```
<210> SEQ ID NO 45
<211> LENGTH: 1410
<212> TYPE: DNA
<213> ORGANISM: Clostridium autoethanogenum

<400> SEQUENCE: 45

atggatttta gaattgaaag tgattccatc ggttcaaagg aagtacctac agaggcttat     60

tatggagttc aaacattgag agcagctgaa aattttaata taacaggata taaattaaat    120

acagagcttg taaaaagcct tgttcaaata aaaaaggcag cagctatagc taattataaa    180

gcaggacttt taaatgaaaa cattgaaaaa gcaataattg aggctagtga taaaatactc    240

ggtggtaatt tgcaagatca attcatacta gaccctattc aaggtggagc tggtacctct    300

gcaaacatga atgcaaatga agtaatcgca aatgaagcta ttcagatttt aggaggtaaa    360

aaaggagact actcaattgt acatcctaat gaccatgtta atatgggaca atctacaaat    420

gatgtcttcc caactgcagg aaaaataact gctttaaaac ttcttttaaa agctatagaa    480

caactaaaga aattagatat gaatttagat ataaaagcaa aagaatttaa taatattata    540

aaaatgggaa gaactcagct tcaagatgcg gttcccatta gattaggaca agaatttaaa    600

gcttatagtt ccgttataaa acgagatatc tcaagacttg aagctgcaaa aaaagaatta    660

gaagtgttaa atttaggtgg tactgcaata ggtactggaa taaatgcaga taataaatat    720

atgaatacag tagtacctat actcagtgat attattggca tacaattaga acaagctgat    780

gatttgatag atgccacaca aaatttagat ggttttgtgt cagtatctgg tgctataaaa    840

acctgtgccg ttaatttatc taaaatggca aatgatttaa gacttatgtc atcaggtcca    900

agaactggtt tagaagaaat aaatcttcca ccaaaacaaa atggatcttc cataatgcca    960

ggaaaagtta atcctgtaat tccagaagta atgactcaag tggcctttaa tattatagga   1020

aatgatgtta caataacaat ggctgctgaa gctggccaac tggaattaaa tgcctttgaa   1080

ccagttatat tcttcaactt atttgaatcc atagaaaccc ttactaacgg tgtaaaaact   1140

tttacagaaa attgtatttc aggtataaca gcaaatacaa atagatgtaa gaagttagtg   1200

gataatagtg ttggcatagt tactgccatt acaccttatg ttggatacga aaaggctgcc   1260
```

```
tcaattgcaa aaagtgctat aaaaacagga aagccagtaa aagaaatcat acttcaaaat   1320

ggtattttaa aagaatctga attagatcgt atactagatc ctataagtat gactgaacct   1380

agggaattaa aaaaatatga atttgcttaa                                    1410
```

<210> SEQ ID NO 46
<211> LENGTH: 1410
<212> TYPE: DNA
<213> ORGANISM: Clostridium ljungdahlii

<400> SEQUENCE: 46

```
atggatttta gaattgaaag tgattccatc ggttcaaagg aagtacctac agaggcttat     60

tatggagttc agacattgag agcagctgaa aattttaata taactggata taaattaaat    120

acagagcttg taaaaagcct tgttcaaata aaaaaggcag cagctatagc taattataaa    180

gcaggtcttt taaatgaaaa cattgaaaaa gcaataattg aggctagtga taaaatactc    240

ggtggtgatt tgcaagatca attcatacta gaccctattc aaggtggagc tggtacctct    300

gcaaacatga atgcaaatga agtaattgca aatgaagcta ttcaaatttt aggtggaaaa    360

aaaggagact actcaattgt acatcctaat gaccatgtta atatgggaca atctacaaat    420

gatgtcttcc caactgcagg aaaaataact gctttaaaac ttcttttaaa agctatagaa    480

caactaaaga aattagatat gaatttagat atgaaagcaa aagaattcaa taatattata    540

aaaatgggaa gaactcagct tcaagatgca gttcccatta gattaggaca agaatttaaa    600

gcttatagtt ccgttataaa acgagatatc tcaagacttg aagccgcaaa aaaagaatta    660

gaagtattaa atttaggtgg tactgcaata ggtactggaa taaatgcaga taataaatat    720

atgaatacag tagtacctat actcagtgat attattggta tacaattaga acaagctgat    780

gatttgatag atgccacaca aaatttagat ggttttgtgt cagtatctgg tgctataaaa    840

acctgtgccg ttaacttatc caaaatggca aatgatttaa ggcttatgtc atcaggtcca    900

agaactggtt tagaagaaat aaatcttcca ccaaaacaaa acggatcttc cataatgccg    960

ggaaaagtta atcctgtaat tccagaagta atgactcaag tggcctttaa tattatagga   1020

aatgatgtta caataacaat ggctgctgaa gctggtcaac tggaattaaa tgcctttgag   1080

ccagttatat tcttcaactt atttgaatcc atagaaaccc ttactaacgg tgtaaaaact   1140

tttacagaaa attgtatttc aggtataaca gcaaatacaa atagatgtaa gaagttagtg   1200

gataatagtg ttggtatagt tactgccatt accccttatg ttggatacga aaaggctgcc   1260

tcaattgcaa aaagtgctat aaaaacagga aagccagtaa aagaaatcat acttcaaaat   1320

ggtattttaa aagaatctga attagatcgt atactagatc ctataagtat gactgaacct   1380

agggaattaa aaaaatatga atttgcttaa                                    1410
```

<210> SEQ ID NO 47
<211> LENGTH: 1410
<212> TYPE: DNA
<213> ORGANISM: Clostridium coskatii

<400> SEQUENCE: 47

```
atggatttta gaattgaaag tgattccatc ggttcaaagg aagtacctac agaggcttat     60

tatggagttc agacattgag agcagctgaa aattttaata taactggata taaattaaat    120

acagagcttg taaaaagcct tgttcaaata aaaaaggcag cagctatagc taattataaa    180

gcaggtcttt taaatgaaaa cattgaaaaa gcaataattg aggctagtga taaaatactc    240

ggtggtgatt tgcaagatca attcatacta gaccctattc aaggtggagc tggtacctct    300
```

```
gcaaacatga atgcaaatga agtaattgca aatgaagcta ttcaaatttt aggtgaaaaa    360
aaaggagact actcaattgt acatcctaat gaccatgtta atatgggaca atctacaaat    420
gatgtcttcc caactgcagg aaaaataact gctttaaaac ttcttttaaa agctatagaa    480
caactaaaga aattagatat gaatttagat atgaaagcaa aagaatttaa taatattata    540
aaaatgggaa gaactcagct tcaagatgca gttcccatta gattaggaca agaatttaaa    600
gcttatagtt ccgttataaa acgagatatc tcaagacttg aagccgcaaa aaaagaatta    660
gaagtattaa atttaggtgg tactgcaata ggtactggaa taaatgcaga taataaatat    720
atgaatacag tagtacctat actcagtgat attattggta tacaattaga acaagctgat    780
gatttgatag atgccacaca aaatttagat ggttttgtgt cagtatctgg tgctataaaa    840
acctgtgccg ttaacttatc caaaatggca aatgatttaa ggcttatgtc atcaggtcca    900
agaactggtt tagaagaaat aaatcttcca ccaaaacaaa acggatcttc cataatgccg    960
ggaaaagtta atcctgtaat tccagaagta atgactcaag tggcctttaa tattatagga   1020
aatgatgtta caataacaat ggctgctgaa gctggtcaac tggaattaaa tgcctttgag   1080
ccagttatat tcttcaactt atttgaatcc atagaaaccc ttactaacgg tgtaaaaact   1140
tttacagaaa attgtatttc aggtataaca gcaaatacaa atagatgtaa gaagttagtg   1200
gataatagtg ttggtatagt tactgccatt acccccttatg ttggatacga aaaggctgcc   1260
tcaattgcaa aaagtgctat aaaaacagga aagccagtaa aagaaatcat acttcaaaat   1320
ggtattttaa aagaatctga attagatcgt atactagatc ctataagtat gactgaacct   1380
agggaattaa aaaaatatga atttgcttaa                                    1410
```

<210> SEQ ID NO 48
<211> LENGTH: 1410
<212> TYPE: DNA
<213> ORGANISM: Clostridium ragsdalei

<400> SEQUENCE: 48

```
atggatttta gaattgaaag tgattccatc ggttcaaagg aagtacctac agaggcttat     60
tatggagttc aaacattgag agcagctgaa aattttaata taacaggata taaattaaat    120
acagagcttg taaaaagcct tgttcaaata aaaaaggcag cagctatagc taattataaa    180
gcaggtcttt taaatgaaaa cattgaaaaa gcaataattg aggctagtga taaaatactc    240
ggaggtaatt tgcaagatca attcatacta gaccctattc aaggtggagc tggtacctct    300
gcaaacatga atgcaaatga agtaattgca aatgaagcta tccagctttt aggtggtaaa    360
aagggagact actcaattgt acatcctaat gatcacgtta atatgggaca atctacaaat    420
gatgtcttcc caactgcagg aaaaataact gctttaaaac ttcttttaaa agctatagaa    480
caactaaaga aattagatat gaaattggaa ataaaagcaa aagaattcaa taatattata    540
aaaatgggaa gaactcagct tcaagatgca gttcccatta gattaggaca agaatttaag    600
gcttatagtt ccgttataaa acgagacatt tcaagacttg aagccgcaaa aaaagaatta    660
gaagtattaa atttaggtgg tactgcaata ggtactggaa taaacgcaga taatagatat    720
atgaatacag tcgtacctat actcagtgat attattggtg tacaattaga acaagctgat    780
gatttgatag atgccacaca aaatttggat ggttttgtgt cagtatctgg cgccataaaa    840
acctgtgccg ttaacttatc caaaatggca aatgatttaa gacttatgtc atcaggtcca    900
agaacaggtt tagaagaaat aaatcttcca ccaaaacaaa acggatcttc cataatgcca    960
```

```
ggaaaagtta atcctgtaat tccagaagta atgactcaag tagcctttaa tattatagga   1020

aatgatgtta caataacaat ggctgctgaa gctggtcaac tggaattaaa tgcatttgaa   1080

ccagttatat tctttaactt atttgaatcc atagaaactc ttactaacgg tgtaaaaact   1140

tttacagaaa attgtatttc aggtataaca gcaaatacaa atagatgtaa gaagttagtg   1200

gataatagtg ttggcatagt tactgccatt acaccttatg ttggatatga aaaggctgcc   1260

tcaattgcaa aaagtgctat aaaaacagga aagccagtaa aagagatcat acttcaaaat   1320

ggtattttaa aagaatctga attagatcgt atactagatc ctataagtat gactgaacct   1380

agggaattaa aaaaatatga atttgcttaa                                     1410
```

```
<210> SEQ ID NO 49
<211> LENGTH: 1215
<212> TYPE: DNA
<213> ORGANISM: Clostridium autoethanogenum

<400> SEQUENCE: 49

atgtgtaaat taaatgataa ttatttaaaa ttgcagggaa gatatttgtt tgcaagtata     60

gcaaaaaagg tagctaactt taaaaaaaat aatccgcata agaaagttat ttcgcttggt    120

attggtgatg taactcagcc attagcacca gttattatag aggcactgca tagttcagtt    180

gatgaaatgg gacataagga tacttttaaa ggatatgcac cggaatttgg ttatgaattt    240

ttaaaaaatg caattataaa aggtgattat aactcccgtg gtgtggacat ttcaatagat    300

gaagtgttta taaatgatgg aataaatgct gatgctggta atattcaaga actatttagt    360

gtagataata agattgcagt ttgtgatcct gtatatcctg tatatgtaga ttcaaatgta    420

atggctggaa ggacaggaac atatgataag gatgcacaaa ggtggagtga agttatatat    480

atgtcctgta ctccggataa taattttgtg ccggatattc cagaagaaaa cccagatatt    540

atatatctat gttttccaaa caatccaaca gggacaacgg ttacaaaaga tcaacttcaa    600

cttttggttg attatgcaaa taaagtggaa gctgttattg tatatgatgg tgcttatgaa    660

gcatatattt cagaagataa tgtatgtcat acaatttatg aatgtgatgg tgcaaaaaat    720

tgtgctgttg agcttaaaag tttttcgaag aaggctggat ttacaggatt aaggcttggg    780

tatacaattg ttccgaagga actaaaatgt tctggagttt ctttgaatag actttgggca    840

agacgttatg gaaccaaata caatggtaca ccatatatag ttcagagggc aggagaagcc    900

gtttattctg aaactggaaa agagcagata aaaaagcaaa ttgattatta taaaaataat    960

gccaaaatca ttttggaagg attgaaatca gcaggctact ctgtgtatgg aggagtgaat   1020

gcaccatatg tatggctaaa gacaccgaac aatatgaatt catgggattt cttttattac   1080

ttattagaaa aagcaaatat tgtaggtacg cctggaagtg gatttggacc gatgggggaa   1140

ggatatttta ggcttacagc ttttggaact tacgaaaata cattggaggc tgttgagagg   1200

attaagaaac tctaa                                                    1215
```

```
<210> SEQ ID NO 50
<211> LENGTH: 1215
<212> TYPE: DNA
<213> ORGANISM: Clostridium ljungdahlii

<400> SEQUENCE: 50

atgtgtaaat taaatgataa ttatttaaaa ttgcaaggaa gatatttgtt tgcaagtata     60

gcaaaaaagg taactaattt taaaaaaagt aatccgcata agaaaattat ttcacttggt    120

attggtgatg taactcagcc attagcacca gttattatag aggcactgca tagttcagtt    180
```

```
gatgaaatgg gacataagga tacttttaaa ggatatgcac cggaatttgg ttatgaattt    240
ttaaaaaatg caattataaa aggtgattat aactcccgtg gtgtggacat ttcaatagat    300
gaagtgttta taaatgatgg aataaatgct gatgctggta atattcaaga actatttagt    360
gtagataata agattgcagt ttgtgaccct gtatatcctg tatatgtaga ttcaaatgta    420
atggctggaa ggacaggaac atatgataag gatgcacaaa ggtggagtga agttatatat    480
atgtcctgta ctccggataa taattttgtg ccggatattc cagaagaaaa cccagatatt    540
atatatctat gttttccaaa taatccaaca gggacaacgg ttacaaaaga tcagcttcaa    600
cttttggttg attatgcaaa taaagtggaa gctgttattg tatatgatgg tgcttatgaa    660
gcatacattt cagaagataa tgtatgtcat acaatttatg aatgtgatgg tgcaaaaaat    720
tgtgctgttg agcttaaaag tttttcaaag aaggctggat ttacaggatt aaggcttgga    780
tatacaattg ttccgaagga actaaaatgt tctggagttt ctttgaatag actttgggca    840
agacgttatg gaaccaaata caatggtaca ccatatatag ttcagagggc aggagaagct    900
gtttattctg agactggaaa agagcagata aaaaagcaaa ttgactatta taaaaataat    960
gccaaaatca ttttggaagg attaaaatca gcaggctact ctgtgtatgg aggagtgaat   1020
gcaccatatg tatggctaaa gacaccgaac aatatgactt catgggattt cttttattac   1080
ttattagaaa gagcaaatat tgtaggtacg cctggaagtg gctttggacc gatgggagaa   1140
gggtatttta ggcttacagc ctttggaact taccaaaata cattagaggc tgttgagaga   1200
attaagaaaa tctaa                                                    1215
```

<210> SEQ ID NO 51
<211> LENGTH: 1215
<212> TYPE: DNA
<213> ORGANISM: Clostridium coskatii

<400> SEQUENCE: 51

```
atgtgtaaat taaatgataa ttatttgaaa ttgcagggaa gatatttgtt tgcaagtata     60
gcaaaaaagg tagctaattt taaaaaaagc aatccgcata agaaaattat ttcacttggt    120
attggtgatg taactcagcc attggcaccg gttattatag aggcactgca tagttcagtt    180
gatgaaatgg gacataagga tacttttaaa ggatatgcac cggaatttgg ttatgaattt    240
ttaaaaaatg caattataaa aggtgactat aactcccgtg gtgtggacat ttcaatagat    300
gaagtgttta taaatgatgg aataaatgct gatgctggta atattcaaga actatttagt    360
gtagataata agattgcagt ttgtgaccct gtatatcctg tatatgtaga ctcaaatgta    420
atggctggaa ggacaggaac atatgataag gatgcacaaa ggtggagtga agttatatat    480
atgtcctgta ctccggataa taattttgtg ccggatattc cagaagaaaa cccagatatt    540
atatatctat gttttccaaa taatccaaca gggacaacgg ttacaaaaga tcagcttcaa    600
cttttggttg attatgcaaa taaagtggaa gctgttattg tatatgatgg tgcttatgaa    660
gcatatattt cagaagataa tgtatgtcat acaatttatg aatgtgatgg tgcaaaaaat    720
tgtgctgttg agcttaaaag tttttcaaag aaggctggat ttacaggatt aaggcttgga    780
tatacaattg ttccgaagga actaaaatgt tctggagttt ctttgaatag actttgggca    840
agacgttatg gaaccaaata caatggtaca ccatatatag ttcagagggc aggagaagcc    900
gtttattctg agactggaaa agagcagata aaaaagcaaa ttgattatta taaaaataat    960
gccaaaatca ttttggaagg attaaaatca gcaggctact ctgtgtatgg aggtgtaaat   1020
```

gcaccctatg tatggctaaa gacaccaaac aatatgactt catgggattt cttttattat 1080
ttattagaaa aagcaaatat tgtaggtacg ccaggaagtg gatttgggcc gatgggagaa 1140
ggatatttta ggcttacagc ctttggaact tatgaaaata cagtagaggc tgttgagagg 1200
attaagaaac tctaa 1215

<210> SEQ ID NO 52
<211> LENGTH: 1215
<212> TYPE: DNA
<213> ORGANISM: Clostridium ragsdalei

<400> SEQUENCE: 52
atgtgtaaat taaatgataa ttatttaaaa ttgcagggaa gatatttgtt tgcaagtata 60
gcaaaaaagg tagctaactt taaaaaaagc aatccgcata agaaaattat ttcgcttggt 120
attggtgatg taactcagcc attggcaccg gttattatag aggcactgca tagttcagtt 180
gatgaaatgg gacataagga tacttttaaa ggatatgcac cggaatttgg ttatgaattt 240
ttaaaaaatg caattataaa aggtgattat aactcccgtg gtgtggacat ttcaatagat 300
gaagtgttta taaatgatgg aataaatgct gatgctggta atattcaaga actatttagt 360
gtagataata agattgcagt ttgtgatcct gtatatcctg tatatgtaga ttcaaatgta 420
atggctggaa ggacaggaac atatgataag gatgcacaaa ggtggagtga agttatatat 480
atgtcctgta ctccggataa taattttgtg ccggatattc cagaagaaaa cccagatatt 540
atatatctat gttttccaaa taatccaaca gggacaacgg ttacaaaaga tcagcttcaa 600
tttttggttg attatgcgaa tagagtggaa gctgttattg tatatgatgg tgcttatgaa 660
gcatatattt cagaagataa tgtatgtcat acaatttatg aatgcgatgg tgcaaaaaat 720
tgtgccattg agcttaaaag cttttcaaaa agagctggat ttacaggatt aaggcttgga 780
tatacgattg ttccaaagga gctaaaatgt tccggaactt ctttgaatag actttgggca 840
agacgttatg gaaccaaata caatggtaca ccatatatag ttcagagggc aggagaagcc 900
gtttattctg aaactggaaa agagcagata aaaaagcaaa ttgattatta taagaataat 960
gccaaaatca ttatggaagg attaaaagca gcaggttact ctgtatacgg aggtgtaaat 1020
gcgccatatg tatggctaaa gacacctaac aatatgactt catgggattt cttttattac 1080
ttattagaaa aagcaaatat tgtaggtacg cctggaagtg gatttggacc gatgggggaa 1140
ggatatttta ggcttacagc ttttggaact tacgaaaata cattagaggc tgttgagagg 1200
attaagaaac tctaa 1215

<210> SEQ ID NO 53
<211> LENGTH: 1221
<212> TYPE: DNA
<213> ORGANISM: Clostridium autoethanogenum

<400> SEQUENCE: 53
atgaattttg aaattataga aggaggggtt acttctccaa aaggatttgt atctgcaggg 60
attagctgtg gtattaaaaa aagaaattca aaggacttgg ctcttataaa atcaattagc 120
ccttgtaatt cagcaggagt ttatacaaag aatatagtta aaggagctcc actcatagtt 180
actaaaaagc atctggaaaa caaaaaagct caagctgtga ttgcaaatag tggaaatgcc 240
aatacttgta ctggtgaaga aggattaaaa aatgcagaag agatgtgtga atatgtagca 300
agagaactta agattgaaaa agaagatgta cttgtagcat ctactggcat tataggagtt 360
aaattaaata ttgaagctat aaagaatgca gtacctgatt tggttaaaaa attagataag 420

```
gatggatata aagatgcatc caaagctata atgactacag atacttttca aaaaactata    480

gccataaaat tagaacttgg aggaaagaca gtaactattg gtgttatggc caaaggatcg    540

ggaatgatac atcctaatat gggaactatg ctttctttta taactacaga tgtaaatata    600

gatccagatc ttttagacaa agctttgaaa gagagtgtac gaataagtta taacagggtt    660

tcagtagatg gagatacttc aaccaacgat atggttgtta tactggcaaa tggattggct    720

gaaaatccac ttataaatga agaaaatgag gattacaaat tatttttaca ggcacttaaa    780

aaattaaata ttgaagtagc caaaatgatt gcaaaagatg gagaaggtgc tactaaatta    840

atagaatgta aagcactaaa tgtttctagt gaagaaaaag gtgagatact tggcaaatct    900

gtaatttgct ctaatttagt aaaaacagct ttatttggat gcaatgcaaa ttggggcaga    960

atacttgatg ctataggata ttcaggagtt gaatttgata taaacaagat ccaggtaaca   1020

atgaaaagta aaaaaggaag tgtcttagta tttgaaaaag gagaacctgt tccattttca   1080

gtgaaagagg caactgatat attatcagaa gatgtaatag atataattat aaactttaat   1140

tcaggtaatt ataatgtatg ctgttgggga tgcgatctaa cctatgatta tgtaaaaatt   1200

aatggagagt atatgtctta a                                              1221
```

```
<210> SEQ ID NO 54
<211> LENGTH: 1221
<212> TYPE: DNA
<213> ORGANISM: Clostridium ljungdahlii

<400> SEQUENCE: 54

atgaattttg aaattataga aggaggggtt acttctccaa aaggatttgt atctgcaggg     60

attagctgtg gtattaaaaa aagaaattca aaggacttgg ctcttataaa atcaattagc    120

ccttgtaatt cagcaggagt ttatacaaag aatatagtta aaggagctcc actcatagtt    180

actaaaaagc atctggaaaa caaaaaagct caagctgtga ttgcaaatag tggaaatgcc    240

aatacttgta ctggtgaaga aggattaaaa aatgcagaag agatgtgtga atatgtagca    300

agagaactta agattgaaaa agaagatgta cttgtagcat ctactggcat tataggagtt    360

aaattaaata ttgaagctat aaagaatgca gtacctgatt tggttaaaaa attagataag    420

gatggatata aagatgcatc caaagctata atgactacag atacttttca aaaaactata    480

gccataaaat tagaacttgg aggaaagaca gtaactattg gtgttatggc caaaggatcg    540

ggaatgatac atcctaatat gggaactatg ctttctttta taactacaga tgtaaatata    600

gatccagatc ttttagacaa agctttgaaa gagagtgtac gaataagtta taacagggtt    660

tcagtagatg gagatacttc aaccaacgat atggttgtta tactggcaaa tggattggct    720

gaaaatccac ttataaatga agaaaatgag gattacaaat tatttttaca ggcacttaaa    780

aaattaaata ttgaagtagc caaaatgatt gcaaaagatg gagaaggtgc tactaaatta    840

atagaatgta aagcactaaa tgtttctagt gaagaaaaag gtgagatact tggcaaatct    900

gtaatttgct ctaatttagt aaaaacagct ttatttggat gcaatgcaaa ttggggcaga    960

atacttgatg ctataggata ttcaggagtt gaatttgata taaacaagat ccaggtaaca   1020

atgaaaagta aaaaaggaag tgtcttagta tttgaaaaag gagaacctgt tccattttca   1080

gtgaaagagg caactgatat attatcagaa gatgtaatag atataattat aaactttaat   1140

tcaggtaatt ataatgtatg ctgttgggga tgcgatctaa cctatgatta tgtaaaaatt   1200

aatggagagt atatgtctta a                                              1221
```

<210> SEQ ID NO 55
<211> LENGTH: 1221
<212> TYPE: DNA
<213> ORGANISM: Clostridium coskatii

<400> SEQUENCE: 55

```
atgaattttg aaattataga aggaggggtt acttctccaa aaggatttgt atctgcaggg     60
attagctgtg gtattaaaaa aagaaattca aaggacttgg ctcttataaa atcaattagc    120
ccttgtaatt cagcaggagt ttatacaaag aatatagtta aaggagctcc actcatagtt    180
actaaaaagc atctggaaaa caaaaaagct caagctgtga ttgcaaatag tggaaatgcc    240
aatacttgta ctggtgaaga aggattaaaa aatgcagaag agatgtgtga atatgtagca    300
agagaactta agattgaaaa agaagatgta cttgtagcat ctactggcat tataggagtt    360
aaattaaata ttgaagctat aaagaatgca gtaccggatt tggttaaaaa attagataag    420
gatggatata aagatgcatc caaagctata atgactacag atacttttca aaaaactata    480
gccataaaat taaaacttgg aggaaagaca gtaactattg gtgttatggc caaaggatcg    540
ggaatgatac atcctaatat gggaactatg ctttctttta taactacaga tgtaaatata    600
gatccagatc ttttagacaa agctttgaaa gagagtgtac gaataagtta taacagggtt    660
tcagtagatg gagatacttc aaccaacgat atggttgtta tacttgcaaa tggattggct    720
gaaaatccac ttataaatga agaaaatgag gattacaaat tatttttaca ggcacttaaa    780
aaattaaata ttgaagtagc caaaatgatt gcaaaagatg gagaaggtgc tactaaatta    840
atagaatgta aagcactaaa tgtttctagt gaagaaaaag gtgagatact tggcaaatct    900
gtaatttgct ctaatttagt aaaaacagct ttatttggat gcaatgcaaa ttggggcaga    960
atacttgatg ctataggata ttcaggagtt gaatttgata taaacaagat ccaggtaaca   1020
atggaaagta aaaaaggaag tgtcttagta tttgaaaaag gagaacctgt tccattttca   1080
gtgaaagagg caactgatat attatcagaa gatgtaatag atataattat aaactttaat   1140
tcaggtaatt ataatgtatg ctgttgggga tgcgatctaa cctatgatta tgtaaaaatt   1200
aatggagagt atatgtctta a                                             1221
```

<210> SEQ ID NO 56
<211> LENGTH: 1221
<212> TYPE: DNA
<213> ORGANISM: Clostridium ragsdalei

<400> SEQUENCE: 56

```
atgaattttg aaattataga aggaggggtt acttctccaa aaggatttgt atctgcaggg     60
attagctgtg gtattaaaaa aagagattcg aaggacctgg ctcttataaa atcaattagc    120
tcttgtaatt cagcaggagt ttatacaaag aatatagtta aaggagctcc acttatagtt    180
actaaaaagc atctggaaaa taaaaaagct caagctgtga ttgcaaatag tggaaatgcc    240
aatacttgta ctggtgaaga aggattaaaa aatgcagaag agatgtgtga atatgtagca    300
agagaactta aaattgaaaa agaagatgta cttgtagcat ctactggcat tataggagtt    360
aaattaaata ttgaagctat aaaaaatgca gtaccggatt tggttaaaaa actagataag    420
gatggatata aagatgcatc caaagctata atgactacag atacttttca aaaaactata    480
gctataaaat tagaacttgg aggaaagaca gcaactattg gtgttatggc caaaggatca    540
ggaatgatac atcctaatat gggaactatg ctttctttta taactacaga cgtaaatata    600
gatccagatc ttttagacaa ggctttgaaa gagagtgtac gaataagtta taatagggtt    660
```

```
tcagtagatg gagatacttc aaccaacgat atggttgtta tactggcaaa tggattggct    720
gaaaatccac ttataaatga agaaaatgag gattacagat tatttttaca ggcacttaaa    780
aaattaaatg ttgaagtagc caaaatgatt gcaaaagatg gagaaggtgc tactaaatta    840
atagaatgta aagcactaaa tgtttctagt gaagaaaaag gtgagatact tggtaaatct    900
gtaatttgct ctaacttagt aaaaacagcc ttatttggat gcaatgcaaa ttggggcaga    960
atacttgatg ctataggata ttcaggagtt gaatttgata taaacaagat tcaggtaaca   1020
atggaaagta aaaaaggaag cgtcttagta tttgaaaaag gagaacctgt tccattttca   1080
gtaaaagaag caactgatat attatcagaa gatgtaatag atataattat aaactttaat   1140
tcaggtaatt ataatgtatg ctgttgggga tgcgatctaa cctatgatta tgtgaaaatt   1200
aatggagaat atatgtctta a                                             1221
```

<210> SEQ ID NO 57
<211> LENGTH: 4539
<212> TYPE: DNA
<213> ORGANISM: Clostridium autoethanogenum

<400> SEQUENCE: 57

```
atgaaatata atttaggatt cccttcaaaa caaggattat atgatcctga ttatgaaaag     60
gattcttgtg gggtaggatt tatagccagt ataaaaggtg aaaaaactca tgatattgta    120
aaaaaaggtg ttaaaatttt agttaactta actcacagag gagcagtagg agctgatact    180
aaaacaggag atggtgcagg tatacttgtc caaattccag atgaattttt tagaataaat    240
tgtgacaatt taggaataga attacctgaa ccaggtgaat atgctgtagg tatggtgttt    300
tttccaaaag aaactgcaat aaggctgcag tgtgagggaa tactcgaaag ggcagcagaa    360
gaagaaggac agaaaatttt aggctggaga gatgtaccta cagataatag aagtattggt    420
gaaacagcta agggtactga acctattata agacagatat ttataggtaa aaatgcacaa    480
aatcaaactg attttgaaag aaaactttat ataatcagaa aaaaagttga aaatgaagtt    540
aaaaaaactc ttgaaagtgc agcaaagtct ttttatgtat gcagcctttc aagtaaaact    600
atagtttata aaggattatt attggcagat caaataaaga aattttatat tgatttaaat    660
gatataaact ttaaaagtgc cattgcacta gtacatcaaa ggtacagcac aaatactttc    720
ccaacttggg atttagcaca accttttagg tttcttggac ataatggtga gataaatact    780
ataagaggaa atagaaactg gatgagatca cgtgaaggcg tactgaaatc tgaggctttc    840
ggaaaggata ttaagaagct cttcccaata ataagtgaag gtggaagtga ctctgcatct    900
cttgataatg tattggagct attatatgaa gatggaaaat ccctaccaca tgcacttatg    960
cttctcatac cagaagcgtg ggaaggaaat aaatatatgg aagaatacaa aagggctttt   1020
tatgagtacc acggttctct tgtagaacct tgggatggac ctgctgcggt tgcattttct   1080
gatggtgtac aagttggtgc tacccttgat agaaatggat taaggccttt aagatatatg   1140
ataactaaaa atggtcttgt agtacttgca tcagaaacag gagtgttaga atttaaagat   1200
gaagatatag aggaaaaggg aaaactaaaa ccaggcaaaa tgttcttggt tgatactgcc   1260
cagggaagaa taatagatga tgaagaatta aaaagagata tatgcaagag taagccttat   1320
gaagaaatgc ttcctaaatt aaaatttact cttgatatgt ttaatgcagt taggacgaga   1380
gaagaaatac cacctgtagt attaaaagaa aaacaacagg cttttggtta ctctcttgaa   1440
gatttgagca aaataatagg acctatggca agggatggta aagagcctgt ggggtctatg   1500
```

```
ggaaatgata cccctcttgc agtgctttca aataaaaatc aattactttt tgcgtatttc   1560
aaacaacttt ttgcccaggt aaccaatcca cctatagatt ctataagaga aagattagta   1620
atgtctcttg caaattatat aggttctact caggctaata tattaaatgg taaagatggg   1680
gaaatctcaa atgatccttt tatagagata aagagtccta cattgactaa tgaagaaata   1740
tcaaaaatca aaagcttgag agataaaaat tttaaaacta ctactattcc tattacattt   1800
aaatgtgata cgggagtaga aggttttaag gaagctcttg aaaaaatttg tgagagggct   1860
tcaaagagaa taaaagaagg atacaatata ttagttttaa gtgataaaaa tgttgattct   1920
tatgaggctg caataccaag tttacttgct gtttcagcag ttcagcacca tttaattaga   1980
gaaaaaacac gtacaaaggt ttcaattatt gtagagactg gagaagcaag agaaactaca   2040
cattttgcac ttttaataag ctatggtgct tctgcagtta acccttatct tgtatatcaa   2100
actatagatg aaatgataaa ggaaaaggat atagttggga ttaaaccaga agaagcaaag   2160
aaaaattata ttaaagctat aaatcaagga atacttaaaa tactttctaa aatgggtata   2220
tccacgctgc aaagttatca tggtgcgcaa atatttgaag caataggtct tgattcagaa   2280
tttgtgaata aatattttga gggtacgtca tctagaatag gcggtatagg tattgatgta   2340
gttgcaaagg aagtacttgc aagacataaa aatgctttta ataaaataag aaaacctatt   2400
tctgagctca atgtaggtgg taactattcc tggagaaaag gaggagagtt tcatctcttt   2460
aatcctgaaa ctatatacaa acttcaagtt gcagcaagaa ctaatgacta tggtatgtat   2520
aagcagtatg ctaaagtaat aaatgaacaa gataaaaatt tatgtacaat aagaggcttg   2580
tttcaattta aaaagggaaa tgaaatacct atagaagaag ttgaaccagt aagtgaaatt   2640
cttaaaagat tctgtacagg agctatgtcc tttggttcta taagcaaaga agctcatgaa   2700
actatagcta tagctatgaa tagaataggt ggaaggagta atactggaga aggtggagaa   2760
gatcctgata gatatgtact agatccaaat ggtgactcca gaagaagtgc cataaaacag   2820
gtggcatcag cacgttttgg tgtaactaca gaatatttgg caaatgcaga tgaaattcag   2880
ataaagatag cacaaggtgc aaaaccagga gaaggtggac aacttccagg taggaaggtt   2940
aataagtata ttgctaaaat aaggtattca acaccaggca tagaccttat ctcaccacca   3000
cctcaccatg atatatattc aatagaggat ttagctcaat taatatatga tttaaaaaat   3060
gtaaatccta gtgcagctat aagtgtaaaa cttgtgtctg aagtaggagt aggaacaatt   3120
gctgctggag ttgcaaaggc tcatgcagat ttaatactta taagtggtca tgatggaggt   3180
acaggggcat cacctatgtc atctgtaaaa aatgcaggaa taccttggga acttggattg   3240
tctgagacac aacaagtact actgttaaat gacctgcgaa gcagagttag aattcaaaca   3300
gatggacagc taaagacagg tagagatgtt gcaattgcag cacttcttgg agctgaagaa   3360
tttggttttg caactactgc tcttgtagta atgggatgta ctatgcttag aaaatgtcat   3420
ttaaatactt gtgatatggg aatagctacc caggatcctg aattaagaaa gaattttaaa   3480
ggaaaaccag agcatataat aaatttcctt acttttatcg cgcaggaagt tagagaatat   3540
atggcaaaac ttggttttaa aacaatgaat gaaatggttg gaagagtaga tatgcttgag   3600
acaaaaaagg ctattactca ttggaaagct aaaggtttgg atttgtctgc tatactttat   3660
aaaccatata tgccaaagag aatcaaatcc tactgtgtaa taccgcagga tcatggactt   3720
gataaggcaa tagattataa actcatccaa atgacacaaa aggcagtaca ggataagata   3780
aaagttactg caaatttaga gataaaaaat gtaaatcgtt ctgtgggaac aatgctaagt   3840
ggaacaattg caaagaaata tggtgccaag ggacttccag aagatactat agtgttaaat   3900
```

```
tttaagggat cagcaggaca gagttttgga gcctttggaa taaatggact tactctactt   3960

cttgaaggag atgccaatga ttatgttgga aaaggtctct ctggtgctaa aatagttata   4020

aaaactcctg agaaggcaac ctttgttgca gaaaagaata tcatagcagg taatactatt   4080

ttatatggag ctacatcagg aaaggtattt gtaaatggta ctgtaggaga aagatttgca   4140

gtaagaaaca gtggtgctat agctgtagct gaaggtgtag gagaccactg ctgtgaatat   4200

atgactggcg gaagagtagt tattatagga caaacaggaa gaaactttgc agctggtatg   4260

agcggcggta tagcttatgt acttgatgaa gatgattctt ttgatagaaa atgcaacatg   4320

gaaatggttg aaattgcaca aatggcagat gaggatgatg taaatacagt atatagttta   4380

atacaggaac attataaata tacagatagt gcaaaagcta aaaaaattct tgaaaaatgg   4440

gatgtatata aaaccaagtt taagagggta atacctactg cgtataaact tatactggaa   4500

caaaccaaat tagaagcagc tgctgcttct aatatgtag                          4539
```

<210> SEQ ID NO 58
<211> LENGTH: 4539
<212> TYPE: DNA
<213> ORGANISM: Clostridium ljungdahlii

<400> SEQUENCE: 58

```
atgaaatata atttaggatt cccttcaaaa caaggattat atgatcctga ttatgaaaag     60

gattcttgtg ggtaggatt tatagccagt ataaaaggtg aaaaaactca tgatattgta    120

aaaaaaggtg ttaaaatttt agttaactta actcacagag gagcagtagg agctgatact    180

aaaacaggag atggtgcagg tatacttgtc caaattccag atgaattttt tagaataaat    240

tgtgacaatt taggaataga attacctgaa ccaggtgaat atgctgtagg tatggtgttt    300

tttccaaaag aaactgcaat aaggctgcag tgtgagggaa tactcgaaag ggcagcagaa    360

gaagaaggac agaaaatttt aggctggaga gatgtaccta cagataatag aagtattggt    420

gaaacagcta agggtactga acctattata agacagatat ttataggtaa aaatgcacaa    480

aatcaaactg attttgaaag aaaactttat ataatcagaa aaaaagttga aaatgaagtt    540

aaaaaaactc ttgaaagtgc agcaaagtct ttttatgtat gcagcctttc aagtaaaact    600

atagtttata aaggattatt attggcagat caaataaaga aattttatat tgatttaaat    660

gatataaact ttaaaagtgc cattgcacta gtacatcaaa gatacagcac aaatactttc    720

ccaacttggg atttagcaca accttttagg tttcttggac ataatggtga gataaatact    780

ataagaggaa atagaaactg gatgagatca cgtgaaggtg tactgaaatc tgaggctttc    840

ggaaaggata ttaagaagct cttcccaata ataagtgaag gtggaagtga ctctgcatct    900

cttgataatg tattggagct attatatgaa gatggaaaat ccctaccaca tgcacttatg    960

cttctcatac cagaagcgtg ggaaggaaat aaatatatgg aagaatacaa aagggctttt   1020

tatgagtacc acggttctct tgtagaacct tgggatggac ctgctgcggt tgcattttct   1080

gatggtgtac aagttggtgc taccccttgat agaaatggat taaggccttt aagatatatg   1140

ataactaaaa atggtcttgt agtacttgca tcagaaacag gagtgttaga atttaaagat   1200

gaagatatag aggaaaaggg aaaactaaaa ccaggcaaaa tgttcttggt tgatactgcc   1260

cagggaagaa taatagatga tgaagaatta aaaagagata tatgcaagag taagccttat   1320

gaagaaatgc ttcctaaatt aaaatttact cttgatatgt ttaatgcagt taggacgaga   1380

gaagaaatac cacctgtagt attaaaagaa aaacaacagg cttttggtta ctctcttgaa   1440
```

-continued

```
gatttgagca aaataatagg acctatggca agggatggta aagagcctgt ggggtctatg   1500
ggaaatgata cccctcttgc agtgctttca aataaaaatc aattactttt tgcgtatttc   1560
aaacaacttt ttgcccaggt aaccaatcca cctatagatt ctataagaga aagattagta   1620
atgtctcttg caaattatat aggttctact caggctaata tattaaatgg taaagatggg   1680
gaaatctcaa atgatccttt tatagagata aagagtccta cattgactaa tgaagaaata   1740
tcaaaaatca aaagcttgag agataaaaat tttaaaacta ctactattcc tattacattt   1800
aaatgtgata cgggagtaga aggttttaag gaagctcttg aaaaaatttg tgagagggct   1860
tcaaagagaa taaaagaagg atataatata ttagttttaa gtgataaaaa tgttgattct   1920
tatgaggctg caataccaag tttacttgct gtttcagcag ttcagcacca tttaattaga   1980
gaaaaaacac gtacaaaggt ttcaattatt gtagagactg gagaagcaag agaaactaca   2040
cattttgcac ttttaataag ctatggtgct tctgcagtta acccttatct tgtatatcaa   2100
actatagatg aaatgataaa ggaaaaggat atagttggga ttaaaccaga agaagcaaag   2160
aaaaattata ttaaagctat aaatcaagga atacttaaaa tactttctaa aatgggtata   2220
tccacgctgc aaagttatca tggtgcgcaa atatttgaag caataggtct tgattcagaa   2280
tttgtgaata aatattttga gggtacgtca tctagaatag gcggtatagg tattgatgta   2340
gttgcaaagg aagtacttgc aagacataaa aatgctttta ataaaataag aaaacctatt   2400
tctgagctca atgtaggtgg taactattcc tggagaaaag gaggagagtt tcatctcttt   2460
aatcctgaaa ctatatacaa acttcaagtt gcagcaagaa ctaatgacta tggtatgtat   2520
aagcagtatg ctaaagtaat aaatgaacaa gataaaaatt tatgtacaat aagaggcttg   2580
tttcaattta aaaagggaaa tgaaatacct atagaagaag ttgaaccagt aagtgaaatt   2640
cttaaaagat tctgtacagg agctatgtcc tttggttcta taagcaaaga agctcatgaa   2700
actatagcta tagctatgaa tagaataggt ggaaggagta atactggaga aggtggagaa   2760
gatcctgata gatatgtact agatccaaat ggtgactcca gaagaagtgc cataaaacag   2820
gtggcatcag cacgttttgg tgtaactaca gaatatttgg caaatgcaga tgaaattcag   2880
ataaagatag cacaaggtgc aaaaccagga gaaggtggac aacttccagg taggaaggtt   2940
aataagtata ttgctaaaat aaggtattca acaccaggca tagaccttat ctcaccacca   3000
cctcaccatg atatatattc aatagaggat ttagctcaat taatatatga tttaaaaaat   3060
gtaaatccta gtgcagctat aagtgtaaaa cttgtgtctg aagtaggagt aggaacaatt   3120
gctgctggag ttgcaaaggc tcatgcagat ttaatactta taagtggtca tgatggaggt   3180
acaggggcat cacctatgtc atctgtaaaa aatgcaggaa taccttggga acttggattg   3240
tctgagacac aacaagtact actgttaaat gacctgcgaa gcagagttag aattcaaaca   3300
gatggacagc taaagacagg tagagatgtt gcaattgcag cacttcttgg agctgaagaa   3360
tttggttttg caactactgc tcttgtagta atgggatgta ctatgcttag aaaatgtcat   3420
ttaaatactt gtgatatggg aatagctacc caggatcctg aattaagaaa gaattttaaa   3480
ggaaaaccag agcatataat aaatttcctt acttttatcg cgcaggaagt tagagaatat   3540
atggcaaaac ttggttttaa aacaatgaat gaaatggttg gaagagtaga tatgcttgag   3600
acaaaaaagg ctattactca ttggaaagct aaaggtttgg atttgtctgc tatactttat   3660
aaaccatata tgccaaagag aatcaaatcc tactgtgtaa taccgcagga tcatggactt   3720
gataaggcaa tagattataa actcatccaa atgacacaaa aggcagtaca ggataagatc   3780
aaagttactg caaatttaga gataaaaaat gtaaatcgtt ctgtgggaac aatgctaagt   3840
```

```
ggaacaattg caaagaaata tggtgccaag ggacttccag aagatactat agtgttaaat   3900

tttaagggat cagcaggaca gagttttgga gcctttggaa taaatggact tactctactt   3960

cttgaaggag atgccaatga ttatgttgga aaaggtctct ctggtgctaa aatagttata   4020

aaaactcctg agaaggcaac ctttgttgca gaaaagaata tcatagcagg taatactatt   4080

ttatatggag ctacatcagg aaaggtattt gtaaatggta ctgtaggaga aagatttgca   4140

gtaagaaaca gtggtgctat agctgtagct gaaggtgtag gagaccactg ctgtgaatat   4200

atgactggcg gaagagtagt tattatagga caaacaggaa gaaactttgc agctggtatg   4260

agcggcggta tagcttatgt acttgatgaa gatgattctt ttgatagaaa atgcaacatg   4320

gaaatggttg aaattgcaca aatggcagat gaggatgatg taaatacagt atatagttta   4380

atacaggaac attataaata tacagatagt gcaaaagcta aaaaaattct tgaaaaatgg   4440

gatgtatata aaaccaagtt taagagggta atacctactg cgtataaact tatactggaa   4500

caaaccaaat tagaagcagc tgctgcttct aatatgtag                          4539
```

<210> SEQ ID NO 59
<211> LENGTH: 4539
<212> TYPE: DNA
<213> ORGANISM: Clostridium coskatii

<400> SEQUENCE: 59

```
atgaaatata atttaggatt cccttcaaaa caaggattat atgatcctga ttatgaaaag     60

gattcttgtg ggtaggattt tatagccagt ataaaaggtg aaaaaactca tgatattgta    120

aaaaaaggtg ttaaaatttt agttaactta actcacagag gagcagtagg agctgatact    180

aaaacaggag atggtgcagg tatacttgtc caaattccag atgaattttt tagaataaat    240

tgtgacaatt taggaataga attacctgaa ccaggtgaat atgctgtagg tatggtgttt    300

tttccaaaag aaactgcaat aaggctgcag tgtgagggaa tactcgaaag ggcagcagaa    360

gaagaaggac agaaaatttt aggctggaga gatgtaccta cagataatag aagtattggt    420

gaaacagcta agggtactga acctattata agacagatat ttataggtaa aaatgcacaa    480

aatcaaactg attttgaaag aaaactttat ataatcagaa aaaaagttga aaatgaagtt    540

aaaaaaactc ttgaaagtgc agcaaagtct ttttatgtat gcagcctttc aagtaaaact    600

atagtttata aaggattatt attggcagat caaataaaga aattttatat tgatttaaat    660

gatataaact ttaaaagtgc cattgcacta gtacatcaaa ggtacagcac aaatactttc    720

ccaacttggg atttagcaca accttttagg tttcttggac ataatggtga gataaatact    780

ataagaggaa atagaaactg gatgagatca cgtgaaggtg tactgaaatc tgaggctttc    840

ggaaaggata ttaagaagct cttcccaata ataagtgaag gtggaagtga ctctgcatct    900

cttgataatg tattggagct attatatgaa gatggaaaat ccctaccaca tgcacttatg    960

cttctcatac cggaagcgtg ggaaggaaat aaatatatgg aagaatacaa aagggctttt   1020

tatgagtacc acggttctct tgtagaacct tgggatggac ctgctgcggt tgcattttct   1080

gatggtgtac aagttggtgc tacccttgat agaaatggat taaggccttt aagatatatg   1140

ataactaaaa atggtcttgt agtacttgca tcagaaacag gagtgttaga atttaaagat   1200

gaagatatag aggaaaaggg aaaactaaaa ccaggcaaaa tgttcttggt tgatactgcc   1260

cagggaagaa taatagatga tgaagaatta aaaagagata tatgcaagag taagccttat   1320

gaagaaatgc ttcctaaatt aaaatttact cttgatatgt ttaatgcagt taggacgaga   1380
```

```
gaagaaatac cacctgtagt attaaaagaa aaacaacagg cttttggtta ctctcttgaa   1440
gatttgagca aaataatagg acctatggca agggatggta aagagcctgt ggggtctatg   1500
ggaaatgata cccctcttgc agtgctttca aataaaaatc aattactttt tgcgtatttc   1560
aaacaacttt ttgcccaggt aaccaatcca cctatagatt ctataagaga aagattagta   1620
atgtctcttg caaattatat aggttctact caggctaata tattaaatgg taaagatggg   1680
gaaatctcaa atgatccttt tatagagata aagagtccta cattgactaa tgaagaaata   1740
tcaaaaatca aagcttgag agataaaaat tttaaaacta ctactattcc tattacattt   1800
aaatgtgata cgggagtaga aggttttaag gaagctcttg aaaaaatttg tgagagggct   1860
tcaaagagaa taaaagaagg atacaatata ttagttttaa gtgataaaaa tgttgattct   1920
tatgaggctg caataccaag tttacttgct gtttcagcag ttcagcacca tttaattaga   1980
gaaaaaacac gtacaaaggt ttcaattatt gtagagactg gagaagcaag agaaactaca   2040
cattttgcac ttttaataag ctatggtgct tctgcagtta acccttatct tgtatatcaa   2100
actatagatg aaatgataaa ggaaaaggat atagttggga ttaaaccaga agaagcaaag   2160
aaaaattata ttaaagctat aaatcaagga atacttaaaa tactttctaa aatgggtata   2220
tccacgctgc aaagttatca tggtgcgcaa atatttgaag caataggtct tgattcagaa   2280
tttgtgaata aatattttga gggtacgtca tctagaatag gcggtatagg tattgatgta   2340
gttgcaaagg aagtacttgc aagacataaa aatgctttta ataaaaataag aaaacctatt   2400
tctgagctca atgtaggtgg taactattcc tggagaaaag gaggagagtt tcatctcttt   2460
aatcctgaaa ctatatacaa acttcaagtt gcagcaagaa ctaatgaata tggtatgtat   2520
aagcagtatg ctaaagtaat aaatgaacaa gataaaaatt tatgtacaat aagaggcttg   2580
tttcaattta aaaagggaaa tgaaatacct atagaagaag ttgaaccagt aagtgaaatt   2640
cttaaaagat tctgtacagg agctatgtcc tttggttcta taagcaaaga agctcatgaa   2700
actatagcta tagctatgaa tagaataggt ggaaggagta atactggaga aggtggagaa   2760
gatcctgata gatatgtact agatccaaat ggtgactcca gaagaagtgc cataaaacag   2820
gtggcatcag cacgttttgg tgtaactaca gaatatttgg caaatgcaga tgaaattcag   2880
ataaagatag cacaaggtgc aaaaccagga gaaggtggac aacttccagg taggaaggtt   2940
aataagtata ttgctaaaat aaggtattca acaccaggca tagaccttat ctcaccacca   3000
cctcaccatg atatatattc aatagaggat ttagctcaat taatatatga tttaaaaaat   3060
gtaaatccta gtgcagctat aagtgtaaaa cttgtgtctg aagtaggagt aggaacaatt   3120
gctgctggag ttgcaaaggc tcatgcagat ttaatactta taagtggtca tgatggaggt   3180
acaggggcat cacctatgtc atctgtaaaa aatgcaggaa taccttggga acttggattg   3240
tctgagacac aacaagtact actgttaaat gacctgcgaa gcagagttag aattcaaaca   3300
gatggacagc taaagacagg tagagatgtt gcaattgcag cacttcttgg agctgaagaa   3360
tttggttttg caactactgc tcttgtagta atgggatgta ctatgcttag aaaatgtcat   3420
ttaaatactt gtgatatggg aatagctacc caggatcctg aattaagaaa gaattttaaa   3480
ggaaaaccag agcatataat aaatttcctt acttttatcg cgcaggaagt tagagaatat   3540
atggcaaaac ttggttttaa aacaatgaat gaaatggttg gaagagtaga tatgcttgag   3600
acaaaaaagg ctattactca ttggaaagct aaaggtttgg atttgtctgc tatactttat   3660
aaaccatata tgccaaagag aatcaaatcc tactgtgtaa taccgcagga tcatggactt   3720
gataaggcaa tagattataa actcatccaa atgacacaaa aggcagtaca ggataagata   3780
```

```
aaagttactg caaatttaga gataaaaaat gtaaatcgtt ctgtgggaac aatgctaagt   3840

ggaacaattg caaagaaata tggtgccaag ggacttccag aagatactat agtgttaaat   3900

tttaagggat cagcaggaca gagttttgga gcctttggaa taaatggact tactctactt   3960

cttgaaggag atgccaatga ttatgttgga aaaggtctct ctggtgctaa aatagttata   4020

aaaactcctg agaaggcaac ctttgttgca gaaaagaata tcatagcagg taatactatt   4080

ttatatggag ctacatcagg aaaggtattt gtaaatggta ctgtaggaga aagatttgca   4140

gtaagaaaca gtggtgctat agctgtagct gaaggtgtag gagaccactg ctgtgaatat   4200

atgactggcg gaagagtagt tattatagga caaacaggaa gaaactttgc agctggtatg   4260

agcggcggta tagcttatgt acttgatgaa gatgattctt ttgatagaaa atgcaacatg   4320

gaaatggttg aaattgcaca aatggcagat gaggatgatg taaatacagt atatagttta   4380

atacaggaac attataaata tacagatagt gcaaaagcta aaaaaattct tgaaaaatgg   4440

gatgtatata aaaccaagtt taagagggta atacctactg cgtataaact tatactggaa   4500

caaaccaaat tagaagcagc tgctgcttct aatatgtag                          4539
```

<210> SEQ ID NO 60
<211> LENGTH: 4539
<212> TYPE: DNA
<213> ORGANISM: Clostridium ragsdalei

<400> SEQUENCE: 60

```
ctacatatta gaagcagcag ctgcttctaa tttggtttgt tccagtataa gtttatacgc     60

agtaggtatt accctcttaa acttggtctt atatatatcc catttttcaa gaattttttt    120

agcttttaca ctatctgtat atttatagtg ttcctgtatt aaactatata ctgtatttac    180

atcatcctca tctgccattt gcgcaatttc aaccatttcc atgttgcatt ttctatcaaa    240

agaatcatct tcatcaagta cataagctat accgccgctc ataccagctg caaaatttct    300

tcccgtttga cccatgataa ctactcttcc accagtcata tattcacagc agtggtctcc    360

tacaccttca actacagctg tagctccact gtttcttact gcaaatcttt ctcctacagt    420

accatttaca aataccttc ctgatgtagc tccatataaa atggtattac ctgctatgat    480

attcttttct gcaacaaaag ttgccttctc aggagtttta ataactattt tagcaccaga    540

aagacctttt ccaacataat cattggcgtc tccttcaagc actagagtaa gtccatttat    600

tccaaaggct ccaaaactct gtcctgctga ccccttaaaa tttaacacta tagtatcttc    660

tggaagtccc ttggcaccat atttctttgc aatcgttccg cttagcattg ttccaacaga    720

acgatttaca ttttttatct ccaaatttgc agtaactttt atcttatcct gtactgcctt    780

ttgtgtcatt tgaatgagtt tataatctat tgccttatca agtccatgat tctgtggtat    840

tacacagtag gatttaattc tctttggcat atatggttta taaagtacag cagacaaatc    900

taaaccttta gctttccaat gagtaatagc ctttttttgtc tccagcatat ctactcttcc    960

aaccatttca ttcattgttc taaagccaag ttttgccata tactctctaa cttcctgtgc   1020

aataaaagta aggaaattta ttatatgctc tggttttcct ttaaaattct ttcttaattc   1080

aggatcttgg gtagctattc ccatatcaca agtatttaaa tggcattttc taagcatagt   1140

acatcccatt actacaaggg cagtagttgc aaaaccaaat tcttcagctc caagaagtgc   1200

tgcaattgca acatctctac ctgtctttaa ctgtccatct gtttgaattc taactctgct   1260

tcgcagatca tttaacagta gtacttgttg tgtctcagat aatccaagtt cccaaggtat   1320
```

```
tcctgcattt tttacagatg acataggtga tgcccctgtg cctccatcat gaccacttat   1380
aagtattaaa tctgcatgag cctttgcaac tccagcagca attgttccta ctcctacttc   1440
agacacaagt tttacactta tagctgcact aggatttaca ttttttaaat catatattaa   1500
ttgagctaaa tcttctattg aatatatatc atggtgaggt ggtggtgaaa taaggtctat   1560
gcctggagtt gaataccita ttttggcgat atacttatta accttcctac ctggaagttg   1620
tccaccttct cctggttttg caccttgtgc tatctttatc tggatttcat ctgcatttgc   1680
caaatattct gtagttacac caaaacgtgc tgatgccacc tgttttatag cacttcttct   1740
ggaatcacca tttggatcta gtacatatct atcaggatcc tctccacctt ctccagtatt   1800
gctccttcca cctattctat tcatagctat agctatagtt tcatgagctt ctttgcttat   1860
agaaccaaag gacatagctc ctgtacagaa tcttttaaga atttcactta ctggttcaac   1920
ttcttctata ggtatctcat ttcccttttt aaattgaaac aagcctctta ttgtacataa   1980
atttttatct tgttcattta ttactttagc atactgctta tacataccat agtcattagt   2040
tcttgctgca acctggagtt tgtatatagt ttcaggatta aagagatgaa actctcctcc   2100
ttttctccaa gaatagttac cacctacatt gagctcagaa ataggttttc ttattttatt   2160
aaaggcattt ttatgtcttg caagtacttc ctttgcaact acatcaatac ctataccacc   2220
tattctagat gatgtaccct caaaatactt atttacaaat tctgaatcaa gacctattgc   2280
ttcaaatatt tgtgcaccgt gataactttg cagcgtggat atacccattt ttgaaagtat   2340
tttaagtatt ccttgattta tagccttaat ataatttttc tttgcttctt ctggtgtaac   2400
tccaactata tcattttcct ttatcatttc atctatagtt tgataaacaa gataaggatt   2460
aactgcagaa gcaccataac ttattaaaag tgcaaaatgc gtagtttctc ttgcttctcc   2520
agtttctacg ataattgaaa cttttgtacg tgtttttttct ctaattagat ggtgctgcac   2580
cgctgaaaca gcaagtaaac ttggtatagc agcctcgtaa gaatccacat ttttatcact   2640
taaaactagt atattgtatc cttcttttat tctctttgaa gctctctcac aaattttttc   2700
aagagcttcc ttaaaacctt ctactcccgt atcacattta aatgtaatag gaatagtagt   2760
agttttaaag tttttatctc tcaagctctt tatttttgat atttcctcat tagttagtgt   2820
aggacttttt atctctataa aaggatcgtt tgagatttct ccatctttac catttaatat   2880
attagcctgg gtagaaccta tataatttgc aagagacatt actaatcttt ctcttataga   2940
atctataggt ggattggtta cctgggcaaa aagttgtttg aaatacgcaa aaagcaattg   3000
atttttattt gaaagcactg caagaggagt atcatttccc atagacccca caggctcttt   3060
accatccttt gccataggtc ctattatctt gctcaaatct tcaagagagt agccaaacgc   3120
ctgttgtttt tcctttaata ctacaggtgg tatttcttct cttgtcctaa ctgccttaaa   3180
catatcaaga gtaaatttta atttaggaag catttcttca taaggcttac tcttgcatat   3240
atctcttttt aattcttcat catctattat tcttccctga gcagtatcaa ccaagaacat   3300
tttgccaggt tttagttttc ccttttcctc tatatcctca tcattaaatt ctagcactcc   3360
tgtctctgat gcaagtacta caagaccatt ttttgttatc atatatctca aaggccttaa   3420
tccattcctg tcaagagtag caccaacttg tacaccatca gaaaatgcaa ccgcagcagg   3480
tccatcccaa ggttctacaa gagaaccgtg atactcataa aaagcccttt tatattcttc   3540
catatatttg tttccttccc acgcttctgg tataagaagc ataagtgcat gtggtaagga   3600
ttttccatct tcatataata attccaatac attatcaaga gatgcagaat cacttccccc   3660
ttcacttatt atagggaaaa gtttcttaat gtcctttccg aaagcttcag atttcagtac   3720
```

```
accttcacgt gatctcatcc agtttcgatt tcctcttatg gtatttatct caccattatg   3780
tccaagaaac ctaaaaggtt gtgccaaatc ccaagttggg aaagtatttg tgctgtacct   3840
ttgatgtact agtgcaatgg cacttttaaa gtttatatca tttaaatcaa tataaaattt   3900
ctttatttga tctgccagta ataatccttt ataaactata gttttacttg aaagactaca   3960
tacataaaaa gattttgatg cactttcaag agttttttta acttcatttt caactttttt   4020
tctgattata taaagttttc tttcaaaatc agtttgattt tgtgcatttt tgcctataaa   4080
tatctgtctt ataataggtt cagtaccctt agctgtttca ccaatacttc tattgtctgt   4140
aggtacatct ctccagccta aaattttctg tccttcttct tctgctgccc tttcaagtat   4200
tccctcacac tgcaacctta ttgcagtttc ttttggaaaa aataccatac ctacagcata   4260
ttcacccggt tcaggtaatt ctattcctaa attgtcacaa tttattctaa aaaattcatc   4320
tggaatttgg acaagtatac ctgcaccatc tcctgtttta gtatcagctc ccactgctcc   4380
tctgtgagtt aagttaacta aaattttaac accttttttt acaatatcat gggttttttc   4440
accttttata ctggctataa atcctacccc acaagaatcc ttttcataag caggatcata   4500
taatccttgt tttgaaggga atcctagatt atatttcat                          4539
```

<210> SEQ ID NO 61
<211> LENGTH: 1434
<212> TYPE: DNA
<213> ORGANISM: Clostridium autoethanogenum

<400> SEQUENCE: 61

```
atgggaaaaa taactggttt taaagaatat aaaagagaaa atccaaaaga acgtccggta     60
gaggaaagaa tcaaagatta taaggaagta tactataaac ttcctaagga taaattgaat    120
gtacaggcag caagatgcat gaattgtgga actccttttt gtaattgggg atgtcctctt    180
gaaaatctaa ttccggattg gaatgatttt gtatataaga atgaatggca caaggcgttt    240
gaaagacttt cattaactaa cactttccct gaatttacag gaagaatatg tcctgctctc    300
tgtgaaggct cttgtacact tggagtaaat agagaacctg tttctgtaag gcagctagaa    360
cttaatataa tcgaaaaggc ttttgaagaa ggatggataa aacctaatcc accaaaagtt    420
agaactggaa aaagggtagc tatagtaggt tcaggaccat ctggactttc aactgctgca    480
gagctcaatt ctgtaggtca tactgttact gtttttgaaa gagcagatga agttggtgga    540
cttttaagat atggtattcc tgattttaaa cttgaaaaac atgtagttga cagaagagta    600
aatattatga aagaagaagg aataatattt aaaacaaaca taaatgtagg agtaaattac    660
gatgtaaatg aacttttagg taattttgat gctgttgttt taacaggagg ttctactatt    720
ccaagagacc ttaaagtgga aggaagagaa cttaaaggca cttattttgc agtagatttt    780
ctaaggcagc aaaataaaag agtttctggt aagaaaatta cagaagaaga gataaatgcc    840
aaaggaaaga tagtcgttgt tatcggtgga ggagatacag gttccgattg tattggtact    900
tctataaggc agggagctaa aaaggtttat caatatgagg ttatgccaaa gccacctgaa    960
aatcgtgata aaacaatgcc gtggcctgtt ttcccaaaaa ctttgaaaac tactacttcc   1020
catgaagagg gatgtatacg tgaatggtgt ataaacacca aaaagcttgt aggagaaaaa   1080
ggtgtattga aatcacttaa aggtgtaaag gttaagtggg aagataacaa tggtaagaga   1140
caaatggtag aagtaccagg tacagaattt gaacaaccag ttgatttgat acttttagct   1200
atgggatttt tgcatcctca gcatgaagga ttgcttgaca gcctaggtgt agaatatgat   1260
```

gctagaggta atgtggtaac ggatgtgaat tatatgactg caaaagaagg ggtatttgca 1320
gcaggagata tgagacgtgg acaatctctt gtagtttggt cactaaatga tggtagaaga 1380
gtggcaaaga atgttgataa atatttaatg ggagaaacat ctctcagagg ataa 1434

<210> SEQ ID NO 62
<211> LENGTH: 1434
<212> TYPE: DNA
<213> ORGANISM: Clostridium ljungdahlii

<400> SEQUENCE: 62
atgggaaaaa taactggttt taaagaatat aaaagagaaa atccaaaaga acgtccggta 60
gaggaaagaa tcaaagatta taaggaagta tactataaac ttcctaagga taaattgaat 120
gtacaggcag caagatgcat gaattgtgga actccttttt gtaattgggg atgtcctctt 180
gaaaatctaa ttccggattg gaatgatttt gtatataaga atgaatggca caaggcgttt 240
gaaagacttt cattaactaa cactttccct gaatttacag gaagaatatg tcctgctctc 300
tgtgaaggct cttgtacact tggagtaaat agagaacctg tttctgtaag gcagctagaa 360
cttaatataa tcgaaaaggc ttttgaagaa ggatggataa aacctaatcc accaaaagtt 420
agaactggaa aaagggtagc tatagtaggt tcaggaccat ctggactttc aactgctgca 480
gagctcaatt ctgtaggtca tactgttact gtttttgaaa gagcagatga agttggtgga 540
cttttaagat atggtattcc tgattttaaa cttgaaaaac atgtagttga cagaagagta 600
aatattatga aagaagaagg aataatattt aaaacaaaca taaatgtagg agtaaattac 660
gatgtaaatg aacttttagg taattttgat gctgttgttt taacaggagg ttctactatt 720
ccaagagacc ttaaagtgga aggaagagaa cttaaaggca cttattttgc agtagatttt 780
ctaaggcagc aaaataaaag agtttctggt aagaaaatta cagaagaaga gataaatgcc 840
aaaggaaaga tagtcgttgt tatcggtgga ggagatacag gttccgattg tattggtact 900
tctataaggc agggagctaa aaaggtttat caatatgagg ttatgccaaa gccacctgaa 960
aatcgtgata aaacaatgcc gtggcctgtt ttcccaaaaa ctttgaaaac tactacttcc 1020
catgaagagg gatgtatacg tgaatggtgt ataaacacca aaaagcttgt aggagaaaaa 1080
ggtgtattga aatcacttaa aggtgtaaag gttaagtggg aagataacaa tggtaagaga 1140
caaatggtag aagtaccagg tacagaattt gaacaaccag ttgatttgat acttttagct 1200
atgggatttt tgcatcctca gcatgaagga ttgcttgaca gcctaggtgt agaatatgat 1260
gctagaggta atgtggtaac ggatgtgaat tatatgactg caaaagaagg ggtatttgca 1320
gcaggagata tgagacgtgg acaatctctt gtagtttggt cactaaatga tggtagaaga 1380
gtggcaaaga atgttgataa atatttaatg ggagaaacat ctctcagagg ataa 1434

<210> SEQ ID NO 63
<211> LENGTH: 1434
<212> TYPE: DNA
<213> ORGANISM: Clostridium coskatii

<400> SEQUENCE: 63
atgggaaaaa taactggttt taaagaatat aaaagagaaa atccaaaaga acgtccggta 60
gaggaaagaa tcaaagatta taaggaagta tactataaac ttcctaagga taaattgaat 120
gtacaggcag caagatgcat gaattgtgga actccttttt gtaattgggg atgtcctctt 180
gaaaatctaa ttccggattg gaatgatttt gtatataaga atgaatggca caaggcgttt 240
gaaagacttt cattaactaa cactttccct gaatttacag gaagaatatg tcctgctctc 300

```
tgtgaaggct cttgtacact tggagtaaat agagaacctg tttctgtaag gcagctagaa    360
cttaatataa tcgaaaaggc ttttgaagaa ggatggataa aacctaatcc accaaaagtt    420
agaactggaa aaagggtagc tatagtaggt tcaggaccat ctggactttc aactgctgca    480
gagctcaatt ctgtaggtca tactgttact gtttttgaaa gagcagatga agttggtgga    540
cttttaagat atggtattcc tgattttaaa cttgaaaaac atgtagttga cagaagagta    600
aatattatga aagaagaagg aataatattt aaaacaaaca taaatgtagg agtaaattac    660
gatgtaaatg aacttttaag taattttgat gctgttgttt taacaggagg ttctactatt    720
ccaagagacc ttaaagtgga aggaagagaa cttaaaggca cttattttgc agtagatttt    780
ctaaggcagc aaaataaaag agtttctggt aagaaaatta cagaagaaga gataaatgcc    840
aaaggaaaga tagtcgttgt tatcggtgga ggagatacag gttccgattg tattggtact    900
tctataaggc agggagctaa aaaggtttat caatatgagg ttatgccaaa gccacctgaa    960
aatcgtgata aaacaatgcc gtggcctgtt ttcccaaaaa ctttgaaaac tactacttcc   1020
catgaagagg gatgtatacg tgaatggtgt ataaacacca aaaagcttgt aggagaaaaa   1080
ggtgtattga aatcacttaa aggtgtaaag gttaagtggg aagataacaa tggtaagaga   1140
caaatggtag aagtaccagg tacagaattt gaacaaccag ttgatttgat acttttagct   1200
atgggatttt tgcatcctca gcatgaagga ttgcttgaca gcctaggtgt agaatatgat   1260
gctagaggta atgtggtaac ggatgtgaat tatatgactg caaaagaagg ggtatttgca   1320
gcaggagata tgagacgtgg acaatctctt gtagtttggt cactaaatga tggtagaaga   1380
gtggcaaaga atgttgataa atatttaatg ggagaaacat ctctcagagg ataa         1434
```

```
<210> SEQ ID NO 64
<211> LENGTH: 1434
<212> TYPE: DNA
<213> ORGANISM: Clostridium ragsdalei

<400> SEQUENCE: 64
```

```
atgggaaaaa taactggttt taaagaatat caaagagaaa atccaaaaga acgtccggta     60
aaggaaagaa tcaaagatta taaggaagta tactataaac ttcctaagga taaattgaat    120
gtacaggcag caagatgcat gaattgtgga actccttttt gtaattgggg atgtcctctt    180
gaaaatctaa ttcccgattg gaatgatttt gtatataaga atgaatggca caaggcgttt    240
gaaagacttt cattaactaa cactttccct gaatttacag gaagaatatg tcctgctctc    300
tgtgaaggtt cttgtacact tggagtaaat agagaacctg tttctgtaag gcagctagaa    360
cttaatataa tcgaaaaggc ttttgaagaa ggatggataa aacctaatcc accaaaagtt    420
agaactggaa aaagggtagc tatagtaggt tcaggaccat ctggactttc aactgctgca    480
gagctcaatt ccgtaggtca tactgttact gtttttgaaa gagcagatga agttggtgga    540
cttttaagat atggtattcc tgattttaaa cttgaaaaac atgtagtgga cagaagagta    600
aatattatga aagaagaagg aatagtattt aaaacaaaca ctaatgtagg agtaaattac    660
gatgtaaatg agcttttaga taattttgat gctgttgttt taacaggagg ttctactatt    720
ccaagggacc ttaaggtgga aggaagagaa cttaaaggca cttattttgc agtagacttc    780
ttaaggcagc aaaataaaag agtttctggt aagaaaatta gggaagaaga gataaatgcc    840
aaaggaaagg tagtcgttgt tatcggtgga ggagatacag gttccgattg tattggtact    900
tctataaggc agggagctaa aaaggtttat caatatgagg ttatgccaaa gccacctgaa    960
```

```
aatcgtgata aaacaatgcc gtggcctgtt ttcccaaaaa ctttgaaaac tactacttcc   1020

catgaagagg gatgtatacg tgaatggtgt ataaatacca aaaagcttgt aggagaaaaa   1080

ggcgtattga aatcacttaa aggtgtaaag gttaagtggg aagataataa tggtaaaagg   1140

caaatggtag aagtaccagg tacagaattt gaacaaccag ttgatttgat acttttagct   1200

atgggatttt tgcatcctca gcatgaagga ctgcttgaca gccttggagt agaatatgat   1260

gctagaggta atgtggtaac ggatgtgaat tatatgactg caaaagaagg ggtatttgca   1320

gcaggagata tgagacgtgg gcaatctctt gtagtttggt cactaaatga tggtagaaga   1380

gtggcaaaga atgttgataa atatttaatg ggagaaacat ctctcagagg ataa         1434
```

<210> SEQ ID NO 65
<211> LENGTH: 1269
<212> TYPE: DNA
<213> ORGANISM: Clostridium autoethanogenum

<400> SEQUENCE: 65

```
ttggataaaa ttgtttttgg tgaagctaat agatgtcttg gatgtaaagt gcctcaatgt     60

aaaaaaggat gccctgtaag caccccctata aatgaagtaa taaaactttt taaagagaat    120

aaaataaaag aagccgggaa acttcttttt gaaaataacc ccatgtcagc tatttgttca    180

caagtttgtc cacatgaaaa gttttgtgaa ggccattgcg tgcttggtaa aaaaggaact    240

cctataaagt ttggtcttat cgaaaaatat atatcagact tttatcttaa ttttataacg    300

tcagctgata taaaaaagtt gaataaaaaa attgcagtag tagggtcagg tccagcagga    360

ttgagtattg cctttataat ggcaagaaag ggatatgatg taactatatt tgaatcccat    420

gaagatatag gaggagtttt gagatacggc atacctgcct ttagacttcc taaagatatt    480

ttggacaggc ttaaggataa acttctccat atgagagtta agataaggcc taatactctt    540

ataggacctg tgataactgt tgaagatttg tttagggatg gatacagggc ggtttatata    600

ggaacaggag tgtggagccc aaggagcttg ggacttaaag gagaaactta tggtaatgtg    660

aattatgcca tagattatct taaaaatcct gaggcctata atttgggaga taaagttgca    720

attataggag caggaaatgt tgctatggat gctgcaagga ctataattag aaatggatca    780

aatgacgtaa ctatcattgc aaggagtgat gaagaacatg caggagcaga taatatagaa    840

attgattatg ccaaacttga tggagtgaaa tttctctata aaatggcacc agttgaaata    900

acagatgatg gaattaaagt agttccaact gaggtgtcct ttgatgaaaa tacagggaaa    960

aagaaagtaa cgttaaaaga tgaggaaaca aagcttttta atgcagattc tataataatt   1020

gctgtaggcc agggacctaa ggcaaatata gtaaacaatt ctgaaggaat agaagtaaat   1080

tccaaaggac ttatacagac agacgattca ggaagaacta caaggtctgg agtttttgca   1140

tcaggtgatg tggtaacagg tgccaaaacc gttgttgaag cagtagaggt ttcaaagcac   1200

cttgtaaatg ctatggaaga atatataaag agtatggata agaaatttga aagttcagat   1260

aaaaattaa                                                           1269
```

<210> SEQ ID NO 66
<211> LENGTH: 1269
<212> TYPE: DNA
<213> ORGANISM: Clostridium ljungdahlii

<400> SEQUENCE: 66

```
ttggataaaa ttgtttttgg tgaagctaat agatgtcttg gatgtaaagt gcctcaatgt     60

aaaaaaggat gccctgtaag taccccctata aatgaagtaa taaaactttt taaagagaat    120
```

```
aaaataaaag aagccgggaa acttcttttt gaaaataacc ccatgtcagc tatttgttca    180
caagtttgtc cacatgaaaa gttttgtgaa ggccattgcg tgcttggtaa aaaaggaact    240
cctataaagt ttggtcttat cgaaaaatat atatcagact tttatcttaa ttttataacg    300
tcagctgata taaaaaagtt gaataaaaaa attgcagtag tagggtcagg tccagcagga    360
ttgagtattg cctttataat ggcaagaaag ggatatgatg taactatatt tgaatcccat    420
gaagatatag gaggagtttt gagatacggc atacctgcct ttagacttcc taaagatatt    480
ttggacaggc ttaaggataa acttctccat atgagagtta agataaggcc taatactctt    540
ataggacctg tgataactgt tgaagatttg tttagggatg gatacagggc ggtttatata    600
ggaacaggag tgtggagccc aaggagcttg ggacttaaag gagaaactta tggtaatgtg    660
aattatgcca tagattatct taaaaatcct gaggcctata atttgggaga taaagttgca    720
attataggag caggaaatgt tgctatggat gctgcaagga ctataattag aaatggatca    780
aatgacgtaa ctatcattgc aaggagtgat gaagaacatg caggagcaga taatatagaa    840
attgattatg ccaaacttga tggagtgaaa tttctctata aaatggcacc agttgaaata    900
acagatgatg gaattaaagt agttccaact gaggtgtcct ttgatgaaaa tacagggaaa    960
aagaaagtaa cgttaaaaga tgaggaaaca aagcttttta atgcagattc tataataatt   1020
gctgtaggcc agggacctaa ggcaaatata gtaaacaatt ctgaaggaat agaagtaaat   1080
tccaaaggac ttatacagac agacgattca ggaagaacta caaggtctgg agtttttgca   1140
tcaggtgatg tggtaacagg tgccaaaacc gttgttgaag cagtagaggt ttcaaagcac   1200
cttgtaaatg ctatggaaga atatataaag agtatggata agaaatttga aagttcagat   1260
aaaaattaa                                                           1269
```

<210> SEQ ID NO 67
<211> LENGTH: 1269
<212> TYPE: DNA
<213> ORGANISM: Clostridium coskatii

<400> SEQUENCE: 67

```
ttggataaaa ttgtttttgg tgaagctaat agatgtcttg gatgtaaagt gcctcaatgt     60
aaaaaaggat gccctgtaag taccccctata aatgaagtaa taaaactttt taaagagaat    120
aaaataaagg aagccggtaa acttcttttt gaaaataacc ctatgtcagc tatttgttcg    180
caagtttgtc ctcatgaaaa gttttgtgaa ggtcattgtg tgcttggtaa aaagggaact    240
cctataaagt ttggccttat cgaaaaatat atatcagact tttatcttaa ttttataacg    300
tcagctgata taaaaaagtt gaataaaaaa attgcagtag tagggtcagg tccagcagga    360
ttgagtattg cttttataat ggcaagaaag ggatatgatg taactatatt tgaatcccat    420
gaagatatag gaggagtttt gagatacggc atacctgcct ttagacttcc taaagatatt    480
ttggacaggc ttaaggataa acttttccat atgggagtta agataaggcc taatactctt    540
ataggacctg taataactgt tgaagatttg tttagggatg gatacagggc agtttatata    600
ggaacaggag tatggagtcc aaggagcttg ggacttaaag gagaaactta tggtaatgtg    660
aattatgcta tagattatct taaaaatcct gaggcttata atttgggaga taaagttgca    720
attataggag caggaaatgt tgctatggat gctgcaagga ctataattag aaatggatca    780
aatgacgtaa ctatcattgc aaggagtgat gaagaacatg caggagcaga taatatagaa    840
attgattatg ccaaacttga tggagtgaaa tttctttata aaatggcacc agttgaaata    900
```

```
acagatgatg gaattaaaat agttccaact gaggtatcct ttgatgaaaa tacagggaaa    960
aagaaggtaa tgctaaaaga tgaggaagca aagcttttta atgcagattc tataataatt   1020
gctgtaggcc agggacctaa ggcaaatata gtaaacaatt ctgaaggaat agaagtaaat   1080
tccaaaggac ttatacagac agacgattca ggaagaacta caaggtctgg agtttttgca   1140
tcaggtgatg tggtaacagg tgccaaaact gttgttgaag cagtagaggt ttcaaagcac   1200
cttgtaagtg ctatggaaga atatataaag agtatggata agaaatttga aagttcagat   1260
aaaaattaa                                                           1269
```

```
<210> SEQ ID NO 68
<211> LENGTH: 1269
<212> TYPE: DNA
<213> ORGANISM: Clostridium ragsdalei
```

```
<400> SEQUENCE: 68
```

```
ttggataaag ttgtttttgg tgaagctaat agatgtctcg gatgcaaagt acctcaatgt     60
aaaaaaggat gccctgtaaa taccccctata aatgaagtaa taaaattttt taaagagaat    120
aaaataaagg aagctgggaa acttcttttt gaaaataacc ccatgtcagc tatttgttca    180
caagtttgtc cgcatgaaaa gttttgtgaa ggccattgtg tgcttggcaa aaaaggaact    240
tctataaagt ttggacttat cgaaaaatat atatcggact tttaccttaa ttttataacg    300
tcagctgata taaaaaagtt gaataaaaaa attgcagtag taggatcagg tccagcagga    360
ttgagtattg cttttataat ggcaagaaag ggatatgatg taactatatt tgaatcccac    420
gaagatatag gaggagtttt gagatacggc atacctgcat ttagactgcc taaagatatt    480
ttggacaggc ttaaggataa acttttccat atgggagtta agataaggcc taataccctt    540
ataggacctg tgataactgt tgaagatttg tttagagatg gatacagggc agtttatata    600
ggaacaggag tatggagccc gaggagcttg ggacttaaag gagaaactta tggtaatgtg    660
aattatgcca tagattatct taaaaaccct gagtcttata atttgggaga taaagttgca    720
attataggcg caggaaatgt tgctatggat gctgcaagga ccataattag aaatggatca    780
aatgacgtaa ctatcattgc aaggagtgat gaagaacatg caggagcaga taacatagaa    840
attgattatg ccaaacttga tggagtgaaa tttctctata aaatggcacc agttgaaata    900
acagatgatg gaataaagat agttccaact gaggtatctt ttgatgaaaa taccggaaaa    960
aagaaagtaa tgctaaagga tgaggaagca aagcttttta atgcagattc tataataatt   1020
gctgtaggcc agggacctaa ggcaaatata gtaaacaatt ctgaaggaat agaagtgaat   1080
ttcagaggac ttatacagac agatgattca ggaagaacta caaggtctgg agtttttgca   1140
tcaggtgatg tggtgacagg tgccaaaact gttgttgaag cagtagaggt ttcaaaacac   1200
cttgtaaatg ctatggaaga atatataaag agtatggata agaaatatga agattcagat   1260
aaaaattaa                                                           1269
```

```
<210> SEQ ID NO 69
<211> LENGTH: 1038
<212> TYPE: DNA
<213> ORGANISM: Clostridium autoethanogenum
```

```
<400> SEQUENCE: 69
```

```
atgtatagtt ttaaaaatga ttatagtgaa ggagctcatc caagaatatt aaatgcttta     60
gttgaatcaa atatggagca aacttcaggt tacggtgaag atatatatac aaaaaaagct    120
gttgagcttt taaagcaaaa aattaagcga gacgatgccc acattcacct gtttgttgga    180
```

```
ggcacacagg caaatctcac tgcaatttca gctttttttaa gacctcatga agcagctatt    240

gctgctaata caggacatat actagttcac gagacaggag ctatagaagc cacggggcat    300

aagattatct ctataaaagt aagcaatggc aaactaagtc ctgaagacat caaacctgcc    360

ttatatgaac atgccgatga acatatggta aaacctaagc tagtgtatat ctcaaactct    420

acagaaattg gttctatata taaaaaaagc gaactagaaa aactaagcaa attttgcaaa    480

gaaaataaac tgcttttata catagatggc gcaaggttag gttcggccct atgttcagaa    540

gaaaatgatg tgggactttc tgatttagct aaattagcag atgcattcta tataggtggg    600

accaaaaatg gtgcgctaat gggtgaggct atggtcatat gtaacaactc acttaaagaa    660

gactttcgat tttatattaa acaaaaggga gcattgcttg caaaaggtag acttcttgga    720

atacaattct tagaactttt caaagatgac ttatattttg atttggcaaa gcatgcaaat    780

gccatggcag atttacttag gaaggaaatc agtaaggctg gatattcatt tttgacccac    840

tcgccttcaa atcagatatt cccaatctta ccaaacagat tgattgaaaa gcttgggaat    900

aaatattctt ttacaatttg gcaaaaatca gatgaatata actctgttat tcgccttgta    960

acttcttggg caacaaaaga gtctatggtt ttagatttta ttaatgatct aaaaaaattt   1020

actgaaatta atatgtaa                                                  1038
```

```
<210> SEQ ID NO 70
<211> LENGTH: 1032
<212> TYPE: DNA
<213> ORGANISM: Clostridium ljungdahlii

<400> SEQUENCE: 70

atgtatagtt ttaaaaatga ttatagtgaa ggagctcatc caagaatatt aaatgcttta     60

gttgaatcaa atatggagca aacttcaggt tacggtgaag atatatatac agaaagagct    120

gttgagcttt tgaagcaaaa aattaagcga gatgatgccc acattcacct gtttgttgga    180

ggcacacagg caaatctcac tgcaatttca gcttttttaa gacctcatga agcagctatt    240

gctgctaata caggacatat actagttcac gagacaggag ctatagaagc tacagggcat    300

aagattatct ctataaaagt aagcaatggc aaactaagtc ccgaagacat caaacctgcc    360

ttagatgaac ataccgatga gcatatggta aagcctaaac tagtgtacat ctcaaactct    420

acagaaattg gttctatata taaaaaaagc gaactagaaa aactaagcaa attttgcaaa    480

gaaaataaac tgcttttata catagatggc gcaaggttag gttcggccct atgttcagaa    540

gaaaatgatg tggaactttc tgatttagct agattagcag atgcgttcta tataggtggg    600

accaaaaatg gtgcgctaat gggtgaggct atggtcatat gtaacaactc acttaaagaa    660

gactttcgat tttatattaa acaaaaggga gcattgcttg caaaaggtag acttcttgga    720

atacaattct tagaactttt caaagatgac ttatattttg atttggcaaa gcatgcaaat    780

gtcatggcag atttacttag gaaggaaatc agtaaggctg gatattcatt tttgacccac    840

tcgccttcaa atcagatatt cccaatctta ccaaacaagt tgattgaaaa gcttggaaat    900

aaatattctt ttacaatttg gcaaaaatca gataaatata actccgttat tcgccttgta    960

acttcttggg caacaaaaga gtctatggct ttagatttta ttaatgattt aaaaaaattt   1020

actgaagtgt aa                                                        1032
```

```
<210> SEQ ID NO 71
<211> LENGTH: 1035
<212> TYPE: DNA
```

<213> ORGANISM: Clostridium coskatii

<400> SEQUENCE: 71

```
atgtatagtt ttaaaaatga ttatagtgaa ggagctcacc caagaatatt aaatgcttta     60
gttgaatcaa atatggagca aacttcaggt tacggtgaag atatatatac agaaaaagct    120
gttgagcttt tgaaacaaag aattaagcaa aacgatgttc acattcacct gtttgttgga    180
ggcacacagg caaatctcac tgcaatttca gctttttttaa gacctcatga agcagctatt    240
gctgctaata caggacatat actagttcac gagacaggag ctatagaagc tacagggcat    300
aagattatct ctataaaagt aagcaatggc aaactaagtc ccgaagacat caaacctgcc    360
ttagatgaac ataccgatga gcatatggta aagcctaaac tagtgtacat ctcaaactct    420
acagaaattg gttctatata taaaaaaagc gaactagaaa aactaagcaa attttgcaaa    480
gaaaataaac tgcttttata catagatggc gcaaggttag gttcggccct atgttcagaa    540
gaaaatgatg tggaactttc tgatttagct agattagcag atgcgttcta tataggtggg    600
accaaaaatg gtgcgctaat gggtgaggct atggtcatat gtaacaactc acttaaagaa    660
gactttcgat tttatattaa acaaaaggga gcattgcttg caaaaggtag acttcttgga    720
atacaattct tagaactttt caaagatgac ttatattttg atttggcaaa gcatgcaaat    780
gtcatggcag atttacttag gaaggaaatc agtaaggctg gatattcatt tttgacccac    840
tcgccttcaa atcagatatt cccaatctta ccaaacaagt tgattaaaaa gcttgggaat    900
aaatattctt ttacaatttg gaaaaaatca gatgaatata actctgttat tcgccttgta    960
acttcttggg caacaaaaga gtctatggtt tcaggcttta ttgaggatct aaaaaaattt   1020
aatgaaatta agtaa                                                    1035
```

<210> SEQ ID NO 72
<211> LENGTH: 1038
<212> TYPE: DNA
<213> ORGANISM: Clostridium ragsdalei

<400> SEQUENCE: 72

```
atgtatagtt ttaaaaatga ttatagtgaa ggagctcatc caagaatatt aaatgcttta     60
gttgaatcaa atatggagca aacttcaggt tacggtgaag atatatatac agaaagagct    120
gttaagcttt tgaagcaaaa aattaagcga gacgatgccc acattcacct gtttgttgga    180
ggcacacagg caaatctcac tgcaatttca gctttttttaa gaccccatga agcagctatt    240
gctgctaata caggacatat actagttcac gagacaggag ctatagaagc tacagggcat    300
aagattatct ctataaaagt aagcaatggc aaactaagtc ccgaagacat caaacctgcc    360
ttagatgaac atgccgatga acatatggta aaacctaagc tagtgtacat ctcaaactct    420
acagaaattg gttctatata taaaaaaagc gaattagaaa aactaagcaa attttgcaaa    480
gaaaataaac tgcttttata catagatggt gcaaggttag gttcggccct atgttcagaa    540
gaaaatgatg ttgaactttc tgatttagct agattagcag atgcgttcta tataggtgga    600
actaaaaatg gtgcgctaat gggtgaggct atggtcatat gtaacaactc acttaaagaa    660
gactttcgat tttatattaa acaaaaggga gcattacttg caaaaggtag gcttcttgga    720
atacaattct tagaactttt caaagatgac ttatattttg atttggcaag gcatgcaaat    780
gccatggcag atttacttag gaaggaaatc agtaaggctg gatattcatt tttgacccac    840
tcgccttcaa atcagatatt cccaatctta ccaaacaaat tgattgaaaa gcttgggaat    900
aaatattctt ttacaatttg gaaaaaatca gatgaatata actctgttat tcgccttgta    960
```

acttcttggg caacaaaaga gtctatggtt ttagatttta ttaatgattt aaaaaaattt 1020
actgaaattg atatgtaa 1038

<210> SEQ ID NO 73
<211> LENGTH: 2274
<212> TYPE: DNA
<213> ORGANISM: Clostridium autoethanogenum

<400> SEQUENCE: 73
atgtacaaga ttgttaacaa aaaagagtta tcaccaaaca tattcttaat ggatattgag 60
gcaccaagag ttgccaagtc ctgtttacca ggacaattta tcatagtcaa aatggatgat 120
aaaggggaaa gaatacctct tactatctgt gattatgatg caggaaaagg aactgttact 180
attgtatttc agacattagg agcttcaact aaaaaaatgg ctaaatatga agtgggagaa 240
tattttgaag attttgttgg accacttgga cattgctcag aacttgtaga gatggatctt 300
aaagaactta agaagaaaaa tataatgttt gtagcaggtg gtgtaggtac tgcaccagtt 360
tatccacagg taaagtggct tcatcagcat ggggtagagg cagatgttat agttggatgt 420
aaatcaaaag attatctatt atttgaagat gaattaaaac caatttgtgg gaatttatat 480
atagcaacgg atgatggaag ttatggatat aaaggatttg ttacggatct tttaaaagag 540
cttattgaca agaaagataa agagtacgat tgtgtagttg ccatagggcc tatgataatg 600
atgaagttta taactcaagt tacgaaacaa tacggaatta aaacaatagt aagtttaaat 660
actataatgg tagatggaac tggaatgtgc ggagcttgta gggttactgt aggtggagaa 720
ttaaaatttg cctgtgtaga tggtcctgaa tttgatggtc atcttgtaaa ttttgacgaa 780
gctatgagaa gacaggctat gtataaaact gaagaaggaa agaaacttct gaaagaagaa 840
gaaggagaca cttttgatag aaaaggctgt gagtgtcaca atgaagataa agctgctagg 900
atgaaaagag tacctataaa ggaacaggat cctaaagtta gagctactaa ttttgatgaa 960
gtttgcttgg gatacactga agaagaagct gtaaaagaag cttcaagatg cttgaattgt 1020
aaaaagccta tgtgtgttac tcagtgccct gttacaataa ctatacctaa gtttgttgaa 1080
caggtaaaaa atagaaactt tgaagaagct gctaaaataa tagcagaatc aagtgcactt 1140
cctgctgtat gtggaagagt atgtcctcag gaaactcagt gtgaaggaaa atgtgtactt 1200
ggcaaaaaag gtgatgctgt tgctataggt aagctggaaa gatttgtagc agattggtca 1260
agaaagaata atatcgattt atctaagact ttacctaaaa acggcaaaaa agtagctgtt 1320
ataggaagtg gtccttcagg acttacttgt gcaggagatt tagcaaagct tggatatgac 1380
gttactatat ttgaagcact tcatgaagca ggaggagtac ttgtatatgg tattccagag 1440
ttcagacttc caaaggatac tgtagtaaaa catgaagttg aaaatgtaaa gaaattagga 1500
gtaaaaatag agacagatgt aataatagga agaactgtta ctatagatga actagtagaa 1560
aaagaaaaat ttgatgctgt atttataggt tcaggagcag gactaccaag gtttatggga 1620
atacctggag aaaacttaaa tggagtattc tctgcaaatg aattcttaac aagaagtaat 1680
ttaatgaaag catataggga tgattatgca actcctataa aagctggtaa gaaagtagct 1740
gtagtaggag gcggaaacgt agctatggac tctgcaagga cagctctaag acttggagca 1800
gaagtataca tagtatacag aagatccgaa gcagaacttc cagcaagagc agaggaagta 1860
caccatgcaa aagaggaagg aataaagttc aatcttttaa ctaatcctgt agaaatatta 1920
ggagatgaaa aaggttgggt taatggaata cgctgtatta agatggaact tggagaacca 1980

```
gatgcatctg gaagaagaaa accagttgca ataaagggct cagaatttga tttagatgta   2040

gatactgtaa ttatggccct tggtacttca ccaaatccac ttatatcaac tacaacaaaa   2100

ggacttgaaa tgaataagcg taaatgctta atagcagaag aagagactgg acttactaca   2160

agagaaggaa tatatgcagg tggagatgca gtaacaggtg ctgctactgt aatacttgcg   2220

atgggtgcag gtaaaaaagc tgctaaggct atagatgaat atctgaaaaa ataa         2274
```

<210> SEQ ID NO 74
<211> LENGTH: 2322
<212> TYPE: DNA
<213> ORGANISM: Clostridium ljungdahlii

<400> SEQUENCE: 74

```
atgggcatag attttatgat ttatgtacta aaaaaatggc ataaaagtat gtacaagatt     60

gttaacaaaa aaaagttatc accaaacata ttcttaatgg atattgaggc accaagagtt    120

gcaaagtcct gtttaccagg acaatttatc atagtcaaaa tggatgataa aggggaaaga    180

atacctctta ctatctgtga ttatgatgca gaaaaaggaa ctgttactat tgtatttcag    240

acattaggag cttcaactaa aaaaatggct aaatatgaag tgggagaata ttttgaagat    300

tttgttggac cacttggaca ttgctcagaa cttgtagaga tggatcttaa agaacttaag    360

aagaaaaata taatgtttgt agcaggtgga gtaggtactg caccagttta tccacaggta    420

aaatggcttc atgaacatgg agttgctgca gatgttatag ttggatgtaa atcaaaagat    480

cttttattat ttgaagatga attgaaacca atttgtggaa atttatatat agcaacggat    540

gatggaagtt atggatataa gggttttgtt acggatcttt taaaagagat tattgacaag    600

aaagataaag agtacgattg tgtagttgcc atagggccta tgataatgat gaagtttata    660

actcaagtta cgaaacaata cggaattaaa acaatagtaa gtttaaatac tataatggta    720

gatggaactg gaatgtgcgg agcttgtagg gttactgtag gtggagaatt aaaatttgcc    780

tgtgtagatg gtcctgaatt tgatggacat cttgtaaatt ttgacgaagc tatgagaaga    840

caggctatgt ataaaactga agaaggaaag aaacttctta aagaagaaga aggggacacc    900

tttgatagaa aaggctgtga atgccacaag gaagataaag ctgatagaat gaaaagagta    960

cctataaagg aacaagatcc aaaggttaga gctactaatt ttgatgaagt ttgcttggga   1020

tacactgaag aagaagctgt aaaagaagct tcaagatgct tgaattgtaa aaagcctatg   1080

tgtgttaccc agtgccctgt tacaataact atacctaagt ttattgaaca ggtaaaaaat   1140

agaaactttg aagaagctgc taaaataata gcagaatcaa gtgcacttcc tgctgtatgt   1200

ggaagagtat gtcctcagga aactcagtgc gaaggaaaat gtgtacttgg caaaaaaggt   1260

gatgctgttg ctataggtaa gctagaaaga tttgtagcag attggtcaag aaagaataat   1320

atcgatttat ctaagacttt acctaaaaac ggcaaaaaag tagctgttat aggaagtggt   1380

ccttcaggac ttacttgcgc aggagattta gcaaaacttg gatatgatgt tactatattt   1440

gaagcacttc atgaagcagg aggggtactt gtatatggta ttccagaatt cagacttcca   1500

aaggacagtg tagtaaaaca tgaagttgaa aatgtaaaga agttaggagt aaaaatagag   1560

acagatgtaa taattgggag aactgttaca atagatgaac ttatagagaa agaaaaattt   1620

gatgctgtat ttataggctc aggagcagga ctaccaagat tcatgggaat acctggagaa   1680

aacttaaatg gagtattctc tgcgaatgaa ttcttaacaa gaagtaattt aatgaaagca   1740

tatagggatg attatgcaac tcctataaaa gcaggcaaaa aagtagctgt agtaggaggc   1800

ggaaacgtag ctatggactc tgcgaggacg gctctaaggc ttggagcaga agtatacata   1860
```

```
gtatacagaa gatctgaagc agaacttcca gcaagagcag aggaagtaca ccatgcaaaa   1920

gaagaaggaa ttaaattcaa tcttttaact aatcctgtag aaatattagg ggatgaaaaa   1980

ggttgggtta aaggaatacg ctgcattaag atggaactag gagaaccaga tgcatctgga   2040

agaagaaaac cagttgcaat aaagggttcg gaatttgatt tagatgtaga tactgtaatt   2100

atggctcttg gtacttcacc aaatccactt atatcaacta caacaaaagg acttgaaatg   2160

aataagcgta aatgcttaat agcagaagaa gagactggac tcactacaag ggaaggaata   2220

tatgcaggtg gagatgcagt aacaggtgct gctactgtaa tacttgcaat gggtgctggt   2280

aaaaaagctg ctaaggctat agatgaatat ctgaaaaaat aa                      2322
```

```
<210> SEQ ID NO 75
<211> LENGTH: 2334
<212> TYPE: DNA
<213> ORGANISM: Clostridium coskatii

<400> SEQUENCE: 75

atgaaaaggg aaatgggcat aaattttatg atttatgtac taaaaaaatg gcataaaagt     60

atgtacaaga ttgttaacaa aaaaaagtta tcaccaaaca tattcttaat ggatattgag    120

gcaccaagag ttgcaaagtc ctgtttacca ggacaattta tcatagtcaa aatggatgat    180

aaaggggaaa gaatacctct tactatctgt gattatgatg cagaaaaagg aactgttact    240

attgtatttc agacattagg agcttcaact aaaaaaatgg ctaaatatga agtgggagaa    300

tattttgaag attttgttgg accacttgga cattgctcag aacttgtaga gatggatctt    360

aaagaactta agaagaaaaa tataatgttt gtagcaggtg gagtaggtac tgcaccagtt    420

tatccacagg taaaatggct tcatgaacat ggagttgctg cagatgttat agttggatgt    480

aaatcaaaag atcttttatt atttgaagat gaattgaaac caatttgtgg aaatttatat    540

atagcaacgg atgatggaag ttatggatat aagggttttg ttacggatct tttaaaagag    600

attattgaca agaaagataa agagtacgat tgtgtagttg ccatagggcc tatgataatg    660

atgaagttta taactcaagt tacgaaacaa tacggaatta aaacaatagt aagtttaaat    720

actataatgg tagatggaac tggaatgtgc ggagcttgta gggttactgt aggtggagaa    780

ttaaaatttg cctgtgtaga tggtcctgaa tttgatggcc atcttgtaaa ttttgacgaa    840

gctatgagaa gacaggctat gtataaaact gaagaaggaa agaaacttct taaagaagaa    900

gaaggggaca cctttgatag aaaaggctgt gaatgccaca aggaagataa agctgataga    960

atgaaaagag tacctataaa ggaacaagat ccaaaggtta gagctactaa ttttgatgaa   1020

gtttgcttgg gatacactga agaagaagct gtaaaagaag cttcaagatg cttgaattgt   1080

aaaaagccta tgtgtgttac ccagtgccct gttacaataa ctatacctaa gtttattgaa   1140

caggtaaaaa atagaaactt tgaagaagct gctaaaataa tagcagaatc aagtgcactt   1200

cctgctgtat gtggaagagt atgtcctcag gaaactcagt gcgaaggaaa atgtgtactt   1260

ggcaaaaaag gtgatgctgt tgctataggt aagctagaaa gatttgtagc agattggtca   1320

agaaagaata atatcgattt atctaagact ttacctaaaa acggcaaaaa agtagctgtt   1380

ataggaagtg gtccttcagg acttacttgc gcaggagatt tagcaaaact tggatatgat   1440

gttactatat ttgaagcact tcatgaagca ggaggggtac ttgtatatgg tattccagaa   1500

ttcagacttc caaaggacag tgtagtaaaa catgaagttg aaaatgtaaa gaagttagga   1560

gtaaaaatag agacagatgt aataattggg agaactgtta caatagatga acttatagag   1620
```

```
aaagaaaaat ttgatgctgt atttataggc tcaggagcag gactaccaag attcatggga   1680
atacctggag aaaacttaaa tggagtattc tctgcgaatg aattcttaac aagaagtaat   1740
ttaatgaaag catataggga tgattatgca actcctataa aagcaggcaa aaaagtagct   1800
gtagtaggag gcggaaacgt agctatggac tctgcgagga cggctctaag gcttggagca   1860
gaagtataca tagtatacag aagatctgaa gcagaacttc cagcaagagc agaggaagta   1920
caccatgcaa aagaagaagg aattaaattc aatcttttaa ctaatcctgt agaaatatta   1980
ggggatgaaa aaggttgggt taaaggaata cgctgcatta agatggaact aggagaacca   2040
gatgcatctg gaagaagaaa accagttgca ataaagggtt cagaatttga tttagatgta   2100
gatactgtaa ttatggctct tggtacttca ccaaatccac ttatatcaac tacaacaaaa   2160
ggacttgaaa tgaataagcg taaatgctta atagcagaag aagagactgg actcactaca   2220
agggaaggaa tatatgcagg tggagatgca gtaacaggtg ctgctactgt aatacttgca   2280
atgggtgctg gtaaaaaagc tgctaaggct atagatgaat atctgaaaaa ataa         2334
```

<210> SEQ ID NO 76
<211> LENGTH: 2274
<212> TYPE: DNA
<213> ORGANISM: Clostridium ragsdalei

<400> SEQUENCE: 76

```
atgtacaaga ttgttaacaa aaaagagtta tcaccaaaca tattcttaat ggatattgag     60
gcaccaagag ttgccaagtc ctgtttacca ggacaattta tcatagtcaa aatggatgat    120
aaaggggaaa gaatacctct tactatctgt gattatgatg cagaaaaagg aactgttact    180
attgtatttc agacattagg agcttcaact aaaaaaatgg ctaaatatga agtgggagag    240
tattttgaag attttgttgg accacttgga cattgctcag aacttgtaga gatggatctt    300
aaagaactta agaagaaaaa tataatgttt gtagcagggg gtgtaggtac tgcaccagtt    360
tatccacagg taaaatggct tcatgaacat ggagttgctg cagatgttat agttggatgt    420
aaatcaaaag atcttttatt atttgaagat gaattgaaac caatttgtgg aaatttatat    480
atagcaacgg atgatgggag ttatggatat aagggctttg ttacgaatct tttgaaagaa    540
cttattgaca agaaagataa agaatatgat tgtgtaattg ccataggacc tatgataatg    600
atgaagttta taactcaagt tacgaaacca tatggaatta aaacaatagt aagtttaaat    660
actataatgg tagatggaac tggaatgtgc ggagcttgta gggttactgt aggtggagaa    720
ttaaaatttg cctgtgtaga tggtcctgaa tttgatggtc atcttgtaaa ttttgatgaa    780
gctatgagaa gacaagctat gtacaagact gaagaaggaa agaaacttct gcaagaagaa    840
gaaggggaca ctggaagtag agaaggtaaa aagtgtagag cagaagaaaa acttgaaaga    900
atgaaaagag tacctataaa ggaacaggat cctaaagtta gagctactaa ttttgatgaa    960
gtttgcttgg gatacactga agaagaagct gtaaaagaag cttcaagatg cttgaattgt   1020
aaaaagccta tgtgtgttac tcagtgccct gttacaataa ctatacctaa gtttgttgaa   1080
caggtaaaaa atagaaactt tgaagaagct gctaaaataa tagcagaatc aagtgcactt   1140
cctgctgtat gtggaagagt atgtcctcag gaaactcagt gtgaaggaaa atgtgtactt   1200
ggcaaaaaag gtgatgctgt tgctataggt aagctggaaa gatttgtagc agattggtca   1260
agaaagaata atatcgattt atctaagact ttacctaaaa acggcaaaaa agtagctgtt   1320
ataggaagtg gtccttcagg acttacttgt gcaggagatt tagcaaagct tggatatgac   1380
gttactatat ttgaagcact tcatgaagca ggaggagtac ttgtatatgg tattccagag   1440
```

```
ttcagacttc caaaggatac tgtagtaaaa catgaagttg aaaatgtaaa gaaattagga   1500

gtaaaaatag agacagatgt aataatagga agaactgtta ctatagatga actagtagaa   1560

aaagaaaaat ttgatgctgt atttataggt tcaggagcag gactaccaag gtttatggga   1620

atacctggag aaaacttaaa tggagtattc tctgcaaatg aattcttaac aagaagtaat   1680

ttaatgaaag catataggga tgattatgca actcctataa aagctggtaa gaaagtagct   1740

gtagtaggag gcggaaacgt agctatggac tctgcaagga cagctctaag acttggagca   1800

gaagtataca tagtatacag aagatccgaa gcagaacttc cagcaagagc agaggaagta   1860

caccatgcaa aagaggaagg aataaagttc aatcttttaa ctaatcctgt agaaatatta   1920

ggagatgaaa aaggttgggt taatggaata cgctgtatta agatggaact tggagaacca   1980

gatgcatctg gaagaagaaa accagttgca ataaagggat cagaatttga tttagatgta   2040

gatactgtaa ttatggccct tggtacttca ccaaatccac ttatatcaac tacaacaaaa   2100

ggacttgaaa tgaataagcg taaatgctta atagcagaag aagagactgg actcactaca   2160

agagaaggaa tatatgcagg tggagatgca gtaacaggtg ctgctactgt aatacttgca   2220

atgggtgcag gtaaaaaagc tgctaaggct atagatgaat atctgaaaaa ataa         2274
```

<210> SEQ ID NO 77
<211> LENGTH: 1185
<212> TYPE: DNA
<213> ORGANISM: Clostridium autoethanogenum

<400> SEQUENCE: 77

```
atgttatctg aggaaagaaa aagtgaagta attgaattgt gcaaaaagct tataagaact     60

agaagttatt ctggacaaga agaaaatgtg gcaaatgtta taaaagtcgc atttaataat    120

atgggttttg acgacttttt tatagatgat tatggtaata taataggcca tataaaaggt    180

aaagaaaagg gaaagtccat attgtttgat ggacatatgg atactgtacc tgtagtggat    240

gagagtgagt ggacataccc tccttttgct gcccaaattc atgatggcaa aatgtacgga    300

aggggaacat cagatatgaa aggcgccctg tgtgccatga tatgtggagt ttcttatttt    360

gctaaggatg ttaagaagaa gtttaaaggt gacatatatg tagcaggagt tgtacatgaa    420

gagtgttttg aaggagttgc ctctagaaaa ataagcgcta aagtaaatcc tgattatgtg    480

gtaattggag aagcatcaaa ctgcaattta aagataggac agaggggaag agctgaaatt    540

ttagttgaaa cctttggaaa gtctgctcac tcagctaatc ctgaaaaggg aataaatgca    600

gtatataaga tgaacaagct tatagaggct ataagaaagt taaaactcag cagccatgat    660

tttctcggcg atggaatact tgaacttaca gatataaaat cttcaccata tccaggggca    720

tctgtagttc ctgattactg tagagcaaca tttgatagaa ggcttcttgt aggagaaact    780

aggaaaagtg tacttaagcc tatacagaat attattacag aacttgaaaa acaagatgaa    840

aattttaaag ctaaagtaag tttttcaagg gggaaagaga tgtgttatac aggtgtggaa    900

atagaagggg aaagattctt tcctgcatgg ctttatgata gaaaagatga atttgttaaa    960

aagtcttatg atggtttagt aaaagctgga attaatcctg aaataactca ctattctttt   1020

tgtacaaatg gaagccatta tgcaggggaa gcaggaataa aggctatagg ttttggacct   1080

tcaaaggaaa atttagcaca tacagtaaat gaatatattg aaatatcaca atttgaaaaa   1140

gctgtagaag ggtattattc aattcttaaa gcagtgcttt cctaa                   1185
```

<210> SEQ ID NO 78

<211> LENGTH: 1185
<212> TYPE: DNA
<213> ORGANISM: Clostridium ljungdahlii

<400> SEQUENCE: 78

```
atgttatctg aggaaagaaa aagtgaagta attgaattgt gcaaaaagct tataagaact     60
agaagttatt ctggacaaga agaaaatgtg gcaaatgtta taaaagtcgc atttaataat    120
atgggttttg acgacttttt tatagatgat tatggtaata taataggcca tataaaaggt    180
aaagaaaagg gaaagtccat attgtttgat ggacatatgg atactgtacc tgtagtggat    240
gagagtgagt ggacataccc tccttttgct gcccaaattc atgatggcaa aatgtacgga    300
aggggaacat cagatatgaa aggcgccctg tgtgccatga tatgtggagt ttcttatttt    360
gctaaggatg ttaagaagaa gtttaaaggt gacatatatg tagcaggagt tgtacatgaa    420
gagtgttttg aaggagttgc ctctagaaaa ataagcgcta aagtaaatcc tgattatgtg    480
gtaattggag aagcatcaaa ctgcaattta aagataggac agaggggaag agctgaaatt    540
ttagttgaaa cctttggaaa gtctgctcac tcagctaatc ctgaaaaggg aataaatgca    600
gtatataaga tgaacaagct tatagaggct ataagaaagt taaaactcag cagccatgat    660
tttctcggcg atggaatact tgaacttaca gatataaaat cttcaccata tccaggggca    720
tctgtagttc ctgattactg tagagcaaca tttgatagaa ggcttcttgt aggagaaact    780
aggaaaagtg tacttaagcc tatacagaat attattacag aacttgaaaa acaagatgaa    840
aattttaaag ctaaagtaag tttttcaagg gggaaagaga tgtgttatac aggtgtggaa    900
atagaagggg aaagattctt tcctgcatgg ctttatgata gaaaagatga atttgttaaa    960
aagtcttatg atggtttagt aaaagctgga attaatcctg aaataactca ctattctttt   1020
tgtacaaatg gaagccatta tgcaggggaa gcaggaataa aggctatagg ttttggacct   1080
tcaaaggaaa atttagcaca tacagtaaat gaatatattg aaatatcaca atttgaaaaa   1140
gctgtagaag ggtattattc aattcttaaa gcagtgcttt cctaa                   1185
```

<210> SEQ ID NO 79
<211> LENGTH: 1185
<212> TYPE: DNA
<213> ORGANISM: Clostridium ragsdalei

<400> SEQUENCE: 79

```
atgttatctg aggaaagaaa aagtgaagta attgaattgt gtaaaaagct tataagaact     60
agaagttatt ctggagaaga agaaaatgtg gcaaatgtta taaaagttgc atttaataat    120
atgggttttg acgacttttt tatagatgat tacggcaata taataggcaa tataaaaggt    180
aaagaaaagg gaaagtccat attgtttgat ggacatatgg atactgtacc tgtagtggat    240
gagagtgagt ggacataccc cccttttgct gcccaaattc atgatggcaa aatgtacggg    300
aggggaacat cagatatgaa aggcgccctg tgtgccatga tatgtggagt ttcttatttt    360
gctaaggatg ttaagaagaa gtttaaaggt gacatatatg tagcaggagt tgtacatgaa    420
gagtgttttg aaggagttgc ctctagaaaa ataagcgcta aagtaaatcc tgattatgtg    480
gtaattggag aagcatcaaa ctgcaattta aagataggac agaggggaag agctgaaatt    540
ttagttgaaa cctttggaaa gtctgcccac tcagctaatc ctgaaaaggg aataaatgca    600
gtatataaga tgaacaagct tatagaggct ataagaaagt taaaactcag cagccatgat    660
tttctcggcg atggaatact tgaacttaca gatataaaat cttcaccata tccaggagca    720
tctgtagttc ctgattactg cagagcaaca tttgatagaa ggcttcttgt aggagaaact    780
```

```
aggaaaagtg tacttaagcc tatacaggat attattacag aacttgaaaa acaagatgaa    840

aattttaaag ctaaagtaag tttttcaagg ggtaaagaga tgtgttatac aggggtggaa    900

atagaagggg aaagattttt tcctgcatgg ctttatgata gaaaagatga atttgttaaa    960

aagtcttatg atggtctagt aaaagctgga attaatcctg aaataactca ctattctttt   1020

tgtacaaatg gaagccatta tgcaggggaa gcagggataa aggctatagg ttttggacct   1080

tcaaaggaaa atttagctca tacagtaaat gaatatattg aaatatcaca atttgaaaaa   1140

gccgtagaag ggtattattc aattcttaaa gcagtgcttt cctaa                   1185
```

<210> SEQ ID NO 80
<211> LENGTH: 1209
<212> TYPE: DNA
<213> ORGANISM: Clostridium autoethanogenum

<400> SEQUENCE: 80

```
atggcattag atttgaataa agaaaaaata ttggatatgg cagaaaagta taaacctgaa     60

atatgtagat ttttaaggga catggctcaa attccaagtg aaagctgtgg agaagaaaaa    120

gttatactta gaataaaaca ggaaatggaa aaagtaggtt ttgacaaagt agaaatagat    180

cccatgggca atgtacttgg atatatagga catggaaaac acctaattgc catggatgct    240

catatagata cagtagggat aggtgataga aatctatgga aatacgatcc ttatgaaggc    300

tatgaagatg atgaggttat tttaggaaga ggtgtcacag accaggaggg aggaatggcc    360

tccatggttt atgcaggtaa gataattaaa gatcttggac ttgaaggaga ttatacatta    420

gtagtaacag gtactgttca agaagaagat tgtgatggat tatgctggca gtatatagtc    480

aatgaagata aagtaaagcc ggaatttgta gttataacag aaccaacttc attaaatata    540

tatagaggac atagaggaag aatggagata aaagttacaa cccatggaat tagctgtcat    600

ggttctgcac cggaaagagg agataatgca atttttaaaa tggctcctat attaaatgag    660

ctaaaggatt taaatgaaaa attaatcaat gatgaatttt taggaaaggg tacattaacc    720

gtatctgaaa tattcttttc atcaccttca agatgtgctg tagcagatgg atgtagtatt    780

tctgttgaca gaaggcttac tgctggtgaa acctgggagt atgcaattga tcagattaag    840

aatttacctt cagttaaggc tgcaaaggct gaagttgaaa tgtacactta tgaaagacct    900

tcttatacag gattaaagta tccaacggaa tgtttcttcc caacctgggt actgcctgaa    960

gatcataaag tatgtcaaaa tgttgtaact tgctataagg atttatttaa gagtgaacca   1020

aaggtagata aatggacatt ttctacaaat gcagtttcca ttatgggaag atataaaata   1080

ccatgtatag gttttggacc aggccacgaa gatcaagcac atgcacctaa tgaaaagaca   1140

tggaaagatg aattagtaaa atgtgcagca atgtatgcgc ttattccaat atcctatgtg   1200

actaaataa                                                           1209
```

<210> SEQ ID NO 81
<211> LENGTH: 1209
<212> TYPE: DNA
<213> ORGANISM: Clostridium ljungdahlii

<400> SEQUENCE: 81

```
atggcattag atttgaataa agaaaaaata ttggatatgg cagaaaagta taaacctgaa     60

atatgtagat ttttaaggga catggctcaa attccaagtg aaagctgtgg agaagaaaaa    120

gttatactta gaataaaaca ggaaatggaa aaagtaggtt ttgacaaagt agaaatagat    180
```

```
cccatgggca atgtacttgg atatatagga catggaaaac acctaattgc catggatgct    240
catatagata cagtagggat aggtgataga aatctatgga aatacgatcc ttatgaaggc    300
tatgaagatg atgaggttat tttaggaaga ggtgtcacag accaggaggg aggaatggcc    360
tccatggttt atgcaggtaa gataattaaa gatcttggac ttgaaggaga ttatacatta    420
gtagtaacag gtactgttca agaagaagat tgtgatggat tatgctggca gtatatagtc    480
aatgaagata aagtaaagcc ggaatttgta gttataacag aaccaacttc attaaatata    540
tatagaggac atagaggaag aatggagata aaagttacaa cccatggaat tagctgtcat    600
ggttctgcac cggaaagagg agataatgca atttttaaaa tggctcctat attaaatgag    660
ctaaaggatt taaatgaaaa attaatcaat gatgaatttt taggaaaggg tacattaacc    720
gtatctgaaa tattcttttc atcaccttca agatgtgctg tagcagatgg atgtagtatt    780
tctgttgaca gaaggcttac tgctggtgaa acctgggagt atgcaattga tcagattaag    840
aatttacctt cagttaaggc tgcaaaggct gaagttgaaa tgtacactta tgaaagacct    900
tcttatacag gattaaagta tccaacggaa tgtttcttcc caacctgggt actgcctgaa    960
gatcataaag tatgtcaaaa tgttgtaact tgctataagg atttatttaa gagtgaacca   1020
aaggtagata aatggacatt ttctacaaat gcagtttcca ttatgggaag atataaaata   1080
ccatgtatag gttttggacc aggccacgaa gatcaagcac atgcacctaa tgaaaagaca   1140
tggaaagatg aattagtaaa atgtgcagca atgtatgcgc ttattccaat atcctatgtg   1200
actaaataa                                                           1209
```

<210> SEQ ID NO 82
<211> LENGTH: 1209
<212> TYPE: DNA
<213> ORGANISM: Clostridium coskatii

<400> SEQUENCE: 82

```
atggcattag atttgaataa agaaaaaata ttggatatgg cagaaaagta taaacctgaa     60
atatgtagat tttaaggga catggctcaa attccaagtg aaagctgtgg agaagaaaaa    120
gttatactta gaataaaaca ggaaatggaa aaagtaggtt ttgacaaagt agaaatagat    180
cccatgggca atgtacttgg atatatagga catggaaaac acctaattgc catggatgct    240
catatagata cagtagggat aggtgataga aatctatgga aatacgatcc ttatgaaggc    300
tatgaagatg atgaggttat tttaggaaga ggtgtcacag accaggaggg aggaatggcc    360
tccatggttt atgcaggtaa gataattaaa gatcttggac ttgaaggaga ttatacatta    420
gtagtaacag gtactgttca agaagaagat tgtgatggat tatgctggca gtatatagtc    480
aatgaagata aagtaaagcc ggaatttgta gttataacag aaccaacttc attaaatata    540
tatagaggac atagaggaag aatggagata aaagttacaa cccatggaat tagctgtcat    600
ggttctgcac cggaaagagg agataatgca atttttaaaa tggctcctat attaaatgag    660
ctaaaggatt taaatgaaaa attaatcaat gatgaatttt taggaaaggg tacattaacc    720
gtatctgaaa tattcttttc atcaccttca agatgtgctg tagcagatgg atgtagtatt    780
tctgttgaca gaaggcttac tgctggtgaa acctgggagt atgcaattga tcagattaag    840
aatttacctt cagttaaggc tgcaaaggct gaagttgaaa tgtacactta tgaaagacct    900
tcttatacag gattaaagta tccaacggaa tgtttcttcc caacctgggt actgcctgaa    960
gatcataaag tatgtcaaaa tgttgtaact tgctataagg atttatttaa gagtgaacca   1020
aaggtagata aatggacatt ttctacaaat gcagtttcca ttatgggaag atataaaata   1080
```

ccatgtatag gttttggacc aggccacgaa gatcaagcac atgcacctaa tgaaaagaca 1140
tggaaagatg aattagtaaa atgtgcagca atgtatgcgc ttattccaat atcctatgtg 1200
actaaataa 1209

<210> SEQ ID NO 83
<211> LENGTH: 1221
<212> TYPE: DNA
<213> ORGANISM: Clostridium ragsdalei

<400> SEQUENCE: 83
atggcattag atttgaataa agaaaaaata ttggatatgg cagaaaagta taaacctgaa 60
atatgtagat ttttaaggga tatggctcga attccaagtg aaagctgcgg cgaagaaaaa 120
gttatactaa gaataaaaga ggaaatggaa aaggtaggtt ttgacaaagt agaaatagat 180
cctatgggaa atgtacttgg atatatagga cacggaaaac accttattgc catggatgcc 240
catatagata cagtagggat aggtgataga aatctatgga aatatgatcc ttatgaaggc 300
tatgaagatg atgaggttat tttaggaaga ggtgtcacag accaggaggg aggaatggcc 360
tccatggttt atgcaggcaa gataattaaa gagcttggac ttgagggaga ttatacatta 420
gtagtaacag gtactgttca agaagaagat tgtgatggct tatgctggca gtatatagtc 480
aatgaagata aagtaaagcc ggaatttgta gttataacag aaccaacttc agtaaatata 540
tatagaggac ataggggaag aatggagata aaagttacaa cccatggaat tagctgccac 600
ggctctgcac cggagagagg agataatgca atttttaaaa tggctcctat attaaatgag 660
ctgaaggatt taaatgaaaa attaattaat gatgaatttt taggaaaggg tacattaacc 720
gtatctgaaa tattcttttc atcaccttca agatgtgccg tagcagatgg atgcagtatt 780
tctgttgaca gaaggcttac tgctggtgaa acctgggagt atgcaattga tcagattaag 840
aatttacctt cagttaaggc tgcaaaggct gaagttgaaa tgtacactta tgaaagacct 900
tcttatacag gattgaagta tccaacggaa tgtttcttcc caacctgggt actgcctgaa 960
gatcataaag tatgtcagaa tgttgtaact tgctataagg atttatttaa gagtgagcca 1020
aaggtagata aatggacatt ctctacaaat gcagtttcca ttatgggaag atataaaata 1080
ccatgtatag gttttggacc aggccatgaa gatcaagcac atgcacctaa tgaaaagacc 1140
tggaaagatg aattagtaaa atgtgcagca atgtatgcac ttattccaat atcctatgta 1200
aataattata cagacaaata a 1221

<210> SEQ ID NO 84
<211> LENGTH: 2145
<212> TYPE: DNA
<213> ORGANISM: Clostridium autoethanogenum

<400> SEQUENCE: 84
atggagaata aagtattaac tgtatgtcct tactgtggtg ctggttgcag actgtattta 60
gtggttgaag atgggaaaat taagagagct gagcctgcta tgggcagaac aaatgaggga 120
gagctttgtc ttaaaggtta ttatggatgg gattatttaa atgatcctaa gcttttaact 180
ccacgtataa ggaagcctaa gatacgaaaa aatggcaagc tcgaagaagt tacttgggat 240
gaagctatca gttttactgc aaaaagattg ggagaaataa gagacaagta tggcgctgat 300
tctataatgg gtactggttg ttctagaggt cctggaaatg aagctaacta tattatgcaa 360
aaatttatga gggctgttat tggaacaaat aatgtggaca actgtgctag agtttgtcat 420

```
ggaccttctg tagctggact tgctaaagtg ttgggaaatg gtgcaatgtc taatagcatt    480

cctgaaattg ataatgcaga cttggtattt atttttgggt ataatcctgc agaatctcat    540

cctatggtag caagaagaat agttaaggca agacaaaaag gtgcaaaaat agtagtagtg    600

gaccctaggg taacagaaag tgtaagaatt tcagatttat ggcttccgat aaagggtggt    660

actaatatgg cacttgtaaa cggttttgcc aatgttctta ttaatgaagg tttatacaat    720

aaagattatg tagaaaaata tacagaagga ttcgatgaat atattaaagt tataaagaaa    780

tatacacctg aatatgtaga aaaaatagta aatgtaccag cagaaaagat taaaaaagct    840

atggaaatgt atgcttcagc taaaaaccca atgatacttt atggtatggg agtatgtcaa    900

tttggtcaag ctgtagatgt ggtaaaagga ttagctggtt tggcactact aacaggaaat    960

tatggaaggc caagtgttgg aataggccct gtaagaggac aaaataatgt tcagggagcc   1020

tgtgatatgg gagcacttcc aaataatttt ccaggatatc agagtgttac agataaaaat   1080

gtgagagaaa aatttgaaaa agcttgggga gtaaaaaatc ttccagacaa aattggctat   1140

catttgactg aagtacctaa agcagtactg gaggaacata aattaaaggc atattatatt   1200

atgggtgaag attgtgttca aagtgatcca aattcaaatg aagtaaggga ggctttggat   1260

gagcttgaat ttgtagtagt tcaggacata tttatgaata aaactacatt acatgcagat   1320

gtaattttgc cagcaactgc ctggggagaa catgaagggg tatatagtgc tgcagataga   1380

ggattgcaaa agtttaacaa ggcagttgaa ccaattggtg aagcaaaacc tgattggcag   1440

ataatttgcg agttatcttc agctatggga tataaaatgc actataataa tacaaaggaa   1500

atatgggatg aaatgagaag cctttcacct aaatttgcag gtgcaactta tgagaaaatg   1560

gaaactttag atggtgtact ttggccatgt cctacagaag atcatccagg aactcctgtt   1620

ttgtatgaaa acaacgagtt tagtactccg agcaaaaagg gtattttatt tgcttcagaa   1680

tggagaccta cagaagaatc accagatgaa aaatatccgc ttagtttgtg tacagttaga   1740

gaaatagggc attactctgt aaggacaatg acaggaaatt gtcgtgctct acagcagcta   1800

gaagatgaac ctggaaaaat acagatgagt atagaagatg cagaagaact tggaattaaa   1860

acaggagatt tagttagagt atcttcaaaa agaggttctg tagtaacaag ggcaaatgtt   1920

acagatagag ttttaaaagg agctacttat atgacttatc aatggtggat tggtgcctgc   1980

aatgaactta cagtagataa tctggaccct atatcaaaaa ctccagaata taaatactgt   2040

gcagttaagg ttgaggcaat agaagatcaa gataaagctg aaaagtatat tgatgatact   2100

tataaagctt tgcgtgaaaa gttgggtatt gtaactgcaa attaa                   2145
```

<210> SEQ ID NO 85
<211> LENGTH: 2106
<212> TYPE: DNA
<213> ORGANISM: Clostridium ljungdahlii

<400> SEQUENCE: 85

```
atgaaaagta tactaactac ttgtccttat tgtggaacag gatgcacatt tttcttaaat     60

gtaagagatg gaaaaattgt tagtgtaacc ccagatgata atgcaaattc agtaaaccaa    120

gggaagctct gctcaaaagg ccgttttggt tttgactttg tacatcataa agatcgttta    180

actagtcctt tgataagaaa agcaggaaag ctggttgagg ttacatggga ggaagcaatt    240

ggctttattg tttctaaaat caaaaaaact gtaaaagaat atggttctga cagtgttgca    300

gcttttagtt cagcacgatg tactaatgaa gaaaactatc ttatgcaaaa attaatgcgc    360

gcagtgattg gtactaataa cgtcgatcat tgtgcccgtt tgtgacatgc tcctacagtg    420
```

```
tctggtctag gcacagcatt tggcagtgga gcaatgacaa actcaataca tgaacttgat    480

gaaatgggac ctgaagatgc tatttttgca attggtacaa ataccacaga atgtcatcct    540

ataattggta ttaaaatgct aaaagctaaa gaacgcggta ctaaactcgt agtggctgat    600

ccccgcaaaa cagatgtggc actacatgct gatgtttggc tgcggcataa accaggtaca    660

gatgtagcac ttctaaatgg aatgtcatat gtcatattga cagaaggact agctgataaa    720

gcatttattg ctgaaagaac tgagaatttt gaggatttca aagaagttgt aatgaaattc    780

acgccaaagt atacatcaag tataactaag gttccagcag acaagataat agaagctgca    840

agaattattg ctaaggctga tgctgctgct ttgtattata ctatgggtat tacgcagcat    900

actactggtg ttgataatgt actatctaca gcaaatatta tgatgcttac tggtaatatt    960

ggcaagccta aggaggagt taaccctctg cgtggtcaga ataacgtgca aggagcatgt   1020

gatatgggag ctttgcctaa tgtctacact ggttaccaat cagtaactaa tcctgatgtg   1080

aaagctaaat ttgaaaaagc atggaatgct cagttaagcg ataaagttgg acttaatatt   1140

ccgtctatct tgaatgcaat tgaaaaagat gaggtcaaaa tgctgtatgt atttggtgaa   1200

aatccaatgc gaagtgaccc tgatataaat catgtggaac actgcttgaa acatttggat   1260

tttttggttg ttcaagatat tttcttaact gaaacagctg aagttgctga tgttgttctt   1320

ccgggcgtat cctatgctga aaaagatgga acttttagta gtactgatcg tacagtgcag   1380

cgtattcgta aggctgtaga gccaataggt aatagtcttc cagattggca aatactcagg   1440

gatatcatga atgcaatgga ttatccagca gattatagtt ctcctgaaga tatatttgat   1500

gaaatgagat ctttaacacc aagttatgct ggtattagtt ataaacggtt ggaggacggt   1560

ggcattccat ggccatgtcc aaatgagaat catcttggga cacctatttt gcatgttggt   1620

aagttttccc gtggtttggg taagttttcc ccaattgagt atagggaacc tgctgagctt   1680

cctgataaag aatatccatt aatgctgact actggacgta tcgttactca ctaccataca   1740

gggactatga cgagacgttg ttggggacta aatggtgcgg atccagaagg atttttggaa   1800

attaacccta cagatgcaaa aaatcttaat attgaagatg gtgatgaaat tagtgcatca   1860

acacgacgtg gctcattaat tacaaaagca caagtaacaa ctagggtacc ggagggatta   1920

acatttatta ctttccattt tactgagagt ccagctaata ttttgactaa tagtgcccct   1980

gatcctgtta ctggaacacc tgaatttaaa gtttgctcgg taaagataaa aaaattagat   2040

ttttcagatt ttggatgtca aaagcgcaag attttccgta aaaagagtat gcgtaaagac   2100

gcttaa                                                              2106
```

<210> SEQ ID NO 86
<211> LENGTH: 2106
<212> TYPE: DNA
<213> ORGANISM: Clostridium coskatii

<400> SEQUENCE: 86

```
atgaagagta tactgactac ttgcccttat tgtggaacag gatgcacatt ttttttaaat     60

gtaagacaag gaaaaattgt tagtgtaacc ccaaataatg atgtaaattc agtaaaccaa    120

gagaagcttt gttcaaaagg gcgttttggg tttgattttg tacatcataa agatcgccta    180

actaatcctt tgatcagaaa agaagaaaag ctagctgaag ttacatgggg agaagcaatt    240

ggttttattg cttctaaaat taaaaaaact gtaaagaaat atggatctga cagcatagca    300

gcttttagtt ccgcacgatg tactaatgaa gaaaactatc ttatgcaaaa attaatgcgt    360
```

```
gcagtaattg gtactaataa cgtcgatcat tgtgcccgct tgtgacatgc tcctaccgtg    420

tctggtctag gcacagcatt tggcagtgga gcaatgacaa actcaataca tgaacttgat    480

gaaatggggc ctaaagatgc tatttttgca attggtacaa ataccacaga atgtcatcct    540

ataattggta ttaaaatgct aaaagctaaa gaacgcggta ctaaactcgt agtagctgat    600

ccacgtaaaa ctgatatggc actacatgct gatatttggc tgcggcataa accaggtaca    660

gacgtagcac ttttgaatgg aatgtcatat gtaatactta cagaagggct ggctgatgaa    720

gtgtttattg ctgaaagaac tgagaacttt gaggctttca aagaggttgc actgagattt    780

aacccagaat atacggccag cataactaaa gttccagcga aaaagataat agaagcggca    840

agaattattg ctaaggctga tgctgctgct ttgtattata ctatgggtat tacgcagcat    900

actacaggtg ttgataatgt actatctaca gcaaatatta tgatgcttac tggtaatatt    960

ggtaagccta aggaggagt taaccctctg cgtggtcaga ataatgtaca aggagcatgt   1020

gatatgggag ctttgcctaa tgtctacact ggttatcaat cagtaactaa tcctgatgtg   1080

aaagcgaaat ttgaaaaagc atggaatgct cagttaagcg atgaggttgg acttaatatt   1140

ccatctatct tgaatgcaat tgaaaaagat aaggtcaaaa tgctgtatgt atttggcgaa   1200

aatccaatgc gcagtgaccc ggatataaat catgtggaac attgtttaaa gcatttggat   1260

tttttagttg ttcaagatat tttcttaact gaaacagctg aagttgctga tgttgttctt   1320

ccgggcgtat cctatgctga aaaagatgga acttttagta gtactgatcg tacagtgcag   1380

cggattcgta aggttgtaga accaataggt aatagtcttc cagattggca aatactccgg   1440

gatatcatga aggcaatgga ttatacagca gattatagtt ctcctgaaga tatatttgat   1500

gaaatgagat ctttaacacc aagttatgct ggtattagtt ataaacggct ggaggatggt   1560

ggcattccat ggccatgtcc aaatgagaat catcctggga cacctatttt gcacgttggt   1620

aagttttccc gtggtttggg taagttttcc ccaattgagt atagagaacc tgctgagctt   1680

cctgataaag aatacccatt aatgctgact actggacgta tcgttactca ctatcataca   1740

ggaactatga cgagacgctg ttggggacta aatggtgtgg atccagaagg atttttggaa   1800

attaaccctg aggatgcaaa aagtcttaat attgaagatg gtgatgaaat tagtgtaaca   1860

acacggcgtg gctcattaat tacaaaagca caagtaacaa ctagggtacc agagggatta   1920

acatttatta ctttccattt tactgagagt ccagctaata ttttgactaa tagtgcccct   1980

gatcctgtta ctggaacacc tgagtttaaa gtttgttcgg taaaagtaaa aaaattagat   2040

ttttcagatt tcggatgtca aaagcgtaaa attttccgta agaagagtgg atacaaagaa   2100

gcttaa                                                              2106
```

<210> SEQ ID NO 87
<211> LENGTH: 1692
<212> TYPE: DNA
<213> ORGANISM: Clostridium ragsdalei

<400> SEQUENCE: 87

```
gtgtctggtc taggcacagc atttggcagt ggagcaatga caaactcaat acatgaactt     60

gatgaaatgg gacctaaaga tgctattttt gcaattggta caaacactac agaatgtcat    120

cctataattg gtattaaaat gctaaaagct aaagagcgcg gtactaagct agtagtggct    180

gatccccgca aaaccgatgt ggcattacat gctgatattt ggctgcggca taaaccaggt    240

acagatgtag cacttctaaa tggaatgtca tatgtcatat tgacagaagg actagctgat    300

gaagcattta ttgctaaaag aactgagaat tttgaggctt tcaaagaagt tgtaatgaaa    360
```

```
ttcacgccaa agtatacatc aagtataact aaggttccag cagacaagat aatagaagcg    420

gcaagaatta ttgctaaggc tgatgctgct gctttgtatt atactatggg tattacacag    480

catactaccg gtgttgataa tgtactatct acagcaaata tcatgatgct tactggtaat    540

attggcaagc ctaaaggagg agttaaccct ctgcgtggtc agaataacgt gcaaggagca    600

tgtgatatgg gagctttgcc taatgtctac actggttacc aaccagtaac taatcctgat    660

gtgaaagcta aattcgaaaa agcatggaat gctcagttaa gtgataaagt tggacttaat    720

attccgtcta tcttgaatgc aattgaaaaa gatgaggtca aaatgctgta tgtatttggt    780

gaaaatccaa tgcgcagcga ccctgatata aatcatgtgg aacattgttt aaagcatttg    840

gattttttgg ttgttcaaga tattttctta actgaaacag ctaaagttgc tgatgttgtt    900

cttccgggcg tatcctatgc tgaaaaagat ggaactttta gtagtactga tcgtacagtg    960

cagcgtattc gtaaggctgt agaaccaata ggtaatagtc ttccagattg gcaaatactc   1020

cgggacatta tgaatgcaat ggattatcca gcagattata gttctcctga ggatatattt   1080

gatgaaatga gatctttaac accaagttat gctggtatta gttataaacg gttggaggat   1140

gggggcattc catggccatg tccaaatgaa aatcatcctg ggacacctat tttgcatatt   1200

ggtaagtttt cccgtggttt gggtaagttt tctccaattg agtataggga gcctgctgaa   1260

cttcctgata aagaatatcc actaatgctg actactggac gtatcgttac tcaatatcat   1320

acagggacta tgacgagacg ttgttgggga ctaaatggtg cggatccaga aggatttttg   1380

gaaattaacc ctgaagatgc aaaaagtctt aatattgagg atggcgatga aattagtgta   1440

acaacacgcc gtggctcatt aattacaaaa gcacaagtaa caactagggt accagaggga   1500

ttaacattta ttacttttca ttttactgag agtccagcta atattttgac taatagtgca   1560

cctgatcctg ttactggaac acctgagttt aaggtttgtt cggtaaaagt aaaaaaatta   1620

gatttctcag attttggatg ccaaaagcgt aagattttcc gtaagaagag taaggcattt   1680

gaaagaaaat aa                                                       1692
```

<210> SEQ ID NO 88
<211> LENGTH: 2130
<212> TYPE: DNA
<213> ORGANISM: Clostridium autoethanogenum

<400> SEQUENCE: 88

```
atggataaaa aagttttaac tgtttgtcct tactgtggcg ctggttgtaa tttatacttg     60

catgtaaaga atggcaaaat aattaaagca gagcctgcta atggtaggac aaatgaagga    120

tcactgtgtt taaaaggaca ctttggttgg gattttttaa acgatcctaa aatattgaca    180

tctagaatta aacatccgat gataagaaaa aacggagagc tagaagaggt aagctgggat    240

gaagctatta gttttacggc ttcaagattg tcacaaataa aagagaaata tggacctgat    300

tccataatgg gaacaggatg tgctaggggt tctggaaacg aagcaaacta cataatgcaa    360

aagtttatga gggcggttat tggaaccaat aacgtagatc actgtgccag agtttgacat    420

gctccttctg tagccggtct ggcttacgtt ttaggaaatg gtgctatgtc aaatggtata    480

catgaaatag atgatacaga tttactactt atttttggat ataatggagc agcttcgcat    540

ccaatagttg ctaagagaat agttagggca aaacaaaagg gtgcaaaggt aatagttgta    600

gatccacgta taacagagtc tggtaggata gcagatttat ggctccctat aaaaaatgga    660

acaaatatgg ttcttgtaaa tacttttgcc aacatactta taaataaaca gttttataac    720
```

```
aaacaatatg tagaagatca tactgttggt tttgaagaat atagatctat agttgaaaat    780
tatactcctg aatatgcaga aaaagttact ggcatacctt cagaggatat agtagaagct    840
atgaaaatgt actcaggtgc taaaaatgcc atgatattat atggtatggg agtatgtcaa    900
tttgctcaag ctgtagatgt agttaaggga ctagcttcta tagcattatt aactggtaat    960
tttggaagac ctaatgtagg tataggacct gtaagaggcc agaacaatgt tcaaggtgct   1020
tgtgatatgg gagcacttcc taatgtatac ccaggttatc aaagtgtaac tgacgatgca   1080
attaggcaaa aatttgaaaa agcttggggt gttaaacttc caaacaaagt tggttatcac   1140
ctgacacaag ttcctgaatt aacgcttaaa gaggataaaa taaaggcata ttatataatg   1200
ggtgaagatc cagttcaaag tgatcctgat tctaatgaaa tgagagagac actggataaa   1260
atggaacttg taatagttca ggatatattt atgaataaaa ctgcactcca tgcagatgta   1320
attttacctt ccacgtcttg gggagaacat gaaggagtct ttagttctgc agatagagga   1380
ttccagagat ttagaaaagc tgtagaacct aagggagatg ttaaaccaga ttgggaaata   1440
atttcaaaaa ttgcctgtgc tatgggttat aatatgcatt ataacaatac tgaggaaata   1500
tggaatgaac ttataaattt atgtccaaat ttcaaaggag caacttataa gagactcgaa   1560
gaattaggag gaatccaatg gccttgtcca tctgaaaatc atcctggaac ttcttatctc   1620
tacaaaggta ataaatttaa tacacctact ggaaaagcaa acttatttgc agcagaatgg   1680
agacctcctg tagagcagac agataaagat tatccactcg ttctttctac agttagagaa   1740
gtaggacatt attctgtaag aacaatgaca ggaaactgta gggcacttca gcagttagcc   1800
gatgaaccag gatatgtaca agttaatcca atggatgcaa aggctaaggg aataatagat   1860
ggtgagctta tgagaataag ttcacgaaga ggttctgtgg ttgcccgtgc acttattact   1920
gaaagggcaa ataaaggagc agtctatatg acctatcaat ggtgggtagg cgcatgtaat   1980
gaacttacat ctaataatct agatccagta tcaaaaactc ctgaattaaa gtattgtgca   2040
gtaaaaatag aagctataaa agatcagaaa gaagctgaaa agtttataaa agatcaatat   2100
gatcttttaa agaaaaagat gaatgtttaa                                    2130
```

<210> SEQ ID NO 89
<211> LENGTH: 2145
<212> TYPE: DNA
<213> ORGANISM: Clostridium ljungdahlii

<400> SEQUENCE: 89

```
atggagaata aagtattaac tgtatgtcct tactgtggtg ctggttgcag actgtattta     60
gtggttgaag atgggaaaat taagagagct gagcctgcta tgggcagaac aaatgaggga    120
gagctttgtc ttaaaggtta ttatggatgg gattatttaa atgatcctaa gcttttaact    180
ccacgtataa ggaagcctaa gatacgaaaa aatggcaagt tcgaagaagt tacttgggat    240
gaagctatca gttttactgc aaaaagattg ggagaaataa gagacaagta tggcgctgat    300
tctataatgg gtactggttg ttctagaggt cctggaaatg aagctaacta tattatgcaa    360
aaatttatga gggctgttat tggaacaaat aatgtggaca actgtgctag agtttgtcat    420
ggaccttctg tagctggact tgctaaagtg ttgggaaatg gtgcaatgtc taatagcatt    480
cctgaaattg ataatgcaga cttggtattt atttttgggt ataatcctgc agaatctcat    540
cctatggtag caagaagaat agttaaggca agacaaaaag gtgcaaaaat agtagtagtg    600
gaccctaggg taacagaaag tgtaagaatt tcagatttat ggcttccgat aaagggtggt    660
actaatatgg cacttgtaaa cggttttgcc aatgttctta ttaatgaagg tttatacaat    720
```

```
aaagattatg tagaaaaata tacagaagga ttcaatgaat atattaaagt tataaagaaa    780

tatacacctg aatatgtaga aaaaatagta aatgtaccag cagaaaagat taaaaaagct    840

atggagatgt atgcttcagc taaaaaccca atgatacttt atggtatggg ggtatgccaa    900

tttggtcaag ctgtagatgt ggtaaaagga ttagctggat tggcactact aacaggaaat    960

tatggaaggc caagtgttgg aataggccct gtaagaggac aaaacaacgt acagggagct   1020

tgtgatatgg gagcacttcc aaataatttt ccaggatatc aaagtgttac ggataaaaat   1080

gtgagagaaa aatttgaaaa agcttggggc gtaaaaaatc ttccagataa gattggatat   1140

catttgactg aagtacctaa agcagtattg gaggaacata aattaaaggc atattatatt   1200

atgggtgaag attgtgttca aagcgatcca aattcaaatg aagtaaggga ggctttggat   1260

gagcttgaat ttgtagtagt tcaggacata tttatgaata aaactacatt acatgcagat   1320

gtaattttgc cagcaactgc ctggggagaa catgaagggg tatatagtgc tgcagataga   1380

ggattgcaaa agtttaacaa ggcagttgaa ccaattggtg aagcaaaacc tgattggcag   1440

ataatttgcg agttatcttc agctatggga tacaaaatgc actataataa tacaaaggaa   1500

atatgggatg aaatgagaag cctttcacct aaatttgcag gtgcaactta tgagaaaatg   1560

gaaactttag atggcgtact ttggccatgt cctacagaag atcatccagg aactcctgtt   1620

ttgtatgaaa acaatgagtt tagtactccg agcaaaaagg gtattttatt tgcttctgaa   1680

tggagaccta cagaagaatc accggatgag aaatatccac ttagcttgtg tacagtcaga   1740

gaaataggac attactctgt aaggacaatg acgggaaatt gtcgtgcttt acagcagcta   1800

gaagacgaac ctggaaaaat acagatgagt atagaagatg cggaagaact tggaattaaa   1860

acaggagatt tagttagagt atcttcaaaa agaggttctg tagtaacaag ggcaaatgtt   1920

acagatagag ttttaaaagg agctacttat atgacttacc aatggtggat tggtgcctgt   1980

aatgaactta cagtggataa tctggatcct atatcaaaaa ctccagaata taaatactgt   2040

gcagttaagg ttgagacaat agaagatcaa gataaagctg aaaagtatat tgatgatact   2100

tataaagctt tgcgtgaaaa gttgggtatt gtaactgcaa attaa                   2145
```

<210> SEQ ID NO 90
<211> LENGTH: 2145
<212> TYPE: DNA
<213> ORGANISM: Clostridium coskatii

<400> SEQUENCE: 90

```
atggagaata aagtattaac tgtatgtcct tactgtggtg ctggttgcag actgtattta     60

gtggttgaag atgggaaaat taagagagct gagcctgcta tgggcagaac aaatgaggga    120

gagctttgtc ttaaaggtta ttatggatgg gattatttaa atgatcctaa gcttttaact    180

ccacgtataa ggaagcctaa gatacgaaaa aatggcaagc tcgaagaagt tacttgggat    240

gaagctatca gttttactgc aaaaagattg ggagaaataa gagacaagta tggcgctgat    300

tctataaatgg gtactggttg ttctagaggt cctggaaatg aagctaacta tattatgcaa    360

aaatttatga gggctgttat tggaacaaat aatgtggaca actgtgctag agtttgtcat    420

ggaccttctg tagctggact tgctaaagtg ttgggaaatg gtgcaatgtc taatagcatt    480

cctgaaattg ataatgcaga cttggtattt atttttgggt ataatcctgc agaatctcat    540

cctatggtag caagaagaat agttaaggca agacaaaaag gtgcaaaaat agtagtagtg    600

gaccctaggg taacagaaag tgtaagaatt tcagatttat ggcttccgat aaagggtggt    660
```

```
actaatatgg cacttgtaaa cggttttgcc aatgttctta ttaatgaagg tttatacaat    720
aaagattatg tagaaaaata tacagaagga ttcgatgaat atattaaagt tataaagaaa    780
tatacacctg aatatgtaga aaaaatagta aatgtaccag cagaaaagat taaaaaagct    840
atggaaatgt atgcttcagc taaaaaccca atgatacttt atggtatggg agtatgtcaa    900
tttggtcaag ctgtagatgt ggtaaaagga ttagctggtt tggcactact aacaggaaat    960
tatggaaggc caagtgttgg aataggccct gtaagaggac aaaataatgt tcagggagcc   1020
tgtgatatgg gagcacttcc aaataatttt ccaggatatc agagtgttac agataaaaat   1080
gtgagagaaa aatttgaaaa agcttgggga gtaaaaaatc ttccagacaa aattggctat   1140
catttgactg aagtacctaa agcagtactg gaggaacata aattaaaggc atattatatt   1200
atgggtgaag attgtgttca aagtgatcca aattcaaatg aagtaaggga ggctttggat   1260
gagcttgaat ttgtagtagt tcaggacata tttatgaata aaactacatt acatgcagat   1320
gtaattttgc cagcaactgc ctggggagaa catgaagggg tatatagtgc tgcagataga   1380
ggattgcaaa agtttaacaa ggcagttgaa ccaattggtg aagcaaaacc tgattggcag   1440
ataatttgcg agttatcttc agctatggga tataaaatgc actataataa tacaaaggaa   1500
atatgggatg aaatgagaag cctttcacct aaatttgcag gtgcaactta tgagaaaatg   1560
gaaactttag atggtgtact ttggccatgt cctacagaag atcatccagg aactcctgtt   1620
ttgtatgaaa acaacgagtt tagtactccg agcaaaaagg gtattttatt tgcttcagaa   1680
tggagaccta cagaagaatc accagatgaa aaatatccgc ttagtttgtg tacagttaga   1740
gaaatagggc attactctgt aaggacaatg acaggaaatt gtcgtgctct acagcagcta   1800
gaagatgaac ctggaaaaat acagatgagt atagaagatg cagaagaact tggaattaaa   1860
acaggagatt tagttagagt atcttcaaaa agagattctg tagtaacaag ggcaaatgtt   1920
acagatagag ttttaaaagg agctacttat atgacttatc aatggtggat tggtgcctgc   1980
aatgaactta cagtagataa tctggaccct atatcaaaaa ctccagaata taaatactgt   2040
gcagttaagg ttgaggcaat agaagatcaa gataaagctg aaaagtatat tgatgatact   2100
tataaagctt tgcgtgaaaa gttgggtatt gtaactgcaa attaa                   2145
```

<210> SEQ ID NO 91
<211> LENGTH: 2130
<212> TYPE: DNA
<213> ORGANISM: Clostridium ragsdalei

<400> SEQUENCE: 91

```
atggataaaa aagttttaac tgtttgtcct tactgcggtg ctggttgtaa gttatacttg     60
catgtaaagg atggcaagat aattaaagca gagcctgcta atggtaggac aaatgaaggg    120
tccttgtgtt taaaaggacg atttggctgg gattttctaa atgatcctaa aatattgaca    180
tctagaatta aacatccaat gataagaaaa aatggagagt tagaagaggt aagttgggat    240
gaagctatta gttttacggc ttcaaaattg tcacaaataa aagagaaata tggacctgat    300
tctataatgg gaacaggatg tgctaggggt tctggaaatg aagcaaacta cgtaatgcaa    360
aagtttatga gggcggttat tggaaccaat aacgtagatc actgtgccag agtttgacat    420
gctccttctg tagccggtct ggcttacgtt ttaggaaatg gtgctatgtc aaatggtata    480
catgaaatag atgatacaga tttactactt atttttggat ataatggagc agcttcgcat    540
ccaatagttg ctaagagaat agttagggca aaacaaaaag gtgcaaaggt aatagttgta    600
gatccacgta taacagagtc tggtaggata gcagatttat ggctccctat aaaaaatgga    660
```

-continued

```
acaaatatgg ttcttgtaaa tacttttgcc aatatactta taaacaagca attttatgac    720
aaacaatatg tagaagatca tactgttggt tttgaagaat ataaatctat agttgaggat    780
tatacgcctg aatatgcaga aaaagttact ggtatacctg cagaggatat agtagaagct    840
atgaaaatgt actccagtgc taaaaatgct atgatattgt acggtatggg agtatgtcag    900
tttgctcaag ctgtagatgt agtaaaaggg ttagcttcaa tagctttatt aactggtaat    960
tttggaagac ctaatgtagg cataggacct gtaagaggcc agaacaatgt gcaaggtgcc   1020
tgcgatatgg gagcacttcc taatgtatac ccaggttatc aaagtgtaac tgacgatgca   1080
attagagaaa aatttgaaaa agcttgggga gttaaacttt caaacaaagt tggttatcac   1140
ctgacacgag ttcctgaatt aacgcttaaa gaggataaaa taaaagcata ttatataatg   1200
ggcgaagatc cagctcaaag tgatcctgat tctaatgaaa tgagggaaac acttgataaa   1260
atggaacttg taatagttca agatatattt atgaataaaa ctgcactcca tgcagatgta   1320
attttacctt ctacgtcttg gggagaacat gaaggagtct tcagttctgc tgatagagga   1380
ttccagagat ttagaaaagc tgtagaacct aagggcgatg ttaaaccaga ttgggagata   1440
atttcagaaa ttgcatgtgc tatgggttat gatatgcatt ataacaatac tgaggaaata   1500
tgggatgaac ttataaattt atgcccaaat ttcaaaggag caacttataa gagattggat   1560
gaattaggag gaattcaatg gccttgtcca tctgaagatc atccaggaac ttcttatctc   1620
tacaaaggaa ataaatttaa tacacctact ggaaaagcaa atttatttgc agcagaatgg   1680
agacctccta tagagaagac agatgaagaa tatccacttg ttctttctac agttagagaa   1740
gtagggcatt actccgtaag aacaatgaca ggaaactgta gggcactcca gcagttagct   1800
gatgaaccag gatatgtaca aattaatcca gtggatgcaa aggctaaaaa aataatagat   1860
ggtgagctta tgagagtaag ttcacgaaga ggttctgtag ttgcccgtgc acttgttact   1920
gaaagggcaa ataaaggagc agtttatatg acctatcaat ggtgggtagg tgcatgtaat   1980
gagcttacag ctaataattt agatccagta tcaaaaactc ctgaattaaa gtattgtgca   2040
gtgaaggtag aagctataga agatcagaaa gaagctgaaa agtttataaa agatcaatat   2100
gcttcaataa agaaaaagat gaatgtttaa                                    2130
```